US011466307B2

(12) United States Patent
Ruan et al.

(10) Patent No.: US 11,466,307 B2
(45) Date of Patent: *Oct. 11, 2022

(54) COMPOSITIONS FOR RNA-CHROMATIN INTERACTION ANALYSIS AND USES THEREOF

(71) Applicant: The Jackson Laboratory, Bar Harbor, ME (US)

(72) Inventors: Yijun Ruan, Farmington, CT (US); Meizhen Zheng, Farmington, CT (US); Junhong Oscar Luo, Avon, CT (US)

(73) Assignee: The Jackson Laboratory, Bar Harbor, ME (US)

( * ) Notice: Subject to any disclaimer, the term of this patent is extended or adjusted under 35 U.S.C. 154(b) by 283 days.

This patent is subject to a terminal disclaimer.

(21) Appl. No.: 15/934,465

(22) Filed: Mar. 23, 2018

(65) Prior Publication Data
US 2018/0312908 A1    Nov. 1, 2018

Related U.S. Application Data

(63) Continuation of application No. 15/059,605, filed on Mar. 3, 2016, now Pat. No. 9,938,565, which is a continuation of application No. PCT/US2014/054185, filed on Sep. 5, 2014.

(60) Provisional application No. 61/873,928, filed on Sep. 5, 2013.

(51) Int. Cl.
*C12Q 1/6809* (2018.01)
*C12Q 1/6806* (2018.01)

(52) U.S. Cl.
CPC ......... *C12Q 1/6809* (2013.01); *C12Q 1/6806* (2013.01)

(58) Field of Classification Search
None
See application file for complete search history.

(56) References Cited

U.S. PATENT DOCUMENTS 5,759,822 A    6/1998 Chenchik et al.
9,938,565 B2 *  4/2018 Ruan .................... C12Q 1/6809

FOREIGN PATENT DOCUMENTS

WO    2012/150317 A1    11/2012

OTHER PUBLICATIONS

Derrien et al., "The GENCODE v7 catalog of human long noncoding RNAs: Analysis of their gene structure, evolution, and expression," Genome Res., 22:1175-1789 (2012).
Faridani et al., "Specific Ligation to double-stranded RNA for analysis of cellular RNA: : RNA interactions", Nucleic Acids Research, vol. 36, No. 16 Aug. 1, 2008.
Fullwood et al., "Next-generation DNA sequencing of paired-end tags (PET) for transciptome and genome analyses," Genome Res., 19:521-532 (2009).
Ruan and Ruan, "Genome Wide Full-Length Transcript Analysis Using 5' and 3' Paired-End-Tag Next Generation Sequencing (RNA-PET)," Transcriptional Regulation: Methods and Protocols, Meth, in Molec. Biol., Chapt. 35, 309:535-562 (2012).
Spicuglia et al., "An update on recent methods applied for deciphering the diversity of the noncoding RNA genome structure and function," Methods, 63:3-17 (2013).
Zhang et al., "ChIA-PET analysis of transcriptional chromatin interactions," Methods, 58(3): 289-299 (2012).

\* cited by examiner

*Primary Examiner* — Nancy J Leith
(74) *Attorney, Agent, or Firm* — Pierce Atwood LLP

(57) ABSTRACT

The invention described herein provides reagents (e.g., kits), compositions, and methods for carrying out an unbiased genome-wide strategy to identify the functional targets for all ncRNAs.

8 Claims, 16 Drawing Sheets

Specification includes a Sequence Listing.

SEQUENCE LISTING

```
<160> NUMBER OF SEQ ID NOS: 23

<210> SEQ ID NO 1
<211> LENGTH: 29299
<212> TYPE: DNA
<213> ORGANISM: Homo sapiens
```

```
<400> SEQUENCE: 1
cactcttggg tagaacgact ctaacagcga ccgtctaaat gaaggtcaca ctaacaacgt      60
tcttaaacag attgtcttac ttactagttg gaactcgtct tctctaatac tttttgaatt     120
atcgtaacat cgttacaccg acaattactt tatgtcaacc gacgagggcg acaaaccgtg     180
gttggttgga ctgtgacagt tgtagtgtta tgctataaat aagggttaat aaaatgccgt     240
tgttgacttt atgttacaca ataattagta taaataatat tcatagttaa actctttaaa     300
gactgtacgg tcttctattt atccaaataa tacttttcgt caagacgaac cacgtacgac     360
cgacgacgac acattattta tcggagacac ccctttcaaa aaattttctt tatttcgttt     420
ttttatcgtg acttttgtct ttccttcgta gttttgagaa gtttatggac gacacaggta     480
accagttcgt gtaagtcctg tagcgtacgg aaatcttgag gtcgtccaag gttgtcgatc     540
atcctgtaag atctgaggaa aatcgggaca gacaccgaag tcttattaaa ggttgcgttg     600
gtaggtttaa aactgggtgt cgcacaatgt aaaccgtaac gccactgagt caaggagtag     660
aaatcacatg aggaagtatt aaatctaatt gaacacactt cgtgacttag gttatatacc     720
acagaaatcc aggttggagt ccagagggat gtacaacagt cttttttctgt aaactcgtaa     780
aattctcact ttagttttca cgtgatggtt ccaaagattg tcgggtcaag acaggaccga     840
aaagaaggac gttgacaaaa gtcgaaccca ctcagtgaaa agagagacct ggaggtaaaa     900
gagtggggtg tagtgtcagg tcactcccga agagaggtag gattttgaaa ggggggacctt     960
gagttcagag agatacaacg ggacgtttta atcgaagtca gggtatatga accgggctaa    1020
tgggtgtctt tcatgtcgtt cgtagtagta ggtgtatccc agaggttta accgaaagga    1080
ccttggtaag tgttccggta aagtcagttt cgggacccctt ttattggtca aggaggttga    1140
cacagagtaa catttttcttt tgtctaataa taacttgaat acattcgttg gtataacggt    1200
atttaattct tataagtgtt tatcaaatgt ttaagatgtc tttagtccgt ctctctcttt    1260
acacgaagtt taagataact gttctcatgt gagatgagtt aacgatttcc aacatttgtc    1320
gagttttctt tttcacaaga ggtctgagac ttttttgtttt gttttttctta gtcgttacaa    1380
agtttcttgg tttttttttt ttttttttttt ttagatttat acatatgtgt gtgtctgtgt    1440
ttctaggtta tcgtaaatgg agttttgaaa tcgatacttt atcgttatct ttgagtggtc    1500
aaatgtttgt ccaagtgtac cgatttgata aaaacggggt tatgtattag tttacttccg    1560
acacttggtt ttaaacccca tctcgtcaag agtaccgtca aacgaaaaat ttccggtatg    1620
gaagggtcta cggtttctcg tgatccaggt ctatcgtggt gtcttttttgt agtagatatt    1680
ggatgattag tccgggttgg gacgaatctt gtcgtcgcat cctcagactg atgtaccttac    1740
aagtagaacg gaagagtaag ttgtcgtttg aggtctaggg tttcttatga ccccggtccg    1800
gttcacgtca ccgattgtgg acgttagagt cgtgaaactc tccgactaca ccctcctggt    1860
gaactcaggt tctcaatctc tggtcggacc cgttgtacta cccttgaata gagaggtttt    1920
taatttttttt tttttttcgat ccgtactacc gtacatggaa atgaggatcg atgaaccctc    1980
cgactcgacc ctcctaggga actcgggtcg tcaaggtccg atgtcactcg gtactactgt    2040
gataacgtga ggtcggaccc gttgtcgcat tctaggacag gagaccggtt ttttcccaga    2100
ccgtggacga atcctcccga aggttttgaa aaagtcgttt ctatcactca ccgttttgga    2160
tcgtacttcg ggtctcatac accgagacgc aatcataaag agtgtcgggt gacattactg    2220
acagtccaac gaaaattcta atactttcag gatataactt aacagtaagc ttaactctgg    2280
aacttcagac ttctgcctta atgaaccctt cttcgtagtg tcatagaatc ttctcacagg    2340
```

```
gaggtacttc gtctaaaccc cagagtaagg caaagacatg aatgtcatta cctggtacaa    2400
tccgttcagt aaattgtgta aacctggggt cgaaggttta gatatgttac cttccatatt    2460
aacctctctc atatttcgga aatcacgggt gaaatgaact ctctaaaagt ctcgtcagtt    2520
actctgaaat ctttattttc acttgaattt tgtatttcac gaaatatttg gggtcgtaac    2580
ggacttcggg actctaacga actaccgggt aacgcatata agtgtccgtg acggggttga    2640
ccgggaatga tgttgagatc tttactgtcc gtaagtaaga aggttaggtg tctactccgt    2700
tgatgcttca caataaaaat tggggagtaa aaaattcctc tttttgactc gaactcgtgt    2760
aattttttac accgggtctc agttatacca tatacaactg gaaccttaag ctcttttcag    2820
aagacagtgt tctcgtcttc ggtgtttgag tttatgaaaa tcccaataca atggttaaca    2880
ccttgtgtac acgtacttta ctcgactcat tctacggttt actggaccat aacctctccg    2940
ttatccctca ccaccccgga catcgtttga tctctctcgt accgagtcaa ttttctctca    3000
ccgtcgttga gttgaggtcg gttaacaacg gtatgttata attcgggtcc ctaaagtctt    3060
gaagatcgat cttttatct ccgatctata catataagga caagttttaa cggagttaat    3120
cttctataat cgttcattaa gtttacgtta tgtgaaaaca taatagtgat atgaccaggt    3180
ggattattcc cctgtcaaac gaaggacgag agtgtttcac aaagtctgat tcaatactgg    3240
tgaattcata cgtttctgtt ttgtcacata gtcattacgt cactaacact cgtacatgaa    3300
gtctttgttt actagaccca agtttaggac cacaactgta attcatcaaa ttattggagc    3360
ccgttcagtg aactgaagag atatggagtc aaagggatag acattttacc ttcattattc    3420
tcatgaatga ggaaagtcac caacactgat agtttactta actgtatcca ttttgttaat    3480
cttgtcaagg actgtgtgcc attctcagta catttatagt tacgaatact ttcgagagta    3540
gggtcctatt cgtagaggat cttttgtaga agcaggtaca tggtctaatt agtataaata    3600
agacgtcaac tataaatacg gtgtacaaga aagaccatc tcttcggact tcaataagac    3660
aaataggact ggaacctttt ctgtttcgtc gagtacaggg gtccctagat ttttaaagtg    3720
acccttacta gtgggtcaca gaggttttgg agtcggtcgt aaagagataa gtgtcgacgt    3780
gacttctcga aggaaggacc gaacacagag gttttcccct atgctaccgt tccagacaaa    3840
taatgagagt ccgactacac cggcccctct acaccttaac acatcttacc ttacgctacc    3900
ttatacttta ccacacctta tgtacacttg aagtacggac gaagagtcca agaaggtga    3960 aggggaaata caccctgttc tatcgacttc acccgacctc aacccaaaag aggaggaggt    4020
aaaccttccg acctcgaacg acctcaactc ataaagaaaa ggagtccagt caatccaaga    4080
ctattttggg atcacccaat ccgagaccaa tctgtcgaag gggactcccg tctggggtga    4140
gactcgtcgt tacggatctt tactaccaag aagtttaggt tcactattgg gtatcattga    4200
ttgagtaatc gaatcaagac ggcatttcag tcttgtttcg ttcctctttg tcttggagac    4260
gtcacttacc tccttaaaga ctcccagtga actttcgtct ttgagttctc ggggtaaagg    4320
ttaaaggatg ataacatgaa ctttatacct aaagtgtata aacccatta gtgaagtagt    4380 catttcaacc ggaagcattc aattttttgtg agtttaaaat ctttgagtta caagacaccc    4440
aatgtttact gacgggtggt acgacacccc gtactgtggg aaaacattaa agactttatg    4500
cttcatgata aaaagaaat tacgtaagag agaaaaatca aagaggtagg acactataca    4560
gacaggtttt cctgaagggt ttttggtgac ataccgtctt ttccaaaagt tttacgtact    4620
ctcttaatat cgtttctctt tattgagtgt gatttcaaaa attttataga ggcctgatac    4680
```

```
cgatccttga taatgatacc gattgttcac attaaagtcg taaaaccctc cggttccgtc    4740
cgtctaggga attcagatcc tcaaactctg gtcgaacccg ttacaccact ttgggggggag   4800 acgttttta  tgttttatta  atcgccccac accaccacgt gtggacacca gggtcgatga   4860
gtacctccga ttcctccctc ctagtgaact cgggccctcc gtctccaacg tcactcgatt    4920
ctaatacggt gacgtggggt cggaccctct gtctaagaca gagttttttt tttttttta    4980 gagacctgat atttgagagt acttagatcg taataaacct agtctttata taagtatcct    5040
atctgacact actgtttatt tagtttaaac cctacggagt tgtgttcttt ataaaaatac    5100
atagtaatac attgtcaggt ccctccgact tttatctcac atacaacgtc cattctttaa    5160
aacgagacgt cagtaagtcc ttaacttcga ctatcactaa gacggtagaa cttgtacacc    5220
gtagcgacag acagacctcc cacggtagtg tcagtcgaaa cctgtcgtgg aacttacgat    5280
agtcccttcg atctcacaag aggacaagaa acgacaggaa cggtcacaga agaggacttg    5340
agtgtagtct tcgtacggtc attcgtccac catggtcgtc ccaagattgg gtccgtgagg    5400
ttaagattcc agttgaaaca atcacaatag atttttttctt ttcgttatta tttaataggt   5460
gttcttttaa aatgttgagt tcaaaaagta tgagaaattt ttccgtaaaa aagtgtacat    5520
gagagtacaa gatactaatc tggattagta acagtgaagt gccgatctct ttgattctgg    5580
tcttctcgaa ggtctagaac tgatcgtggt gagttactca ccctactggt cttgggacat    5640
gactagtacg tttgaagtgg tgtattgtcg aacactataa ctcactcaac aaagtggata    5700
tgctggggag atttggttaa ataattagat cttttaccct tattatcgtt aaagatacat    5760
tattcaacaa cctcgtgttc tatttcaata tacatatttt gtaaatcgtg tcaaggacca    5820
cgtattgtcc agacatcatt tataaacaac attaatcgtc gttttagtag agggagtaat    5880
gacgtcaact aaaaggaaat aataaccttt ctttaaagag ttgactcaaa gtcaacttat    5940
gtcataatct aataaggaat tgactcaaag tcgtaaaatt tacatatgag ggatgagttt    6000
tgatggatga tttagtgcgg acattaaggt cgtgagaccg tccggttccg cccacctagt    6060
actccagtcc tctagttctg gtaggaccga ttgtgctact ttggggtaga gatgatttt    6120 tacgtttttt taatcggtcc gcaccaccga ccgtggacat cagggtcgat gaaccctccg    6180
actccgtcct cttaccacac ttgggccctc cgtctcgaac gtcacccggc tctagcacgg    6240
tgacgtggtg tcggacccgc tgtctcactc tgaggcagag ttttttgtttg ttttttttgtg   6300 tttttagatg gatgattttt cttcaagaag ttacgaatct gaaactcgtt tcttttttcag   6360 acgagattgt ccttcgacca ctatatcttt ccatttcaaa gtgaagtgtc cgtgaaacta    6420
aagggaagct ccacctatga cttactaaac acacacgcgt gtaaaaagat acgtaataag    6480
ttttaatttt aaggaatctc ctttggtgac tttcggttag taaatgtttt gaaatttta     6540 ctgtagaact tctcaagaaa ccacgagtaa gtagtttgaa tcgttactaa attgacatta    6600
agaaataagt ctaagtagag ggtgttttat ttttacggta tttcgaaatg tcatgacata    6660
ggattactta tctctttgat ttcttttca ttctactcgt tcactctcct tttgggcttt     6720
tactcggaca ggaccgtaca aagatttttc tttctttgtt tgtttgttcg tcggggagga    6780
gagtcgagaa cccttttcttt ataacttaga actgttatag acgtgaagta tcaactaagt   6840
atcgtactgg atagagtttg ttaaattcta agtttacttc aaacgttaat tagaaagcta    6900
tagtgaaacg ttttgtaaga gtattggaat aggtcgggaa aatgtttagt taggacactc    6960
cacttgtagt gacacaaggg taaatgtcct cttttccgtga ctcggtgtct ctccaatata   7020
tgagtactag ttattcgacc attctgattc ttggtcctta ctatgacaga aggaagaggt    7080
```

```
ttataggaca agaaataata ctcatggatt tgtcataatt tttaattaat gtcgagttgt   7140
tatcattcat ttacaggagt acactttagg tggcaaattt tgaattccaa tagataaata   7200
gtttatttaa tttaggatga gtgaattgtt ataagtaact cgagtaagac atttgttggt   7260
aatccggtcc ccgtctatac tttatactcc gagttagaca ctagtgtctc tactttatat   7320
gttaaatctc tctctttcta ttcgtactac tgtttattta ttacatactt ttaatcggta   7380
atagaatccg gttgaaaaag attcgacatt cgacagacgg atgaagacgg tccacaatca   7440
ttaacaaaat ttttcacccc cttcttctca tgaagtacca cccttctata agtaactcct   7500
gtattcgtag aaggagaatc tttaattgtt acgtgtcacc ggataacgtt caaaactttc   7560
gggacgtttg ttattttcgg actaatcaaa ataacttag tcatagagga tttgtgaaaa    7620
agtactttgt tccaatgagt gtttagaaca gctccttgat tacaggatcc tttcaccaaa   7680
agttcgaact cgtacatgta ttcatagtaa cctttccaac gttttatgt ttacacaccc    7740
gaggtgaggt ctttaagact aacttcacca gagtagacag tagactcttg aacgtaaaaa   7800
cagtctaagg atcgactaga ctacaaagtc ctgactcttg aattaaactc atcatagaga   7860
tgtcttgtca aaattttac aagaggacct catcctacta atatgaattg ttttacatt     7920
atgtgagtcc actacctgtg ggaatcatag gactaaccta gtgatgtgta atatatgtac   7980
attgtgtaaa agagttcatg gggtatttaa acgtgtttat ttatttattt attttaatat   8040
gaaagagtt tatttttta ttttatttac aaggagaact taccatctta gaaacaaaaa     8100
aacactatta gtatttatgt atatttataa gagtagtaat gtacgtacat caatggaagg   8160
aaatgtacta cgtggtcttt cttatgggtg agattcttcc tttcttactt ctcttcttcc   8220
gtaacaaatt ttctggataa taatcttatt cagtttaaga tacagatggt aataattcga   8280
caaactgaaa ctcgtcccta accttccgta aaatttaact ccacctctat acgtgtttcg   8340
gtgcacccct tacagtacac agggacgtat ttctcttgtt cgataaaacg aaccaacctc   8400
tactcctctg tctccgacat gtattcttac acaagttaaa tttcgttgtt ttatatagct   8460
ggtttgatga aactcgttag ttcccctata taaccgagtg tagtgacttt atatatgacc   8520
gtgtcgtcta aaggtcaatc cagactagac gatcgagaca ggggaggtct tatgtccgag   8580
gtccgtccgt ccttccttct cctgtagtca agagaaccac agatcgtgcg acggacataa   8640
ttccatccag gagttattta agtacaacat cctttactta cgtacaagag tttctacgcc   8700
aatgaaagtc atagtgacga aaggagtacc aaaggtgaag ttataatcag attgaacgga   8760
atccctgggt tctaccgacg ataagtgaag ttaatcgatt tgtgaagaga aaagtaccga   8820
cactctctga tcgatggaga aggtatttac ttaaaagaga agaaagaccc gtgttatcag   8880
agataaaggg tcggagaaaa tgttaatcca cataggtacg ttgagtcaag atcggttacc   8940
gcacactcat catcactata ggtggtgaac gtctggatgt gtatttccga gggtctgtgt   9000
agaagacacg agaaatgacc ttgtgaacga actaaggtta tttatgtcgt tggaatcgtc   9060
gatgtataac gtcaaccgtc tcgaaagtac aaagtcgaag aagtataaaa aatcaaaaca   9120
acagtgacaa ccaaaaaaaa aattaactaa gtcctctact ggattatttt ttaacttctt   9180
tttatttcgt aaaacaagac ctaaagagta atccttgtac tccaaatgag ataacgttga   9240
ccgaatcaag tatactagta ggggactcca ctccctttt ctacgcactt aactaattcg     9300
gttccagtgt accagctta catcttaacc caaaactcca gtcaagggga tttagtgggt    9360
ctataggttc acctttagtc cgaggtaact gttttccctt gtcaagaatc tttacgttga   9420
```

```
tgtttacagg ttagggtcaa ccgttcaagc ttcgttcctt cccgaaaggt aatttcttac   9480
acctacgatg gaccacccgt tgacctccgg tgaccgtata taaaaaaaac ccccccaaa    9540 gtatttgata accaaaaaaa ttaataataa tatgaaattc aaaatcccat gtacacgtgt   9600
tacacgtcca atcaatgtat acatatgcac acggtacgac cacacgacgt gggtaattga   9660
gtagtaaatc gtaatccata tagaggatta cgatagggag ggggagggg ggtggggtgt    9720 tgtcagggt ctcacactac aaggggaagg acacaggtac acaaaagtaa caagtcaagg    9780
gtggatactc actcttgtac gccacaaacc aaaaacagga acgctatcaa atgactctta   9840
ctactaaagg ttaaagtagg tacagggatg tttcctgtac ttgagtagta aaaaataccg   9900
acgtatcata aggtaccaca tatacacggt gtaagagaat taggtcagat agtaacaacc   9960
tgtaaaccga accaaggttc agaaacgata acacttatca cggtgttatt tgtatgcata  10020
cgtacacaga aatatcgtcg tactaaatat caggaaaccc atatatgggt cattacccta  10080
ccgacccagt ttaccataaa gatcaagatc tagggactcc ttagcggtgt gactgaaggt  10140
gttaccaact tgatcaaatg tcagggtgat tgtcacattt tcacaaggat aaagaggtgt  10200
aggagagctc gtggacaaca aaggactgaa aaattactaa cggtaagatt gaccacactc  10260
taccatagag taacaccaaa actaaacgta aagagactac cggtcactac tactcgtaaa  10320
aaagtacaca aaaaaccgac gtatttacag aagaaaactc ttcacagaca agtacaggaa  10380
acgggtgaaa aactacccca acaaacaaaa aaagaacatt taaacaaact caagtaacat  10440
ctaagaccta taatcgggaa acagtctact catccaacac ttttaaaaga gggtaaaaca  10500
tccaacggac aagtgagact accatcaaag aaaacgacac gtcttcgaga agtcaaatta  10560
atctagggga aacagttaaa acagaaaaca acggtaacga aaaccacaaa atctgtactt  10620
caggaacggg tacggataca ggacttacca ttacggatcc aaaagaagat cccaaaaata  10680
ccaaaatcca gattgtaaat tcagaaatta ggtagaactt aattaaaaac atattccaca  10740
ttccttccct aggtcaaagt cgaaagaggt ataccgatcg gtcaaaggg tcgtggtaaa   10800 taatttatcc cttaggaaag gggtaacgaa caaaaagagt ccaaacagtt tctagtctct  10860
caacatctat acaccgcaat aaagactccc gagacaagac aaggtaacta gatatagaga  10920
caaaaccatg gtcatggtac gacaaaccca atgacatcgg aacatcatat caaacttcag  10980
tccatcacac tacggaggtc gaaacaagaa aaccgaatcc taactgaacc actacgcccg  11040
agaaaaaacc acggtatact tgaaatttcg tcaaaaaagg ttaagacact tctttcagta  11100
accatcgaac tacccctacc gtaacttaga tatttaatgg aacccgtcat accggtaaaa  11160
gtgctataac taagaaggat gggtactcgt accttacaag aaggtaaaca aacataggag  11220
aaaataaagt aactcgtcac caaacatcaa gaggaacttc tcaaggaagt acagggaaca  11280
ttcaacctaa ggatccataa aataagagaa acttcgttaa cacttaccct caagtgagta  11340
ctaaaccgag agacaaacag acaacaacca catattctta cgaagactaa aaacatgtaa  11400
ctaaaaatat aggactctga aacgacttca acgaatagtc gaattcctct aaaacccgac  11460
tctgttaccc caaaagatct atatgtacag tagacgtttg tccctgttaa actaaaggag  11520
aaaaggatta acttatggga aataaaggaa gaggacggat taacgggacc ggtcttgaag  11580
gttgtggtac aacttatcct caccactctc tcccgtaggg acagaacacg gtcaaaagtt  11640
tcccttacga aggtcaaaaa cgggtaagtc atactataac cgacacccaa aaagtatcta  11700
ttgagaataa taaaactcta tgcagggtag ttatgaatta aataactctc aaaaccgta   11760 cttctcaaca acttaaaaca gtttccggaa aagacgtaga taactctatt agtacaccaa  11820
```

```
aaacagaaac caagacaaat atacgaccta atgtaaataa ctaaacgaat ataacttggt   11880
cggaacgtag ggtccctact tcgggtgaac tagtaccacc tattcgaaaa actacacgac   11940
gacctaaacc aaactggtga ccgtataaaa ttcgtaccct cattgtgaca gtccaaaaaa   12000
tttaatgttt tacgaaatcg tatctctttt aatatttctt gttatattca ttgtctatac   12060
gtgagtgata ggacgaatta gtttacagtg tgaaacggtt cgaactaagt ttaaaaaatt   12120
tcgtttcttt gtaatgtcta taccgacgtt gtaggataca cggggtggcg actatgtatg   12180
gagagaaggg ttcccattgg tgaaagactg aaactatgaa tagtaagggt ccgtactaat   12240
ttacgataac gacttaaacg tatatatgta tttattatat atgtcaacaa acgtacaaga   12300
ttttgaaacg taatttatta tagtttatta atttttaaaa gtgtttaacg taaaaattga   12360
gtcagaaaat attctaacgg ttattactat agagaagtct agtaagtaaa actgataata   12420
taataaaaag taacatactg atacggtacc gagtgaatag gtaagacaat aactatttgt   12480
aaacacaaca aaggtgttaa aacgataatt ttattaccgt aacacttgta agaacacaca   12540
tatagtgaca catgtgtacg atctcaaaga gattacataa taccacatat aacgacccgg   12600
tttccgatac attcagaagt tgaagggatc tacagtatgg ttgagtatgt atatactggt   12660
cacactcgta agagtcacga gatgtaacag gtctaagatg tacttcgtga ccaccggata   12720
accagtccaa ctgactataa tcttccaata acggtttcag atacactctc tctgactccc   12780
agactttatg gatctacatt ccctatattt cactctctcc tttcttcaat tgtataaatc   12840
ctcgttttag gtgtactgaa acactaacta atacctcttt tattcctctt cttcccttgt   12900
ccttctgaga gttcagaggt ctaacttgtg ttctccttcg aatacacggc actctgacta   12960
ctgtttaagg aaaacttgta tcacggaaac tcccgaacca tcattttttc tttcgtgata   13020
ggtagtccgt aaacctataa atccagacct tctgacttttt ctctagtttt gtcttttatg   13080
tttaatatct tagtagctct acccatttta gtcttctcaa cctagttctt ttcatggatc   13140
ttagtcatct cttcactcaa ttcttttata gagacccttt gtaattataa atttccatat   13200
attttccttc tcttctgaca cctcttctgt ctctgacttc ttcctctgtt ttacacagta   13260
tgacatcatc ggtctcctta tctcgaagtt tcttactcac cagttggtgt aatttgtgtc   13320
gatcttttgg ttcttccatt tctttacttt taatttgtaa ttgtatgtta cttcaataac   13380
tcaggtacaa ttttaccaaa gttacctta cgtagttacc tttattaacg ttaatcattt   13440
tcttaaaatc tttttctttt ttaattatgt cgattgaaag agtttaattt aaaaaacttt   13500
tattttgtca ctctacctta agctcacgtt ctacaaacaa cttttagttg tgtgtacttt   13560
cctttctctc acttggatttt ttttaaccga ggtctcagat aattacattt ctgatacaat   13620
ataacagaga gatagaaatc cctttgtata tgggttaagt agaacacagt ggtcttagtc   13680
taagtagttt gggtaagacc tggtgagact agtgatcaaa gtgggagtgt cagtatcatt   13740
tctttgattt cgtttttctga tgttctcgtt tcctgtcttt ccctttacaa taaaagaggg   13800
gagtggaaac gggagaaact aaaagaggta acaacgattt tccttgtgaa tcttttgata   13860
ctttctttga agacggacat ttacgtcgag gtactaatac ttaagactta ggaacattgt   13920
cttcttggtt atcctgacta ggtactgaag ataatcatct ctgacccttc catccactga   13980
aatcgagtgg ttcggactag tgtcgtttta tcttttacta gtgtcacagg ggaaaaatag   14040
gaccccattg ttacttgtaa gtcaccctcg gttgatgaca taatttcagg acccacgtcg   14100
aggaccgtgt actgtaccgg gtgttccatc atcaagactc atgggaacgg atagtcacca   14160
```

```
cgaccccgct cttccctccc gtcggacgag tgatccctct cgtccttact ccgatccttc   14220
atgtccctgg accgtttcta cagaggacaa actctctctg aagtcaatta caagtcagtt   14280
gaaggacacc acgattcttc actttcaact tgaactgata gttccttgtc tccgtccaac   14340
aatcgacccg gggaccctcc ttcagttgtt cgaggtggtg tagactgttg tggatgacga   14400
acgtcgggaa gggggtccag tccgtcgacg tgtggagtac gaaggttgac tcccccttac   14460
ttacccatgg ttctcatcca ctcagatgaa gaaagggtcc ccactcatcg cccacttctt   14520
tagtcgtaca tcacctgtaa atgtacacgg cctatggagt atatacgtca caccatagta   14580
ataggagtga cacgtctact tctgtgactc cgagtccctg aacaagttct gtgtgtagac   14640
cagttatccc tcggtcctaa gttttagtgc agtcagatca tgagttcagg agacaagaaa   14700
ggtgctgatg taatctacat agggatctat cagatccaca ttgtcgtact cagagggtac   14760
tttccttcac ccccgagaac cttgtatgga gaaatccttc ggaaggtagt aacacgacgg   14820
aaggaggaga cacgtcggag tcgtgagtga caactcggga agagatcctc aaacgttaga   14880
tgcccctcac tacccgtgta ttcctttatt aaagttacat cataccgttt acgactcgat   14940
ctatttacgc gcttactgat acttcttgtc tcctaacccc agtggattga gttgtactct   15000
gagtaccttc agaggactcc tctttggaga ctcaggatct ctcactctta accggtcttt   15060
ttaattcttc cccgtccctt aaggtctctc ttcattgtcc atttgttttc gtttctccgt   15120
attctatcag acctcagacc agtttaatgt tagtcaacct tcatcatctc ttatttatg    15180 tttcacctct ctcccctctt catttcgact tatctatttg tcccagtcga atgtctccca   15240
ggatacgtcc gatttaaggt ctacgacgat attttatgt cctttctttt gagtacttta    15300
taaaattcta aaaacacctt ataaaattct cgaaaacact tgtagagtac ttcgtgagga   15360
cacaaacctc cgtcgtgacc gtcgtttagt ttgtattatt ttccagacat gtagtttgta   15420
actgtgtaaa taagttgttc gtgtataact cgtggatgat acaccgtcct tgagagaagt   15480
agtcgttcat aaaaccgtga tttattttgt gtcttgtgtg gcgggagaaa ctttactgtt   15540
atttctttta ttcacttaat atataataga gtcgtctata acgtaccata tacctttcgt   15600
atagtccctt cccccacatt tcacagtact ctccttaatg ttataattat cctacaattc   15660
tgtcgaggat gacttcggta caaatttgtc tgtgaacctc ctctcctccc tcaaccgatt   15720
caactataaa ccccattccg taaggtcctt cccctagtc ggtcaagttt cgggaccccc    15780
cacccccgac acgaaccgta taaactcctc accattcctc cggtcacacc gaccttgtct   15840
tactagtttc ttttttccacc atcatttact ccagtctatt tgtcattctc tgttccctaa   15900
aaatccagta gatcttaaat ctaaaaaagg actctcccgt ctcctcggtg ctctttcgag   15960
actctactcc tactctacta gattaagtcc aaaattgacc tatcaagtct cgttctcacc   16020
cccgtccctt ggtcactcct ctgacaccgt tattagtgct tttcaccacg tcgccgaacc   16080
tggtccctca atcgtcacct tcgtctctct tcactgttgt gagacgtata ccctttccca   16140
cccgtcctct cttgtcacgg gttctactag gtcataaaac cggactcttc gacccctttt   16200
tctttgttgt tgttgttgta gtcaccttcc ccaaagtccc tcaggtccac aagaccaacg   16260
tcgaaacaaa acggaatttt tataaactca tgcattgatc attaccctaa cgacccaact   16320
taccattaag gcaaaaatca ggaaactctt taacggtgtc acgaaaggaa tcgtttgatt   16380
ccgtccttgt cttttggttt acggtgtaca agagtgaaca ttcaccctcg atttactatt   16440
cttgagtact tgtgtatctc cccttgttct ctatgactcc ggatggactc ccacctccaa   16500
ccctcctccc tctcctagtc ctttttattg attactcgtg atccgaatta tggacccact   16560
```

```
actttcatag acatattgtt tcaggacact gcactcaaag ggatccattg tttgaacgtg   16620
tacacgggga cttgaatttt attttgatat atgtatatat atgtataatc tttcttaata   16680
tgaaaactca aaattatcgt gtaaaagaca ttctaaaacg ttaaatttga agtgatataa   16740
aatatatttg ttaattctca actcaactgg aactataatg tataatgtct ataaaataat   16800
tgtagataat taaaaattaa taaactaaaa aagttttaaa gtttattata tggataaaaa   16860
gtctaaagtc cgtccggtaa cttttcgagg atcaagatta atgacaagga cattacgaaa   16920
tacttatatt gtcaggccgg aaaggagaat ctcaaacgtc agattccatc tctttatatt   16980
attttctttt acgtacttaa aaattgatta taccacaccc aagatttcga gtctatttaa   17040
taaagcaaat caagagtgtt gttgggagac tacgtccgtg ataataaagg gggtaaaatt   17100
attactcctt tgacttcgtg tctctcgaac caactgaacg ggttataatg gtgtgagaca   17160
caccgattcg accctaaact tggttctttt gagagaaggg tatccagcaa ctttttaata   17220
cttcccaatt cggtggagag acgaacacaa cggataaagg tggtacactc aggttacaca   17280
ccactgtctc ttcccatcta caaaccgtag acacttaaga cacctaacac acagtactaa   17340
gaaataaaga caggagacat aggacttaac ggtgatggga ctcgtccact attctcattt   17400
taaggtaatg taaccagaac tcccctaccc gtttgtgaaa cctgagagaa ctataagatc   17460
aataatttat aacgagtcgc attcaatctg ttacttactc tgaacaacta caaagtaaa   17520 gttaaacaga atattactag acacgagttg tacattttgg ttatctacat tgtggaaacc   17580
ttataaagac tcatttgtac cccgtggttg agtttctcgt tctccatttt tacggatcac   17640
acctagtttt agatgagata ctgtcccctta gagtacccga gacttcctaa gaccagtgta   17700
tccctcattt atcgtctgag agttaagtct cagtctacac tcaagtgtgc gttacaaaac   17760
cctgaagtag gacagaaaag ggacgagacc ctcagtattc ttaattcaag attaggatta   17820
agacaacaat agatggactc actgtgatta atctatatat tgaagagact ccgagctgta   17880
aatgtagatg tttatttctt ccgatcttat gatttcggag aagataaaga aggttaataa   17940
ctaacatagc cgagaatgag atatttacca aagaagataa aatccctta attaataaaa   18000 caagaatacc acaacgacct ggacaacgaa aagtaacgac attaatgaag agaaacaact   18060
tctggaaacg gtctgcttta cactaccac atattccgag accgtaaaac gggtccagac   18120
atcgtgtatc ttaaggtgat tacccagacg acccgtagac tctggtgtct cggtaaacag   18180
tattgtactg ttaaggtcaa cccgtcccta tttacaatcg aaattgctaa aacctggtct   18240
caaacagatc tctctctcgt ctcatgtttc ggttttcgta gtagaaatct cgattcgtcc   18300
gtactcaagt ttagggttgg gtcggtgaat gatctataca tcggtgtcgg tggcggttca   18360
gagttaaatt tacagtgaaa gagtttgtcc ggaggatccc agagggtgca accgaatcag   18420
gtcttatgac caaataggaa tgccatattt taaataaggt agtaatacgt ggtcataaat   18480
tatttacgac tccttacacc ttgtttataa acaatttatt tttcactgaa ttaggaagag   18540
acagagtcag gagtgaagtc acttcacccg ttttcccatc ttgttcaaag gacacgtttt   18600
tcttagtcca gtttcacggg atctttatcg tttgtgacag tgttgggatc tatcgtacta   18660
atgttagact ttatttgatc aagttttttcg tttagagtct gagttcaccc cgaaaaagat   18720
caaatcttga acctcaatct tcttctttct tcccccgatt tcacacgacg cacagatcta   18780
cacggtccgt gacatgcatt atcttacagt gtgtaaatta taaacagatt ttcacacttt   18840
cacacttaaa ggtattctcc ctgtgtccaa gaaccatttt ggttccaaac gagattgaaa   18900
```

```
agtgtgtgaa accgtctgcc aaaacggaaa aagaggattc aaccttgaaa actccggtaa    18960
tgacggtcct cccttttcaa tcactacgaa tagatacaag tcttgatctt ttaccgggga    19020
agaccagggg tcaaccgggt gtaacaataa gtgtacgacg gatattttc tgttttggag    19080 gtcttccacc ttttctactt atacgtctta cgatgtgtat ctatgagtac atccactcta    19140
ccgcttgtgt cgtctaaatc cagatggtta ttctatgatg gggtaaaccc tactgtgtgg    19200
aaggaatctt cactgtcacc gtcttgtatc tgtttccctg attaattttc atacacccaa    19260
gacgtctaac gtagacctca ttctcaggtc actagattta acatccggtt ccggagaacg    19320
aacgattgta ggagacagac ggagtcaaaa gaatggacgt tttacctagt gacttgtagt    19380
gtaaagagaa ataattaaat aagtaagtga cttcttcgtt cgacagtttt tcgttgacga    19440
tgtatacagt tcttctacg gtctacgatt ttatttatg ttttaaact aatgatgttt    19500 aacgatggta gctcctcagt atcagattac tttctctttt tgtactctca cttattactt    19560
cagtcgtttt tcaagttttc tttttattta ttttccgtat ctataatttt tacttcttca    19620
ttttgataga ataagtcttt cctatactaa tacatgcctc ttttagggtt tcttagatgt    19680
tgtagtctga gtagtcactt agatcgttct agtgacctat gtcaaatata tatttacaat    19740
agttattaac ataaagacac ggactgttgt tttttaactt ctgttgaaaa ttttgttgtt    19800
acaaatatta ctgtggcttt ttatagttta atcttcaagt acatttaaca tcaaaggttc    19860
tcgagggcga cctttaacct tcggtaacaa ctttatttaa tttcttctaa attcgtttac    19920
ctctctgaat ggtaccaata ccaagctttc tgagatgtaa cgattctacg ttaaatgagg    19980
ttttaacaga tgtctaagtt atgttaaagt caatttcaaa gactttgaaa gtaaacaaca    20040
acaacaaaaa ccttatctgt tcgactaaga cttcaaatat atgtttacgt ttcctgcatt    20100
ttgtcgattt cttttaaacg tcttctttct ttgattttct taatgtgaca gtctaaagct    20160
ctggatgatg tttcgatgct aataattgtg tcacgtataa ccatgttctt atccgtttat    20220
ctgatttctt tgtcttctgt ctcaggtctt tgacttgatg tgtatgtgct agtagactaa    20280
ataatgtttc cacggttccg ttaactcatc cttctcttgc tacaagatgc atttaccgtt    20340
ataactcata gacataccat tttttattta gaaccgatat acagtatatt ataccttgttt    20400 aattaatgtt tacatcatat gtggtttaca cttttccattt tgttttattg tacaattttt    20460
ttcatatcat agaatggaac cctatcgtct ataaagaatt tgtcctgtgt tcttcacttt    20520
tccgttcggt gtcggagtga aaacagaagg agtacggaag agaagatcac accgagtcac    20580
gaatcacgtc ctctttggtc attgggactt aacgtcgaga aggaagagtg atgtacttaa    20640
gttaaaggag tagacagttt actcatatgg ttaagtatag agctttcgac aacgacactc    20700
ttagtctatt cgtattggag tgtcgaatac agataatctt gtcgtgaacc gtgtaccatt    20760
tgtgaggttt cataaacaat ttacttactt atctaatttt ccaccgtaca aaacatgatt    20820
tgacaagtta ctatcacatt ttggtaaacc agtattacgc ctttcccttc attccgcctt    20880
aaggaaatta gacacaaaat gcgtccaagg tttcctcgca ccacctctct tcctacgtct    20940
atcagaccca ctctcgatct ccgacctcag tcgtccttcc tgactccggc aaccacgaac    21000
ccctcactcc cgaggaaaga cgagacagga tccgattcaa ggggtgggta aggaagaact    21060
ctagatggag tttgtgttta gggagttaac tggtgtcccc cgcgggaag atacttaaac    21120 cgcgactatc gacactagac gggtcgtgtc accccttttg tgttttaaat gtctagtccg    21180
tacaggcccg agtctaagga tgaggtcgtg gaccaccggt tccctggggt tgacaattta    21240
tccgtaccac tacggacgaa aggttcggac aaccctttct ctctcccctc gccctcctt    21300
```

```
accctctctc tctctctgac tcgttcgtac ggttctgaat tatatgaata taaatataat    21360
tttctttatt tatagtctac taatgttaaa ccaacttgat tctatgtgtc atcttatacc    21420
ttgattatag gttatagtgt ttcataagat cgctcggaag gatgtctttc ttaacaccca    21480
ccgaccccte atccgtaatc gatgatacac tcacgtctct tatgagtcgg aagaaggtct    21540
accactcgat ttcaagtttc tagttcagtg catgtgtgga agaaagagta gggtccagga    21600
tcagacgaac ttaagtttac cggtaggtgt ggaacggact ttatgaacgt tattaattct    21660
atgccgaaag acggacgaac cccaaaccag gtgttaaggg aattctccgg agtaaagtta    21720
atcctgagtg tgtagggaag ttgtcattaa aacacagtcc gaaccaatcg ttgagttccg    21780
agttcgtatt taccctgtct taagaaaagg aaaactttga gtggttatat cactaacatc    21840
gttgatcgat gtaacaaaaa caaaaaaaaa agggggagtt aagattcgtg atacgtttcc    21900
gaaatttcgt caccagggtt cggaaaaacc gtggtccctg gtcaaaacac cttctgttaa    21960
aacacttttc tgttttacac cttctggcac ctgaccctac caaacccta ctaagttcgt    22020
gtaatgtaaa caacacgtga cacaaagata ataataatgt aacataatat attactttat    22080
taatatgttg agtggtatta catcttagtc accttcggga ctcgaacaaa ggacgttgat    22140
ctgtgagggt agatccccac taccctctgc cactgtccag taatccgtaa tctaagagta    22200
ttcctcgcgt gttggatcta gggagcgtac acgtcaagta ctgtcccaaa cacgacgata    22260
ctcttaaatt acggtgacga ctagactgtc ctccacctcg agtccgtcat ccactcgtt    22320
accctcgtc gacatttatt gcgactagag tgagtgggtg acgagtggag gacgacacac    22380
cgggtcaagg attgtccggt gttttaccat ggacagacac aggggtccca acccctggtg    22440
acggaatttc cggaagtaga gtaagtcaaa agtagtttta agacacacca tccatgagag    22500
taatctgggt aaaatacccca ttccttgact ccatttaac caatatattg aacggatttt    22560
attcagttca gagactactc tcccggtcct aagttcaagt tcgtcagact gaggttttag    22620
agtttcgtga agacaccatc cttctctttt acttacctta ccgtatctca gtagatttac    22680
tgacgtcatc cttccctcgt aaagggcaca cgtcacaata aaaaggccc gaaactttct    22740
attatcctc gtacgtcaat ttttttctctc ctcttccgta agatccgtct ttccggtcac    22800
gaatgtgtct tagagtctta acattgtcaa ggataatgtg ggaccgtctc actacggttc    22860
cgacaataac agttcgtggg aggacggagg gtcaccccaa ctcttcccca cttccctgtg    22920
accgtcttca cttcgaccct tcaaacgtga acgatcaacc ctgaacgtat cggtagaaga    22980
gttacggttt ctcctggagt cagagacaca cgcgaaacaa aaaacaacaa caacaacaac    23040
aactaaacac cgggtccgat ctcacgccac cacactagag acgagtgacg ttggaggtag    23100
agggtccaag ttccctaaga ggacggaggt ctgagggttc atcgaaccta atgtccgcgg    23160
gcggtggtgt ggacctatta aaaatatgaa aatcatcccc acctcaaagt ggcacaaccg    23220
gtccgaccag acacacacga aacctaaact ctgtgagact actaaatctc aacttttacc    23280
ctcatctaac ccactaagag atcaatagta caaatcagtt tagtctaggc acgtaagttt    23340
tagtattccg ttcaaaagga cacaccgagt cattgtagga atttctttat caagactaca    23400
ggtaggccac aaaaaagtct ttctcgcagt cccaactgtc atcgacacta cgaggtctac    23460
ctcgacgcct attgtcgtat attcaaagtc ccgtcaccaa ctccccgaca ccctcccacc    23520
cctcccttct acctactgaa aagagttggt agacataaac taaccttata acacactgaa    23580
cactttatct taatttctat actagaagaa taccagaaga gtgtcaaaag ttccctaaaa    23640
```

```
tcctcttttg cgaatcggta tgtctcgggt tggaccattc accgtcccga ccggtccagt   23700
cacgttgaag tttcagctac aacagtcact tacgaggtct acctaacgtc tcttctggtt   23760
tcaagtacag agccgtggaa agggttacat gtcccgaata caaccctgt ctcatcacgg    23820 accggatctt caatttgtaa gtaggtcgat cgataattcc gaacttacgg aagtttcttg   23880
tcgtacctaa aaagacactt agcactcgca aaagcgttac gaattgtgcc gtcgaccatt   23940
actactaacg aggacaaagg gaaacttaaa gcacaagcaa atgaattgtc ccgtaacgat   24000
tagatcttct tccctcaccc acttcttagg gtaaacattt ctcctatcgt ccaattactt   24060
ttcttcgtct ccatacgcat ccactatcac aaagatgttc cgagccaagt taaccatact   24120
aaatttccgt tcggaaccga ccgaccagta ttattcccgg tgtattacct ccctaaatg    24180 caccgttaat ggtaccagga acgatcaccc tatgttacaa atcccgagg gacctatgaa    24240 ttctaattac agacttagtc atcacaataa caacgttcta gaatcacact accctcggta   24300
cactccgtgc ttaaaaatag ggaatagtct tacattttat agagtatcag acgttcttgt   24360
ggtcactgat accggacttc aacgggattc tgtcaaattt gtaggacaac taacaaaaca   24420
aaaaaaaagg aaaggaacc gttggtctta cgtacttact cagatcgcaa tgaaaacaag    24480
taggtccatt atactaactt taccctaat atgtacaagt tagtaaatct cttcttcctg    24540
atttttagta tctggatatc gtttaattta ctaatatctc ttagatggta catttactga   24600
cgttaattcc tgaagaagta catggggccc ggtctaagtg tcgtagaccc tgtttgagag   24660
gtaccaaaaa gggagccaca taaataattc ttactactag gacttgaagt tcctctgaac   24720
cccttaaaaa cctaaggacg gtccatacat ggaccggttc taattaaacc acttagtctt   24780
caagggtcct tggtatagta ctcatgattc tcttgtttaa ctaaatagat catcatacaa    24840
agaggttgaa tctatagaca cgttttttc acgtcgcctg taccacgtgt aaggttcttc    24900
aagaggaggt tccttcacca gttttataca ttacgaataa ataataggta aaactctggg    24960
tttaataggt cagtcaccct agttatggaa tgaggagaag gggtcttcgg agtgtttatt    25020
tcagaattgt ggtagagttg ttttttattct atccctggat ctgtacctct tataccgaca   25080
gagtacctaa gattcgttag tccatctcat aactctttac aataactttg tccttcaagg    25140
acgatttcca caaccaccct aaccctacgg tcacgtctca ctgtgtcata aacctgttct    25200
tgtgtattgt gctttcacag acttaggaca agaacagata ttaccgtaga acggtaattt    25260
aggaaccgtg cacggacatt agggtcgaag accccctccga cttcgtcctc ttaacgaact   25320
ttggccctcc acctccaacg tcactcggcc ctagtgtggt gacgtgaggt cggacccact   25380
gtctcactct gagggagagt tttttttttt tttttttttt tttttttttt tcttttttcct   25440 ttttcttttt tttcgttggt actctgctcg ttcttcgatt caaatgttta tttacactag    25500
gtgtgaagag ttgtagtcct gtccaggaag tacgaatcta aggtccagag aagaacgctt   25560
acccttgtca gtagtgaata ggttactacg taaattctcg tggttcaaaa ttttctctg    25620 tttacagctt ttctttacgg taaatagtag tttgtggtaa taatttgtga tcgaacaacc   25680
gtatagacat tcagaccaac agtaaaacga tccacctctc ccgtcttaaa acctttcata   25740
gatccggtgt gggtacaaag tcttatcatt catgtttttcg gtgttacata actagtgaat   25800
ctgagtagta tacaaacagg aaaataaaat ttatggggtt cctacctcca gaaagatcgg   25860
attaaaaggt cgattctttt agttccatt ttttaaaaga acacaacaat gaaataggaa    25920
tcatgggggg acccttcatc catattaatc ggagtagaat ctctactctt ttgactccga   25980
gtctctcctg acaggacatt ggtctttctc ctacacaatc ctagacttgg gtagactgct   26040
```

```
ttccgatacg agaattaatc attgtaaagg gacggaacgt tcctgtgtac atccagtgtc   26100
ctatgggtcc cttccattta cgagacagga aaagagtggg catgatgttg aatcattgtc   26160
ggagaccggg ttttactctg acctgtaact gaaattacct accttcatgt gtaaggattg   26220
tacctaagta agtcttcgtg ggtctaaagt gttctccttt actactccgt aaaaagactc   26280
cacaacttta acacgggaaa cagtcagtgt ttggttggtt tttttttttt tttccgaaac   26340
ttttaaggag tttccatttt ccatcggaaa gaagagagta tcaagactat atcagggttt   26400
tcctttgttt tcgaacgtat taagatcggg gtcactaaga agaaaggaag aataattgat   26460
gtttagaagt ggtgtaaaaa agaatgatta atcagtgtac gaattcgagg actcagtgcc   26520
tcaacagatg accaatatcg aacaagatcg agaaggtggg agtttacctt gaacgttcct   26580
taatccggga gacttctagc gtgtaagttc agtactttg ttcggttgtt actttagtta    26640
gtgacggctc ttcccacctg ttcgtgttcg taattctggg tgatgacaac tcagtcccgg   26700
aagtctatac gacggttacc cttcttctct cttttaata caaataagta aatatttata    26760
cacgtaagaa cggaggtttc cagggttaaa gtgtgaccag gtcaacccaa gagaaaggaa   26820
acgacgtaag tcctcgtgtc aacataaagt agatgacgaa ctcttacgtc acctcgaaca   26880
gcggtcgtca ctacctcggt ttgtatttcg gttaatggaa agggatccac cgattacctc   26940
cgaggttctt cggtctcaaa cgggtgtcgg tataccaggc tctcttatct ggtacgtaaa   27000
gacctccgaa atggactgaa agcggttttc gtacgtgtct tgcaccttga accggaggac   27060
ttttccgcac agaagtcgaa tccaataagg aaagagctac gagtggtact acagtccgag   27120
gatcatcctc tcggtaatta ttggacggat agagtggtaa tctgacacat gaagatcttc   27180
cgtctttaga aaaagattac taagaataaa agggtcttgg gaagccactg aaccgtaaac   27240
tacccgttag aaccggtagg atttcgtaag gtacggtagt ctatatggga cgtaacggta   27300
ctcgaaatag taaccgaaaa tcttgtagta ggagggtgaa acttatttac cagatcgtct   27360
gttatgtcag ggaacacggt ccgttgtaag acctacgaaa tacatgtaat cgagtaactt   27420
agtaaagtta agttagtaag ttgcgtcccc aaacttagaa tcgacaaact ccagtaacag   27480
gtacgtgagt ggatattgta acaagacaga gaaagacgtt tacattctat ttttataatg   27540
gaagtaagat cttttgtggg gaaacatctt atccaaatat ggaagtccgt acacctgaaa   27600
ggttaggttt gaggtcctca tctgtctatg ggtggtcctg atccgttacg tcctttaga   27660
gtccgaagtc gatcctgaca aagtatgtta aaggacgtac cggtccttgt tcccacttcc   27720
gtacgtgaga cactcgtcgg gtaaacacct gtcacccagt accctgactt ccttggtaca   27780
atgtgtacgg actcaaaaga aaggttcgag tctttggtat agcttgtggg gagggaaccc   27840
ctcttcactc actcgtccac ctctctgcta tcattacaat cataccacct tgaagaaggg   27900
gtatctacct ttgtgactcc cgattcttct tcccggagag gaggttgtac acaatagatc   27960
gttccgacca agataaattc ttactatata tcagatcaca ttatcttatg ttatacggat   28020
cgagatttta atacaacctt ttttagttg taatgctaca cgatataagt cagttactca   28080
tttataaaga cacggacggt gtacgagtcg taatattaat ctcggtggca cttttatga   28140
ataggcacta ggaaatacga cagtttcgga tttaaggggt gaattggttc ttaggaccta   28200
ttaagggttt tttgtttaaa taataaacaa agataccaac acacaaacag tttttaactt   28260
cgtaattatc tttattcttg ttaaatctga tattttcggt atccgaatat ttttacgatc   28320
gtagtcgtgt aaggttttga cggacggggt agggaactac catacacact aacgacagtg   28380
```

```
ttttgatcgt caatcttaga aaacattgac tcctatattt ggtttaaatc tttatacaga    28440
aatgatttcc cacctttgaa tctttgactt cacctaaatg gtgttacttg atcttgattt    28500
acatggttgt gtccgagttt tgtgagattc tattaaaaag tttaaataaa ttttaattct    28560
tttcttttga cccattgtaa cttagtgttt gtcaacttt gtgaccccaa tgtatcataa     28620
ttgtatatta atgtactagt aaacactatt tgtcttttaa attttttct ttttcctctt     28680
tttttatttt ttatttcttt ttgtttttg tttttttatc ttttacttta ctcttttttt     28740
aactagttac cgtttagtga cctctattta gtaacacatg tctaaaggga taacttttt    28800
tattgttatt aatttgtggt cgattcggaa gaaagaagaa aactaaaaac acttttagc     28860
gttattctac atagagatct agcacacgaa cggtcttaga aacgacaaag aatccacttt    28920
ctagtaacta ttcttagacc gtacctcttg tcagttcctt cgtaacgtcg agttatgttt    28980
tgccaccggt ccctctagg tgacttaatc ctcagtcgtc agtaataaga tgatggacga    29040
ttagaagata ctcgaagcag ttcagtaaat tcgaaccatg ggcagtcaaa ggagtagact    29100
tttgactctt ttcaacaaag tttaacagat tcaggtaagg tcgaactagt atgatcgtag    29160
aatacacgtc gaagaatttc aggtcgagtg tggagacagt tgagggacat attatactga    29220
aggttttttt gtggacacca aaccaatatg tatatatacc tgtatatata caatatgtat    29280
atataaccaa tatggatat                                                 29299

<210> SEQ ID NO 2
<211> LENGTH: 25265
<212> TYPE: DNA
<213> ORGANISM: Homo sapiens

<400> SEQUENCE: 2
cactcttggg tagaacgact ctaacagcga ccgtctaaat gaaggtcaca ctaacaacgt      60
tcttaaacag attgtcttac ttactagttg gaactcgtct tctctaatac ttttttgaatt   120
atcgtaacat cgttacaccg acaattactt tatgtcaacc gacgagggcg acaaaccgtg    180
gttggttgga ctgtgacagt tgtagtgtta tgctataaat aagggttaat aaaatgccgt    240
tgttgacttt atgttacaca ataattagta taaataatat tcatagttaa actcttaaa    300
gactgtacgg tcttctatttt atccaaataa tacttttcgt caagacgaac cacgtacgac    360
cgacgacgac acattattta tcggagacac ccctttcaaa aaattttctt tatttcgttt     420
ttttatcgtg acttttgtct ttccttcgta gttttgagaa gtttatggac gacacaggta    480
accagttcgt gtaagtcctg tagcgtacgg aaatcttgag gtcgtccaag gttgtcgatc    540
atcctgtaag atctgaggaa atcgggaca gacaccgaag tcttattaaa ggttgcgttg     600
gtaggtttaa aactgggtgt cgcacaatgt aaaccgtaac gccactgagt caaggagtag    660
aaatcacatg aggaagtatt aaatctaatt gaacacactt cgtgacttag gttatatacc    720
acagaaatcc aggttggagt ccagagggat gtacaacagt cttttctgt aaactcgtaa     780
aattctcact ttagttttca cgtgatggtt ccaaagattg tcgggtcaag acaggaccga    840
aaagaaggac gttgacaaaa gtcgaaccca ctcagtgaaa agagagacct ggaggtaaaa    900
gagtggggtg tagtgtcagg tcactcccga agagaggtag gattttgaaa gggggacctt    960
gagttcagag agatacaacg ggacgtttta atcgaagtca gggtatatga accgggctaa   1020
tgggtgtctt tcatgtcgtt cgtagtagta ggtgtatccc agaggtttta accgaaagga   1080
ccttggtaag tgttccggta aagtcagttt cgggacccct ttattggtca aggaggttga   1140
cacagagtaa cattttcttt tgtctaataa taacttgaat acattcgttg gtataacggt   1200
```

```
atttaattct tataagtgtt tatcaaatgt ttaagatgtc tttagtccgt ctctctcttt    1260
acacgaagtt taagataact gttctcatgt gagatgagtt aacgatttcc aacatttgtc    1320
gagttttctt tttcacaaga ggtctgagac ttttttgttt gtttttctta gtcgttacaa    1380
agtttcttgg ttttttttttt tttttttttt ttagatttat acatatgtgt gtgtctgtgt    1440
ttctaggtta tcgtaaatgg agttttgaaa tcgatacttt atcgttatct ttgagtggtc    1500
aaatgtttgt ccaagtgtac cgatttgata aaaacggggt tatgtattag tttacttccg    1560
acacttggtt ttaaacccca tctcgtcaag agtaccgtca aacgaaaaat ttccggtatg    1620
gaagggtcta cggtttctcg tgatccaggt ctatcgtggt gtcttttttgt agtagatatt    1680 ggatgattag tccgggttgg gacgaatctt gtcgtcgcat cctcagactg atgtacctta    1740
aagtagaacg gaagagtaag ttgtcgttttg aggtctaggg tttcttatga ccccggtccg    1800
gttcacgtca ccgattgtgg acgttagagt cgtgaaactc tccgactaca ccctcctggt    1860
gaactcaggt tctcaatctc tggtcggacc cgttgtacta cccttgaata gagaggtttt    1920 taatttttt tttttttcgat ccgtactacc gtacatggaa atgaggatcg atgaaccctc    1980
cgactcgacc ctcctaggga actcgggtcg tcaaggtccg atgtcactcg gtactactgt    2040
gataacgtga ggtcggaccc gttgtcgcat tctaggacag gagaccggtt ttttcccaga    2100
ccgtggacga atcctcccga aggttttgaa aaagtcgttt ctatcactca ccgttttgga    2160
tcgtacttcg ggtctcatac accgagacgc aatcataaag agtgtcgggt gacattactg    2220
acagtccaac gaaaattcta atactttcag gatataactt aacagtaagc ttaactctgg    2280
aacttcagac ttctgcctta atgaaccctt cttcgtagtg tcatagaatc ttctcacagg    2340
gaggtacttc gtctaaaccc cagagtaagg caaagacatg aatgtcatta cctggtacaa    2400
tccgttcagt aaattgtgta aacctggggt cgaaggttta gatatgttac cttccatatt    2460
aacctctctc atatttcgga aatcacgggt gaaatgaact ctctaaaagt ctcgtcagtt    2520
actctgaaat ctttatttttc acttgaattt tgtatttcac gaaatatttg gggtcgtaac    2580
ggacttcggg actctaacga actaccgggt aacgcatata agtgtccgtg acggggttga    2640
ccgggaatga tgttgagatc tttactgtcc gtaagtaaga aggttaggtg tctactccgt    2700
tgatgcttca caataaaaat tggggagtaa aaaattcctc ttttttgactc gaactcgtgt    2760 aattttttac accgggtctc agttatacca tatacaactg gaaccttaag ctcttttcag    2820
aagacagtgt tctcgtcttc ggtgtttgag tttatgaaaa tcccaataca atggttaaca    2880
ccttgtgtac acgtacttta ctcgactcat tctacggttt actggaccat aacctctccg    2940
ttatccctca ccaccccgga catcgtttga tctctctcgt accgagtcaa ttttctctca    3000
ccgtcgttga gttgaggtcg gttaacaacg gtatgttata attcgggtcc ctaaagtctt    3060
gaagatcgat cttttttatct ccgatctata catataagga caagttttaa cggagttaat    3120
cttctataat cgttcattaa gtttacgtta tgtgaaaaca taatagtgat atgaccaggt    3180
ggattattcc cctgtcaaac gaaggacgag agtgtttcac aaagtctgat tcaatactgg    3240
tgaattcata cgtttctgtt ttgtcacata gtcattacgt cactaacact cgtacatgaa    3300
gtctttgttt actagaccca agtttaggac cacaactgta attcatcaaa ttattggagc    3360
ccgttcagtg aactgaagag atatggagtc aaagggatag acatttttacc ttcattattc    3420 tcatgaatga ggaaagtcac caacactgat agtttactta actgtatcca ttttgttaat    3480
cttgtcaagg actgtgtgcc attctcagta catttatagt tacgaatact ttcgagagta    3540
```

```
gggtcctatt cgtagaggat cttttgtaga agcaggtaca tggtctaatt agtataaata    3600
agacgtcaac tataaatacg gtgtacaaga aagacccatc tcttcggact tcaataagac    3660
aaataggact ggaaccttt ctgtttcgtc gagtacaggg gtccctagat ttttaaagtg     3720
acccttacta gtgggtcaca gaggttttgg agtcggtcgt aaagagataa gtgtcgacgt    3780
gacttctcga aggaaggacc gaacacagag gttttcccct atgctaccgt tccagacaaa    3840
taatgagagt ccgactacac cggcccctct acaccttaac acatcttacc ttacgctacc    3900
ttatacttta ccacaccta tgtacacttg aagtacggac gaagagtcca agaaggtga     3960 agggaaata caccctgttc tatcgacttc acccgacctc aacccaaaag aggaggaggt     4020
aaaccttccg acctcgaacg acctcaactc ataaagaaaa ggagtccagt caatccaaga    4080
ctattttggg atcacccaat ccgagaccaa tctgtcgaag gggactcccg tctggggtga    4140
gactcgtcgt tacggatctt tactaccaag aagtttaggt tcactattgg gtatcattga    4200
ttgagtaatc gaatcaagac ggcatttcag tcttgtttcg ttcctctttg tcttggagac    4260
gtcacttacc tccttaaaga ctcccagtga actttcgtct ttgagttctc ggggtaaagg    4320
ttaaaggatg ataacatgaa ctttataccct aaagtgtata aacccccatta gtgaagtagt    4380 catttcaacg gaagcattc aatttttgtg agtttaaaat ctttgagtta caagacaccc     4440
aatgtttact gacgggtggt acgacacccc gtactgtggg aaaacattaa agactttatg    4500
cttcatgata aaaagaaat tacgtaagag agaaaaatca aagaggtagg acactataca    4560
gacaggtttt cctgaagggt ttttggtgac ataccgtctt ttccaaaagt tttacgtact    4620
ctcttaatat cgtttctctt tattgagtgt gatttcaaaa atttttataga ggcctgatac    4680 cgatccttga taatgatacc gattgttcac attaaagtcg taaaaccctc cggttccgtc    4740
cgtctaggga attcagatcc tcaaactctg gtcgaacccg ttacaccact ttgggggggag   4800 acgtttttta tgttttatta atcgccccac accaccacgt gtggacacca gggtcgatga    4860
gtacctccga ttcctccctc ctagtgaact cgggccctcc gtctccaacg tcactcgatt    4920
ctaatacggt gacgtggggt cggaccctct gtctaagaca gagtttttt ttttttttta     4980 gagacctgat atttgagagt acttagatcg taataaaccct agtctttata taagtatcct    5040
atctgacact actgtttatt tagtttaaac cctacggagt tgtgttcttt ataaaaatac    5100
atagtaatac attgtcaggt ccctccgact tttatctcac atacaacgtc cattctttaa    5160
aacgagacgt cagtaagtcc ttaacttcga ctatcactaa gacggtagaa cttgtacacc    5220
gtagcgacag acagacctcc cacggtagtg tcagtcgaaa cctgtcgtgg aacttacgat    5280 agtccctcg atctcacaag aggacaagaa acgacaggaa cggtcacaga agaggacttg    5340
agtgtagtct tcgtacggtc attcgtccac catggtcgtc ccaagattgg gtccgtgagg    5400
ttaagattcc agttgaaaca atcacaatag attttttctt ttcgttatta tttaataggt    5460
gttcttttaa aatgttgagt tcaaaaagta tgagaaattt ttccgtaaaa aagtgtacat    5520
gagagtacaa gatactaatc tggattagta acagtgaagt gccgatctct ttgattctgg    5580
tcttctcgaa ggtctagaac tgatcgtggt gagttactca ccctactggt cttgggacat    5640
gactagtacg tttgaagtgg tgtattgtcg aacactataa ctcactcaac aaagtggata    5700
tgctggggag atttggttaa ataattagat cttttaccct tattatcgtt aaagatacat    5760
tattcaacaa cctcgtgttc tatttcaata tacatatttt gtaaatcgtg tcaaggacca    5820
cgtattgtcc agacatcatt tataaacaac attaatcgtc gttttagtag agggagtaat    5880
gacgtcaact aaaaggaaat aataaccttt ctttaaagag ttgactcaaa gtcaacttat    5940
```

```
gtcataatct aataaggaat tgactcaaag tcgtaaaatt tacatatgag ggatgagttt    6000
tgatggatga tttagtgcgg acattaaggt cgtgagaccg tccggttccg cccacctagt    6060
actccagtcc tctagttctg gtaggaccga ttgtgctact ttggggtaga gatgattttt    6120 tacgttttt  taatcggtcc gcaccaccga ccgtggacat cagggtcgat gaaccctccg    6180
actccgtcct cttaccacac ttgggccctc cgtctcgaac gtcacccggc tctagcacgg    6240
tgacgtggtg tcggacccgc tgtctcactc tgaggcagag ttttttgtttg ttttttttgtg    6300 tttttagatg gatgattttt cttcaagaag ttacgaatct gaaactcgtt tcttttttcag    6360 acgagattgt ccttcgacca ctatatcttt ccatttcaaa gtgaagtgtc cgtgaaacta    6420
aagggaagct ccacctatga cttactaaac acacgcgt gtaaaaagat acgtaataag     6480
ttttaatttt aaggaatctc ctttggtgac tttcggttag taaatgtttt gaaattttta    6540
ctgtagaact tctcaagaaa ccacgagtaa gtagtttgaa tcgttactaa attgacatta    6600
agaaataagt ctaagtagag ggtgttttat ttttacggta tttcgaaatg tcatgacata    6660
ggattactta tctctttgat ttctttttca ttctactcgt tcactctcct tttgggctttt    6720 tactcggaca ggaccgtaca aagattttc tttctttgtt tgtttgttcg tcggggagga    6780
gagtcgagaa cccttttcttt ataacttaga actgttatag acgtgaagta tcaactaagt   6840
atcgtactgg atagagtttg ttaaattcta agtttacttc aaacgttaat tagaaagcta   6900
tagtgaaacg ttttgtaaga gtattggaat aggtcgggaa aatgtttagt taggacactc   6960
cacttgtagt gacacaaggg taaaatgtct ctttccgtga ctcggtgtct ctccaatata   7020
tgagtactag ttattcgacc attctgattc ttggtcctta ctatgacaga aggaagaggt   7080
ttataggaca agaaataata ctcatggatt tgtcataatt tttaattaat gtcgagttgt   7140
tatcattcat ttacaggagt acactttagg tggcaaattt tgaattccaa tagataaata   7200
gtttatttaa tttaggatga gtgaattgtt ataagtaact cgagtaagac atttgttggt   7260
aatccggtcc ccgtctatac tttatactcc gagttagaca ctagtgtctc tactttatat   7320
gttaaatctc tctcttttcta ttcgtactac tgttttattta ttacatactt ttaatcggta  7380
atagaatccg gttgaaaaag attcgacatt cgacagacgg atgaagacgg tccacaatca   7440
ttaacaaaat ttttcaccc cttcttctca tgaagtacca cccttctata agtaactcct    7500
gtattcgtag aaggagaatc tttaattgtt acgtgtcacc ggataacgtt caaaactttc    7560
gggacgtttg ttattttcgg actaatcaaa aataacttag tcatagagga tttgtgaaaa   7620
agtactttgt tccaatgagt gttagaaca gctccttgat tacaggatcc tttcaccaaa    7680
agttcgaact cgtacatgta ttcatagtaa ccttttccaac gttttttatgt ttacacaccc  7740 gaggtgaggt ctttaagact aacttccacca gagtagacag tagactcttg aacgtaaaaa    7800
cagtctaagg atcgactaga ctacaaagtc ctgactcttg aattaaactc atcatagaga   7860
tgtcttgtca aaatttac aagaggacct catcctacta atatgaattg tttttacatt    7920
atgtgagtcc actacctgtg ggaatcatag gactaaccta gtgatgtgta atatatgtac    7980
attgtgtaaa agagttcatg gggtattaa  acgtgtttat ttatttattt attttaatat   8040
gaaaagagtt tattttttta tttttatttac aaggagaact taccatctta gaaacaaaaa   8100
aacactatta gtatttatgt atatttataa gagtagtaat gtacgtacat caatggaagg    8160
aaatgtacta cgtggtcttt cttatgggtg agattcttcc tttcttactt ctcttcttcc    8220
gtaacaaatt ttctggataa taatcttatt cagtttaaga tacagatggt aataattcga   8280
```

```
caaactgaaa ctcgtcccta accttccgta aaatttaact ccacctctat acgtgtttcg    8340
gtgcacccct tacagtacac agggacgtat ttctcttgtt cgataaaacg aaccaacctc    8400
tactcctctg tctccgacat gtattcttac acaagttaaa tttcgttgtt ttatatagct    8460
ggtttgatga aactcgttag ttcccctata taaccgagtg tagtgacttt atatatgacc    8520
gtgtcgtcta aaggtcaatc cagactagac gatcgagaca ggggaggtct tatgtccgag    8580
gtccgtccgt ccttccttct cctgtagtca agagaaccac agatcgtgcg acggacataa    8640
ttccatccag gagttattta agtacaacat cctttactta cgtacaagag tttctacgcc    8700
aatgaaagtc atagtgacga aaggagtacc aaaggtgaag ttataatcag attgaacgga    8760
atccctgggt tctaccgacg ataagtgaag ttaatcgatt tgtgaagaga aaagtaccga    8820
cactctctga tcgatggaga aggtatttac ttaaaagaga agaaagaccc gtgttatcag    8880
agataaaggg tcggagaaaa tgttaatcca cataggtacg ttgagtcaag atcggttacc    8940
gcacactcat catcactata ggtggtgaac gtctggatgt gtatttccga gggtctgtgt    9000
agaagacacg agaaatgacc ttgtgaacga actaaggtta tttatgtcgt tggaatcgtc    9060
gatgtataac gtcaaccgtc tcgaaagtac aaagtcgaag aagtataaaa aatcaaaaca    9120
acagtgacaa ccaaaaaaaa aattaactaa gtcctctact ggattatttt ttaacttctt    9180
tttatttcgt aaaacaagac ctaaagagta atccttgtac tccaaatgag ataacgttga    9240
ccgaatcaag tatactagta ggggactcca ctcccttttt ctacgcactt aactaattcg    9300
gttccagtgt accagcttta catcttaacc caaaactcca gtcaaaggga tttagtgggt    9360
ctataggttc acctttagtc cgaggtaact gttttccctt gtcaagaatc tttacgttga    9420
tgtttacagg ttagggtcaa ccgttcaagc ttcgttcctt cccgaaaggt aatttcttac    9480
acctacgatg gaccacccgt tgacctccgg tgaccgtata taaaaaaaac ccccccaaa    9540
gtatttgata accaaaaaaa ttaataataa tatgaaattc aaaatcccat gtacacgtgt    9600
tacacgtcca atcaatgtat acatatgcac acgtacgac cacacgacgt gggtaattga    9660
gtagtaaatc gtaatccata tagaggatta cgatagggag ggggagggg ggtggggtgt    9720
tgtcaggggt ctcacactac aaggggaagg acacaggtac acaaaagtaa caagtcaagg    9780
gtggatactc actcttgtac gccacaaacc aaaaacagga acgctatcaa atgactctta    9840
ctactaaagg ttaaagtagg tacagggatg tttcctgtac ttgagtagta aaaaataccg    9900
acgtatcata aggtaccaca tatacacggt gtaagagaat taggtcagat agtaacaacc    9960
tgtaaaccga accaaggttc agaaacgata acacttatca cggtgttatt tgtatgcata   10020
cgtacacaga aatatcgtcg tactaaatat caggaaaccc atatatgggt cattacccta   10080
ccgacccagt ttaccataaa gatcaagatc tagggactcc ttagcggtgt gactgaaggt   10140
gttaccaact tgatcaaatg tcagggtgat tgtcacattt tcacaaggat aaagaggtgt   10200
aggagagctc gtggacaaca aaggactgaa aaattactaa cggtaagatt gaccacactc   10260
taccatagag taacaccaaa actaaacgta aagagactac cggtcactac tactcgtaaa   10320
aaagtacaca aaaaaccgac gtatttacag aagaaaactc ttcacagaca agtacaggaa   10380
acgggtgaaa aactacccca acaaacaaaa aaagaacatt taaacaaact caagtaacat   10440
ctaagaccta taatcgggaa acagtctact catccaacac ttttaaaaga gggtaaaaca   10500
tccaacggac aagtgagact accatcaaag aaaacgacac gtcttcgaga agtcaaatta   10560
atctagggga aacagttaaa acagaaaaca acgtaacgaa aaaccacaaa atctgtactt   10620
caggaacggg tacggataca ggacttacca ttacggatcc aaaagaagat cccaaaaata   10680
```

```
ccaaaatcca gattgtaaat tcagaaatta ggtagaactt aattaaaaac atattccaca   10740
ttccttccct aggtcaaagt cgaaagaggt ataccgatcg gtcaaaaggg tcgtggtaaa   10800
taatttatcc cttaggaaag gggtaacgaa caaaaagagt ccaaacagtt tctagtctct   10860
caacatctat acaccgcaat aaagactccc gagacaagac aaggtaacta gatatagaga   10920
caaaaccatg gtcatggtac gacaaaccca atgacatcgg aacatcatat caaacttcag   10980
tccatcacac tacggaggtc gaaacaagaa accgaatcc taactgaacc actacgcccg    11040
agaaaaaacc acggtatact tgaaatttcg tcaaaaaagg ttaagacact tctttcagta   11100
accatcgaac taccctacc gtaacttaga tatttaatgg aacccgtcat accggtaaaa    11160
gtgctataac taagaaggat gggtactcgt accttacaag aaggtaaaca acataggag    11220
aaaataaagt aactcgtcac caaacatcaa gaggaacttc tcaaggaagt acagggaaca   11280
ttcaacctaa ggatccataa aataagagaa acttcgttaa cacttaccct caagtgagta   11340
ctaaaccgag agacaaacag acaacaacca catattctta cgaagactaa aaacatgtaa   11400
ctaaaaatat aggactctga aacgacttca acgaatagtc gaattcctct aaaacccgac   11460
tctgttaccc caaagatct atatgtacag tagacgtttg tccctgttaa actaaaggag    11520
aaaaggatta acttatggga aataaaggaa gaggacggat taacgggacc ggtcttgaag   11580
gttgtggtac aacttatcct caccactctc tcccgtaggg acagaacacg gtcaaagtt    11640
tcccttacga aggtcaaaaa cgggtaagtc atactataac cgacacccaa aaagtatcta   11700
ttgagaataa taaaactcta tgcagggtag ttatgaatta ataactctc aaaaaccgta    11760
cttctcaaca acttaaaaca gtttccggaa aagacgtaga taactctatt agtacaccaa   11820
aaacagaaac caagacaaat atacgaccta atgtaaataa ctaaacgaat ataacttggt   11880
cggaacgtag ggtccctact tcgggtgaac tagtaccacc tattcgaaaa actacacgac   11940
gacctaaacc aaactggtga ccgtataaaa ttcgtaccct cattgtgaca gtccaaaaaa   12000
tttaatgttt tacgaaatcg tatctctttt aatatttctt gttatattca ttgtctatac   12060
gtgagtgata ggacgaatta gtttacagtg tgaaacggtt cgaactaagt ttaaaaaatt   12120
tcgtttcttt gtaatgtcta taccgacgtt gtaggataca cggggtggcg actatgtatg   12180
gagagaaggg ttcccattgg tgaaagactg aaactatgaa tagtaagggt ccgtactaat   12240
ttacgataac gacttaaacg tatatatgta tttattatat atgtcaacaa acgtacaaga   12300
ttttgaaacg taatttatta tagtttatta atttttaaaa gtgtttaacg taaaaattga   12360
gtcagaaaat attctaacgg ttattactat agagaagtct agtaagtaaa actgataata   12420
taataaaaag taacatactg atacggtacc gagtgaatag gtaagacaat aactatttgt   12480
aaacacaaca aaggtgttaa aacgataatt ttattaccgt aacacttgta agaacacaca   12540
tatagtgaca catgtgtacg atctcaaaga gattacataa taccacatat aacgacccgg   12600
tttccgatac attcagaagt tgaagggatc tacagtatgg ttgagtatgt atatactggt   12660
cacactcgta agagtcacga gatgtaacag gtctaagatg tacttcgtga ccaccggata   12720
accagtccaa ctgactataa tcttccaata acggtttcag atacactctc tctgactccc   12780
agactttatg gatctacatt ccctatattt cactctctcc tttcttcaat tgtataaatc   12840
ctcgttttag gtgtactgaa acactaacta atacctcttt tattcctctt cttcccttgt   12900
ccttctgaga gttcagaggt ctaacttgtg ttctccttcg aatacacggc actctgacta   12960
ctgtttaagg aaaacttgta tcacggaaac tcccgaacca tcatttttc tttcgtgata    13020
```

```
ggtagtccgt aaacctataa atccagacct tctgactttt ctctagtttt gtcttttatg    13080
tttaatatct tagtagctct acccatttta gtcttctcaa cctagttctt ttcatggatc    13140
ttagtcatct cttcactcaa ttcttttata gagacccttt gtaattataa atttccatat    13200
attttccttc tcttctgaca cctcttctgt ctctgacttc ttcctctgtt ttacacagta    13260
tgacatcatc ggtctcctta tctcgaagtt tcttactcac cagttggtgt aatttgtgtc    13320
gatcttttgg ttcttccatt tctttacttt taatttgtaa ttgtatgtta cttcaataac    13380
tcaggtacaa ttttaccaaa gttaccttat cgtagttacc tttattaacg ttaatcatt    13440 tcttaaaatc ttttcttt ttaattatgt cgattgaaag agtttaattt aaaaaacttt    13500
tattttgtca ctctacctta agctcacgtt ctacaaacaa cttttagttg tgtgtacttt    13560
cctttctctc acttggattt ttttaaccga ggtctcagat aattacattt ctgatacaat    13620
ataacagaga gatagaaatc cctttgtata tgggttaagt agaacacagt ggtcttagtc    13680
taagtagttt gggtaagacc tggtgagact agtgatcaaa gtgggagtgt cagtatcatt    13740
tctttgattt cgttttctga tgttctcgtt tcctgtcttt cccttacaa taaaagaggg    13800 gagtggaaac gggagaaact aaaagaggta acaacgattt tccttgtgaa tcttttgata    13860
cttctcttga agacggacat ttacgtcgag gtactaatac ttaagactta ggaacattgt    13920
cttcttggtt atcctgacta ggtactgaag ataatcatct ctgacccttc catccactga    13980
aatcgagtgg ttcggactag tgtcgtttta tcttttacta gtgtcacagg ggaaaaatag    14040
gaccccattg ttacttgtaa gtcaccctcg gttgatgaca taatttcagg acccacgtcg    14100
aggaccgtgt actgtaccgg gtgttccatc atcaagactc atgggaacgg atagtcacca    14160 cgacccgct cttccctccc gtcggacgag tgatccctct cgtccttact ccgatccttc    14220
atgtccctgg accgtttcta cagaggacaa actctctctg aagtcaatta caagtcagtt    14280
gaaggacacc acgattcttc actttcaact tgaactgata gttccttgtc tccgtccaac    14340
aatcgacccg ggaccctcc ttcagttgtt cgaggtggtg tagactgttg tggatgacga    14400
acgtcgggaa gggggtccag tccgtcgacg tgtggagtac gaaggttgac tccccttac    14460 ttacccatgg ttctcatcca ctcagatgaa gaaagggtcc ccactcatcg cccacttctt    14520
tagtcgtaca tcacctgtaa atgtacacgg cctatggagt atatacgtca caccatagta    14580
ataggagtga cacgtctact tctgtgactc cgagtcctg aacaagttct gtgtgtagac    14640
cagttatccc tcggtcctaa gttttagtgc agtcagatca tgagttcagg agacaagaaa    14700
ggtgctgatg taatctacat agggatctat cagatccaca ttgtcgtact cagagggtac    14760
tttccttcac ccccgagaac cttgtatgga gaaatccttc ggaaggtagt aacacgacgg    14820
aaggaggaga cacgtcggag tcgtgagtga caactcggga agagatcctc aaacgttaga    14880
tgcccctcac tacccgtgta ttcctttatt aaagttacat cataccgttt acgactcgat    14940
ctatttacgc gcttactgat acttcttgtc tcctaaccc agtggattga gttgtactct    15000
gagtaccttc agaggactcc tctttggaga ctcaggatct ctcactctta accggtcttt    15060
ttaattcttc cccgtcccctt aaggtctctc ttcattgtcc atttgttttc gtttctccgt    15120
attctatcag acctcagacc agtttaatgt tagtcaacct tcatcatctc ttattttatg    15180
tttcacctct ctcccctctt catttcgact tatctatttg tcccagtcga atgtctccca    15240
ggatacgtcc gatttaaggt ctacgacgat attttttatgt cctttctttt gagtacttta    15300
taaaattcta aaaacacctt ataaaattct cgaaaacact tgtagagtac ttcgtgagga    15360
cacaaacctc cgtcgtgacc gtcgtttagt ttgtattatt ttccagacat gtagtttgta    15420
```

```
actgtgtaaa taagttgttc gtgtataact cgtggatgat acaccgtcct tgagagaagt    15480
agtcgttcat aaaaccgtga tttattttgt gtcttgtgtg gcgggagaaa ctttactgtt    15540
atttctttta ttcacttaat atataataga gtcgtctata acgtaccata tacctttcgt    15600
atagtccctt cccccacatt tcacagtact ctccttaatg ttataattat cctacaattc    15660
tgtcgaggat gacttcggta caaatttgtc tgtgaacctc ctctcctccc tcaaccgatt    15720
caactataaa ccccattccg taaggtcctt cccctagtc ggtcaagttt cgggaccccc    15780
cacccccgac acgaaccgta taaactcctc accattcctc cggtcacacc gaccttgtct    15840
tactagtttc tttttccacc atcatttact ccagtctatt tgtcattctc tgttccctaa    15900
aaatccagta gatcttaaat ctaaaaaagg actctcccgt ctcctcggtg ctctttcgag    15960
actctactcc tactctacta gattaagtcc aaaattgacc tatcaagtct cgttctcacc    16020
cccgtccctt ggtcactcct ctgacaccgt tattagtgct tttcaccacg tcgccgaacc    16080
tggtccctca atcgtcacct tcgtctctct tcactgttgt gagacgtata ccctttccca    16140
cccgtcctct cttgtcacgg gttctactag gtcataaaac cggactcttc gaccccttt    16200 tctttgttgt tgttgttgta gtcaccttcc ccaaagtccc tcaggtccac aagaccaacg    16260
tcgaaacaaa acggaatttt tataaactca tgcattgatc attaccctaa cgacccaact    16320
taccattaag gcaaaaatca ggaaactctt taacggtgtc acgaaaggaa tcgtttgatt    16380
ccgtccttgt cttttggttt acggtgtaca agagtgaaca ttcaccctcg atttactatt    16440
cttgagtact tgtgtatctc cccttgttct ctatgactcc ggatggactc ccacctccaa    16500
ccctcctccc tctcctagtc ctttttattg attactcgtg atccgaatta tggacccact    16560
actttcatag acatattgtt tcaggacact gcactcaaag ggatccattg tttgaacgtg    16620
tacacgggga cttgaattt attttgatat atgtatatat atgtataatc tttcttaata    16680
tgaaaactca aaattatcgt gtaaaagaca ttctaaaacg ttaaatttga agtgatataa    16740
aatatatttg ttaattctca actcaactgg aactataatg tataatgtct ataaaataat    16800
tgtagataat taaaaattaa taaactaaaa aagtttaaaa gtttattata tggataaaaa    16860
gtctaaagtc cgtccggtaa cttttcgagg atcaagatta atgacaagga cattacgaaa    16920
tacttatatt gtcaggccgg aaaggagaat ctcaaacgtc agattccatc tctttatatt    16980
attttctttt acgtacttaa aaattgatta taccacaccc aagatttcga gtctatttaa    17040
taaagcaaat caagagtgtt gttgggagac tacgtccgtg ataataaagg gggtaaaatt    17100
attactcctt tgacttcgtg tctctcgaac caactgaacg ggttataatg gtgtgagaca    17160
caccgattcg accctaaact tggttctttt gagagaaggg tatccagcaa ctttttaata    17220 cttttccaatt cggtggagag acgaaacacaa cggataaagg tggtacactc aggttacaca    17280
ccactgtctc ttcccatcta caaaccgtag acacttaaga cacctaacac acagtactaa    17340
gaaataaaga caggagacat aggacttaac ggtgatggga ctcgtccact attctcatt    17400 taaggtaatg taaccagaac tcccctaccc gtttgtgaaa cctgagagaa ctataagatc    17460 ataatttat aacgagtcgc attcaatctg ttacttactc tgaacaacta caaaagtaaa    17520
gttaaacaga atattactag acacgagttg tacattttgg ttatctacat tgtggaaacc    17580
ttataaagac tcatttgtac cccgtggttg agtttctcgt tctccatttt tacggatcac    17640
acctagtttt agatgagata ctgtccctta gagtacccga gacttcctaa gaccagtgta    17700
tccctcattt atcgtctgag agttaagtct cagtctacac tcaagtgtgc gttacaaaac    17760
```

```
cctgaagtag gacagaaaag ggacgagacc ctcagtattc ttaattcaag attaggatta   17820
agacaacaat agatggactc actgtgatta atctatatat tgaagagact ccgagctgta   17880
aatgtagatg tttatttctt ccgatcttat gatttcggag aagataaaga aggttaataa   17940
ctaacatagc cgagaatgag atatttacca aagaagataa aatccctta attaataaaa    18000 caagaatacc acaacgacct ggacaacgaa aagtaacgac attaatgaag agaaacaact   18060
tctggaaacg gtctgcttta cactacccac atattccgag accgtaaaac gggtccagac   18120
atcgtgtatc ttaaggtgat tacccagacg acccgtagac tctggtgtct cggtaaacag   18180
tattgtactg ttaaggtcaa cccgtcccta tttacaatcg aaattgctaa aacctggtct   18240
caaacagatc tctctctcgt ctcatgtttc ggttttcgta gtagaaatct cgattcgtcc   18300
gtactcaagt ttagggttgg gtcggtgaat gatctataca tcggtgtcgg tggcggttca   18360
gagttaaatt tacagtgaaa gagtttgtcc ggaggatccc agagggtgca accgaatcag   18420
gtcttatgac caaataggaa tgccatattt taaataaggt agtaatacgt ggtcataaat   18480
tatttacgac tccttacacc ttgtttataa acaatttatt tttcactgaa ttaggaagag   18540
acagagtcag gagtgaagtc acttcacccg ttttcccatc ttgttcaaag gacacgtttt   18600
tcttagtcca gtttcacggg atctttatcg tttgtgacag tgttgggatc tatcgtacta   18660
atgttagact ttatttgatc aagttttttcg tttagagtct gagttcaccc cgaaaaagat   18720
caaatcttga acctcaatct tcttctttct tcccccgatt tcacacgacg cacagatcta   18780
cacggtccgt gacatgcatt atcttacagt gtgtaaatta taaacagatt ttcacacttt   18840
cacacttaaa ggtattctcc ctgtgtccaa gaaccatttt ggttccaaac gagattgaaa   18900
agtgtgtgaa accgtctgcc aaaacggaaa aagaggattc aaccttgaaa actccggtaa   18960
tgacggtcct cccttttcaa tcactacgaa tagatacaag tcttgatctt ttaccgggga   19020
agaccagggg tcaaaccggg gtaacaataa gtgtacgacg gatatttttc tgttttggag   19080
gtcttccacc ttttctactt atacgtctta cgatgtgtat ctatgagtac atccactcta   19140
ccgcttgtgt cgtctaaatc cagatggtta ttctatgatg gggtaaaccc tactgtgtgg   19200
aaggaatctt cactgtcacc gtcttgtatc tgtttccctg attaattttc atacacccaa   19260
gacgtctaac gtagacctca ttctcaggtc actagattta acatccggtt ccggagaacg   19320
aacgattgta ggagacagac ggagtcaaaa gaatggacgt tttacctagt gacttgtagt   19380
gtaaagagaa ataattaaat aagtaagtga cttcttcgtt cgacagtttt tcgttgacga   19440
tgtatacagt tctttctacg gtctacgatt ttattttatg ttttttaaact aatgatgttt   19500 aacgatggta gctcctcagt atcagattac tttctctttt tgtactctca cttattactt   19560
cagtcgtttt tcaagttttc ttttttattta tttttccgtat ctataatttt tacttcttca   19620
ttttgataga ataagtcttt cctatactaa tacatgcctc tttagggtt tcttagatgt     19680 tgtagtctga gtagtcactt agatcgttct agtgacctat gtcaaatata tatttacaat   19740
agttattaac ataaagacac ggactgttgt tttttaactt ctgttgaaaa ttttgttgtt   19800
acaaatatta ctgtggcttt ttatagttta atcttcaagt acatttaaca tcaaaggttc   19860
tcgagggcga cctttaacct tcggtaacaa ctttatttaa tttcttctaa attcgtttac   19920
ctctctgaat ggtaccaata ccaagctttc tgagatgtaa cgattctacg ttaaatgagg   19980
ttttaacaga tgtctaagtt atgttaaagt caatttcaaa gactttgaaa gtaaacaaca   20040
acaacaaaaa ccttatctgt tcgactaaga cttcaaatat atgtttacgt ttcctgcatt   20100
ttgtcgattt cttttaaacg tcttctttct ttgatttttct taatgtgaca gtctaaagct   20160
```

```
ctggatgatg tttcgatgct aataattgtg tcacgtataa ccatgttctt atccgtttat   20220
ctgatttctt tgtcttctgt ctcaggtctt tgacttgatg tgtatgtgct agtagactaa   20280
ataatgtttc cacggttccg ttaactcatc cttctcttgc tacaagatgc atttaccgtt   20340
ataactcata gacataccat tttttattta gaaccgatat acagtatatt ataccttgttt  20400 aattaatgtt tacatcatat gtggtttaca ctttccattt tgtttttattg tacaatttt   20460 ttcatatcat agaatggaac cctatcgtct ataaagaatt tgtcctgtgt tcttcacttt   20520
tccgttcggt gtcggagtga aaacagaagg agtacggaag agaagatcac accgagtcac   20580
gaatcacgtc ctctttggtc attgggactt aacgtcgaga aggaagagtg atgtacttaa   20640
gttaaaggag tagacagttt actcatatgg ttaagtatag agctttcgac aacgacactc   20700
ttagtctatt cgtattggag tgtcgaatac agataatctt gtcgtgaacc gtgtaccatt   20760
tgtgaggttt cataaacaat ttacttactt atctaatttt ccaccgtaca aaacatgatt   20820
tgacaagtta ctatcacatt ttggtaaacc agtattacgc cttccctc attccgcctt    20880 aaggaaatta gacacaaaat gcgtccaagg tttcctcgca ccacctctct tcctacgtct   20940
atcagaccca ctctcgatct ccgacctcag tcgtccttcc tgactccggc aaccacgaac   21000
ccctcactcc cgaggaaaga cgagacagga tccgattcaa ggggtgggta aggaagaact   21060
ctagatggag tttgtgttta gggagttaac tggtgtcccc cgcggggaag atacttaaac   21120
cgcgactatc gacactagac gggtcgtgtc accccttttg tgttttaaat gtctagtccg   21180
tacaggcccg agtctaagga tgaggtcgtg gaccaccggt tccctggggt tgacaattta   21240
tccgtaccac tacggacgaa aggttcggac aacccttct ctctcccctc gcccctcctt    21300
accctctctc tctctctgac tcgttcgtac ggttctgaat tatatgaata taaatataat   21360
tttctttatt tatagtctac taatgttaaa ccaacttgat tctatgtgtc atcttatacc   21420
ttgattatag gttatagtgt ttcataagat cgctcggaag gatgtctttc ttaacaccca   21480
ccgacccctc atccgtaatc gatgatacac tcacgtctct tatgagtcgg aagaaggtct   21540
accactcgat ttcaagtttc tagttcagtg catgtgtgga agaaagagta gggtccagga   21600
tcagacgaac ttaagtttac cggtaggtgt ggaacggact ttatgaacgt tattaattct   21660
atgccgaaag acggacgaac cccaaaccag gtgttaaggg aattctccgg agtaaagtta   21720
atcctgagtg tgtagggaag ttgtcattaa aacacagtcc gaaccaatcg ttgagttccg   21780
agttcgtatt taccctgtct taagaaaagg aaaactttga gtggttatat cactaacatc   21840
gttgatcgat gtaacaaaaa caaaaaaaaa agggggagtt aagattcgtg atacgtttcc   21900
gaaatttcgt caccagggtt cggaaaaacc gtggtccctg gtcaaaacac cttctgttaa   21960
aacacttttc tgttttacac cttctggcac ctgaccctac caaacccta ctaagttcgt    22020 gtaatgtaaa caacacgtga cacaaagata ataataatgt aacataatat attactttat   22080
taatatgttg agtggtatta catcttagtc accttcggga ctcgaacaaa ggacgttgat   22140
ctgtgagggt agatccccac taccctctgc cactgtccag taatccgtaa tctaagagta   22200
ttcctcgcgt gttggatcta gggagcgtac acgtcaagta ctgtcccaaa cacgacgata   22260
ctcttaaatt acggtgacga ctagactgtc ctccacctcg agtccgtcat tccactcgtt   22320
acccctcgtc gacatttatt gcgactagag tgagtgggtg acgagtggag gacgacacac   22380
cgggtcaagg attgtccggt gttttaccat ggacagacac aggggtccca accctggtg    22440 acggaatttc cggaagtaga gtaagtcaaa agtagtttta agacacacca tccatgagag   22500
```

-continued

```
taatctgggt aaaataccca ttccttgact ccattttaac caatatattg aacggatttt    22560
attcagttca gagactactc tcccggtcct aagttcaagt tcgtcagact gaggttttag    22620
agtttcgtga agacaccatc ctttctcttt acttacctta ccgtatctca gtagatttac    22680
tgacgtcatc cttccctcgt aaagggcaca cgtcacaata aaaaaggccc gaaactttct    22740
atttatcctc gtacgtcaat ttttctctc ctcttccgta agatccgtct ttccggtcac     22800
gaatgtgtct tagagtctta acattgtcaa ggataatgtg ggaccgtctc actacggttc    22860
cgacaataac agttcgtggg aggacggagg gtcaccccaa ctcttcccca cttccctgtg    22920
accgtcttca cttcgaccct tcaaacgtga acgatcaacc ctgaacgtat cggtagaaga    22980
gttacggttt ctcctggagt cagagacaca cgcgaaacaa aaaacaacaa caacaacaac    23040
aactaaacac cgggtccgat ctcacgccac cacactagag acgagtgacg ttggaggtag    23100
agggtccaag ttccctaaga ggacggaggt ctgagggttc atcgaaccta atgtccgcgg    23160
gcggtggtgt ggacctatta aaaatatgaa aatcatcccc acctcaaagt ggcacaaccg    23220
gtccgaccag acacacacga aacctaaact ctgtgagact actaaatctc aacttttacc    23280
ctcatctaac ccactaagag atcaatagta caaatcagtt tagtctaggc acgtaagttt    23340
tagtattccg ttcaaaagga cacaccgagt cattgtagga atttctttat caagactaca    23400
ggtaggccac aaaaaagtct ttctcgcagt cccaactgtc atcgacacta cgaggtctac    23460
ctcgacgcct attgtcgtat attcaaagtc ccgtcaccaa ctccccgaca ccctcccacc    23520
cctcccttct acctactgaa aagagttggt agacataaac taaccttata acacactgaa    23580
cactttatct taatttctat actagaagaa taccagaaga gtgtcaaaag ttccctaaaa    23640
tcctcttttg cgaatcggta tgtctcgggt tggaccattc accgtcccga ccggtccagt    23700
cacgttgaag tttcagctac aacagtcact tacgaggtct acctaacgtc tcttctggtt    23760
tcaagtacag agccgtggaa agggttacat gtcccgaata caaccctgt ctcatcacgg      23820 accgatctt caatttgtaa gtaggtcgat cgataattcc gaacttacgg aagtttcttg      23880
tcgtacctaa aaagacactt agcactcgca aaagcgttac gaattgtgcc gtcgaccatt    23940
actactaacg aggacaaagg gaaacttaaa gcacaagcaa atgaattgtc ccgtaacgat    24000
tagatcttct tccctcaccc acttcttagg gtaaacattt ctcctatcgt ccaattactt    24060
ttcttcgtct ccatacgcat ccactatcac aaagatgttc cgagccaagt taaccatact    24120
aaatttccgt tcggaaccga ccgaccagta ttattcccgg tgtattacct cccctaaatg    24180
caccgttaat ggtaccagga acgatcaccc tatgttacaa aatcccgagg gacctatgaa    24240
ttctaattac agacttagtc atcacaataa caacgttcta gaatcacact accctcggta    24300
cactccgtgc ttaaaaatag ggaatagtct tacattttat agagtatcag acgttcttgt    24360
ggtcactgat accggacttc aacgggattc tgtcaaattt gtaggacaac taacaaaaca    24420
aaaaaaaagg aaaaggaacc gttggtctta cgtacttact cagatcgcaa tgaaaacaag    24480
taggtccatt atactaactt tacccttaat atgtacaagt tagtaaatct cttcttcctg    24540
atttttagta tctggatatc gtttaattta ctaatatctc ttagatggta catttactga    24600
cgttaattcc tgaagaagta catgggggcc ggtctaagtg tcgtagaccc tgtttggagag   24660 gtaccaaaaa gggagccaca taaataattc ttactactag gacttgaagt tcctctgaac    24720
cccttaaaaa cctaaggacg gtccatacat ggaccggttc taattaaacc acttagtctt    24780
caagggtcct tggtatagta ctcatgattc tcttgtttaa ctaaatagat catcatacaa    24840
agaggttgaa tctatagaca cgtttttttc acgtcgcctg taccacgtgt aaggttcttc    24900
```

```
aagaggaggt tccttcacca gttttataca ttacgaataa ataataggta aaactctggg   24960
tttaataggt cagtcaccct agttatggaa tgaggagaag gggtcttcgg agtgtttatt   25020
tcagaattgt ggtagagttg tttttattct atccctggat ctgtacctct ataccgaca    25080 gagtacctaa gattcgttag tccatctcat aactctttac aataactttg tccttcaagg   25140
acgatttcca caaccaccct aaccctacgg tcacgtctca ctgtgtcata aacctgttct   25200
tgtgtattgt gctttcacag acttaggaca agaacagata ttaccgtaga acggtaattt   25260
aggaa                                                               25265

<210> SEQ ID NO 3
<211> LENGTH: 465
<212> TYPE: DNA
<213> ORGANISM: Homo sapiens

<400> SEQUENCE: 3
gaaaatcggg acagacaccg aagtcttatt aaaggttgcg ttggtaggtt taaaactggg     60
tgtcgcacaa tgtaaaccgt aacgccactg agtcaaggag tagaaatcac atgaggaagt    120
agttccaaag attgtcgggt caagacagga ccgaaaagaa ggacgttgac aaaagtcgaa    180
cccactcagt gaaaagagag acctggaggt aaaagagtgg gtgtagtgtc aggtcactcc    240
cgaagagagg taggattttg aaaggggggac cttgagttca gagagataca acggacgttt   300
taatcgaagt cagggtatat gaaccgggct aatgggtgtc tttcatgtcg ttcgtagtag    360
taggtgtatc ccagaggttt taaccgaaag gaccttggta agtgttccgg taaagtcagt    420
ttcggggttg gaccattcac cgtcccgacc ggtccagtca cgttg                    465

<210> SEQ ID NO 4
<211> LENGTH: 8066
<212> TYPE: DNA
<213> ORGANISM: Homo sapiens

<400> SEQUENCE: 4
agatttatac atatgtgtgt gtctgtgttt ctaggttatc gtaaatggag ttttgaaatc      60
gatactttat cgttatcttt gagtggtcaa atgtttgtcc aagtgtaccg atttgataaa    120
aacggggtta tgtattagtt tacttccgac acttggtttt aaaccccatc tcgtcaagag    180
taccgtcaaa cgaaaaattt ccggtatgga agggtctacg gttctcgtg atccaggtct     240 atcgtggtgt ctttttgtag tagatattgg atgattagtc cgggttggga cgaatcttgt    300
cgtcgcatcc tcagactgat gtaccttaaa gtagaacgga agagtaagtt gtcgtttgag    360
gtctagggtt tcttatgacc ccggtccggt tcacgtcacc gattgtggac gttagagtcg    420
tgaaactctc cgactacacc ctcctggtga actcaggttc tcaatctctg gtcggacccg    480
ttgtactacc cttgaataga gaggttttta atttttttt ttttcgatcc gtactaccgt    540
acatggaaat gaggatcgat gaaccctccg actcgaccct cctagggaac tcgggtcgtc   600
aaggtccgat gtcactcggt actactgtga taacgtgagg tcggaccgt tgtcgcattc     660 taggacagag accggttttt tcccagaccg tggacgaatc ctcccgaagg ttttgaaaaa    720
gtcggagaaa tccttcggaa ggtagtaaca cgacggaagg aggagacacg tcggagtcgt    780
gagtgacaac tcgggaagag atcctcaaac gttagatgcc cctcactacc cgtgtattcc    840
tttattaaag ttcatcata ccgtttacga ctcgatctat ttacgcgctt actgatactt     900
cttgtctcct aaccccagtg gattgagttg tactctgagt accttcagag gactcctctt    960
```

-continued

```
tggagactca ggatctctca ctcttaaccg gtcttttaa ttcttccccg tcccttaagg     1020
tctctcttca ttgtccattt gttttcgttt ctccgtattc tatcagacct cagaccagtt     1080
taatgttagt caaccttcat catctcttat tttatgtttc acctctctcc cctcttcatt     1140
tcgacttatc tatttgtccc agtcgaatgt ctcccaggat acgtccgatt taaggtctac     1200
gacgatattt ttatgtcctt tcttttgagt actttataaa attctaaaaa caccttataa     1260
aattctcgaa aacacttgta gagtactccg tgaggacaca aacctccgtc gtgaccgtcg     1320
tttagtttgt attattttcc agacatgtag tttgtaactg tgtaaataag ttgttcgtgt     1380
ataactcgtg gatgatacac cgtccttgag agaagtagtc gttcataaaa ccgtgattta     1440
ttttgtgtct tgtgtggcgg gagaaacttt actgttattt cttttattca cttaatatat     1500
aatagagtcg tctataacgt accatatacc tttcgtatag tcccttcccc cacatttcac     1560
agtactctcc ttaatgttat aattatccta caattctgtc gaggatgact tcggtacaaa     1620
tttgtctgtg aacctcctct cctccctcaa ccgattcaac tataaacccc attccgtaag     1680
gtccttcccc ctagtcggtc aagtttcggg accccccacc cccgacacga accgtataaa     1740
ctcctcacca ttcctccggt cacaccgacc ttgtcttact agtttctttt tccaccatca     1800
tttactccag tctatttgtc attctctgtt ccctaaaaat ccagtagatc ttaaatctaa     1860
aaaaggactc tcccgtctcc tcggtgctct ttcgagactc tactcctact ctactagatt     1920
aagtccaaaa ttgacctatc aagtctcgtt ctcaccccccg tcccttggtc actcctctga     1980
caccgttatt agtgcttttc accacgtcgc cgaacctggt ccctcaatcg tcaccttcgt     2040
ctctcttcac tgttgtgaga cgtataccct ttcccaccccg tcctctcttg tcacgggttc     2100
tactaggtca taaaaccgga ctcttcgacc ccttttttctt tgttgttgtt gttgtagtca     2160
ccttccccaa agtccctcag gtccacaaga ccaacgtcga aacaaaacgg aattttttata     2220 aactcatgca ttgatcatta ccctaacgac ccaacttacc attaaggcaa aaatcaggaa     2280 actcttttaac ggtgtcacga aaggaatcgt ttgattccgt ccttgtcttt tggtttacgg     2340
tgtacaagag tgaacattca ccctcgattt actattcttg agtacttgtg tatctcccct     2400
tgttctctat gactccggat ggactcccac ctccaacccct cctccctctc ctagtccttt     2460
ttattgatta ctcgtgatcc gaattatgga cccactactt tcatagacat attgtttcag     2520
gacactgcac tcaaagggat ccattgtttg aacgtgtaca cggggacttg aattttattt     2580
tgatatatgt atatatatgt ataatctttc ttaatatgaa aactcaaaat tatcgtgtaa     2640
aagacattct aaaacgttaa atttgaagtg atataaaata tatttgttaa ttctcaactc     2700
aactggaact ataatgtata atgtctataa aataattgta gataattaaa aattaataaa     2760
ctaaaaaagt tttaaagttt attatatgga taaaaagtct aaagtccgtc cggtaacttt     2820
tcgaggatca agattaatga caaggacatt acgaaatact tatattgtca ggccggaaag     2880
gagaatctca aacgtcagat tccatctctt tatattattt tcttttacgt acttaaaaat     2940
tgattatacc acacccaaga tttcgagtct atttaataaa gcaaatcaag agtgttgttg     3000
ggagactacg tccgtgataa taaaggggggt aaaattatta ctcctttgac ttcgtgtctc     3060
tcgaaccaac tgaacgggtt ataatggtgt gagacacacc gattcgaccc taaacttggt     3120
tcttttgaga gaagggtatc cagcaacttt ttaatacttt ccaattcggt ggagagacga     3180
acacaacgga taaggtggt acactcaggt tacacaccac tgtctcttcc catctacaaa     3240
ccgtagacac ttaagacacc taacacacag tactaagaaa taaagacagg agacatagga     3300
cttaacggtg atgggactcg tccactattc tcattttaag gtaatgtaac cagaactccc     3360
```

```
ctacccgttt gtgaaacctg agagaactat aagatcaata atttataacg agtcgcattc    3420
aatctgttac ttactctgaa caactacaaa agtaaagtta aacagaatat tactagacac    3480
gagttgtaca ttttggttat ctacattgtg gaaaccttat aaagactcat ttgtaccccg    3540
tggttgagtt tctcgttctc cattttacg gatcacacct agtttagat gagatactgt    3600 cccttagagt acccgagact tcctaagacc agtgtatccc tcatttatcg tctgagagtt    3660
aagtctcagt ctacactcaa gtgtgcgtta caaaccctg aagtaggaca gaaaagggac    3720
gagaccctca gtattcttaa ttcaagatta ggattaagac aacaatagat ggactcactg    3780
tgattaatct atatattgaa gagactccga gctgtaaatg tagatgttta tttcttccga    3840
tcttatgatt tcggagaaga taaagaaggt taataactaa catagccgag aatgagatat    3900
ttaccaaaga agataaaatc cctttaatta ataaaacaag aataccacaa cgacctggac    3960
aacgaaaagt aacgacatta atgaagagaa acaacttctg gaaacggtct gctttacact    4020
acccacatat tccgagaccg taaaacgggt ccagacatcg tgtatcttaa ggtgattacc    4080
cagacgaccc gtagactctg gtgtctcggt aaacagtatt gtactgttaa ggtcaacccg    4140
tccctattta caatcgaaat tgctaaaacc tggtctcaaa cagatctctc tctcgtctca    4200
tgtttcggtt ttcgtagtag aaatctcgat tcgtccgtac tcaagtttag ggttgggtcg    4260
gtgaatgatc tatacatcgg tgtcggtggc ggttcagagt taaatttaca gtgaaagagt    4320
ttgtccggag gatcccagag ggtgcaaccg aatcaggtct tatgaccaaa taggaatgcc    4380
atattttaaa taaggtagta atacgtggtc ataaattatt tacgactcct tacaccttgt    4440
ttataaacaa tttatttttc actgaattag gaagagacag agtcaggagt gaagtcactt    4500
cacccgtttt cccatcttgt tcaaaggaca cgttttcctt agtccagttt cacgggatct    4560
ttatcgtttg tgacagtgtt gggatctatc gtactaatgt tagactttat ttgatcaagt    4620
ttttcgttta gagtctgagt tcaccccgaa aaagatcaaa tcttgaacct caatcttctt    4680
ctttcttccc ccgatttcac acgacgcaca gatctacacg gtccgtgaca tgcattatct    4740
tacagtgtgt aaattataaa cagatttttca cactttcaca cttaaaggta ttctccctgt    4800
gtccaagaac cattttggtt ccaaacgaga ttgaaaagtg tgtgaaaccg tctgccaaaa    4860
cggaaaaaga ggattcaacc ttgaaaactc cggtaatgac ggtcctccct tttcaatcac    4920
tacgaataga tacaagtctt gatcttttac cggggaagac caggggtcaa accgggtaa    4980 caataagtgt acgacggata ttttctgtt ttggaggtct tccaccttt ctacttatac    5040 gtcttacgat gtgtatctat gagtacatcc actctaccgc ttgtgtcgtc taaatccaga    5100
tggttattct atgatggggt aaaccctact gtgtggaagg aatcttcact gtcaccgtct    5160
tgtatctgtt tccctgatta attttcatac acccaagacg tctaacgtag acctcattct    5220
caggtcacta gatttaacat ccggttccgg agaacgaacg attgtaggag acagacggag    5280
tcaaaagaat ggacgtttta cctagtgact tgtagtgtaa agagaaataa ttaaataagt    5340
aagtgacttc ttcgttcgac agttttcgt tgacgatgta tacagttctt tctacggtct    5400
acgattttat tttatgtttt taaactaatg atgtttaacg atggtagctc ctcagtatca    5460 gattacttc tcttttgta ctctcactta ttacttcagt cgttttcaa gttttctttt    5520 tatttatttt ccgtatctat aattttact tcttcatttt gatagaataa gtctttccta    5580
tactaataca tgcctctttt agggtttctt agatgttgta gtctgagtag tcacttagat    5640
cgttctagtg acctatgtca aatatatatt tacaatagtt attaacataa agacacggac    5700
```

```
tgttgttttt taacttctgt tgaaaatttt gttgttacaa atattactgt ggctttttat    5760
agtttaatct tcaagtacat ttaacatcaa aggttctcga gggcgacctt taaccttcgg    5820
taacaacttt atttaatttc ttctaaattc gtttacctct ctgaatggta ccaataccaa    5880
gctttctgag atgtaacgat tctacgttaa atgaggtttt aacagatgtc taagttatgt    5940
taaagtcaat ttcaaagact ttgaaagtaa acaacaacaa caaaaacctt atctgttcga    6000
ctaagacttc aaatatatgt ttacgtttcc tgcattttgt cgattctttt taaacgtctt    6060 cttctttga ttttcttaat gtgacagtct aaagctctgg atgatgtttc gatgctaata    6120
attgtgtcac gtataaccat gttcttatcc gtttatctga tttctttgtc ttctgtctca    6180
ggtctttgac ttgatgtgta tgtgctagta gactaaataa tgtttccacg gttccgttaa    6240 ctcatcctc tcttgctaca agatgcattt accgttataa ctcatagaca taccattttt    6300
tatttagaac cgatatacag tatattatac ctgtttaatt aatgtttaca tcatatgtgg    6360
tttacacttt ccatttttgtt ttattgtaca atttttttca tatcatagaa tggaaccccta   6420 tcgtctataa agaatttgtc ctgtgttctt cacttttccg ttcggtgtcg ggttggacca    6480
ttcaccgtcc cgaccggtcc agtcacgttg aagtttcagc tacaacagtc acttacgagg    6540
tctacctaac gtctcttctg gtttcaagta cagagccgtg gaaagggtta catgtcccga    6600
ataacaaccc tgtctcatca cggaccggat cttcaatttg taagtaggtc gatcgataat    6660
tccgaactta cggaagtttc ttgtcgtacc taaaaagaca cttagcactc gcaaaagcgt    6720
tacgaattgt gccgtcgacc attactacta acgaggacaa agggaaactt aaagcacaag    6780
caaatgaatt gtcccgtaac gattagatct tcttccctca cccacttctt agggtaaaca    6840
tttctcctat cgtccaatta cttttcttcg tctccatacg catccactat cacaaagatg    6900
ttccgagcca agttaccata ctaaatttcc gttcggaacc gaccgaccag tattattccc    6960
ggtgtattac ctcccctaaa tgcaccgtta atggtaccag gaacgatcac cctatgttac    7020
aaaatcccga gggacctatg aattctaatt acagacttag tcatcacaat aacaacgttc    7080
tagaatcaca ctaccctcgg tacactccgt gcttaaaaat agggaatagt cttacatttt    7140
atagagtatc agacgttctt gtggtcactg ataccggact tcaacgggat tctgtcaaat    7200
ttgtaggaca actaacaaaa caaaaaaaag gaaaaggaac cgttggtctt acgtacttac    7260
tcagatcgca atgaaaacaa gtaggtccat tatactaact ttacccttaa tatgtacaag    7320
ttagtaaatc tcttcttcct gattttagt atctggatat cgtttaattt actaatatct    7380
cttagatggt acatttactg acgttaattc ctgaagaagt acatgggggcc cggtctaagt    7440 gtcgtagacc ctgtttgaga ggtaccaaaa agggagccac ataaataatt cttactacta    7500
ggacttgaag ttcctctgaa ccccttaaaa acctaaggac ggtccataca tggaccggtt    7560
ctaattaaac cacttagtct tcaagggtcc ttggtatagt actcatgatt ctcttgttta    7620
actaaataga tcatcataca aagaggttga atctatagac acgttttttt cacgtcgcct    7680
gtaccacgtg taaggttctt caagaggagg ttccttcacc agttttatac attacgaata    7740
aataataggt aaaactctgg gtttaatagg tcagtcaccc tagttatgga atgaggagaa    7800
ggggtcttcg gagtgtttat ttcagaattg tggtagagtt gtttttattc tatccctgga    7860
tctgtacctc ttataccgac agagtaccta agattcgtta gtccatctca taactcttta    7920
caataacttt gtccttcaag gacgatttcc acaaccaccc taaccctacg gtcacgtctc    7980
actgtgtcat aaacctgttc ttgtgtattg tgctttcaca gacttaggac aagaacagat    8040
attaccgtag aacggtaatt taggaa                                         8066
```

<210> SEQ ID NO 5
<211> LENGTH: 1824
<212> TYPE: DNA
<213> ORGANISM: Homo sapiens

<400> SEQUENCE: 5

```
ttctatcact caccgttttg gatcgtactt cgggtctcat acaccgagac gcaatcataa      60
agagtgtcgg gtgacattac tgacagtcca acgaaaattc taatactttc aggatataac     120
ttaacagtaa gcttaactct ggaacttcag acttctgcct taatgaaccc ttcttcgtag     180
tgtcatagaa tcttctcaca gggaggtact tcgtctaaac cccagagtaa ggcaaagaca     240
tgaatgtcat tacctggtac aatccgttca gtaaattgtg taaacctggg gtcgaaggtt     300
tagatatgtt accttccata ttaacctctc tcatatttcg gaaatcacgg gtgaaatgaa     360
ctctctaaaa gtctcgtcag ttactctgaa atctttattt tcacttgaat tttgtatttc     420
acgaaatatt tggggtcgta acggacttcg ggactctaac gaactaccgg gtaacgcata     480
taagtgtccg tgacggggtt gaccgggaat gatgttgaga tctttactgt ccgtaagtaa     540
gaaggttagg tgtctactcc gttgatgctt cacaataaaa attggggagt aaaaaattcc     600
tcttttgac tcgaactcgt gtaatttttt acaccgggtc tcagttatac catatacaac     660
tggaacctta agctcttttc agaagacagt gttctcgtct tcggtgtttg agtttatgaa     720
aatcccaata caatggttaa caccttgtgt acacgtactt tactcgactc attctacggt     780
ttactggacc ataacctctc cgttatccct caccaccccg gacatcgttt gatctctctc     840
gtaccgagtc aattttctct caccgtcgtt gagttgaggt cggttaacaa cggtatgtta     900
taattcgggt ccctaaagtc ttgaagatcg atctttttat ctccgatcta tacatataag     960
gacaagttt aacggagtta atcttctata atcgttcatt aagtttacgt tatgtgaaaa    1020
cataatagtg atatgaccag gtggattatt ccccctgtcaa acgaaggacg agagtgtttc    1080
acaaagtctg attcaatact ggtgaattca tacgtttctg ttttgtcaca tagtcattac    1140
gtcactaaca ctcgtacatg aagtctttgt ttactagacc caagtttagg accacaactg    1200
taattcatca aattattgga gcccgttcag tgaactgaag agatatggag tcaaagggat    1260
agacatttta ccttcattat tctcatgaat gaggaaagtc accaacactg atagtttact    1320
taactgtatc cattttgtta atcttgtcaa ggactgtgtg ccattctcag tacatttata    1380
gttacgaata ctttcgagag tagggtccta ttcgtagagg atcttttgta gaagcaggta    1440
catggtctaa ttagtataaa taagacgtca actataaata cggtgtacaa gaaagaccca    1500
tctcttcgga cttcaataag acaaatagga ctggaacctt ttctgtttcg tcgagtacag    1560
gggtccctag atttttaaag tgacccttac tagtgggtca cagaggtttt ggagtcggtc    1620
gtaaagagat aagtgtcgac gtgacttctc gaaggaagga ccgaacacag aggttttccc    1680
ctatgctacc gttccaacaa ataatgagag tccgactaca ccggcccctc tacacccttaa    1740
cacatcttac cttacgctac cttatacttt accacacctt atgtggttgg accattcacc    1800
gtcccgaccg gtccagtcac gttg                                           1824
```

<210> SEQ ID NO 6
<211> LENGTH: 11053
<212> TYPE: DNA
<213> ORGANISM: Homo sapiens

<400> SEQUENCE: 6

```
actgtttatt tagtttaaac cctacggagt tgtgttcttt ataaaaatac atagtaatac    60
attgtcaggt ccctccgact tttatctcac atacaacgtc cattctttaa aacgagacgt   120
cagtaagtcc ttaacttcga ctatcactaa gacggtagaa cttgtacacc gtagcgacag   180
acagacctcc cacggtagtg tcagtcaaac ctgtcgtgga acttacgata gtcccttcga   240
tctcacaaga ggacaagaaa cgacaggaac ggtcacagaa gaggacttga gtgtagtctt   300
cgtacgtcat tcgtccacca tggtcgtccc aagattgggt ccgtgaggtt aagattccag   360
ttgaaacaat cacaatagat tttttctttt cgttattatt taataggtgt tcttttaaaa   420
tgttgagttc aaaaagtatg agaaattttt ccgtaaaaaa gtgtacatga gagtacaaga   480
tactaatctg gattagtaac agtgaagtgc cgatctcttt gattctggtc ttctcgaagg   540
tctagaactg atcgtggtga gttactcacc ctactggtct tgggacatga ctagtacgtt   600
tgaagtggtg tattgtcgaa cactataact cactcaacaa agtggatatg ctggggagat   660
ttggttaaat aattagatct tttaccctta ttatcgttaa agatacatta ttcaacaacc   720
tcgtgttcta tttcaatata catattttgt aaatcgtgtc aaggaccacg tattgtccag   780
acatcattta taaacaacat taatcgtcgt tttagtagag ggagtaatga cgtcaactaa   840
aaggaaataa taacctttct ttaaagagtt gactcaaagt caacttatgt cataatctaa   900
taaggaattg actcaaagtc gtaaaattta catatgaggg atgagttttg atggatgatt   960
tagtgcggac attaaggtcg tgagaccgtc cggttccgcc cacctagtac tccagtcctc  1020
tagttctggt aggaccgatt gtgctacttt ggggtagaga tgattttta cgttttttta  1080 atcggtccgc accaccgacc gtggacatca gggtcgatga accctccgac tccgtcctct  1140
taccacactt gggccctccg tctcgaacgt caccccggctc tagcacggtg acgtggtgtc  1200
ggacccgctg tctcactctg aggcagagtt tttgtttgtt tttttgtgtt tttagatgga  1260 tgattttct tcaagaagtt acgaatctga aactcgtttc ttttttcagac gagattgtcc  1320 ttcgaccact atatctttcc atttcaaagt gaagtgtccg tgaaactaaa gggaagctcc  1380
acctatgact tactaaacac acacgcgtgt aaaaagatac gtaataagtt ttaattttaa  1440
ggaatctcct ttggtgactt tcggttagta aatgttttga aatttttact gtagaacttc  1500
tcaagaaacc acgagtaagt agtttgaatc gttactaaat tgacattaag aaataagtct  1560
aagtagaggg tgtttattt ttacggtatt tcgaaatgtc atgacatagg attacttatc  1620
tctttgattt ctttttcatt ctactcgttc actctccttt tgggctttta ctcggacagg  1680
accgtacaaa gattttctt tctttgtttg tttgttcgtc ggggaggaga gtcgagaacc  1740
ctttctttat aacttagaac tgttatagac gtgaagtatc aactaagtat cgtactggat  1800
agagtttgtt aaattctaag tttacttcaa acgttaatta gaaagctata gtgaaacgtt  1860
ttgtaagagt attggaatag gtcgggaaaa tgtttagtta ggacactcca cttgtagtga  1920
cacaagggta aaatgtctct ttccgtgact cggtgtctct ccaatatatg agtactagtt  1980
attcgaccat tctgattctt ggtccttact atgcagaag gaagaggttt ataggacaag  2040
aaataatact catggatttg tcataatttt taattaatgt cgagttgtta tcattcattt  2100
acaggagtac actttaggtg gcaaattttg aattccaata gataaatagt ttatttaatt  2160
taggatgagt gaattgttat aagtaactcg agtaagacat ttgttggtaa tccggtcccc  2220
gtctatactt tatactccga gttagacact agtgtctcta ctttatatgt taaatctctc  2280
tctttctatt cgtactactg tttatttatt acatactttt aatcggtaat agaatccggt  2340
tgaaaaagat tcgacattcg acagacggat gaagacggtc cacaatcatt aacaaaattt  2400
```

```
ttcaccccct tcttctcatg aagtaccacc cttctataag taactcctgt attcgtagaa    2460
ggagaatctt taattgttac gtgtcaccgg ataacgttca aaactttcgg gacgtttgtt    2520
attttcggac taatcaaaaa taacttagtc atagaggatt tgtgaaaaag tactttgttc    2580
caatgagtgt ttagaacagc tccttgatta caggatcctt tcaccaaaag ttcgaactcg    2640
tacatgtatt catagtaacc tttccaacgt ttttatgttt acacacccga ggtgaggtct    2700
ttaagactaa cttcaccaga gtagacagta gactcttgaa cgtaaaaaca gtctaaggat    2760
cgactagact acaaagtcct gactcttgaa ttaaactcat catagagatg tcttgtcaaa    2820
aattttacaa gaggacctca tcctactaat atgaattgtt tttacattat gtgagtccac    2880
tacctgtggg aatcatagga ctaacctagt gatgtgtaat atatgtacat tgtgtaaaag    2940
agttcatggg gtatttaaac gtgtttattt atttatttat tttaatatga aaagagttta    3000 ttttttttatt ttatttacaa ggagaactta ccatcttaga aacaaaaaaa cactattagt    3060
atttatgtat atttataaga gtagtaatgt acgtacatca atggaaggaa atgtactacg    3120
tggtctttct tatgggtgag attcttcctt tcttacttct cttcttccgt aacaaatttt    3180
ctggataata atcttattca gtttaagata cagatggtaa taattcgaca aactgaaact    3240
cgtccctaac cttccgtaaa atttaactcc acctctatac gtgtttcggt gcacccttta    3300
cagtacacag ggacgtattt ctcttgttcg ataaaacgaa ccaacctcta ctcctctgtc    3360
tccgacatgt attcttacac aagttaaatt tcgttgtttt atatagctgg tttgatgaaa    3420
ctcgttagtt ccctatata accgagtgta gtgactttat atatgaccgt gtcgtctaaa    3480
ggtcaatcca gactagacga tcgagacagg ggaggtctta tgtccgaggt ccgtccgtcc    3540
ttccttctcc tgtagtcaag agaaccacag atcgtgcgac ggacataatt ccatccagga    3600
gttatttaag tacaacatcc tttacttacg tacaagagtt tctacgccaa tgaaagtcat    3660
agtgacgaaa ggagtaccaa aggtgaagtt ataatcagat tgaacggaat ccctgggttc    3720
taccgacgat aagtgaagtt aatcgatttg tgaagagaaa agtaccgaca ctctctgatc    3780
gatggagaag gtatttactt aaaagagaag aaagacccgt gttatcagag ataaagggtc    3840
ggagaaaatg ttaatccaca taggtacgtt gagtcaagat cggttaccgc acactcatca    3900
tcactatagg tggtgaacgt ctggatgtgt atttccgagg gtctgtgtag aagacacgag    3960
aaatgacctt gtgaacgaac taaggttatt tatgtcgttg gaatcgtcga tgtataacgt    4020
caaccgtctc gaaagtacaa agtcgaagaa gtataaaaaa tcaaaacaac agtgacaacc    4080
aaaaaaaaaa ttaactaagt cctctactgg attattttt aacttctttt tatttcgtaa    4140
aacaagacct aaagagtaat ccttgtactc caaatgagat aacgttgacc gaatcaagta    4200
tactagtagg ggactccact ccctttttct acgcacttaa ctaattcggt tccagtgtac    4260
cagctttaca tcttaaccca aaactccagt caaagggatt tagtgggtct ataggttcac    4320
ctttagtccg aggtaactgt tttcccttgt caagaatctt tacgttgatg tttacaggtt    4380
agggtcaacc gttcaagctt cgttccttcc cgaaaggtaa tttcttacac ctacgatgga    4440
ccacccgttg acctccggtg accgtatata aaaaaaaccc ccccaaagt atttgataac    4500 caaaaaaatt aataataata tgaaattcaa atcccatgt acacgtgtta cacgtccaat    4560
caatgtatac atatgcacac ggtacgacca cacgacgtgg gtaattgagt agtaaatcgt    4620
aatccatata gaggattacg ataggggaggg ggaggggggg tggggtgttg tcagggtct    4680 cacactacaa ggggaaggac acaggtacac aaaagtaaca agtcagggt ggatactcac    4740
```

```
tcttgtacgc cacaaaccaa aaacaggaac gctatcaaat gactcttact actaaaggtt   4800
aaagtaggta cagggatgtt tcctgtactt gagtagtaaa aaataccgac gtatcataag   4860
gtaccacata tacacggtgt aagagaatta ggtcagatag taacaacctg taaaccgaac   4920
caaggttcag aaacgataac acttatcacg gtgttatttg tatgcatacg tacacagaaa   4980
tatcgtcgta ctaaatatca ggaaacccat atatgggtca ttaccctacc gacccagttt   5040
accataaaga tcaagatcta gggactcctt agcggtgtga ctgaaggtgt taccaacttg   5100
atcaaatgtc agggtgattg tcacattttc acaaggataa agaggtgtag gagagctcgt   5160
ggacaacaaa ggactgaaaa attactaacg gtaagattga ccacactcta ccatagagta   5220
acaccaaaac taaacgtaaa gagactaccg gtcactacta ctcgtaaaaa agtacacaaa   5280
aaaccgacgt atttacagaa gaaaactctt cacagacaag tacaggaaac gggtgaaaaa   5340
ctaccccaac aaacaaaaaa agaacattta acaaactca agtaacatct aagacctata    5400
atcgggaaac agtctactca tccaacactt ttaaaagagg gtaaaacatc caacggacaa   5460
gtgagactac catcaaagaa aacgacacgt cttcgagaag tcaaattaat ctaggggaaa   5520
cagttaaaac agaaaacaac ggtaacgaaa accacaaaat ctgtacttca ggaacgggta   5580
cggatacagg acttaccatt acggatccaa aagaagatcc caaaaatacc aaaatccaga   5640
ttgtaaattc agaaattagg tagaacttaa ttaaaaacat attccacatt ccttccctag   5700
gtcaaagtcg aaagaggtat accgatcggt caaaagggtc gtggtaaata atttatccct   5760
taggaaaggg gtaacgaaca aaaagagtcc aaacagtttc tagtctctca acatctatac   5820
accgcaataa agactcccga acaagacaa ggtaactaga tatagagaca aaaccatggt    5880
catggtacga caaacccaat gacatcggaa catcatatca aacttcagtc catcacacta   5940
cggaggtcga aacaagaaaa ccgaatccta actgaaccac tacgcccgag aaaaaaccac   6000
ggtatacttg aaatttcgtc aaaaaaggtt aagacacttc tttcagtaac catcgaacta   6060
cccctaccgt aacttagata tttaatggaa cccgtcatac cggtaaaagt gctataacta   6120
agaaggatgg gtactcgtac cttacaagaa ggtaaacaaa cataggagaa aataaagtaa   6180
ctcgtcacca acatcaaga ggaacttctc aaggaagtac agggaacatt caacctaagg    6240
atccataaaa taagagaaac ttcgttaaca cttaccctca agtgagtact aaaccgagag   6300
acaaacagac aacaaccaca tattcttacg aagactaaaa acatgtaact aaaaatatag   6360
gactctgaaa cgacttcaac gaatagtcga attcctctaa aacccgactc tgttaccca    6420 aaagatctat atgtacagta gacgtttgtc cctgttaaac taaaggagaa aaggattaac   6480
ttatgggaaa taaggaaga ggacggatta acgggaccgg tcttgaaggt tgtggtacaa    6540
cttatcctca ccactctctc ccgtagggac agaacgggt caaaagtttc ccttacgaag    6600
gtcaaaaacg ggtaagtcat actataaccg acacccaaaa agtatctatt gagaataata   6660
aaactctatg cagggtagtt atgaattaaa taactctcaa aaaccgtact tctcaacaac   6720
ttaaaacagt ttccggaaaa gacgtagata actctattag tacaccaaaa acagaaacca   6780
agacaaatat acgacctaat gtaaataact aaacgaatat aacttggtcg gaacgtaggg   6840
tccctacttc gggtgaacta gtaccaccta ttcgaaaaac tacacgacga cctaaaccaa   6900
actggtgacc gtataaaatt cgtacccctca ttgtgacagt ccaaaaaatt taatgtttta   6960
cgaaatcgta tctcttttaa tatttcttgt tatattcatt gtctatacgt gagtgatagg   7020
acgaattagt ttacagtgtg aaacggttcg aactaagttt aaaaaattc gtttctttgt    7080 aatgtctata ccgacgttgt aggatacacg gggtggcgac tatgtatgga gagaagggtt   7140
```

```
cccattggtg aaagactgaa actatgaata gtaagggtcc gtactaattt acgataacga   7200
cttaaacgta tatatgtatt tattatatat gtcaacaaac gtacaagatt ttgaaacgta   7260
atttattata gtttattaat ttttaaaagt gtttaacgta aaaattgagt cagaaaatat   7320
tctaacggtt attactatag agaagtctag taagtaaaac tgataatata ataaaaagta   7380
acatactgat acggtaccga gtgaataggt aagacaataa ctatttgtaa acacaacaaa   7440
ggtgttaaaa cgataatttt attaccgtaa cacttgtaag aacacacata tagtgacaca   7500
tgtgtacgat ctcaaagaga ttacataata ccacatataa cgacccggtt tccgatacat   7560
tcagaagttg aagggatcta cagtatggtt gagtatgtat atactggtca cactcgtaag   7620
agtcacgaga tgtaacaggt ctaagatgta cttcgtgacc accggataac cagtccaact   7680
gactataatc ttccaataac ggtttcgat acactctctc tgactcccag acttatgga    7740 tctacattcc ctatatttca ctctctcctt tcttcaattg tataaatcct cgttttaggt   7800
gtactgaaac actaactaat acctctttta ttcctcttct tcccttgtcc ttctgagagt   7860
tcagaggtct aacttgtgtt ctccttcgaa tacacggcac tctgactact gtttaaggaa   7920
aacttgtatc acggaaactc ccgaaccatc atttttcct tcgtgatagg tagtccgtaa    7980
acctataaat ccagaccttc tgactttct ctagttttgt cttttatgtt taatatctta    8040
gtagctctac ccattttagt cttctcaacc tagttctttt catggatctt agtcatctct   8100
tcactcaatt cttttataga gacccttgt aattataaat ttccatatat tttccttctc    8160
ttctgacacc tcttctgtct ctgacttctt cctctgtttt acacagtatg acatcatcgg   8220
tctccttatc tcgaagtttc ttactcacca gttggtgtaa tttgtgtcga tcttttggtt   8280
cttccatttc tttactttta atttgtaatt gtatgttact tcaataactc aggtacaatt   8340
ttaccaaagt taccttatcg tagttacctt tattaacgtt aatcattttc ttaaaatctt   8400 tttcttttt aattatgtcg attgaaagag tttaatttaa aaaactttta ttttgtcact    8460
ctaccttaag ctcacgttct acaaacaact tttagttgtg tgtactttcc tttctctcac   8520 ttggatttt ttaaccgagg tctcagataa ttacatttct gatacaatat aacagagaga    8580
tagaaatccc tttgtatatg ggttaagtag aacacagtgg tcttagtcta agtagtttgg   8640
gtaagacctg gtgagactag tgatcaaagt gggagtgtca gtatcatttc tttgatttcg   8700
ttttctgatg ttctcgtttc ctgtctttcc ctttacaata aaagagggga gtggaaacgg   8760
gagaaactaa aagaggtaac aacgattttc cttgtgaatc ttttgatact ttctttgaag   8820
acggacattt acgtcgaggt actaatactt aagacttagg aacattgtct tcttggttat   8880
cctgactagg tactgaagat aatcatctct gacccttcca tccactgaaa tcgagtggtt   8940
cggactagtg tcgttttatc ttttactagt gtcacagggg aaaaatagga ccccattgtt   9000
acttgtaagt caccctcggt tgatgacata atttcaggac ccacgtcgag gaccgtgtac   9060
tgtaccgggt gttccatcat caagactcat gggaacggat agtcaccacg accccgctct   9120
tccctcccgt cggacgagtg atccctctcg tccttactcc gatccttcat gtccctggac   9180
cgtttctaca gaggacaaac tctctctgaa gtcaattaca agtcagttga aggacaccac   9240
gattcttcac tttcaacttg aactgatagt tccttgtctc cgtccaacaa tcgacccggg   9300
gaccctcctt cagttgttcg aggtggtgta gactgttgtg gatgacgaac gtcgggaagg   9360
gggtccagtc cgtcgacgtg tggagtacga aggttgactc cccttactt acccatggtt    9420 ctcatccact cagatgaaga aagggtcccc actcatcgcc cacttcttta gtcgtacatc   9480
```

| | |
|---|---|
| acctgtaaat gtacacggcc tatggagtat atacgtcaca ccatagtaat aggagtgaca | 9540 |
| cgtctacttc tgtgactccg agtccctgaa caagttctgt gtgtagacca gttatccctc | 9600 |
| ggtcctaagt tttagtgcag tcagatcatg agttcaggag acaagaaagg tgctgatgta | 9660 |
| atctacatag ggatctatca gatccacatt gtcgtactca gagggtactt tccttcaccc | 9720 |
| ccgagaacct tgtatggaga aatccttcgg aaggtagtaa cacgacggaa ggaggagaca | 9780 |
| cgtcggagtc gtgagtgaca actcgggaag agatcctcaa acgttagaac cctatcgtct | 9840 |
| ataaagaatt tgtcctgtgt tcttcacttt tccgttcggt gtcgggttgg accattcacc | 9900 |
| gtcccgaccg gtccagtcac gttgaagttc agctacaaca gtcacttacg aggtctacct | 9960 |
| aacgtctctt ctggtttcaa gtacagagcc gtggaaaggg ttacatgtcc cgaataacaa | 10020 |
| ccctgtctca tcacggaccg gactgaaagc ggttttcgta cgtgtcttgc accttgaacc | 10080 |
| ggaggacttt tccgcacaga agtcgaatcc aataaggaaa gagctacgag tggtactaca | 10140 |
| gtccgaggat catcctctcg gtaattattg aagccactga accgtaaact acccgttaga | 10200 |
| accggtagga tttcgtaagg tacgtagtc tatatggac gtaacggtac tcgaaatagt | 10260 |
| aaccgaaaat cttgtagtag gagggtgaaa cttatttacc agatcgtctg ttatgtcagg | 10320 |
| aacacggtcc gttgtaagac ctacgaaata catgtaatcg agtaacttag taaagttaag | 10380 |
| ttagtaagtt gcgtccccaa acttagaatc gacaaactcc agtaacaggt acgtgagtgg | 10440 |
| atattgtaac aagacagaga aagacgttta cattctattt ttataatgga agtaagatct | 10500 |
| tttgtgggga aacatcttat ccaaatatgg aagtccgtac acctgaaagg ttaggtttga | 10560 |
| ggtcctcatc tgtctatggg tggtcctgat ccgttacgtc cttttagagt ccgaagtcga | 10620 |
| tcctgacaaa gtatgttaaa ggacgtaccg gtccttgttc ccacttccgt acgtgagaca | 10680 |
| ctcgtcgggt aaaacctgt cacccagtac cctgacttcc ttggtacaat gtgtacggac | 10740 |
| tcaaagaaa ggttcgagtc tttggtatag cttgtgggga gggaacccct cttcactcac | 10800 |
| tcgtccacct ctctgctatc attacaatca taccaccttg aagaagggggt atctaccttt | 10860 |
| gtgactcccg attcttcttc ccggagagga ggttgtacac aatagatcgt tccgaccaag | 10920 |
| ataaattctt actatatatc agatcacatt atcttatgtt atacggatcg agatttaat | 10980 |
| acaacctttt tttagttgta atgctacacg atataagtca gttactcatt tataaagaca | 11040 |
| cggacggtgt acg | 11053 |

<210> SEQ ID NO 7
<211> LENGTH: 1166
<212> TYPE: DNA
<213> ORGANISM: Homo sapiens

<400> SEQUENCE: 7

| | |
|---|---|
| cgtcgttacg gatctttact accaagaagt ttaggttcac tattgggtat cattgattga | 60 |
| gtaatcgaat caagacggca tttcagtctt gtttcgttcc tctttgtctt ggagacgtca | 120 |
| cttacctcct taaagactcc cagtgaactt tcgtctttga gttctcgggt tggaccattc | 180 |
| accgtcccga ccggtccagt cacgttgaag ttcagctaca acagtcactt acgaggtcta | 240 |
| cctaacgtct cttctggttt caagtacaga gccgtggaaa gggttacatg tcccgaataa | 300 |
| caaccctgtc tcatcacgga ccggactgaa agcggttttc gtacgtgtct tgcaccttga | 360 |
| accggaggac ttttccgcac agaagtcgaa tccaataagg aaagagctac gagtggtact | 420 |
| acagtccgag gatcatcctc tcggtaatta ttgaagccac tgaaccgtaa actacccgtt | 480 |
| agaaccggta ggatttcgta aggtacggta gtctatatgg gacgtaacgg tactcgaaat | 540 |

```
agtaaccgaa aatcttgtag taggagggtg aaacttattt accagatcgt ctgttatgtc      600
aggatattgt aacaagacag agaaagacgt ttacattcta tttttataat ggaagtaaga      660
tcttttgtgg ggaaacatct tatccaaata tggaagtccg tacacctgaa aggttaggtt      720
tgaggtcctc atctgtctat gggtggtcct gatccgttac gtccttttag agtccgaagt      780
cgatcctgac aaagtatgtt aaaggacgta ccggtccttg ttcccacttc cgtacgtgag      840
acactcgtcg ggtaaacacc tgtcacccag taccctgact ccttggtac aatgtgtacg       900
gactcaaaag aaaggttcga gtctttggta tagcttgtgg ggagggaacc cctcttcact      960
cactcgtcca cctctctgct atcattacaa tcataccacc ttgaagaagg ggtatctacc     1020
tttgtgactc ccgattcttc ttcccggaga ggaggttgta cacaatagat cgttccgacc     1080
aagataaatt cttactatat atcagatcac attatcttat gttatacgga tcgagatttt     1140
aatacaacct ttttttagtt gtaatg                                          1166

<210> SEQ ID NO 8
<211> LENGTH: 4103
<212> TYPE: DNA
<213> ORGANISM: Homo sapiens

<400> SEQUENCE: 8
tgaaaacaga aggagtacgg aagagaagat cacaccgagt cacgaatcac gtcctctttg       60
gtcattggga cttaacgtcg agaaggaaag tgatgtactt aagttaaagg agtagacagt      120
ttactcatat ggttaagtat agagctttcg acaacgacac tcttagtcta ttcgtattgg      180
agtgtcgaat acagataatc ttgtcgtgaa ccgtgtacca tttgtgaggt ttcataaaca      240
atttacttac ttatctaatt ttccaccgta caaaacatga tttgacaagt tactatcaca      300
ttttggtaaa ccagtattac gcctttccct tcattccgcc ttaaggaaat tagacacaaa      360
atgcgtccaa ggtttcctcg caccacctct cttcctacgt ctatcagacc cactctcgat      420
ctccgacctc agtcgtcctt cctgactccg gcaaccacga ccccctcact cccgaggaaa      480
gacgagacag gatccgattc aaggggtggg taaggaagaa ctctagatgg agtttgtgtt      540
tagggagtta actggtgtcc cccgcgggga agatacttaa accgcgacta tcgacactag      600
acgggtcgtg tcacccctttt tgtgttttaa atgtctagtc cgtacaggcc cgagtctaag      660
gatgaggtcg tggaccaccg gttccctggg gttgacaatt tatccgtacc actacggacg      720
aaaggttcgg acaaccctttt ctctctcccc tcgcccctcc ttaccctctc tctctctctg      780
actcgttcgt acggttctga attatatgaa tataaatata atttctctta tttatagtct      840
actaatgtta aaccaacttg attctatgtg tcatcttata ccttgattat aggttatagt      900
gtttcataag atcgctcgga aggatgtctt tcttaacacc caccgaccc tcatccgtaa       960
tcgatgatac actcacgtct cttatgagtc ggaagaaggt ctaccactcg atttcaagtt     1020
tctagttcag tgcatgtgtg gaagaaagag tagggtccag gatcagacga acttaagttt     1080
accggtaggt gtggaacgga ctttatgaac gttattaatt ctatgccgaa agacggacga     1140
accccaaacc aggtgttaag ggaattctcc ggagtaaagt taatcctgag tgtgtaggga     1200
agttgtcatt aaaacacagt ccgaaccaat cgttgagttc cgagttcgta tttaccctgt     1260
cttaagaaaa ggaaaacttt gagtggttat atcactaaca tcgttgatcg atgtaacaaa     1320
aacaaaaaaa aaggggggag ttaagattcg tgatacgttt ccgaaatttc gtcaccaggg     1380
ttcggaaaaa ccgtggtccc tggtcaaaac accttctgtt aaaacacttt tctgttttac     1440
```

```
accttctggc acctgacccct accaaacccc tactaagttc gtgtaatgta aacaacacgt    1500
gacacaaaga taataataat gtaacataat atattacttt attaatatgt tgagtggtat    1560
tacatcttag tcaccttcgg gactcgaaca aaggacgttg atctgtgagg gtagatcccc    1620
actaccctct gccactgtcc agtaatccgt aatctaagag tattcctcgc gtgttggatc    1680
tagggagcgt acacgtcaag tactgtccca aacacgacga tactcttaaa ttacggtgac    1740
gactagactg tcctccacct cgagtccgtc attccactcg ttacccctcg tcgacattta    1800

ttgcgactag agtgagtggg tgacgagtgg aggacgacac accgggtcaa ggattgtccg    1860
gtgttttacc atggacagac acaggggtcc caacccctgg tgacggaatt tccggaagta    1920
gagtaagtca aaagtagttt taagacacac catccatgag agtaatctgg gtaaaatacc    1980
cattccttga ctccatttta accaatatat tgaacggatt ttattcagtt cagagactac    2040
tctcccggtc ctaagttcaa gttcgtcaga ctgaggtttt agagtttcgt gaagacacca    2100
tcctttctct ttacttacct taccgtatct cagtagaтттт actgacgtca tccttccctc    2160
gtaaagggca cacgtcacaa taaaaaaggc ccgaaacтттт ctatttatcc tcgtacgtca    2220

attttttctc tcctcttccg taagatccgt ctttccggtc acgaatgtgt cttagagtct    2280
taacattgtc aaggataatg tgggaccgtc tcactacggt tccgacaata acagttcgtg    2340
ggaggacgga gggtcacccc aactcttccc cacttccctg tgaccgtctt cacttcgacc    2400
cttcaaacgt gaacgatcaa ccctgaacgt atcggtagaa gagttacggt ttctcctgga    2460
gtcagagaca cacgcgaaac aaaaaacaac aacaacaaca acaactaaac accgggtccg    2520
atctcacgcc accacactag agacgagtga cgttggaggg agagggtcca agttccctaa    2580
gaggacggag gtctgagggt tcatcgaacc taatgtccgc gggcggtggt gtggacctat    2640
taaaaatatg aaaatcatcc ccacctcaaa gtggcacaac cggtccgacc agacacacac    2700
gaaacctaaa ctctgtgaga ctactaaatc tcaactttta ccctcatcta acccactaag    2760
agatcaatag tacaaatcag tttagtctag gcacgtaagt tttagtattc cgttcaaaag    2820
gacacaccga gtcattgtag gaatttcttt atcaagacta caggtaggcc acaaaaaagt    2880
ctttctcgca gtcccaactg tcatcgacac tacgagtctt acctcgacgc ctattgtcgt    2940
atattcaaag tccgtcacc aactccccga caccctccca ccctcccttt ctacctactg    3000
aaaagagttg gtagacataa actaacctta taacacactg aacactttat cttaatttct    3060
atactagaag aataccagaa gagtgtcaaa agttccctaa aatcctcttt tgcgaatcgg    3120 tatgtctcgg тттggaccaтт caccgtcccg accggtccag tcacgttgaa gttcagctac    3180
aacagtcact tacgaggtct acctaacgtc tcttctggtt tcaagtacag agccgtggaa    3240
agggttacat gtcccgaata acaaccctgt ctcatcacgg accggactga aagcggtttt    3300
cgtacgtgtc ttgcaccttg aaccggagga cтттттccgca cagaagtcga atccaataag    3360
gaaagagcta cgagtggtac tacagtccga ggatcatcct ctcggtaatt attgacggat    3420
agagtggtaa tctgacacat gaagatcttc cgtctttaga aaaagattac taaagaataa    3480
agggtcttgg atattgtaac aagacagaga aagacgttta cattctattt ttataatgga    3540
agtaagatct tttgtgggga aacatcttat ccaaatatgg aagtccgtac acctgaaagg    3600

ttagttttga ggtcctcatc tgtctatggg tggtcctgat ccgttacgtc cтттттagagт    3660 ccgaagtcga tcctgacaaa gtatgttaaa ggacgtaccg gtccttgttc ccacttccgt    3720
acgtgagaca ctcgtcgggt aaacacctgt cacccagtac cctgacttcc ttggtacaat    3780
gtgtacggac tcaaaagaaa ggttcgagtc tttggtatag cttgtgggga gggaacccct    3840
```

```
cttcactcac tcgtccacct ctctgctatc attacaatca taccaccttg aagaagggt      3900 atctaccttt gtgactcccg attcttcttc ccggagagga ggttgtacac aatagatcgt      3960
tccgaccaag ataaattctt actatatatc agatcacatt atcttatgtt atacggatcg      4020
agattttaat acaacctttt tttagttgta atgctacacg atataagtca gttactcatt      4080
tataaagaca cggacggtgt acg                                              4103

<210> SEQ ID NO 9
<211> LENGTH: 2612
<212> TYPE: DNA
<213> ORGANISM: Homo sapiens

<400> SEQUENCE: 9
tcatcattac cagctgccgt gttaagcatt gcgaaaacgc tcacgattca cagaaaaatc        60
catgctgttc tttgaaggca ttcaagcctt aatagctagc tggatgaatg tttaacttct       120
aggccaggca ctactctgtc ccaacaataa gccctgtaca ttgggaaagg tgccgagaca       180
tgaactttgg tcttctctgc aatccatctg gagcattcac tgacaacatc gactttgaag       240
ttgcactgac ctggccagcc ctgccactta ccaggttggc tctgtatggc taagcgtttt       300
ctcctaaaat cccttgaaaa ctgtgagaag accataagaa gatcatatct ttaattctat       360
ttcacaagtc acacaatatt ccaatcaaat acagatggtt gagaaaagtc atccatcttc       420 cctcccacc ctcccacagc ccctcaacca ctgccctgaa acttatatgc tgttatccgc        480
agctccatct ggagcatcac agctactgtc aaccctgacg ctctttctga aaaaacaccg       540
gatggacatc agaactattt ctttaaggat gttactgagc cacacaggaa aacttgcctt       600
atgattttga atgcacggat ctgatttgac taaacatgat aactagagga tcacccaatc       660
tactcccatt ttcaactcta aatcatcaga gtgtctcaaa tccaaagcac acacagacca       720
gcctggccaa cgcggtgaaa ctccacccct actaaaagta taaaaattat ccaggtgtgg       780
tggcgggcgc ctgtaatcca agctacttgg gagtctgagg caggagaatc ccttgaacct       840
gggagatgga ggttgcagtg agcagagatc acaccaccgc actctagcct gggccacaaa       900
tcaacaacaa caacaacaac aaaaaacaaa gcgcacacag agactgaggt cctctttggc       960
attgagaaga tggctatgca agtcccaact agcaagtgca aacttcccag cttcacttct      1020
gccagtgtcc cttcacccct tctcaacccc actgggagc aggagggtgc ttgacaataa       1080
cagccttggc atcactctgc cagggtgtaa taggaactgt tacaattctg agattctgtg      1140
taagcactgg ccttttctgcc tagaatgcct tctcctctct tttttaactg catgctccta      1200
tttatctttc aaagcccgga aaaaataaca ctgcacacgg gaaatgctcc cttcctactg      1260
cagtcattta tgatgactcta tgccattcca ttcatttctc tttcctacca cagaagtgct      1320
ttgagatttt ggagtcagac tgcttgaact tgaatcctgg ccctctcatc agagacttga      1380
cttattttag gcaagttata taaccaattt tacctcagtt ccttacccat aaaatgggtc      1440
taatgagagt acctaccaca cagaattttg atgaaaactg aatgagatga aggcctttaa      1500
ggcagtggtc cccaaccctg gggacacaga caggtaccat tttgtggcct gttaggaact      1560
gggccacaca gcaggaggtg agcagtgggt gagtgagatc agcgttattt acagctgctc      1620
cccattgctc accttactgc ctgagctcca cctcctgtca gatcagcagt ggcattaaat      1680
tctcatagca gcacaaaccc tgtcatgaac tgcacatgcg agggatctag gttgtgcgct      1740
ccttatgaga atctaatgcc taatgacctg tcaccgtctc ccatcacccc tagatgggag      1800
```

```
tgtctagttg caggaaacaa gctcagggct tccactgatt ctacattatg gtgagttgta    1860
taattatttc attatataat acaatgtaat aataatagaa acacagtgca caacaaatgt    1920
aatgtgcttg aatcatcccc aaaccatccc agtccacggt cttccacatt ttgtctttc    1980 acaaaattgt cttccacaaa actggtccct ggtgccaaaa aggcttggga ccactgcttt    2040
aaagcctttg catagtgctt agaattgagg gggaaaaaaa aaacaaaaac aatgtagcta    2100
gttgctacaa tcactatatt ggtgagtttc aaaaggaaaa gaattctgtc ccatttatgc    2160
ttgagccttg agttgctaac caagcctgac acaaaattac tgttgaaggg atgtgtgagt    2220
cctaattgaa atgaggcctc ttaagggaat tgtggaccaa accccaagca ggcagaaagc    2280
cgtatcttaa ttattgcaag tatttcaggc aaggtgtgga tggccatttg aattcaagca    2340
gactaggacc tgggatgaga aagaaggtgt gtacgtgact tgatctttga actttagctc    2400
accatctgga agaaggctga gtattctctg cactcacata gtagctaatg cctactcccc    2460
agccacccac aattctttct gtaggaaggc tcgctagaat actttgtgat attggatatt    2520
agttccatat tctactgtgt atcttagttc aaccaaattg taatcatctg atatttattt    2580
cttttaatat aaatataagt atattaagtc tt                                 2612
```

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5'-Phos"

<400> SEQUENCE: 10
gttggacttg tacgatagct ctc                                            23

<210> SEQ ID NO 11
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5'-OH"
<220> FEATURE:
<221> NAME/KEY: modified_base
<222> LOCATION: (5)..(5)
<223> OTHER INFORMATION: iBIOdT
<220> FEATURE:
<221> NAME/KEY: modified_base
<222> LOCATION: (20)..(24)
<223> OTHER INFORMATION: a, c, t, g, unknown or other

<400> SEQUENCE: 11
gctancgtac aagtccaacn nnnnv                                          25

<210> SEQ ID NO 12
<211> LENGTH: 19
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5'-OH"

<400> SEQUENCE: 12
gcgatatcac tgttccaac                                                    19

<210> SEQ ID NO 13
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5'-OH"

<400> SEQUENCE: 13
gttggaacag tgatatcgcg aga                                               23

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ggccgcgata tcggatccaa c                                                 21

<210> SEQ ID NO 15
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gttggatccg atatcgc                                                      17

<210> SEQ ID NO 16
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (45)..(46)
<223> OTHER INFORMATION: a, c, t, g, unknown or other

<400> SEQUENCE: 16
ccatctcatc cctgcgtgtc ccatctgttc cctccctgtc tcagnn                      46

<210> SEQ ID NO 17
<211> LENGTH: 44
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
ctgagacagg gagggaacag atgggacacg cagggatgag atgg             44

<210> SEQ ID NO 18
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ctgagacacg caacagggga taggcaaggc acacagggga tagg             44

<210> SEQ ID NO 19
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (45)..(46)
<223> OTHER INFORMATION: a, c, t, g, unknown or other

<400> SEQUENCE: 19
cctatcccct gtgtgccttg cctatcccct gttgcgtgtc tcagnn          46

<210> SEQ ID NO 20
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aatgatacgg cgaccaccga gatctacacc ctatcccctg tgtgccttg        49

<210> SEQ ID NO 21
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
caagcagaag acggcatacg agatcggtcc atctcatccc tgcgtgtc         48

<210> SEQ ID NO 22
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 22
gtgccttgcc tatccctgt tgcgtgtctc ag                                    32

<210> SEQ ID NO 23
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tgcgtgtccc atctgttccc tccctgtctc ag                                   32
```

COMPOSITIONS FOR RNA-CHROMATIN INTERACTION ANALYSIS AND USES THEREOF

REFERENCE TO RELATED APPLICATION

This application claims priority to and the benefit of the filing date of U.S. Provisional Application No. 61/873,928, filed on Sep. 5, 2013, the entire content of which is incorporated herein by reference.

SEQUENCE LISTING

The instant application incorporates by reference the Sequence Listing in the ASCII textfile filed Mar. 23, 2018, entitled "SeqList.txt", which file was created on Mar. 23, 2018, the size of which file is 114,511 bytes.

BACKGROUND OF THE INVENTION

Noncoding RNAs (ncRNAs) are now believed to be transcribed pervasively in the genome, and large numbers of ncRNAs have been identified. However, disproportionally, still very little is known about their functional roles. Many of the known ncRNA functions were inferred by perturbation experiments, which lack the details of what specific target an ncRNA interact with. Technologies like CLIP/RIP-Seq and ChiRP-Seq have provided tremendous insights of what the protein factors and chromatin loci for some ncRNAs to interact with. However, current methods are limited to examine ncRNA or interacting target one at a time. Thus it is desirable to have an unbiased genome-wide strategy to identify the functional targets for all ncRNAs.

SUMMARY OF THE INVENTION

One aspect of the invention provides a kit comprising: (1) an RNA linker comprising: (i) a first polynucleotide, and, (ii) a second polynucleotide, wherein the first and the second polynucleotides form a first double stranded region flanked by a first ligation compatible end, and a 3'-overhang at the 3'-end of the first polynucleotide, wherein the 3'-overhang comprises a random-sequence primer; and, (2) a DNA linker comprising: (iii) a third polynucleotide, and, (iv) a fourth polynucleotide, wherein the third and the fourth polynucleotides form a second double stranded region flanked by a blunt end and a second ligation compatible end, wherein the first and the second ligation compatible ends ligate to each other, or are adaptable to ligate to each other.

In certain embodiments, the first ligation compatible end is a 3'-overhang at the 3'-end of the second polynucleotide, and the second ligation compatible end is a 3'-overhang at the 3'-end of the third polynucleotide, wherein both 3'-overhangs anneal to each other for ligation.

In certain embodiments, the first double stranded region comprises a first recognition site for a first restriction enzyme (RE) that cleaves 3' to the random-sequence primer.

In certain embodiments, the second double stranded region comprises a second recognition site for a second restriction enzyme (RE) that cleaves 5' to the third polynucleotide.

In certain embodiments, one or more of said first, second, third, and fourth polynucleotides are DNA.

In certain embodiments, one or more of said first, second, third, and fourth polynucleotides comprise a modified nucleotide.

In certain embodiments, the modified nucleotide is a biotinylated T (Thymidine).

In certain embodiments, the first polynucleotide comprises a plurality of polynucleotides, each differing only at the random-sequence primer region.

In certain embodiments, the first polynucleotide comprises a homogeneous population of polynucleotides having identical random-sequence primer.

In certain embodiments, the random-sequence primer comprises 4, 5, 6, 7, 8, or more nucleotides.

In certain embodiments, the first double stranded region comprises a unique sequence that distinguishes the RNA linker from the DNA linker.

In certain embodiments, the second double stranded region comprises a unique sequence that distinguishes the RNA linker from the DNA linker.

In certain embodiments, the last nucleotide of the first recognition site is the last base-paired nucleotide 5' to the random-sequence primer.

In certain embodiments, the last nucleotide of the second recognition site is a base-paired nucleotide at the blunt end.

In certain embodiments, the first and the second restriction enzymes are the same.

In certain embodiments, the first or the second restriction enzyme is independently selected from: AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, EcoP15I, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI or Tth111I.

In certain embodiments, the cleavage site of the first or the second restriction enzyme is at least about 10, 12, 14, 16, 18, 20, 22, 24, 26, 28, 30 or more nucleotides 3' to the last nucleotide of the recognition site.

In certain embodiments, the first and the fourth polynucleotides are dephosphorylated.

In certain embodiments, the kit further comprises a reagent that cross-links protein and polynucleotide.

In certain embodiments, the reagent comprises formaldehyde.

In certain embodiments, the kit further comprises an affinity reagent (e.g., an antibody, or a monoclonal antibody) that specifically or selectively binds a component of chromatin (e.g., histone).

In certain embodiments, the kit further comprises an end-repairing mixture that converts DNA containing damaged or incompatible 5'- and/or 3'-protruding ends to 5'-phosphorylated, blunt-ended DNA.

In certain embodiments, the kit further comprises a DNA ligase (e.g., T4 ligase).

In certain embodiments, the kit further comprises a reagent that reverses cross-linking of protein and polynucleotide (e.g., Proteinase K).

In certain embodiments, the kit further comprises the first and/or the second restriction enzyme(s).

In certain embodiments, the kit further comprises a pair of concatenating adapters for PCR amplification of blunt-ended double stranded DNA.

In certain embodiments, the kit further comprises a Taq DNA polymerase.

In certain embodiments, the kit further comprises a reverse transcriptase.

Another aspect of the invention provides a paired-end tag (PET) polynucleotide comprising a central region comprising the first and second double stranded regions of the subject RNA and DNA linkers, said central region being flanked by: (1) at a site proximal to said first double stranded region, a sequence tag of a non-coding RNA (ncRNA); and (2) at a site proximal to said second double stranded region, a sequence tag of a genomic DNA.

In certain embodiments, the sequence tag of the non-coding RNA (ncRNA) has a free end resulting from digestion by said first restriction enzyme.

In certain embodiments, the sequence tag of the non-coding RNA (ncRNA) uniquely identifies a genomic region from which the ncRNA is transcribed.

In certain embodiments, the sequence tag of the non-coding RNA (ncRNA) is about 8-30 base pairs in length.

In certain embodiments, the sequence tag of the genomic DNA has a free end resulting from digestion by said second restriction enzyme.

In certain embodiments, the sequence tag of the genomic DNA uniquely identifies a genomic region at which the genomic DNA is located.

In certain embodiments, the sequence tag of the genomic DNA is about 8-30 base pairs in length.

Another aspect of the invention provides a paired-end tag (PET) library comprising two or more members of the subject PET polynucleotide, wherein each member of the PET library comprises the same said central region, and different said sequence tag of the subject non-coding RNA (ncRNA) or different said sequence tag of the subject genomic DNA or both.

Another aspect of the invention provides a vector comprising a subject PET polynucleotide.

In certain embodiments, the vector comprises a plurality of concatenated subject PET polynucleotide.

Another aspect of the invention provides a concatemer of two or more subject PET polynucleotides.

Another aspect of the invention provides a method of identifying functional interaction loci within a genome for non-coding RNAs (ncRNAs) of the genome, the method comprising: (1) providing chromatin fragments comprising cross-linked genomic DNA fragments and cross-linked ncRNAs; (2) using the RNA linker and the DNA linker of claim 1, ligating an end of a cross-linked genomic DNA fragment to an end of a cDNA of a cross-linked ncRNA, under a condition for proximity ligation, wherein said end of the cross-linked genomic DNA fragment is ligated to the DNA linker, and said end of the cDNA of the cross-linked ncRNA comprises the RNA linker; (3) isolating a PET polynucleotide of claim 29 for sequencing analysis; and, (4) mapping the sequence tag of the genomic DNA and the sequence tag of the ncRNA within each said PET polynucleotide to a reference genome, thereby identifying functional interaction loci within the reference genome for said non-coding RNAs (ncRNAs) of the reference genome.

In certain embodiments, the ncRNAs and the genomic DNA are cross-linked in live cells through formaldehyde-mediated cross-linking.

In certain embodiments, chromatin fragments are generated by sonication.

In certain embodiments, the cDNA of the cross-linked ncRNA comprises a first strand cDNA reverse transcribed from the random-sequence primer of the RNA linker, and the ncRNA template.

In certain embodiments, $2^{nd}$ strand cDNA synthesis is carried out after proximity ligation but before step (3).

In certain embodiments, the method further comprises repairing the ends of the cross-linked genomic DNA fragments to 5'-phosphorylated, blunt-ended DNA prior to step (2).

In certain embodiments, the third polynucleotide of the DNA linker is dephosphorylated and the DNA linker does not self-ligate.

In certain embodiments, the method further comprises identifying clusters of two or more PET polynucleotides having overlapping sequence tags of the genomic DNA and overlapping sequence tags of the ncRNA.

In certain embodiments, the method further comprises excluding PET polynucleotides comprising sequence tags of rRNA.

In certain embodiments, the method further comprises isolating or enriching a subset of chromatin fragments prior to step (2).

In certain embodiments, the subset of chromatin fragments is isolated or enriched by immunoprecipitation using an antibody specific for a protein component of the subset of chromatin fragments.

In certain embodiments, the protein component is a histone, a transcription factor, a polycomb-group (PcG) family protein; a recombination involved factor; a chromatin insulator or chromatin waver; a methyl-CpG-binding protein; or an RNA binding protein.

It should be understood that any description disclosed for the purpose of carrying out one embodiment of this invention (such as embodiments only described in the example section only), including but not limited to any technique(s), reagents, experimental conditions, restrictions sites, enzymes, vectors, primers, and the like, may also be used in combination with other embodiments of the invention, including those embodiments described only in detail in one (but not any other) aspect of the invention. It will be evident to any skilled person how to adapt techniques and material disclosed for the other embodiments to the present embodiment of the invention.

BRIEF DESCRIPTION OF THE DRAWINGS

FIG. 2A shows proportions of singleton PET (no overlap with other PET sequences) and PET clusters. Using the PET cluster data, approximately 700 RNA loci and about 5000 DNA loci were identified. FIG. 2B shows RNA-Seq data intensity at the RNA and DNA loci identified by the RICh-PET data. FIG. 2C shows that most of the RICh-PET data defined ncRNA interactions were trans-acting and inter-chromosomal.

FIG. 4A shows that both NEAT1 and MALAT1 are expressed in HeLa S3 cells, and are abundantly detected in RICh-PET data. NEAT1 is restricted only in cis-acting, in that both RNA and DNA tags were mapped in short distances within the same locus. MALAT1 is mostly trans-acting, in that most of the DNA tags were mapped in large distances in the same chromosome or in different chromosomes (inset). FIG. 4B shows RNA-FISH experiments in human A549 and HeLa S3. The NEAT1 probe generated few fluorescent spots (1-2 per nucleus in HeLa S3 cells), whereas the MALAT1 probe generated much more spots (13 per nucleus in HeLa S3 cells). Counts were based on 100 nuclei per probe per experiment.

FIG. 5A shows pie charts of categories of RNA tag cluster locations in the genome, showing that the vast majority of RNA tags were found in putative ncRNA regions, only 3% were overlap with protein-coding exons. Many know ncRNAs were detected, and many new ones were identified. FIG. 5B shows pie charts of categories of DNA tag cluster locations in the genome, showing that the majority of DNA tag clusters were mapped to protein coding regions, mostly in either promoters or introns.

FIG. 6A is a connectivity map of MALAT1 interacting with 59 genomic loci. FIG. 6B is a box plot showing genes with MALAT1 presence at their promoter regions have higher RNA-seq reads than the genes with MALAT1 interactions at their intron regions. In an aggregation plot of RNAPII ChIP-Seq intensity (not shown), genes with MALAT1 presence at their promoter regions have higher RNA-seq reads than the genes with MALAT1 interactions at their intron regions.

DETAILED DESCRIPTION OF THE INVENTION

1. Overview

Figure 1A:
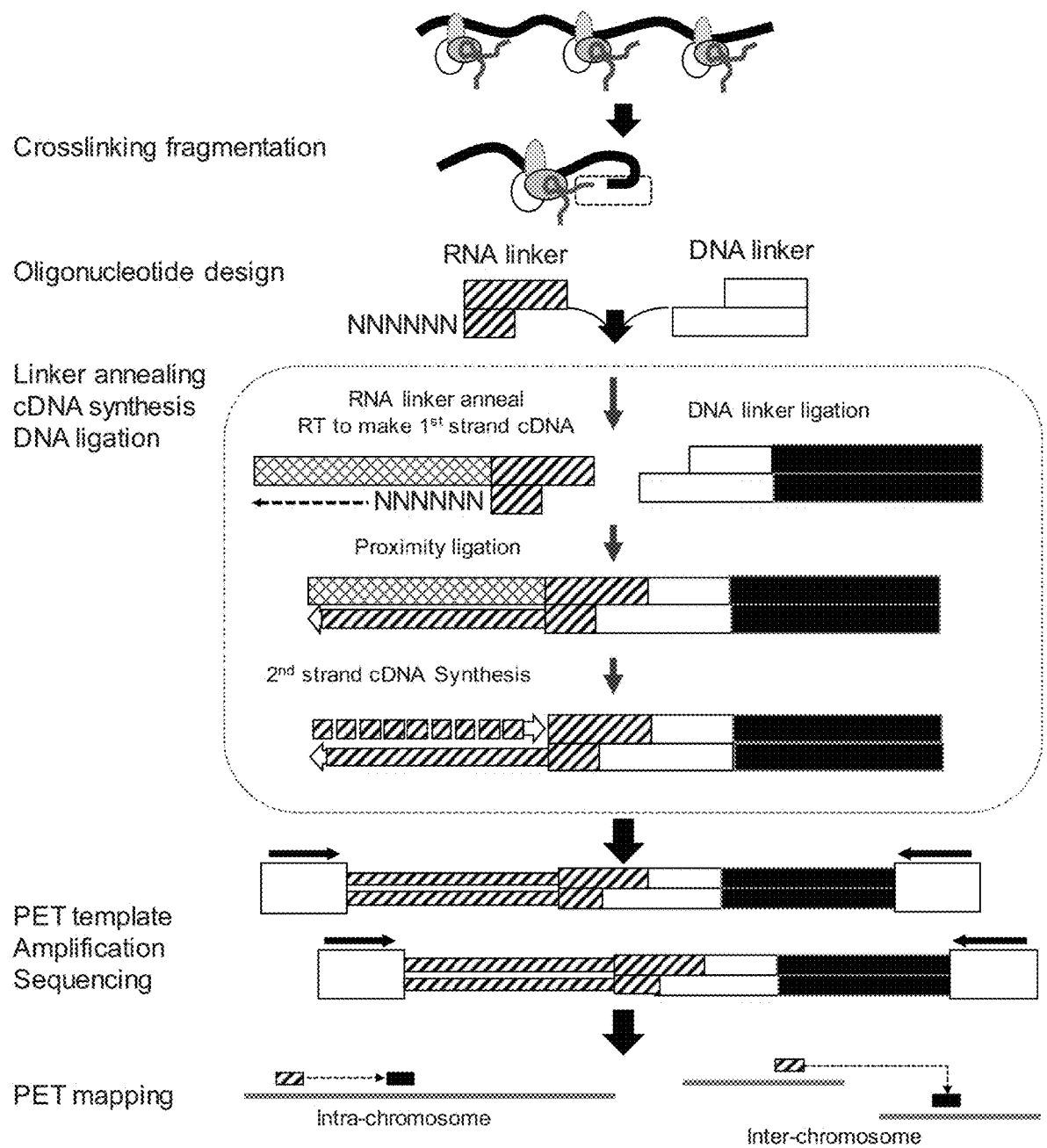
FIG. 1A shows a schematic flow of a typical setting of the RICh-PET method using the RNA linker and DNA linker pair. The interactions of ncRNA to chromatin are captured by crosslinking, followed by sonication to break up the chromatin fibers into tethering complexes with RNA, DNA and protein components. The tethered RNA and DNA in each of the chromatin fragment complex are then connected by a set of ligation reactions mediated by specifically designed RNA linker and DNA linker oligonucleotides that may also have unique sequence barcodes for orientation and specificity. Within each of the chromatin complexes, the 3'-end of RNA is annealed to the random hexamer protruding portion of the RNA linker followed by reverse transcription for cDNA synthesis. Meanwhile, the DNA linker is added to the blunt ends of the tethered DNA fragments by ligation. After wash of the excess linker oligos, the attached RNA and DNA linkers are ligated to each other, thus linking the tethered RNA and DNA molecules. After reverse cross-linking, the hybrid ligation products are fragmented either by shearing or restriction digestion into desired sizes for further amplification, sequencing, and mapping analysis to identify the locations where the RNA was transcribed and where it interacted in the genome.

The invention described herein is partly based on the realization that, if an ncRNA had an epigenetic regulatory role in the nuclear space, it would have to either directly or indirectly interact with chromatin at certain locations in chromosomes, in which functions take place for modulating chromatin states and target gene activity. Hence, the invention described herein provides a new approach to globally map ncRNA-chromatin interactions through RNA-DNA ligation, followed by paired-end-tag sequencing (RICh-PET).

In brief, compositions described herein can be used in a method comprising three main parts: 1) chromatin cross-linking to capture (preferably all) molecular interaction events between RNA, DNA and proteins in a live cell (such as one cultured in vitro, or a primary cell obtained from a tissue sample); 2) ligation of the tethered interactive RNA and the chromatin DNA fragment (e.g., through specifically designed linker, such as the RNA linker and DNA linker pairs, or through ligating RNA 3' end to 5' adenylated ssDNA or 5' adenylated overhang); and, 3) sequencing and mapping analysis of the RNA-DNA ligation products or tag sequences derived therefrom (e.g., PET polynucleotide) to localize ncRNAs' transcription sites and their chromatin target sites in the genome.

Thus one aspect of the invention provides a method of identifying functional interaction loci within a genome for non-coding RNAs (ncRNAs) of the genome, the method comprising: (1) providing a chromatin fragment comprising a cross-linked genomic DNA fragment and a cross-linked ncRNA (or a fragment thereof); (2) ligating an end of the cross-linked genomic DNA fragment to an end of the cross-linked ncRNA, under a condition for proximity ligation; (3) isolating a paired-end tag (PET) polynucleotide for sequencing analysis, wherein the PET polynucleotide comprises a sequence tag of a non-coding RNA (ncRNA), and a sequence tag of a genomic DNA; and, (4) mapping the sequence tag of the genomic DNA and the sequence tag of the ncRNA to a reference genome, thereby identifying functional interaction loci within the reference genome for the non-coding RNAs (ncRNAs) of the reference genome.

This RNA-DNA ligation approach not only applies to global study of all ncRNA-chromatin interactions, but can also be applied to studying RNA-protein interaction at specific chromatin locations. Thus, a chromosomal immunoprecipitation (ChIP)-based RICh-PET method could provide additional specificity of RNA-protein-chromatin interaction information.

The reagents and methods of the invention have a wide range of potential uses in research, development, drug target identification, drug screening, diagnosis, treatment/efficacy monitoring, prognosis, etc. For example, the reagents and methods of the invention can be used to comprehensively characterize ncRNA-chromatin interactomes for a number of established cell lines, stem cells, iPS cells, and cells from primary tissues, such as those derived from cancer and healthy tissue control; and to significantly increase our capability of investigating the immense complex world of RNA functions in regulating the output of the genome. The successful completion of the characterization of RNA-chromatin interactomes would provide a comprehensive chromatin address book for most (if not all) of the ncRNA species, which would add another dimension of genomic information to help understand how the genome functions in healthy and disease conditions.

Several specific embodiments of the invention are described in more details below.

a) RNA Linker and DNA Linker Pairs

In the first specific embodiment, the method of the invention can be carried out using an RNA linker and DNA linker pair to ligate the crosslinked RNA and chromosomal DNA in the same chromatin fragment.

Thus one aspect of the invention provides a kit comprising: (1) an RNA linker comprising: (i) a first polynucleotide, and, (ii) a second polynucleotide, wherein the first and the second polynucleotides form a first double stranded region flanked by a first ligation compatible end, and a 3'-overhang at the 3'-end of the first polynucleotide, wherein the 3'-overhang comprises a random-sequence primer; and, (2) a DNA linker comprising: (iii) a third polynucleotide, and, (iv) a fourth polynucleotide, wherein the third and the fourth polynucleotides form a second double stranded region flanked by a blunt end and a second ligation compatible end, wherein the first and the second ligation compatible ends ligate to each other, or are adaptable to ligate to each other.

In certain embodiments, the first ligation compatible end is a 3'-overhang at the 3'-end of the second polynucleotide, and the second ligation compatible end is a 3'-overhang at the 3'-end of the third polynucleotide, wherein both 3'-overhangs anneal to each other for ligation.

In certain embodiments, the first ligation compatible end is a 5'-overhang at the 5'-end of the first polynucleotide, and the second ligation compatible end is a 5'-overhang at the 5'-end of the fourth polynucleotide, wherein both 5'-overhangs anneal to each other for ligation.

In certain embodiments, the first and/or the second ligation compatible ends are adaptable for ligation. For example, instead of having the requisite 3' or 5' overhangs for ligation, the first and/or the second ligation compatible ends may comprise a restriction enzyme (RE) site, which can be cleaved by the RE to produce the requisite 3' or 5' overhangs required for ligation. Prior to cleavage by the restriction enzyme, however, the ligation compatible ends may be blunt ended (e.g., dephosphorylated blunt end to prevent self-ligation), or have non-compatible overhang that prevents self-ligation or ligation with the other ligation compatible end.

In certain embodiments, the two 5'- or 3'-overhangs at the compatible ligation ends do not self-anneal and do not anneal with each other. This can be accomplished, for example, by designing the sequences of the overhangs such that the overhang sequences do not self-anneal or anneal with each other, at least when under the conditions the linkers are to be used.

This design may be advantageous in certain embodiments, in which, for example, a downstream step includes PCR amplification. One frequently observed type of non-specific amplification product is a template-independent artifact of amplification reactions referred to as "primer dimer," which is a double-stranded fragment whose length typically is close to the sum of the two primer lengths and appears to occur when one primer is extended over the other primer. The resulting extension product forms an undesired template which, because of its short length, is amplified efficiently.

Each of the first, second, third, and fourth polynucleotides may be provided in separate containers, such as synthesized polynucleotides, either in freeze dried, lyophilized form or in water or a suitable buffer solution. Alternatively, the first and the second polynucleotides may be combined in the same container (lyophilized or in solution), for example, in 1:1 molar ratio, such that they can be used as pre-annealed RNA linker. Similarly, the third and the fourth polynucleotides may be combined in the same container (lyophilized or in solution), for example, in 1:1 molar ratio, such that they can be used as pre-annealed DNA linker.

The second, third, and fourth polynucleotides are substantially homogeneous or pure (e.g., individual polynucleotide molecules within the same container are the same), while the 3'-end of the first polynucleotide in the 3'-overhang region comprises a random-sequence primer (e.g., individual first polynucleotide molecules within the same container are the same except that each may have a different random sequence primer within the 3'-overhang region). Thus the first polynucleotide may be unique in that it is in fact a mixture of polynucleotides differing only at the random-sequence primer region of the individual polynucleotides.

In a related embodiment, however, when a specific ncRNA with a defined 3'-end sequence is of interest, and first polynucleotide of the invention may be homogenously containing the same matching sequence at the random-sequence primer region, in order to initiate first strand cDNA synthesis specifically from the specific ncRNA with the defined 3'-end sequence.

The random-sequence primer generally has sufficient length (e.g., hexamer), so as to be capable of directing $1^{st}$ strand cDNA synthesis from the 3'-end of a non-coding RNA. Although hexamer random sequences can be used, other lengths, such as 4, 5, 7, 8, 9, 10, 11, 12 random sequence primers may also be used.

In certain embodiments, the most 3'-end of the random-sequence primer is not deoxythymidine (T) or Uridine (U), or other nucleotide analog that can base pair with adenine (A) in the poly A tail of mRNA. Such design may further help to avoid reverse transcription from the polyA tail of an mRNA.

The 5'- or 3'-overhangs at the 3'-end of the second and third polynucleotides (the first and second ligation compatible ends) are designed to be complementary such that they anneal to each other. The length of the overhang regions in the second and third polynucleotides can be the same, but need not be the same. In certain embodiments, about 2, 3, 4, 5, 6, 7, 8, or more nucleotides in the overhang regions of both polynucleotides are complementary and can form base pairs (Watson-Crick or wobble base pairs).

In certain embodiments, the length of the first double stranded region on the RNA linker is about 6, 7, 8, 9, 10, 15, 20, 25, 30, 35, 40, 50, 60 or more base pairs.

In certain embodiments, the length of the second double stranded region on the DNA linker is about 6, 7, 8, 9, 10, 15, 20, 25, 30, 35, 40, 50, 60 or more base pairs.

In certain embodiments, the total length of the first and the second double stranded regions, in the ligated RNA-DNA linker, is about 10, 15, 20, 25, 30, 35, 40, 45, 50, 55, 60, 65, 70, 75, 80 or more base pairs.

In certain embodiments, the first double stranded region may comprise a first recognition site for a first restriction enzyme, such as a Type II restriction enzyme (RE). The RE recognition site may be strategically placed such that, when the RE cleaves, it cleaves outside the RE site, 3' to the random-sequence primer. This allows the generation of an RNA tag linked to the RNA linker. For example, a MmeI recognition site may be placed at the end of the first double stranded region, distal to the other end of the first double stranded region (where the RNA linker and the DNA linker are linked via their respective 3'-overhang regions). The MmeI site is designed to be in the orientation such that when MmeI cuts, an RNA tag comprising a 18-bp fragment with a 2 bp overhang is generated in the cDNA derived from a linked ncRNA. However, the placement of the RE site does not need to be at the end of the first double stranded region. A more internal placement generates a correspondingly shorter RNA tag sequence.

In certain embodiments, the last nucleotide of the first recognition site (for the first (Type II) restriction enzyme) is the last base-paired nucleotide 5' to the random-sequence primer.

Likewise, in certain embodiments, the second double stranded region may comprise a second recognition site for a second restriction enzyme, such as a Type II restriction enzyme (RE), which may cleave 3' to the second RE recognition site and 5' to the third polynucleotide. The orientation of the RE recognition site is arranged in such a way that it generates a DNA tag based on the terminal sequence of a linked genomic DNA. In certain embodiments, the placement of the RE site does not need to be at the end of the second double stranded region. A more internal placement generates a correspondingly shorter DNA tag sequence.

In certain embodiments, the last nucleotide of the second recognition site (for the second (Type II) restriction enzyme) is a base-paired nucleotide at the blunt end.

In certain embodiments, the first and the second (Type II) restriction enzymes are the same. In other embodiments, the first and the second (Type II) restriction enzymes are different.

For RE that generates relatively long tag sequences, such as Type I or Type III RE, the orientation of the first and second RE recognition sequences may be reversed, such that the RE site in the RNA linker directs the generation of a DNA tag, while the RE site in the DNA linker directs the generation of an RNA tag.

For RE that recognizes two recognition sites (such as Type IIB RE), one of the RE site may be in the RNA linker, and the other may be in the DNA linker, such that the RE only cleaves when the RNA and DNA linkers are correctly ligated as designed to reconstitute the full RE recognition site.

Suitable restriction enzymes that may be used according to the instant invention are described in more details below. In certain embodiments, the cleavage site of the first or the second restriction enzyme is at least about 10, 11, 12, 13, 14, 15, 16, 17, 18, 19, 20, 21, 22, 23, 24, 25, 26, 27, 28, 29, 30 or more nucleotides 3' to the last nucleotide of the recognition site.

In certain embodiments, the RNA linker, the DNA linker, or both, does not have a restriction enzyme recognition site for generating the RNA tag or DNA tag.

In certain embodiments, one or more of the first, second, third, and fourth polynucleotides are DNA (e.g., all are DNA), or comprise both DNA and RNA nucleotides.

In other embodiments, any of them may be RNA.

In certain embodiments, one or more of the first, second, third, and fourth polynucleotides may comprise a modified nucleotide. The modified nucleotide may be at the 5'-end, 3'-end, and/or at an internal position.

In certain embodiments, the modified nucleotide is a biotinylated nucleotide, such as biotinylated dT (deoxythymidine). The presence of the biotinylated nucleotide allows affinity purification of the polynucleotide comprising one or more of such biotinylated nucleotides by, for example, using resins, agarose, nanoparticles, metal or magnetic beads conjugated to a biotin binding partner, such as avidin or streptavidin. Such beads can then be isolated by magnets. The biotinylated nucleotide may be present in the RNA linker, the DNA linker, or both. This technique may also be combined with high throughput next generation sequencing, such as single-molecule real-time sequencing (Pacific Bio); ion semiconductor (Ion Torrent sequencing); pyrosequencing (454); sequencing by synthesis (Illumina); sequencing by ligation (SOLiD sequencing); polony sequencing; massively parallel signature sequencing (MPSS); DNA nanoball sequencing; Heliscope single molecule sequencing, or be used with a Luminex-type system, using color beads or other antibodies for laser- or FACS-based sorting.

In certain embodiments, the modified nucleotide enhances the ability of the random sequence primer to synthesize first strand cDNA via reverse transcription, such as by enhancing the stability and/or specificity of the hybridization between the random primer with the 3'-end of the ncRNA.

In certain embodiments, the random priming sequence may include at least one nucleotide containing a sugar other than the conventional 2'-deoxy-D-ribose or D-ribose found in naturally occurring DNA and RNA, such as a nucleotide in which the sugar is modified by the addition or substitution of a side group, or in which the sugar is a stereoisomer of the conventional 2'-deoxy-D-ribose or D-ribose found in naturally occurring DNA and RNA, or both. See U.S. Pat. No. 6,794,142 (incorporated herein by reference). Such modified nucleotide may be at or near the 3'-end of the random priming sequence. In one embodiment, the modified random primer sequence consists essentially of an oligonucleotide in which at least one of the three 3' terminal nucleotides is a modified nucleotide selected from the group consisting of 2'-O-methyl-nucleotides, 2'-amino-nucleotides, and 2'-fluoro-nucleotides. In one embodiment, the modified primer sequence consists essentially of an oligonucleotide in which at least one of the three 3' terminal nucleotides is a modified nucleotide selected from the group consisting of 2'-O-methyl-ribonucleotides, 2'-deoxy-2'-amino-nucleotides, and 2'-deoxy-2'-fluoro-nucleotides. These modifications represent the addition of a moiety to the 2' OH, or the replacement of the 2'-OH by an alternative moiety.

In certain embodiments, the random priming sequence comprises one or more LNA or PNA. The presence of unusually thermodynamically stable structural fragments in RNAs, such as hairpins, can makes it nearly impossible to carry out primer extension. Replacement of DNA primers with LNA-modified primers may overcome this limitation (see Fratczak et al., *Biochemistry*, 48(3):514-6, 2009; Uppuladinne et al., *Biomol. Struct. Dyn.*, 31(6):539-60, 2013).

Other modified nucleotide, such as thiophosphate (or phosphorothioate, a family of compounds and anions with the general chemical formula $PS_{4-x}OR_x^{3-}$ (x=0, 1, 2, or 3)) modification that renders the internucleotide linkage resistant to nuclease degradation, morpholino oligonucleotides, 2' F-ANA, 2'-O-alkyl, etc., may also be incorporate to the linkers to enhance the stability and nuclease resistant ability of the linkers. See Verma & Eckstein, "Modified oligonucleotides: synthesis and strategy for users," Annu. Rev. Biochem., 67:99-134, 1998 (incorporated herein by reference).

In certain embodiments, the RNA linker and/or the DNA linker may comprise a unique sequence (e.g., a "bar code") that distinguishes the RNA linker from the DNA linker, or the RNA/DNA linker from other RNA/DNA linker (e.g., when two or more sets of RNA linkers are used together). For example, the first and/or the second double stranded region(s) may comprise a unique sequence that distinguishes the RNA linker from the DNA linker. Such bar code may simply be a small stretch of unique sequence, such as a 2-, 3-, 4-, 5-, 6-, 7-, 8-, 9-, 10-nucleotide sequence (or more). In certain embodiments, the difference in the sequence of the RNA linker and the DNA linker may be sufficient to distinguish the RNA linker from the DNA linker. In certain embodiments, only the RNA linker or only the DNA linker has the unique sequence/bar code. In certain embodiments, both the RNA linker and the DNA linker have their respective unique sequences/bar codes.

In certain embodiments, the first polynucleotide is dephosphorylated. In certain embodiments, the second polynucleotide is dephosphorylated. In certain embodiments, the third polynucleotide is dephosphorylated. In certain embodiments, the fourth polynucleotide is dephosphorylated. The dephosphorylation may help to avoid self-ligation of the polynucleotides or the DNA/RNA linkers, such as self-ligation through the blunt ends of two DNA linkers, each may be ligated to a chromosomal DNA fragment in the same chromatin fragment. In addition, if the linkers or the ligatable ends of the linkers are dephosphorylated, it is expected that the linkers are unlikely to ligate to form dimers or concatemers of linkers. Furthermore, it is expected that the DNA linker may ligate to the phosphorylated ends of the chromosomal DNA molecule but cannot ligate to link together the ends of the chromosomal DNA molecules until they are phosphorylated.

In an alternative embodiment, the first and the second polynucleotides may hybridize and form an RNA linker that has, at one end, the 3'-overhang comprising the random priming sequence of the first polynucleotide, and, at the other end, the first ligation compatible site comprising a recognition site for a restriction enzyme. Similarly, the third and the fourth polynucleotides may hybridize and form a DNA linker that has, at one end, the blunt end for ligating to a free end of a chromosomal fragment, and, at the other end, the second ligation compatible end comprising a recognition site for the same restriction enzyme, or a recognition site for a compatible restriction enzyme that generates a compatible ligatable end. Thus digestion by the restriction enzyme and/or its compatible RE produces the overhang (could be 3' or 5' overhang) that can be used to ligate the DNA and RNA linkers. In this embodiment, prior to the restriction enzyme digestion, the ends of the DNA and RNA linkers may not be ligatable (for example, the RNA linker may have a 5' overhang and the DNA linker may have a blunt end of 3' overhang, or vice versa), and such ends may be further dephosphorylated. After the RE digestion, ligatable ends at the DNA and RNA linker ends are generated, with proper phosphorylation. The ligatable ends of the DNA and RNA linker(s) may then be ligated. The ligatable end after restriction may be a blunt end, or have a cohesive end with a 5' or 3' overhang. In particular, a restriction enzyme which cuts rarely may be used so as to reduce the possibility of cutting the nucleic acid material at unintended locations and/or to produce very short fragments.

The subject polynucleotides can be prepared by any suitable method, including direct chemical synthesis by a method such as the phosphotriester method of Narang et al., 1979, Meth. Enzymol., 68:90-99; the phosphodiester method of Brown et al., 1979, Meth. Enzymol., 68:109-151; the diethylphosphoramidite method of Beaucage et al., 1981, Tetrahedron Lett., 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry, 1(3):165-187, incorporated herein by reference.

One or more additional reagents for carrying out the methods of the invention may also be included in the kit of the invention.

In certain embodiments, the kit further comprises a reagent that cross-links protein and polynucleotide, such as formaldehyde (e.g., 1% formaldehyde).

In certain embodiments, the kit further comprises an affinity reagent that specifically or selectively binds a component of chromatin (e.g., histone or a specific ncRNA of interest). For example, the affinity reagent may be an antibody (such as a monoclonal antibody), or any of the functional antigen-binding fragments or derivatives thereof. The affinity reagent may also be a polynucleotide (such as an antisense polynucleotide) that can hybridize/bind to the polynucleotide component of the chromatin. The antisense polynucleotide may be labeled to facilitate subsequent capture of the hybridization complex formed between the antisense polynucleotide and its complement target sequence. For example, the label can be a biotin label (such as biotinylated U or T) that can be captured by avidin or streptavidin coated beads. The antisense polynucleotide may also be immobilized on a solid support, such as on the surface of a microbeads or nanoparticles, which may be packed into a column or used in batch mixture for affinity capture of the complement target sequence.

In certain embodiments, the kit further comprises an end-repairing mixture that converts DNA containing damaged or incompatible 5'- and/or 3'-protruding ends to 5'-phosphorylated, blunt-ended DNA. Such reagents are readily available commercially, such as the End-It™ DNA End-Repair Kit from Epicentre.

In certain embodiments, the kit further comprises a DNA ligase (e.g., T4 DNA ligase from various commercial sources, such as New England Biolabs (NEB)).

In certain embodiments, the kit further comprises a reagent that reverses cross-linking of protein and polynucleotide (e.g., Proteinase K from various commercial sources, such as New England Biolabs (NEB)).

In certain embodiments, the kit further comprises the first and/or the second restriction enzyme(s), and optionally any suitable buffers or cofactors required for RE digestion.

In certain embodiments, the kit further comprises a pair of concatenating adapters for PCR amplification of blunt-ended double stranded DNA. The adapters may comprise restriction enzyme sites useful for concatemerization, and may comprise PCR primer sequences suitable for PCR amplification.

In certain embodiments, the kit further comprises a Taq DNA polymerase for PCR amplification, or other DNA polymerases required for other forms of amplification (e.g., rolling circle amplification).

In certain embodiments, the kit further comprises a reverse transcriptase for first strand cDNA synthesis.

Another aspect of the invention provides a paired-end tag (PET) polynucleotide comprising a central region comprising the first and second double stranded regions linked through the first and the second ligation compatible ends, said central region being flanked by: (1) at a site proximal to the first double stranded region, a sequence tag of a non-coding RNA (ncRNA); and (2) at a site proximal to the second double stranded region, a sequence tag of a genomic DNA.

Such PET polynucleotides comprise both the RNA tag and the DNA tag, each derived from the end sequence of the respective ncRNA and genomic DNA (paired-end tag). Together, the paired-end tag represents an observed event or incident where the ncRNA and the genomic DNA fragment are at close proximity of each other in a chromosomal fragment.

In certain embodiments, the sequence tag of the non-coding RNA (ncRNA) has a free end resulting from digestion by the first restriction enzyme.

The restriction enzyme may be any of the ones described above, such as a Type II RE (Type IIS, IIB, IIG, etc.), Type I RE, or a Type III RE, which may digest outside their recognition site. Alternatively, the free end may be generated by a naturally existing RE site on the cDNA corresponding to the ncRNA. Preferably, the RE is selected based on the sequence of the central region such that the RE does not cut inside the central region to disrupt the structure of the linked DNA linker and RNA linker.

In certain embodiments, the RNA sequence tag of the ncRNA or the DNA sequence tag of the genomic DNA has a free end resulting from physical shearing, such as shearing by sonication, hydroshearing, repeated drawing through a hypodermic syringe needle, etc.

In certain embodiments, the RNA sequence tag of the ncRNA or the DNA sequence tag of the genomic DNA has a free end resulting from limited digestion of a non-specific endonuclease, such as Micrococcal Nuclease (NEB Catalog M0247S), DNase I (NEB Catalog M0303S), or exonucleases that progressively digests from one end of a double stranded DNA, or a combination of endo- and exonucleases (e.g., Exonuclease III and Mung Bean Nuclease) to reduce the average length of the cross-linked genomic DNA or cDNA of ncRNA. The extend of digestion may be controlled by limiting enzyme or substrate concentration, temperature and/or pH of digestion, availability of co-factors, or a combination thereof. Suitable digestion conditions may be pre-tested using standard substrates of defined length, and examining digestion products (by electrophoresis of CE (capillary electrophoresis), etc.) before and after digestion.

The length of the RNA or DNA sequence tags should be sufficient to uniquely identify a genomic region from which the ncRNA is transcribed, or at which the genomic DNA is located. For example, the RNA sequence tag of the non-coding RNA (ncRNA) and/or the DNA sequence tag may be about 10-100 base pairs in length (or 15-50 bp, 20-40 bp, 20-30 bp, 20-25 bp) for relatively complicated genomes of higher eukaryotes, but may be shorter (e.g., 6-10 bp, 8-10 bp, 8-12 bp) for relatively simple genomes of bacteria, or lower eukaryotes.

In a related aspect, the invention provides a paired-end tag (PET) polynucleotide library comprising two or more members of the subject PET polynucleotides, wherein each member of the PET library comprises the same central region, and different RNA sequence tag of the non-coding RNA (ncRNA), different DNA sequence tag of the genomic DNA, or both.

In yet another related aspect, the invention provides a vector or recombinant vector comprising the subject PET polynucleotides.

In certain embodiments, the vector comprises a plurality of concatenated subject PET polynucleotides.

Another aspect of the invention provides a method of identifying functional interaction loci within a genome for non-coding RNAs (ncRNAs) of the genome, the method comprising: (1) providing chromatin fragments comprising cross-linked genomic DNA fragments and cross-linked ncRNAs; (2) using the RNA linker and the DNA linker of the invention, ligating an end of a cross-linked genomic DNA fragment to an end of a cDNA of a cross-linked ncRNA, under a condition for proximity ligation, wherein the end of the cross-linked genomic DNA fragment is ligated to the DNA linker, and the end of the cDNA of the cross-linked ncRNA comprises the RNA linker; (3) isolating a PET polynucleotide of the invention for sequencing analysis; and, (4) mapping the sequence tag of the genomic DNA and the sequence tag of the ncRNA within each PET polynucleotides to a reference genome, thereby identifying functional interaction loci within the reference genome for the non-coding RNAs (ncRNAs) of the reference genome.

In certain embodiments, the methods of the invention are performed using live cells, such as tissue culture cells or cell isolated from freshly dissected tissues. In certain embodiments, the ncRNAs and the genomic DNA in live cells are cross-linked through formaldehyde- and/or EGS (Ethylene glycol bis [succinimidylsuccinate])-mediated cross-linking. Other similar bifunctional crosslinking reagents suitable for crosslinking protein-DNA, protein-RNA and/or protein-protein (e.g., those having two or more reactive chemical groups suitable for reacting with the amide and/or thiol groups) may also be used. If EGS is used, the spacer region between the two NHS-ester may be a 12-atom spacer, although longer or shorter spacers (e.g., 6, 7, 8, 9, 10, 11, 12, 13, 14, 15, 16, 17, 18, 19, 20 atom spacers) may be used as well.

If formaldehyde or EGS (typically about 1-2 mM, or 1.5 mM) are used, EGS may be added first followed by (about 1%) formaldehyde. Reaction may be quenched by glycine. Alternatively, about 1% formaldehyde or about 1% glutaraldehyde may be used.

In other embodiments, the nucleic acids are cross-linked to the chromatin via UV cross-linking. For example, tissue culture cells may be UV-crosslinked at about 150 mJ/cm$^2$ at 254 nm (e.g., by using a UV crosslinker, such as STRATALINKER® UV crosslinker).

For example, about $1-2 \times 10^8$ live tissue culture cells or isolated cells may be first collected and cross-linked with EGS with shaking for 40 min., then formaldehyde (final concentration of about 1%; Sigma) for 10 minutes at room temperature.

Proteinase inhibitor and/or RNase inhibitor may be added to prevent non-specific proteinase or RNase digestion.

The cells are then lysed in a suitable lysis buffer (e.g., 50 mM HEPES, 1 mM EDTA, 0.15 M NaCl, 1% SDS, 1% Triton X-100, 0.1% sodium deoxycholate, all from Ambion).

Once the crosslinking step is complete, various methods may be used to produce chromatin fragments comprising cross-linked genomic DNA and ncRNA.

For example, in certain embodiments, chromatin fragments are generated by physical shearing, such as sonication, hydroshearing, or repeated drawing through a hypodermic syringe needle. Sonication may be advantageous for breaking up the chromatin fibers into tethering complexes with RNA, DNA and protein components, while "shaking off" spurious, random, or week ncRNA-chromatin-DNA interaction.

Alternatively, in certain embodiments, chromatin fragments may be generated by restriction enzyme digestion, or partial or limited endo- and/or exo-nuclease digestion under controlled conditions, in order to produce RNA and DNA tags of suitable length.

To generate chromatin fragments comprising cross-linked genomic DNA fragments and cross-linked ncRNAs, the chromatin can be solubilized by sonication (e.g., using a Branson 450 ultrasonic cell disruptor, operated at 20% duty power output, 30 second, 5 to 8 times; or using a probe sonicator operating at 35% power for 1.5 min, with 20 sec on/30 sec off cycles).

Other commercially available instruments may be used for sonication. For example, the S220 Focused-ultrasonicator from Covaris, Inc. utilizes the Adaptive Focused Acoustics™ (AFA) technology for DNA, RNA, and chromatin shearing. According to the manufacturer, its software incorporates various preset protocols for standard methods, such as DNA shearing to specific fragment lengths. Alternatively, the BIORUPTOR® UCD-200 (Life Technologies Corp.), a benchtop sonication device, may also be used for sonication shearing. The device consists of a high-power ultrasound generating element located below a water bath, and operates at a 20 kHz frequency (similar to a probe sonicator) to provide automated sonication steps suitable for standardized protocols such as ChIP, MeDIP, etc.

Once sheared, the chromatin is diluted (e.g., 10 times) to lower the SDS concentration (e.g., to about 0.1-0.5%). The extract is then cleared by centrifugation (e.g., at 14,000 rpm for 10 minutes at 4° C.). This extract can be stored at −80° C. until use.

If immunoprecipitation is desired, about 2 µg of monoclonal antibody (specific for a chromatin component) can be bound to protein G sepharose (Pharmacia). The antibody coated beads are then incubated with the chromatin extract at 4° C. for 16 hours. The beads are then washed (e.g., with the following reagents from Sigma Chemical Company: Wash buffer 1 (50 mM HEPES, 1 mM EDTA, 0.15 M NaCl, 0.1% SDS, 1% Triton X-100, 0.1% sodium deoxycholate); 2 times Wash buffer 2 (50 mM HEPES, 1 mM EDTA, 0.5 M NaCl, 0.1% SDS, 1% Triton X-100, 0.1% sodium deoxycholate); 1 time Wash buffer 3 (20 mM Tris.HCl pH 8.0, 1 mM EDTA, 0.25 M LiCl, 0.5% NP40, 0.5% sodium deoxycholate); 1 time Wash buffer 4 (20 mM Tris.HCl pH 8.0, 1 mM EDTA). The protein-DNA complexes are then eluted from the beads with elution buffer (e.g., 50 mM Tris.HCl pH 8.0, 1 mM EDTA, 1% SDS) for 20 min at 65° C. The eluent is then dialyzed in PBS (Ambion) to remove SDS (e.g., for 3 hours at 4° C.).

Optionally, the chromatin fragments may also be biotinylated (for example, by using EZlink Iodoacetyl-PEG2-Biotin (IPB) (Thermo Scientific, cat. 21334)), and be isolated as streptavidin beads-bound chromatin fragments. For example, DYNABEADS® with streptavidin (DYNABEADS® MyOne™ Streptavidin C1/T1) may be used to enrich biotinylated chromatin fragments.

In addition, beads with silica like coating may be used to enrich the crosslinked nucleic acid on the chromatin fragments.

The chromatin fragments, after shearing or RE digestion, may have damaged ends or ends otherwise unsuitable for ligation with the DNA linker. Thus end-repair may be performed using, for example, the End-It kit from Epicentre or the T4 polymerase (Promega, R0191), according to the manufacture's suggestion.

First-strand cDNA synthesis can be performed using a reverse transcriptase and the RNA linker (or the modified RNA linker in the second specific embodiment below), such as the Superscript III First Strand Synthesis System (Life Technologies, cat. 18080051).

The repaired chromatin DNA with 5' phosphorylation at its blunt end can then be used in ligation with the DNA linker. This can be carried out in the same container for reverse transcription using the RNA linker, provided that the proper buffer and other reaction conditions for DNA ligation are provided. A DNA ligase, such as the T4 DNA ligase, may be used for this reaction. If necessary, the dephosphorylated DNA linker can then be phosphorylated (e.g., by T4 polynucleotide kinase).

In certain embodiments, first strand cDNA synthesis is performed (either before or after or concurrent with the DNA linker ligation) using the RNA linker.

In certain embodiments, the cDNA of the cross-linked ncRNA comprises a first strand cDNA reverse transcribed from the random-sequence primer of the RNA linker, and the ncRNA template. Due to the presence of the RNA linker, this first strand cDNA and ncRNA template hybrid molecule can be ligated to the DNA linker already ligated to the free end of the chromosomal DNA fragment.

Once the RNA linker and the DNA linker have been properly ligated to their respective ends of the target nucleic acid, proximity ligation can be performed to connect the DNA linker and the RNA linker on the same chromatin fragment. Proximity ligation is usually carried out at a diluted environment such that RNA and DNA linkers on the same chromatin fragment, due to their proximity to one another, are much more likely to be ligated as compared to RNA and DNA linkers on different chromatin fragments.

In certain embodiments, proximity ligation is carried out with about 2, 3, 4, 5, 6, 7, 8, 9, 10, 12, 13, 14, 15, 16, 70, 18, 19, 20-fold or more dilution with respect to the linker ligation steps.

In certain embodiments, proximity ligation is carried out in a total ligation volume of about 5, 6, 7, 8, 9, 10, 11, 12, 13, 14, 15, 16, 17, 18, 19, 20 mL or more, for each equivalent amount of captured chromatin fragments derived from about $1 \times 10^8$ human cells. Ligation volumes may be adjusted accordingly based on the type of cells (e.g., species of origin or genome size).

The proximity ligation conditions may be modified or adjusted, as required, so as to maximize the ligation of the DNA and RNA linkers. Any ligation condition may be modified or adjusted, including but not limited to increasing or decreasing the time for the ligation reaction and/or concentration of the reagents. In other words, the ligation reactions are adjusted or modified to maximize intermolecular ligation of separate nucleic acid molecules cross-linked to the same chromatin fragment. In particular, the ligation may be performed under very dilute conditions of the nucleic acid molecules to maximize the ligation of the ends of different nucleic acid molecules and to reduce the formation of circular multimers.

In certain embodiments, the method includes assessing the extent or frequency of undesired or false positive ligation events between genomic DNA and ncRNA crosslinked to different chromatin fragments. Under ideal proximity ligation conditions, only genomic DNA and ncRNA crosslinked to the same chromatin fragment should be ligated.

For example, one set of DNA and RNA linkers (e.g., linker set A) can be used for ligating to the genomic DNA and RNA ends, respectively, in one reaction container. Meanwhile, a second set of DNA and RNA linkers (e.g., linker set B) can be used for ligating to the genomic DNA and RNA ends, respectively, in a second reaction container. The contents of the two reaction containers are then pooled for the proximity ligation. If the RNA linker in linker set A can be ligated to the DNA linkers of both linker sets (and the DNA linker in linker set A can be ligated to the RNA linkers of both linker sets), then proximity ligation condition is optimum if there is no or very infrequent ligation between linkers of sets A and B (e.g., RNA linker in set A ligate to DNA linker in set B). Conversely, proximity ligation condition is less than optimum if there is significant ligation between linkers of sets A and B.

In certain embodiments, the ratio of the RNA and DNA linkers in linker sets A and B can be further adjusted (e.g., not necessarily 1:1). For example, the molar ratio of RNA and DNA linkers in linker set A compared to that in linker set B may be 2:1, 3:1, 4:1, 5:1, 6:1, 7:1, 8:1, 9:1, 10:1, or vice versa.

In certain embodiments, the first, second, third, and/or the fourth polynucleotide of the invention is dephosphorylated and the DNA linker or RNA linker does not self-ligate.

Second strand cDNA synthesis can be completed either before or after the RNA linker-DNA linker ligation, using, for example, the Superscript Double-stranded cDNA Synthesis Kit (Life Technologies, cat. 1197-020). In certain embodiments, $2^{nd}$ strand cDNA synthesis is carried out after proximity ligation but before step (3).

In certain embodiments, a DNA polymerase, such as T4 DNA polymerase, may be added after the $2^{nd}$ strand cDNA synthesis.

Next, the cross-linked nucleic acid and protein component of the chromatin fragment can be reverse cross-linked with proteinase K. In a typical reaction condition, for example, sample can be reverse cross-linked as 20 µL aliquots by overnight incubation at 65° C. in the presence of 15 µl of 20 mg/ml proteinase K (Ambion) and optionally 0.3% SDS (Ambion). The following day, about 1 µL of 10 mg/ml RNase A (Qiagen) may be added to degrade RNA (e.g., for 45 min at 37° C.), followed by phenol extraction and ethanol precipitation of DNA.

Optionally, purification or enrichment of at least one linked and reverse cross-linked nucleic acid molecule may be performed using a binding system comprising at least two components, wherein at least one first component is coupled to the linker (e.g., a biotinylated nucleotide incorporated into the RNA or DNA linker, for example), and at least a second component binds the first component. The components include but are not limited to streptavidin-biotin, avidin-biotin, protein-antibody and/or magnet/magnetic material.

In particular, biotinylated linker-ligated nucleic acid material may be purified using streptavidin beads, such as streptavidin-conjugated magnetic DYNABEADS™ (Life Technologies, cat. 11206D-10ML). Only the nucleic acid material that contains biotinylated linkers will be immobilized on the streptavidin beads. If another component is bound to the linkers used, other systems of purifying the nucleic acid molecules suitable for the component may be used.

Alternatively, streptavidin columns may be used instead to capture the biotinylated beads. In yet another alternative, the beads may be color or fluorescently coated such that they can be sorted or collected by FACS, etc., on a flow-based detection instrument (e.g., LUMINEX® 100™, LUMINEX® 200™ or BIO-RAD® BIO-PLEX® type analyzer).

The resulting released DNA can be used to produce PET polynucleotides having paired DNA and RNA tags through, for example, RE enzyme digestion. Optionally, the released PET polynucleotides may be further amplified by PCR before sequencing analysis. PCR adapters may be ligated to both ends of the PET polynucleotides (such as by T4 DNA ligase) before carrying out the PCR amplification. Only blunt ended, non-circularized nucleic acids can be ligated to the adapters. Self-ligated nucleic acid molecules and circular multimers cannot be ligated to the adapters.

The PCR adapters may also comprise modified nucleotides for PCR product purification. Similarly, streptavidin-biotin, avidin-biotin, protein-antibody and/or magnet/magnetic material may be used for this purpose.

The PET polynucleotides (with or without amplification) may be directly sequenced, such as according to the protocols for the various next-generation sequencing, such as 454 sequencing using the 454 multiplex sequencing machine (454 life sciences). The technique is taught in Margulies et al (2005) and US Application No. 20030068629 (both incorporated herein by reference). Any other high throughput or next-generation sequencing (NGS) methods may be used to determine the sequences of the PET polynucleotides.

Mapping of the obtained RNA/DNA tag sequences to their respective genomic locations can be performed using any of many commercially available tools, software, or services.

Once the RNA and DNA tags of the PET polynucleotides are sequenced and mapped to the reference genome, each linked RNA tag and DNA tag represents a putative ncRNA-chromatin interaction. The collection of all such observed interactions constitute the functional interaction loci within the reference genome for the non-coding RNAs (ncRNAs) of the reference genome.

In certain embodiments, the method further comprises identifying clusters of two or more PET polynucleotides having overlapping sequence tags of the genomic DNA and overlapping sequence tags of the ncRNA.

The PET clusters are considered as high confidence data, reflecting recurrent detection of more reliable events of ncRNA-chromatin interactions. In contrast, the singleton PETs with no overlap on both the RNA tag and the DNA tag with other PET sequences may represent weak linking signals, and may be indistinguishable from random background noises.

In certain embodiments, the method further comprises excluding PET polynucleotides comprising sequence tags of rRNA. Although some rRNA-chromatin-gDNA (genomic DNA) interactions may be of true biological significance, the presence of large amount (about ¼ in some data set) of rRNA-chromatin-DNA interactions may obscure the other less abundant interactions. Thus such digital subtraction before further data analysis may be desirable for analyzing less frequent ncRNA-chromatin interactions.

In certain embodiments, the method further comprises isolating or enriching a subset of chromatin fragments prior to the proximity ligation step. For example, the subset of chromatin fragments can be isolated or enriched by immunoprecipitation using an antibody specific for a protein component of the subset of chromatin fragments, or by hybridization using a (labeled) polynucleotide specific for a nucleic acid component of the subset of chromatin fragments. This may be useful for identifying specific interactions between a known chromatin component and ncRNA.

In certain embodiments, the protein component is a histone, a transcription factor (such as a general transcription factor RNAPII, RNAPI, RNAPIII), a polycomb-group (PcG) family protein that remodels chromatin (such as EZH2, and others from insects, mammals, and plants); a recombination involved factor (such as PRDM9); a chromatin insulator or chromatin waver (such as CTCF); a methyl-CpG-binding protein (such as MeCP2); or an RNA binding protein.

In a variation of the method, a specific labeled ncRNA (such as biotyinylation) may be added to the cell before crosslinking. Such labeled ncRNA can be isolated or enriched by using magnetic beads coated with avidin or streptavidin.

In yet another variation of the method, complementary sequences to one or more specific ncRNAs of interest may be used to isolate or enrich such specific ncRNAs (using an array or column) cross-linked to chromatin fragments. Once isolated or enriched, such chromatin fragments can be subject to the remaining steps of the method to identify the regions of genomic DNA that interacts with the specific ncRNA.

In certain embodiments, the method further comprises validating one or more observed ncRNA-chromatin interaction by, for example, DNA/RNA FISH and immunofluorescence assays. For instance, if a specific ncRNA is linked to a particular genomic locus, DNA/RNA FISH and immunofluorescence assays may be performed using the ncRNA to confirm the observation (see, for example, FIG. 4B).

b) Modified RNA Linker

In another/second specific embodiment, the method of the invention can be carried out using one modified RNA linker (and no DNA linker) to ligate the crosslinked RNA and chromosomal DNA in the same chromatin fragment.

Thus another aspect of the invention provides a modified RNA linker comprising: (i) a first polynucleotide, and, (ii) a second polynucleotide, wherein the first and the second polynucleotides form a double stranded region flanked by a genomic DNA ligation compatible end, and a 3'-overhang at the 3'-end of the first polynucleotide, wherein the 3'-overhang comprises a random-sequence primer.

According to this aspect of the invention, the 3'-overhang at the 3'-end of the first polynucleotide has a similar function as that of the RNA linker in the specific embodiment described in subsection a) (RNA and DNA linker pair), while the genomic DNA ligation compatible end can be used ligate blunt ended genomic DNA crosslinked to the same chromatin fragment.

In certain embodiments, the ligation compatible end may be blunt ended for direct ligation to the blunt end of the crosslinked genomic DNA fragment.

In another embodiment, the ligation compatible end may comprise a restriction enzyme site, which can be cleaved by the RE to produce the requisite blunt end required for ligation to the blunt end of the crosslinked genomic DNA fragment. Prior to cleavage by the restriction enzyme, however, the ligation compatible ends may be blunt ended (e.g., dephosphorylated blunt end to prevent self-ligation), or have non-compatible overhang that prevents self-ligation.

In certain embodiments, the modified RNA linker does not self-ligate, either through its 3'-overhang or its ligation compatible end.

The first and second polynucleotides may be provided in separate containers, such as synthesized polynucleotides, either in freeze dried, lyophilized form or in water or a suitable buffer solution. Alternatively, the first and the second polynucleotides may be combined in the same container (lyophilized or in solution), for example, in 1:1 molar ratio, such that they can be used as pre-annealed modified RNA linker.

The second polynucleotide is substantially homogeneous or pure (e.g., individual polynucleotide molecules within the same container are the same), while the 3'-end of the first polynucleotide in the 3'-overhang region comprises a random-sequence primer.

In a related embodiment, the first polynucleotide may be homogenously containing the same matching sequence at the random-sequence primer region, in order to initiate first strand cDNA synthesis specifically from the specific ncRNA with the defined 3'-end sequence.

In certain embodiments, the double stranded region may comprise a first recognition site for a first restriction enzyme, such as a Type II restriction enzyme (RE). The RE recognition site may be strategically placed such that, when the RE cleaves, it cleaves outside the RE site, 3' to the random-sequence primer. This allows the generation of an RNA tag linked to the RNA linker. For example, a MmeI recognition site may be placed at the end of the double stranded region, proximal to the 3' overhang comprising the random-sequence primer. The MmeI site is designed to be in the orientation such that when MmeI cuts, an RNA tag comprising a 18-bp fragment with a 2 bp overhang is generated in the cDNA derived from a linked ncRNA. However, the placement of the RE site does not need to be at the end of the first double stranded region. A more internal placement generates a correspondingly shorter RNA tag sequence.

In certain embodiments, the last nucleotide of the first recognition site (for the first (Type II) restriction enzyme) is the last base-paired nucleotide 5' to the random-sequence primer.

In certain embodiments, the double stranded region may comprise a second recognition site for a second restriction enzyme, such as a Type II restriction enzyme (RE), at or near the ligation compatible end. The RE may cleave 3' to the second RE recognition site and 5' to the first polynucleotide (e.g., into the ligated genomic DNA). The orientation of the RE recognition site is arranged in such a way that it generates a DNA tag based on the terminal sequence of a linked genomic DNA. In certain embodiments, the placement of the RE site does not need to be at the end of the double stranded region. A more internal placement generates a correspondingly shorter DNA tag sequence.

In certain embodiments, the last nucleotide of the second recognition site (for the second (Type II) restriction enzyme) is a base-paired nucleotide at the ligation compatible/blunt end.

In certain embodiments, the modified RNA linker does not have a restriction enzyme recognition site for generating the RNA tag or DNA tag.

In certain embodiments, the modified RNA linker may comprise a unique sequence (e.g., a "bar code") that distinguishes the modified RNA linker from other modified RNA linker(s).

In certain embodiments, the first and/or the second polynucleotide is dephosphorylated.

Another aspect of the invention provides a paired-end tag (PET) polynucleotide comprising a central region comprising the double stranded region (of the modified RNA linker) flanked by: (1) at a site proximal to the random-sequence primer, a sequence tag of a non-coding RNA (ncRNA); and (2) at a site proximal to the ligation compatible end, a sequence tag of a genomic DNA.

In a related aspect, the invention provides a paired-end tag (PET) polynucleotide library comprising two or more members of the subject PET polynucleotides, wherein each member of the PET library comprises the same central region, and different RNA sequence tag of the non-coding RNA (ncRNA), different DNA sequence tag of the genomic DNA, or both.

In yet another related aspect, the invention provides a vector or recombinant vector comprising the subject PET polynucleotides.

Another aspect of the invention provides a method of identifying functional interaction loci within a genome for non-coding RNAs (ncRNAs) of the genome, the method comprising: (1) providing chromatin fragments comprising cross-linked genomic DNA fragments and cross-linked ncRNAs; (2) using the modified RNA linker of the invention, ligating an end of a cross-linked genomic DNA fragment to an end of a cDNA of a cross-linked ncRNA, under a condition for proximity ligation, wherein the end of the cross-linked genomic DNA fragment is ligated to the ligation compatible end of the modified RNA linker, and the end of the cDNA of the cross-linked ncRNA comprises the modified RNA linker; (3) isolating a PET polynucleotide of the invention for sequencing analysis; and, (4) mapping the sequence tag of the genomic DNA and the sequence tag of the ncRNA within each PET polynucleotides to a reference genome, thereby identifying functional interaction loci within the reference genome for the non-coding RNAs (ncRNAs) of the reference genome.

In certain embodiments, the cDNA of the cross-linked ncRNA comprises a first strand cDNA reverse transcribed from the random-sequence primer of the modified RNA linker, and the ncRNA template. Due to the presence of the modified RNA linker, this first strand cDNA and ncRNA template hybrid molecule can be ligated to the free end of the chromosomal DNA fragment.

In certain embodiments, the length of the double stranded region on the modified RNA linker is about 6, 7, 8, 9, 10, 15, 20, 25, 30, 35, 40, 50, 60 or more base pairs.

Other embodiments as described in the first specific embodiment described in subsection a) (RNA and DNA linker pair) are generally applicable, and are incorporated (but not reiterated) herein.

c) Direct RNA-DNA Ligation

In another/third specific embodiment, the method of the invention can be carried out using certain enzymes (such as the truncated RNA Ligase 2 or RNL2) that directly ligate the 3'-OH group of the ncRNA to a 5' adenylated single-stranded DNA (5' App-ssDNA), such as a ssDNA linker that is later hybridized to a complement polynucleotide, or a dsDNA with a 5' adenylated overhang that can serve as a substrate of the enzyme for direct ligation to the 3'-OH group of the ncRNA.

Thus the invention also provides an alternative way to ligate the 3'-end of the cross-linked ncRNA and a free end of a cross-linked genomic DNA fragment in the same chromatin fragment. According to this aspect of the invention, a single stranded DNA oligonucleotide is provided with its 5' pre-Adenylated (5' App ssDNA). An RNA-DNA ligase (such as the Thermostable 5' AppDNA/RNA Ligase, NEB Catalog M0319S or M0319L) can then be used to directly link the 3'-OH of the ncRNA to the 5' App ssDNA.

According to the manufacture, the thermostable 5' App DNA/RNA Ligase is a point mutant of catalytic lysine of RNA ligase from *Methanobacterium thermoautotrophicum* (Zhelkovsky and McReynolds, *BMC Mol. Biol.*, 13:24, 2012). This enzyme is ATP independent, but requires a 5' pre-adenylated linker for ligation to the 3'-OH end of either RNA or single stranded DNA (ssDNA). The enzyme is also active in ligation of RNA with 2'-O-methylated 3' end to 5'-adenylated linkers (Zhelkovsky and McReynolds, supra). The mutant ligase is unable to adenylate the 5'-phosphate of RNA or ssDNA, which reduces the formation of undesired ligation products (concatemers and circles). The ability of the ligase to function at 65° C. might further reduce the constraints of RNA secondary structure in RNA ligation reactions.

Another suitable ligase for this embodiment of the invention is RNA Ligase 2, such as the AIR™ RNA Ligase 2 (RNL2) from Bioo Scientific (Austin, Tex.), which specifically ligates the adenylated 5' end of an adapter to the 3' end of RNA. Similarly, the enzyme does not require ATP for ligation but does need an adenylated substrate, which dramatically reduces the amount of ligation between random RNA molecules. The ligase is a truncated version of T4 RNA Ligase 2. Unlike the full length RNA ligase 2, AIR™ Ligase does not ligate the phosphorylated 5' end of RNA or DNA without the adenylated substrate.

Alternatively, T4 RNA ligase 1 (NEB Cat. No. M0204S or M0204L) may be used to ligate the ncRNA 3'-OH to the 5' phosphoryl-terminated ssDNA.

Once the 3'-end of the ncRNA is ligated to the ssDNA, a complementary ssDNA can be anneal to the ligated ssDNA to initiate $2^{nd}$ strand cDNA synthesis, and/or to form a blunt end suitable for ligation with the free end of a cross-linked genomic DNA fragment in the same chromatin fragment.

In an alternative embodiment, a dsDNA linker having a blunt end (or a ligation compatible end) at one end and a 5' adenylated overhang (that can serve as the single strand substrate for the various RNA ligases above) at the other end can first be ligated to the free end of the crosslinked genomic DNA fragment, before the protruding adenylated 5' end is directly ligated to the 3'-OH of the ncRNA.

Likewise, all the embodiments or variations described above for the ligated RNA linker-DNA linker or the modified RNA linker are generally applicable to the double stranded region formed between the 5' App ssDNA and its complementary sequence.

For example, in certain embodiments, the double stranded region formed between the 5' App ssDNA and its complementary sequence may comprise one or more RE recognition sites to facilitate the generation of RNA and DNA tag sequences. Two MmeI sites can be situated at both ends of the double stranded region and direct the cleavage outside the double stranded region to generate 18-20 bp RNA and DNA tags flanking the double stranded region. Alternatively, one RE site may be used to generate the RNA tag (or the DNA tag), and the DNA tag (or the RNA tag) may be generated by physical shearing or limited non-specific enzyme digestion (see above).

Thus another aspect of the invention provides a direct RNA linker comprising: (i) a first polynucleotide, and, (ii) a second polynucleotide, wherein the first and the second polynucleotides form a double stranded region flanked by a genomic DNA ligation compatible end, and a 5'-overhang at the 5'-end of the first polynucleotide.

The 5'-overhang is optionally 5' adenylated, or can be adenylated by a suitable enzyme, such as the Mth RNA Ligase in the 5' DNA adenylation kit (Cat. No. E2610S or E2610L). If the RNA ligation is to be performed with the 5'-overhang, as opposed to the first polynucleotide as a ssDNA (before its annealing with the second polynucleotide), the 5'-overhang is of sufficient length (e.g., 4, 5, 6, 7, 8, 9, 10, 11, 12, 13, 14, 15 bases or more) to be used as a substrate for the enzyme for direct RNA ligation.

In certain embodiments, the ligation compatible end may be blunt ended for direct ligation to the blunt end of the crosslinked genomic DNA fragment.

In another embodiment, the ligation compatible end may comprise a restriction enzyme site, which can be cleaved by the RE to produce the requisite blunt end required for ligation to the blunt end of the crosslinked genomic DNA fragment. Prior to cleavage by the restriction enzyme, however, the ligation compatible ends may be blunt ended (e.g., dephosphorylated blunt end to prevent self-ligation), or have non-compatible overhang that prevents self-ligation.

In certain embodiments, the direct RNA linker does not self-ligate. For example, the 3' end of the first polynucleotide may be blocked by a dideoxynucleotide or other modified nucleotide to prevent self-ligation (self-circularization) of the first polynucleotide. Upon completion of RNA-DNA ligation, the blocked 3' end of the first polynucleotide becomes part of the ligation compatible end, and may be cleaved off through RE digestion to create a blunt end for genomic DNA ligation.

In certain embodiments, the double stranded region may comprise a first recognition site for a first restriction enzyme, such as a Type II restriction enzyme (RE). The RE recognition site may be strategically placed such that, when the RE cleaves, it cleaves outside the RE site, 5' to the 5' adenylated end of the first polynucleotide. This allows the generation of an RNA tag linked to the direct RNA linker. For example, a MmeI recognition site may be placed at the end of the double stranded region, proximal to the 5' end of the 5'-overhang of the first polynucleotide. The MmeI site is designed to be in the orientation such that when MmeI cuts, an RNA tag comprising a 18-bp fragment with a 2 bp overhang is generated in the cDNA derived from a linked ncRNA. However, the placement of the RE site does not need to be at the end of the first polynucleotide. A more internal placement generates a correspondingly shorter RNA tag sequence. Longer RNA tag sequences can be generated if the first polynucleotide is used as a ssDNA substrate (as opposed to its 5'-overhang is used as substrate), since the RE site can be placed at the 5'-end of the first polynucleotide.

Thus in certain embodiments, the last nucleotide of the first recognition site (for the first (Type II) restriction enzyme) is the 5'-end of the first polynucleotide.

In certain embodiments, the double stranded region may comprise a second recognition site for a second restriction enzyme, such as a Type II restriction enzyme (RE), at or near the ligation compatible end. The RE may cleave 3' to the second RE recognition site and 3' to the first polynucleotide (e.g., into the ligated genomic DNA). The orientation of the RE recognition site is arranged in such a way that it generates a DNA tag based on the terminal sequence of a linked genomic DNA. In certain embodiments, the placement of the RE site does not need to be at the end of the double stranded region. A more internal placement generates a correspondingly shorter DNA tag sequence.

In certain embodiments, the last nucleotide of the second recognition site (for the second (Type II) restriction enzyme) is a base-paired nucleotide at the ligation compatible/blunt end.

In certain embodiments, the direct RNA linker does not have a restriction enzyme recognition site for generating the RNA tag or DNA tag.

In certain embodiments, the direct RNA linker may comprise a unique sequence (e.g., a "bar code") that distinguishes the direct RNA linker from other direct RNA linker(s).

In certain embodiments, the second polynucleotide is dephosphorylated.

The PET polynucleotides generated according to this aspect of the invention comprises a central region corresponding to the double stranded region formed between the 5' App ssDNA and its complementary sequence (i.e., the second polynucleotide). There is no specific sequence requirement for this region, and the length of the region is flexible (e.g., as short as a few bp, sufficient long to support the substrate requirement of the RNA-DNA ligase, and that for the reverse transcriptase), although longer sequences may be used to incorporate any desired RE recognition sites, bar code sequences, or modified nucleotide (e.g., biotinylated nucleotide for affinity purification).

Thus another aspect of the invention provides a paired-end tag (PET) polynucleotide comprising a central region comprising the double stranded region (of the direct RNA linker) flanked by: (1) at a site proximal to the 5' end of the first polynucleotide (either 5' adenylated or suitable to be 5' adenylated), a sequence tag of a non-coding RNA (ncRNA); and (2) at a site proximal to the ligation compatible end, a sequence tag of a genomic DNA.

In a related aspect, the invention provides a paired-end tag (PET) polynucleotide library comprising two or more members of the subject PET polynucleotides, wherein each member of the PET library comprises the same central region, and different RNA sequence tag of the non-coding RNA (ncRNA), different DNA sequence tag of the genomic DNA, or both.

In yet another related aspect, the invention provides a vector or recombinant vector comprising the subject PET polynucleotides.

Yet another aspect of the invention provides a method of identifying functional interaction loci within a genome for non-coding RNAs (ncRNAs) of the genome, the method comprising: (1) providing chromatin fragments comprising a cross-linked genomic DNA fragment and a cross-linked ncRNA; (2) ligating the 3'-OH of the ncRNA to a 5' pre-adenylated ssDNA; (3) providing a complement of the ssDNA to form a double stranded region between the ssDNA and the complement, (4) if necessary, producing a blunt end at the end of the double stranded region; (5) ligating the blunt end to an end of the cross-linked genomic DNA fragment under a condition for proximity ligation; (6) isolating a PET polynucleotide for sequencing analysis, wherein the PET polynucleotide comprises the double stranded region flanked by a DNA tag of the cross-linked genomic DNA fragment and an RNA tag of the ncRNA; and, (7) mapping the DNA tag and the RNA tag to a reference genome, thereby identifying functional interaction loci within the reference genome for the non-coding RNAs (ncRNAs) of the reference genome.

An alternative aspect of the invention provides a method of identifying functional interaction loci within a genome for non-coding RNAs (ncRNAs) of the genome, the method comprising: (1) providing chromatin fragments comprising a cross-linked genomic DNA fragment and a cross-linked ncRNA; (2) ligating the 3'-OH of the ncRNA to a 5' pre-adenylated overhang of a dsDNA having a double stranded region, (4) if necessary, producing a blunt end at the end of the double stranded region distal to the 5' pre-adenylated overhang; (5) ligating the blunt end to an end of the cross-linked genomic DNA fragment under a condition for proximity ligation; (6) isolating a PET polynucleotide for sequencing analysis, wherein the PET polynucleotide comprises the double stranded region flanked by a DNA tag of the cross-linked genomic DNA fragment and an RNA tag of the ncRNA; and, (7) mapping the DNA tag and the RNA tag to a reference genome, thereby identifying functional interaction loci within the reference genome for the non-coding RNAs (ncRNAs) of the reference genome.

In certain embodiments, the complement of the ssDNA (i.e., the second polynucleotide) has the same length as the ssDNA. In certain embodiments, the complement is longer or shorter than the ssDNA, and forms a double stranded region with a protruding 3' or 5' end. In the latter case, the overhang can be filled-in by enzyme to generate a ligation suitable blunt end, or by cut off from the end by a restriction enzyme that generates a blunt end. The RE site can be engineered into the sequence of the ssDNA.

In certain embodiments, the length of the first polynucleotide of the direct RNA linker is about 6, 7, 8, 9, 10, 15, 20, 25, 30, 35, 40, 50, 60 or more bases.

Other embodiments as described in the first and second specific embodiments described in subsection a) (RNA and DNA linker pair) and subsection b) (modified RNA linker), respectively, are generally applicable, and are incorporated (but not reiterated) herein.

With the general aspects of the invention so described, the following sections provide additional details and specific quantities and parameters relating to specific embodiments of the present invention. It shall be apparent to one of skill in the art that the invention may be practiced without such details or with minor modifications without departing from the general scope of the invention.

2. Definitions

"Non-coding RNA (ncRNA)" includes an RNA molecule that is not translated into a protein. Less frequently, it may also be referred to as non-protein-coding RNA (npcRNA), non-messenger RNA (nmRNA) and functional RNA (fRNA). It is usually a functional RNA having a function other than encoding protein, but some may be non-functional or without a known function. Sometimes, the term small RNA (sRNA) is often used for short bacterial ncRNAs. The DNA sequence from which a non-coding RNA is transcribed is often called an RNA gene.

Non-coding RNA genes include highly abundant and functionally important RNAs, such as transfer RNA (tRNA) and ribosomal RNA (rRNA), as well as RNAs such as snoRNAs (including scRNA; for nucleotide modification of RNAs), snRNA (for splicing and other functions), gRNA (guide RNA; for mRNA nucleotide modification), RNase P (for tRNA maturation), RNase MRP (for rRNA maturation, and/or DNA replication), Y RNA (for RNA processing, and/or DNA replication), telomerase RNA (for Telomere synthesis), spliced leader RNA, SmY RNA (for mRNA trans-splicing), antisense RNA, cis-natural antisense transcript, microRNA (for gene regulation), siRNA (including trans-acting siRNA; for gene regulation), exRNAs, and piRNA (including repeat associated siRNA; for transposon defense, and maybe other functions), 7SK RNA (for negatively regulating CDK9/cyclin T complex), and the long ncRNAs that include examples such as Xist and HOTAIR. The number of ncRNAs encoded within the human genome is unknown, but recent transcriptomic and bioinformatic studies suggest the existence of thousands of ncRNAs. Since many of the newly identified ncRNAs have not been validated for their function, it is possible that many are non-functional.

In certain embodiments, ncRNA of the invention does not include any one or more of the above-referenced species. For example, in certain embodiments, ncRNA of the invention does not include rRNA. In certain embodiments, ncRNA of the invention does not include tRNA. In certain embodiments, ncRNA of the invention does not include tRNA.

"Restriction enzyme (RE)" and "restriction endonuclease" are used interchangeably herein to include an enzyme that cleaves double-stranded DNA. The enzyme typically makes two incisions, at, within, or near (e.g., from about a few bases to about a few kilobases) specific recognition nucleotide sequences known as "restriction sites" or "RE recognition sites," one through each of the phosphate backbones of the double helix without damaging the bases.

Restriction enzymes are commonly classified into three types, which differ in their structure and whether they cut their DNA substrate at their recognition site, or if the recognition and cleavage sites are separate from one another. Over 3000 restriction enzymes have been studied in detail so far, and more than 600 of these are available commercially, many of which are routinely used for DNA modification and manipulation in molecular biology.

Type I restriction enzymes cut at a site that differs, and is a random distance (at least 1000 bp) away, from their recognition site. The Type I restriction enzyme recognition site is asymmetrical, and is composed of two specific portions—one containing 3-4 nucleotides, and another containing 4-5 nucleotides—separated by a non-specific spacer of about 6-8 nucleotides. These enzymes are multifunctional and are capable of both restriction and modification activities, depending upon the methylation status of the target DNA. Cofactors S-Adenosyl methionine (AdoMet), hydrolyzed adenosine triphosphate (ATP), and magnesium ($Mg^{2+}$) ions are required for their full activity.

Typical type II restriction enzymes are homodimers, with recognition sites that are usually undivided, palindromic, and 4-8 nucleotides in length. They recognize and cleave DNA at the same site, and they do not use ATP or AdoMet for their activity—they usually require only $Mg^{2+}$ as a cofactor. Recently, new subfamily nomenclature (defined using a letter suffix) was developed to divide this large family into subcategories based on deviations from typical characteristics of type II enzymes. For example, Type IIB restriction enzymes (e.g., BcgI and BpII) are multimers requiring both AdoMet and $Mg^{2+}$ cofactors, and they cleave DNA on both sides of their recognition to cut out the recognition site. Type IIE restriction endonucleases (e.g., NaeI) cleave DNA following interaction with two copies of their recognition sequence. One recognition site acts as the target for cleavage, while the other acts as an allosteric effector that speeds up or improves the efficiency of enzyme cleavage. Similar to type IE enzymes, type IIF restriction endonucleases (e.g., NgoMIV) interact with two copies of their recognition sequence but cleave both sequences at the same time. Type IIG restriction endonucleases (Eco57I) do have a single subunit, like classical Type II restriction enzymes, but require the cofactor AdoMet to be active. Type IIM restriction endonucleases, such as DpnI, are able to recognize and cut methylated DNA. Type IIS restriction endonucleases (e.g., FokI) cleave DNA at a defined distance from their non-palindromic asymmetric recognition sites. That is, Type IIS enzymes cleave outside of their recognition sequence to one side. MmeI as well as most of the type IIS restriction enzymes produce variable end lengths. Dunn et al. (2002) showed that MmeI can cut 18/20 or 19/21 bases away in a rough proportion of 1:1. Therefore, when 18/20 is used to describe MmeI restriction cleavage site, 19/21 is also contemplated. Type IIT restriction enzymes (e.g., Bpu10I and BslI) are composed of two different subunits. Some recognize palindromic sequences while others have asymmetric recognition sites.

Type III restriction enzymes (e.g., EcoP15) recognize two separate non-palindromic sequences that are inversely oriented. They cut DNA about 20-30 base pairs after the recognition site. These enzymes contain more than one subunit and require AdoMet and ATP cofactors for their roles in DNA methylation and restriction, respectively. Type III enzymes recognize short 5-6 bp long asymmetric DNA sequences and cleave 25-27 bp downstream to leave short, single-stranded 5' protrusions. They require the presence of two inversely oriented unmethylated recognition sites for restriction to occur.

Restriction enzyme cleavage products may be blunt-ended or have sticky ends with 5' or 3' overhangs, which sticky-end fragment can be ligated not only to the fragment from which it was originally cleaved, but also to any other fragment with a compatible cohesive or sticky end.

"Nucleotide" as used herein includes a phosphoric ester of nucleoside—the basic structural unit of nucleic acids (DNA or RNA). Short strands of two or more nucleotides (e.g., 2-30, 5-25, 10-15 nucleotides) are sometimes referred to as "oligonucleotides," while longer strands are referred to as polynucleotides, although there is no definitive length limitation between the two terms. The term nucleotide may be used interchangeably with the term "nucleic acid." A polynucleotide may be either single-stranded, or double-stranded with each strand having a 5' end and a 3' end. The end regions of a stretch of nucleic acid may be referred to as the 5' terminus and the 3' terminus respectively. The nucleotides in a polynucleotide may be natural nucleotides (deoxyribonucleotides A, T, C, or G for DNA, and ribonucleotides A, U, C, G for RNA), or may include modified nucleotides, which may be incorporated into a polynucleotide by, for example, chemical synthesis. Such modified nucleotides may confer additional desirable properties absent or lacking in the natural nucleotides, and polynucleotides comprising modified nucleotides may be used in the compositions and methods of the invention.

The term "primer" or "priming sequence" refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer may be a single-stranded DNA. The appropriate length of a primer depends on the intended use of the primer but typically ranges from 10 to 50 nucleotides, such as from 15-35 nucleotides. Short primer molecules generally require lower temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in, for example, the literature cited herein.

A "probe" generally refers to a nucleic acid molecule or a sequence complementary therewith, used to detect the presence of at least a portion of the cDNA or an mRNA of a target sequence, such as the CCAT1 ncRNA sequence or cDNA thereof. The detection may be carried out by identification of hybridization complexes between the probe and the assayed target sequence. The probe can be attached to a solid support or to a detectable label. The probe will generally be single stranded. The probe(s) typically comprise 10 to 200 nucleotides. The particular properties of a probe will depend upon the particular use and are within the competence of one of ordinary skill in the art to determine. Generally, the probe will hybridize to at least a portion of the target cDNA or RNA under conditions of high stringency hybridization.

"Adapter" refers to an oligonucleotide molecule to be ligated or is ligated to an end of a nucleic acid molecule. Adapters may be used for amplification (PCR adapter having PCR primer sequences), sequencing (having sequencing primer sequences), and/or inserting a nucleic acid fragment into a vector (having suitable cloning sequences, such as RE recognition sites).

"Concatemer" is usually composed of at least two nucleotide monomer sequences linked end to end, optionally separated by a linker or spacer. The monomers may or may not be the same in sequence, but may have similar structural elements (such as the RNA and DNA linkers of the invention). The monomers may also be in the same or different orientation (e.g., monomers within a concatemer may be linked to one another head-to-head, head-to-tail, or a mixture of both). A concatemer of the invention comprises at least two oligonucleotides (e.g., PET polynucleotides) prepared according to the method of the invention.

"Library" includes a collection of like nucleic acid sequences, oligonucleotides, or polynucleotides, with each member of the library sharing one or more defining characteristics. For example, a library of PET polynucleotide of the invention comprises two or more (e.g., tens of thousands, hundreds of thousands, millions, tens of millions, etc.) PET polynucleotides of the invention, with each PET polynucleotide sharing a similar or identical structure but having different DNA and/or RNA tag sequences.

"Vector" or "recombinant vector" is an art-recognized term referring to a bacteriophage, plasmid, or other agent that is capable of transferring or amplifying a genetic material contained within (e.g., a cloned genetic information or cloned DNA) from one cell to another. Such vectors, depending on specific nature and characteristics, may be introduced into different host cells by transfection and/or transformation, such as lipofection, calcium phosphate precipitation, retroviral deliver, electroporation, and biolistic transformation, and any other molecular biology techniques available in the art.

Suitable vectors may include a plasmid, a viral vector or other vehicle known in the art that has been manipulated by insertion or incorporation of heterologous genetic sequences. Such vectors may contain a replication origin for suitable host amplification, a promoter sequence that may facilitate the efficient transcription of the cloned sequences, flanking PCR primers for direct amplification of the cloned sequences. The vector may also comprise specific genes that allow phenotypic selection of the transformed cells. Vectors suitable for use in the present invention include for example, pBlueScript (Stratagene, La Jolla, Calif.); pBC, pZErO-1 (Invitrogen, Carlsbad, Calif.) and pGEM3z (Promega, Madison, Wis.) or modified vectors thereof as well as other similar vectors known to those of skill in the art. See, for example, the pGEM vectors disclosed in U.S. Pat. No. 4,766,072, herein incorporated by reference.

"Chromatin" is used to describe a complex of nucleic acids and proteins, primarily histones, in the cell nucleus that stains readily with basic dyes and condenses to form chromosomes during cell division. Chromatin is an example of a nucleic acid-protein complex.

"Tag" as used herein includes an identifiable stretch of sequence of nucleic acids that may uniquely identify the origin of the sequence within a reference genome. The tag may be of sufficient length (usually 18-20 bp, but can be shorter depending on the sequence composition and reference genome size and complexity, etc.) that uniquely or unambiguously maps the tag to one or several locations (such as duplicate copies of one gene or related genes with high sequence identity) in a reference genome. A DNA tag of the invention originates from a genomic DNA sequence. It may be linked to an ncRNA, or a cDNA of the ncRNA, through, for example, the DNA linker and RNA linker of the invention (or the modified RNA linker of the invention, or the direct RNA linker of the invention). An RNA tag of the invention originates from an ncRNA, or a cDNA reverse transcribed from the ncRNA. The RNA tag may be linked to genomic DNA through, for example, the DNA linker and RNA linker of the invention (or the modified RNA linker of the invention, or the direct RNA linker of the invention).

The RNA or DNA tags of the invention can be of any size, but needs to be meaningful and advantageous over the size of the parental sequence from which it is derived. In certain embodiments, the size of a DNA or RNA tag is determined by genome complexity. For a bacterial genome, a tag from about 8 bp to about 16 bp may be sufficient, whereas for a complex genome like the human genome, a 16-20 bp tag may be considered.

"Linker" is usually an artificial sequence of nucleic acids designed for a specific purpose, such as linking two polynucleotides together. The "RNA linker" of the invention is designed to be linked to the DNA linker of the invention and to the cDNA synthesized from the free 3'-end of an RNA, such as a cross-linked non-coding RNA. The "DNA linker" of the invention is designed to be linked to the RNA linker of the invention and to a free end of a DNA, such as a chromosomal DNA cross-linked to a chromatin fragment. The "modified RNA linker" of the invention is designed to be linked to a genomic DNA fragment at one end (e.g., a blunt end or a ligation compatible end capable of generating a blunt end), and to the cDNA synthesized from the free 3'-end of an RNA, such as a cross-linked non-coding RNA, at the other end. The "direct RNA linker" of the invention is designed to be directly linked to the 3'-OH of ncRNA through a pre-adenylated 5'-end, and to be linked to genomic DNA fragment at the other end (e.g., a blunt end or a ligation compatible end capable of generating a blunt end).

"Sequencing" refers to the various methods used to determine the order of constituents in a biopolymer, in this case, a nucleic acid. Suitable sequencing techniques that can be used with the instant invention includes the traditional chain termination Sanger method, as well as the so-called next-generation (high throughput) sequencing available from a number of commercial sources, such as massively parallel signature sequencing (or MPSS, by Lynx Therapeutics/Solexa/Illumina), polony sequencing (Life Technologies), pyrosequencing or "454 sequencing" (454 Life Sciences/Roche Diagnostics), sequencing by ligation (SOLiD sequencing, by Applied Biosystems/Life Technologies), sequencing by synthesis (Solexa/Illumina), DNA nanoball sequencing, heliscope sequencing (Helicos Biosciences), ion semiconductor or Ion Torrent sequencing (Ion Torrent Systems Inc./Life Technologies), and single-molecule real-time (SMRT) sequencing (Pacific Bio), etc. Numerous other high throughput sequencing methods are still being developed or perfected, with may also be used to sequence the PET polynucleotides of the invention, including nanopore DNA sequencing, sequencing by hybridization, sequencing with mass spectrometry, microfluidic Sanger sequencing, transmission electron microscopy DNA sequencing, RNAP sequencing, and In vitro virus high-throughput sequencing, etc.

In certain embodiments, the sequencing method is capable of sequencing tags from both sides of the subject PET polynucleotides, thus providing paired end tag information. In certain embodiments, the sequencing method is capable of performing reads on long DNA fragments of variable length, such as concatemers of the subject PET polynucleotides.

"Reference genome" refers to the genome of the organism of interest, or the genome from which the ncRNA and genomic DNA originates. The method and compositions of the invention apply to any reference genomes for which a complete or substantially complete sequence is available, including numerous archaeal or eubacterial, protist, fungi (e.g., *S. cerevisae* or *S. pombe*), plant, animal genomes. For example, the genome sequences of human, mouse and numerous other mammals and non-mammalian species are now readily available in the public domain. See, for example, Venter et al., "The Sequence of the Human Genome," *Science*, 291(5507):1304-1351, 2001. Other non-limiting reference genomes include those for numerous non-human primates, mammals, rodents (rats, mice, hamsters, rabbits, etc.), livestock animals (cattle, pigs, horses, sheep, goat), birds (chickens), reptiles, amphibians (*Xenopus*), fish (zebrafish (*Danio rerio*), puffer fish), insects (*Drosophila*, mosquito), nematodes, parasites, fungi (e.g., yeast, such as *S. cerevisae* or *S. pombe*), various plants, virus (such as those integrated into a host genome), etc.

Locked nucleic acid (LNA) is a modified RNA nucleotide in which the ribose moiety of an LNA nucleotide is modified with an extra bridge connecting the 2' oxygen and 4' carbon. The bridge "locks" the ribose in the 3'-endo conformation. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides.

Peptide nucleic acid (PNA) is an artificially synthesized polymer similar to DNA or RNA. PNA oligomers show greater specificity in binding to complementary DNAs, with a PNA/DNA base mismatch being more destabilizing than a similar mismatch in a DNA/DNA duplex. This binding strength and specificity also applies to PNA/RNA duplexes.

A "paired-end tag (PET) polynucleotide" of the invention is a polynucleotide that, at or near one end, an RNA tag originating from a ncRNA, and at or near the other end, a DNA tag originating from a genomic DNA, wherein the ncRNA and the genomic DNA preferably are crosslinked to the same chromatin fragment. In that sense, the RNA and DNA tags at the two ends of the PET polynucleotide are paired, and reflects an event of physical proximity between the ncRNA and the genomic DNA at the time of crosslinking.

"Proximity ligation condition" refers to a condition for polynucleotide ligation reaction under which ligatable polynucleotide ends in close proximity, such as those genomic DNA and ncRNA crosslinked to the same chromatin fragment, are ligated preferentially. Meanwhile, ligatable polynucleotide ends not in close proximity, such as those genomic DNA and ncRNA crosslinked to different chromatin fragments, are not ligated or substantially not ligated. Such ligation condition include large volume ligation, such that ligatable ends on the same chromatin fragment, due to their physical proximity to one another, are much more likely to be ligated than ligation between ligatable ends on different chromatin fragments.

"Mapping (a sequence tag to a genome)" includes the identification of the genomic location of the sequence tag in the genome.

A "bifunctional crosslinking agent/reagent" or "crosslinking agent/reagent" includes modifying agents that possess two or more reactive groups, each is capable of reacting with one moiety (such as a DNA, an RNA, or a protein), thus crosslinking the two moieties together when the two moieties represent separate molecules. Such bifunctional crosslinkers are well known in the art (see, for example, Isalm and Dent in Bioconjugation, Chapter 5, pp. 218-363, Groves Dictionaries Inc., New York, 1999). For example, formaldehyde, glutaraldehyde or other similar reagents having aldehyde reactive groups may cross-link primary amino groups in proteins with other nearby nitrogen atoms in protein or DNA through a methylene (—$CH_2$—) linkage. Other bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a polypeptide are well known in the art (see US Patent Applications 2008/0050310, 2005/0169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(7-maleimidobutryloxy)sulfosuccinimde ester (sulfo-GMBS), N-(ε-maleimidocaproyloxy) sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents that may be used for crosslinking may contain an amine-reactive N-hydroxysuccinimide group (NHS group), and/or a carbonyl-reactive hydrazine group. Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Other bifunctional crosslinking agents that enable crosslinking via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 2009/0274713 and 2010/0129314, all of which are incorporated herein by reference. Alternatively, crosslinking agents such as 2-iminothiolane, homocysteine thiolactone or S-acetylsuccinic anhydride that introduce thiol groups can also be used.

Two or more of the above bifunctional crosslinking reagents may be used together to crosslink DNA, RNA, and protein in a chromatin fragment.

3. Restriction Enzymes

It is not required that the DNA and/or RNA linkers of the invention comprise restriction enzyme recognition sites. Indeed, in certain embodiments, it may even be desired that the DNA and/or RNA linkers of the invention comprise no restriction enzyme recognition sites. However, in certain embodiments, the DNA and/or the RNA linkers of the invention may comprise at least one RE recognition site, such as a Type II RE recognition site (e.g., Type IIS RE site).

In general, any RE and their recognition sites known in the art may be used, if the result of the RE cleavage produces a DNA or RNA tag of desired length, such as 10-20 bp. Such restriction enzymes recognizing at least one recognition site within the nucleic acid molecule and which may be used with the instant invention will be evident to those skilled in the art, particularly in view of the guidance provided herein and the illustrative examples. See, for example, Current Protocols in Molecular Biology, Vol. 2, 1995, Ed. Ausubel, et al., Greene Publish. Assoc. & Wiley Interscience, Unit 3.1.15; and the most up-to-date New England Biolabs Catalog or website information, 2005 and beyond.

A non-exclusive list of possible restriction enzyme recognition sites and the corresponding restriction enzymes recognizing the same is reported below.

As an example, a Type IIS RE, such as MmeI, may be used to generate a fixed length DNA or RNA tag that flanks the ligated RNA-DNA linkers. In particular, an MmeI recognition site may be placed at the end of the double-stranded region of the RNA or DNA linker, such that, upon MmeI cleavage, an 17-21 bp tag sequence originating from the RNA or DNA sequence is linked to the now ligated RNA linker and DNA linker. If one MmeI site appears in each of the RNA and DNA linkers, the two generated tags—one being a DNA tag, another being an RNA tag—flanks the now ligated RNA linker and DNA linker. The two tags may be additionally processed by blunting such that further downstream operation, such as PCR amplification, concatenation, or sequencing, may be performed.

Examples of some non-exhaustive Type II restriction enzymes that may be used with the instant invention include: AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (see the list in the web site of Rebase Enzymes: rebase dot neb dot com slash cgi-bin slash outsidelist; see also Szybalski, W., 1985, Gene, 40:169). Other suitable RE enzymes known in the art or those later discovered, which have the similar property of being able to generate a tag sequence of desired length (e.g., 10-25 bp to hundreds of bps) may also be used to practice the present invention.

In certain embodiments, the restriction enzyme is a Type IIS enzyme. In certain embodiments, the RE produces a DNA or an RNA tag sequence of about 10-25 bp or 15-20 bp. In certain embodiments, the RE is MmeI or GsuI.

Other examples of recognition sites and cleavage sites of several class II restriction enzymes include (into parenthesis are the recognition site and the cleavage site): BbvI (GCAGC 8/12), HgaI (GACGC 5/10), BsmFI (GGGAC 10/14) SfaNI (GCATC 5/9), and Bsp I (ACCTGC 4/8).

Artificial restriction endonucleases may also be used. These endonucleases may be prepared by protein engineering. For example, the endonuclease FokI has been engineered by insertions so that it cleaves one nucleotide further away from its recognition site on both strands of the DNA substrates. See Li and Chandrasegaran, Proc. Nat. Acad. Sciences USA, 90:2764-8, 1993. Such techniques may be applied to prepare restriction endonucleases with desirable recognition sequences and desirable distances from recognition site to cleavage site.

Thus in certain embodiments, the RE enzymes that may be useful for the composition and methods of the invention includes artificial restriction endonucleases, such as those capable of generating Type IIS type cleavage fragments outside the recognition sites. In certain other embodiments, however, the RE enzymes that may be useful for the composition and methods of the invention excludes artificial restriction endonucleases.

In certain embodiments, Type IIB restriction enzyme recognition sites may be incorporated into the design DNA and/or RNA linkers. Type IIB restriction enzymes (e.g., BcgI and BplI) are multimers requiring both AdoMet and $Mg^{2+}$ cofactors, and they cleave DNA on both sides of their recognition to cut out the recognition site. Thus, a Type IIB RE site may be engineered to span or straddle the linked RNA and DNA linkers (e.g., part of the RE site is on the RNA linker, and the remaining part of the RE site is on the DNA linker, such that the ligated DNA and RNA linkers reconstitute a complete Type IIB RE site), or completely within the RNA linker or the DNA linker. Upon digestion with the Type IIB RE, both the RNA and DNA tags can be generated.

In certain embodiments, Type IIG RE (such as AcuI) recognition sites may be used instead of the Type IIS RE sites. Such Type IIG RE recognize continuous sequences and cleave on just one side (AcuI).

A list of all suitable Type II RE recognition sites, e.g., Type II RE that cleaves outside its recognition sequence on one or both sides, may be obtained from various sources. See, for example, Restriction Endonucleases (Nucleic Acids and Molecular Biology), edited by A. Pingoud, Springer; 2004 edition (Dec. 1, 2004), incorporated herein by reference. Also see, New England Biolabs' 2010 catalog and subsequent updates (incorporated herein by reference).

In certain embodiments, Type I restriction enzymes may also be used to generate RNA or DNA tags, particularly DNA tags. For example, the Type I RE recognition sites may be included in the DNA linker such that the RE cuts at a random distance in the linked chromosomal DNA.

In certain embodiments, Type III RE recognition sites (e.g., EcoP15I site) may be used in the RNA and/or DNA linkers. Type III RE enzymes cleave outside of their recognition sequences and require two such sequences in opposite orientations within the same DNA molecule to accomplish cleavage. The two required recognition site for each cleavage may be contained completely within the DNA linker, or completely within the RNA linker, or in both linkers (such that only correctly linked RNA-DNA linkers regenerate the RE recognition site.

Examples of Type III restriction site(s) and Type III enzyme(s) have been described in, for example, Matsumura et al., SuperSAGE, Proc. Natl. Acad. Sci., USA 100(26): 15718-23 (December 2003; Moencke-Buchner et al., J. Biotechnol., 114: 99-106, 2004; Mucke et al., J. Mol. Biol., 312: 687-698, 2001; Rao et al., J. Mol. Biol., 209: 599-606, 1989; Hadi et al., J. Mol. Biol., 134: 655-666, 1979, all incorporated herein by reference. Type III restriction enzymes can also by purchased from New England Biolabs (NEB). In particular, an exemplary Type III RE for carrying out an embodiment of the present invention is the type III enzyme EcoP15I. The recognition site(s) of EcoP15I is CAGCAG (25/27).

Any of the above restriction sites may be used together in the DNA or RNA linkers. For example, the RNA linker may comprise a Type IIS RE site, and the corresponding DNA linker may have no RE site, a Type IIG site, or a Type III RE site, etc.

4. Concatemers and Libraries

In certain embodiments, the isolated PET polynucleotides of the present invention may be joined or concatenated with other isolated PET polynucleotides to form a concatemer of PET polynucleotides. Any number of PET polynucleotides may be joined together for the purposes of sequencing or for cloning into a suitable plasmid or vector.

Accordingly, in another aspect, the present invention provides a concatemer of PET polynucleotides comprising at least two PET polynucleotides, each comprising at least a DNA tag and at least one RNA tag, wherein the DNA tag is obtained from a chromosomal or genomic DNA and the RNA tag obtained from a cDNA of a ncRNA, wherein the DNA and the cDNA of the ncRNA are obtained from a cross-linked nucleic acid-protein complex, using the RNA/DNA linkers and methods of the invention.

Each PET polynucleotide of the concatemer of PET polynucleotides may thus has the general structure of RNA tag-RNA linker-DNA linker-DNA tag (or the reverse orientation).

The concatemers may be formed by any of many art recognized methods. In particular, the length controlled concatenation method (Ruan et al., U.S. patent application publication US 2008/0124707 A1, incorporated herein by reference) may be used. In another example, the isolated PET polynucleotides may be polished at both ends, if necessary, before the ends are linked to one or more adapter oligonucleotide(s) that can be digested by a (Type II) restriction enzyme. The digestion products may have compatible sticky ends that can facilitate the concatemerization of the individual PET polynucleotides. If the RE sites are the same for all the adapters linked to the ends of the PET polynucleotides, all sticky ends are compatible for ligation and concatemerization, and the individual PET polynucleotides may be independently linked together either in head-to-tail manner or head-to-head manner. If the adapters are different, for example, a first adapter having a first RE site may be linked to the RNA tag, while a second adapter having a second (different) RE site may be linked to the DNA tag. Upon concatemerization, all PET polynucleotides will be linked in a head-to-head manner.

Thus each PET polynucleotide of the concatemer of PET polynucleotides may be independently linked to one (for the terminal PET polynucleotides) or two (for the internal PET polynucleotides) another PET polynucleotide in a head-to-tail or head-to-head manner. In certain embodiments, all PET polynucleotides within the concatemer are linked in a head-to-head manner.

The DNA and/or RNA linkers of the PET polynucleotides may comprise at least one restriction enzyme recognition site, such as an RE recognition site for a type IIS restriction enzyme (e.g., MmeI or GsuI).

The concatemer of PET polynucleotides may be inserted into or cloned in a vector or a cell; the cell may be a bacterial cell. The cloned concatemer of PET polynucleotides may be digested by RE and isolated individually if desired.

It will be apparent that the number of PET polynucleotides of the present invention that may be concatenated depends on the length of the PET polynucleotides, which may be readily determined by those of skilled in the art without undue experimentation. After formation of concatemers, multiple tags may be cloned into a vector for sequence analysis, or the concatemers may be directly sequenced without cloning by methods known to those of skill in the art, such as by any of the so called next-generation high throughput sequencing methods described herein or known in the art, including single molecule sequencing methods. Hence, the concatenation of the PET polynucleotides allows an efficient analysis of the nucleic acid molecules in a serial manner by sequencing multiple PET polynucleotides within a single vector or clone.

In a related aspect, the present invention provides a library of PET polynucleotides comprising at least two PET polynucleotides, each comprising at least a DNA tag and at least one RNA tag, wherein the DNA tag is obtained from a chromosomal or genomic DNA and the RNA tag obtained from a cDNA of a ncRNA, wherein the DNA and the cDNA of the ncRNA are obtained from a cross-linked nucleic acid-protein complex, using the RNA/DNA linkers and methods of the invention.

In certain embodiments, the library may comprise up to 10 million PET polynucleotides, or up to 1 million, 100 thousand, 10 thousand, 1 thousand, 100 hundred, or 10 PET polynucleotides.

In certain embodiments, the library has not been through any amplification, such as PCR amplification.

In certain embodiments, the library has been amplified, such that at least two members within the library originate from amplification, such as PCR amplification, rolling circle amplification, biological amplification of cloned genetic materials, or any other known amplification methods. The PCR primers and the probes sequences may be prepared based on the information of the PCR adapters linked to the end of the PET polynucleotides, or based on the primer sequences on the cloning vector flanking the cloned PET polynucleotides or concatemers thereof.

The PCR or other amplification products that contain the PET polynucleotides may then be isolated with an enzyme recognizing the flanking RE restriction site (inside the adaptors) to give rise to the amplified library, which may be used for any of many downstream analysis.

In certain embodiments, the PET polynucleotide concatemers, before or after amplification, may be selected for suitable sizes, by any standard method, including gel electrophoresis and gel excision. The main considerations in selection for the appropriate sizes are that the sizes should be above the size of primer dimers and unannealed adapters and below the sizes of certain long linear multimers. In particular, concatemers with sizes of approximately 100-1000 bp, or 200-500 bp may be selected. Accordingly, with size selection, an advantage is that long linear multimers may be eliminated as their sizes will be above the size range. Similarly, fragments that are too short, unannealed adapters and primer dimers may also be eliminated.

5. Chromatin Immunoprecipitation (ChIP)

In certain embodiments, the methods of the invention may be used to identify specific ncRNA-chromatin/protein-DNA interaction. For example, in certain embodiments, it may be of interest to determine any ncRNA-DNA-chromatin interaction associated with a particular chromatin component or protein. The methods of the invention may further comprising using ChIP to immunoprecipitate the protein of interest.

ChIP has been used to enrich and thereby allow the identification of genomic regions associated with specific proteins such as histones and other proteins binding to nucleic acids in nucleic-acid protein complexes (reviewed in Taverner et al., *Genome Biol.*, 2004, 5(3):210). The aim is to cross-link proteins with DNA at their sites of interaction.

This may be accomplished quickly and efficiently by adding a suitable fixative such as formaldehyde, paraformaldehyde, glutaraldehyde, acetone, methanol, or other bifunctional crosslinking reagents (or mixtures thereof) directly to living cells in culture. Crude extracts of these fixed cells are then prepared, and the chromatin fragmented according to the methods of the invention. For example, fragmentation may be achieved either by physical sheering (e.g., shearing by sonication, hydroshearing, repeated drawing through a hypodermic syringe needle), or by enzymatic digestion (such as restriction enzyme digestion, or digestion with endonuclease with controlled timing, enzyme concentration, temperature, pH, etc.) so as to achieve a desired average size (e.g., usually about 1 kb). The cross-linked and sheered chromatin fragments are then used in immunoprecipitation reactions with antibodies raised against the specific protein of interest (e.g. transcription factors or histones). Crosslinked ncRNA and DNA fragments enriched in each immunoprecipitation are subsequently linked using the DNA and RNA linkers of the invention through proximity ligation, then de-linked or reverse cross-linked from the protein components (e.g., through heat and/or Protease K digestion), and purified to allow their identification by the methods of the invention.

The advantage of using ChIP is that this approach is able to "freeze" the ncRNA or gene regulatory network in live cells, as such interactions exist in their natural states, by rapid cross-linking of chromatin and other non-histone proteins, thereby in theory representing a "true" picture of the specific ncRNA or gene regulatory system at any point in time, free of potential artifacts imposed by heterologous expression, for instance.

6. Applications

The methods and compositions of the invention allow one to identify interaction between ncRNA and genomic loci, either at a non-biased global level, or at the level of specific ncRNA or specific chromatin components of interest. Information obtained using the instant methods can be used in a wide variety of research and development settings.

For example, the invention provides a method to identify chromatin targets of a specific ncRNA, which may previously have unknown or incompletely understood function, the method comprising determining interaction between the specific ncRNA and its genomic target sequences using the methods and compositions of the invention. The identified genomic target sequences represent candidate targets upon which the ncRNA exerts its biological function.

In a related aspect, the invention provides a method to identify ncRNAs that interact with a specific gene or genomic region, such as gene or genomic region harboring a tumor suppressor gene or an oncogene, the method comprising determining interaction between the specific gene or genomic region and ncRNAs of the genome using the methods and compositions of the invention. The identified ncRNAs represent candidate modulators (e.g., suppressors, enhancers or co-activators) of gene function.

In certain embodiments, the method further comprises comparing the presence/absence or the extent of the interaction between the ncRNA and the gene/genomic region, among two or more samples. Such comparison may help to further decipher the biological significance of the interaction and any observed differences between the samples.

For example, one of the samples may be a healthy control sample, and the other samples may be disease samples, such as disease samples from animal models (e.g., mouse or rat models); disease samples before and after a particular treatment; disease samples over different stages of treatment; disease samples from patients who have responded to a particular treatment, or patients who are resistant to a treatment, or patients who has relapsed after a treatment.

In certain embodiments, one of the samples is a stem cell or induced pluripotent stem (iPS) cell derived from the patient, and, optionally, the other samples may be cell lines differentiated from such stem cells or iPS cells. Here, a specific ncRNA-chromatin interaction may be associated with the initiation of a developmental or differentiation program.

In certain embodiments, the sample(s) may be from a human, a non-human primate/mammal, a livestock animal (cattle, horse, pig, sheep, goat, chicken, camel, donkey, cat, and dog), a mammalian model organism (mouse, rat, hamster, guinea pig, rabbit or other rodents), an amphibian (e.g., *Xenopus*), fish (e.g., zebrafish), an insect (*Drosophila*), a nematode (e.g., *C. elegans*), a plant, an algae, a fungus (yeast, such as *S. cerevisae* or *S. pombe*). The sample(s) may be a tissue culture of established cell lines, cultured primary cells, tissue biopsies (freshly dissected or frozen), etc.

As shown in Example 9, the methods of the invention identified an ncRNA—CCAT1 (Colon Cancer Associated Transcript 1)—as having a very complicated transcript isoform structures in this locus. The RICh-PET data provides important insights of potential function and underlying mechanism of CCAT1. Specifically, it was found that CCAT1 locus itself has significant enhancer features, that CCAT1 locus is highly transcribed in cervical cancer cell line HeLa cells, and the RICh-PET data shows that the transcribed product from this locus targets other enhancer and promoter regions. For example, for 122 loci targeted by CCAT1 ncRNA transcript (each with ≥3 RNA tags), 88 loci are enhancer regions, including six enhancer loci with RNAPII interaction. Another 34 loci are within promoter regions. This is consistent with the observation that CCAT1 target genes on average are more highly expressed than randomly selected groups of genes. Thus the lncRNA CCAT1 may act as a transcription co-factor to activate a network of genes, including the oncogene c-myc.

Thus another aspect of the invention provides a method to treat a cancer expressing CCAT1, the method comprising administering an antagonist of the CCAT1-encoded lncRNA.

In a related aspect, the invention provides a method to disrupt transcription activation or co-activation mediated by a gene product of CCAT1 (e.g., a transcribed lncRNA), comprising contacting the gene product with an antagonist of the CCAT1-encoded lncRNA. In certain embodiments, the transcription activation or co-activation occurs in a cancer cell. In certain embodiments, the transcription activation or co-activation is for c-myc, FAN84B, and/or SNX14. In certain embodiments, the transcription activation or co-activation is effected by bringing the CCAT1 genomic locus to physical proximity of a target gene locus.

In certain embodiments, the cancer is a colon cancer (e.g., adenocarcinoma of the colon), a rectal cancer, a cervical cancer, a lung cancer, a gastric carcinoma, a liver cancer, and a metastase thereof. In certain embodiments, the cancer expresses CCAT1 transcript at a level that is 2-fold, 3-, 5-, 10-, 15-, 20-, 30-, 40-, 50-, 60-, 70-, 80-, 90-, 100-, 120-, 150-, 175-, 200-, 250-, 300-, 500-, 1000-fold higher compared to a matching or control sample.

In certain embodiments, the antagonist is an antisense polynucleotide that may optionally comprise modified nucleotides to, for example, improve serum stability, pharmacological or pharmacokinetic properties, etc. The modified nucleotide may comprise PNA, LNA, 2'-O-alkyl or other 2' modifications, and/or modifications on the sugar-phosphate backbone.

In certain embodiments, the antagonist is an siRNA or miRNA construct that targets the encoded CCAT1 lncRNA.

The invention also provides an antagonist of the CCAT1 lncRNA (antisense, siRNA, miRNA, or vector encoding/expressing the same).

In another aspect, the invention provides a method for drug screening, the method comprises establishing a statistically significant association or correlation between drug efficacy and a specific observed ncRNA-chromatin interaction identified by the methods of the invention (such as an interaction identified in a responsive patient but not in a resistant patient), determining the effect of a plurality of candidate drugs on the statistically significant association or correlation, and identifying candidate drugs that promote the statistically significant association or correlation.

In certain embodiments, effects of the candidate drugs are tested using samples from the resistant patient. This may allow the identification of candidate drugs that restores the statistically significant association in the resistant patient.

In another aspect, the invention provide a method to identify a target gene for treating a disease, the method comprising: (1) using the methods of the invention, identifying (from among the observed ncRNA—genomic DNA interactions), a statistically significantly association between the efficacy of a drug and a particular ncRNA-genomic DNA (gene) interaction (e.g., whenever efficacy is observed in a patient responsive to treatment, a particular ncRNA-genomic DNA (gene) interaction(s) is observed; whenever efficacy is not observed in a patient not responsive to treatment, the particular ncRNA-genomic DNA (gene) interaction(s) is not observed), (2) determining the expression level of the involved ncRNA and/or the DNA (gene); wherein the DNA (gene) is identified as a potential target gene for treating the disease when drug efficacy is associated with increased ncRNA expression and inhibition of DNA (gene) expression.

The compositions and methods of the invention can also be used to identify as yet unknown ncRNA in a particular genome, since the method of the invention is an unbiased approach for identifying such ncRNAs. If a cluster of PET polynucleotides consistently identify a cluster of RNA tags in one region of genome that does not encode any protein, and consistently link these RNA tags to a (remote, e.g., an interchromosomal) locus that is represented by the corresponding DNA tags, it is likely that the RNA tags reveal an ncRNA.

Any candidate therapeutic reagents or target genes identified by the screening methods of the invention can be validated in vitro and/or in vivo, using well-known experimental models correlating to a disease or condition. For example, if a particular ncRNA is identified as promoting the expression of an oncogene (or as inhibiting the expression of a tumor suppressor gene), thus becoming a candidate drug target, a potential therapy using antagonists of the ncRNA, such as siRNA, miRNA, antisense, etc., may be further validated in vitro and/or in vivo, the latter may be carried out in an established cancer model, e.g., in a model animal, such as a mouse model of the cancer to be treated.

The mouse is a well-established model for drug discovery and development, with many different strains available. For example, a large number of useful models for studying cancer can be found at Mouse Models of Human Cancers Consortium, which has developed several databases, e.g., Emice (emice dot nci dot nih dot gov), Cancer Models Database (cancermodels dot nci dot nih dot gov) and Cancer Images Database (cancerimages dot nci dot nih dot gov), or other resource such as cancer research models distributed via The Jackson Laboratory (see jaxmice dot jax dot org slash list slash rax3 dot html). Further xenograft models, using either primary cancer biopsies or cell lines, are useful to investigate cancer.

For example, to develop a lung cancer model in which the efficacy of a potential antagonist against a candidate ncRNA can be verified, six to eight 8-week-old female immunodeficient mice, such as CB17-SCID beige mice (Taconic, cat. no. CBSCBG) or NOD/SCID (The Jackson Laboratory cat. 001303) or NOD SCID Gamma mice, also known as NSG (The Jackson Laboratory cat. 5557) are injected either subcutaneously or transthoracically (orthotopic; $10^4$/sup cells/25 µL) via the left lung with human lung carcinoma A549 cells (ATCC® CCL-185). Tumor-bearing mice are intraperitoneally injected with neutralizing anti-CXCL12 or preimmune serum, or receive no treatment. Alternatively, tumor-bearing mice may be treated with Platinol (Cisplatin) or Abitrexate (Methotrexate) or Paclitaxel, or other compounds. Tumors are isolated at various time points, treated and untreated. Noncoding RNAs are identified according to the method described previously.

7. CCAT1 Transcripts, Antagonists, and Uses Thereof

In another aspect, the invention provides various CCAT1 transcripts identified by the methods of the invention, their cDNA sequences (both strands), antagonist (e.g., antisense sequences, siRNA or miRNA constructs that antagonizes the function of these CCAT1 ncRNA transcripts.

The eight identified cDNA sequences representing different isoforms of the CCAT1 ncRNA are provided below in SEQ ID NOs: 1-8.

```
>CCAT1_JAX_1 Transcript sequence; Genomic location:
chr8:128128655-128241571 strand:-
<128241571>
                                              (SEQ ID NO: 1)
3'-

TATAGGTATAACCAATATATATGTATAACATATATATGTCCATATATATGTATAACCAAACC

ACAGGTGTTTTTTTGGAAGTCATATTTATACAGGGAGTTGACAGAGGTGTGAGCTGGACTTTA

AGAAGCTGCACATAAGATGCTAGTATGATCAAGCTGGAATGGACTTAGACAATTTGAAACAA

CTTTTCTCAGTTTTCAGATGAGGAAACTGACGGGTACCAAGCTTAAATGACTTGACGAAGCT

CATAGAAGATTAGCAGGTAGTAGAATAATGACTGCTGACTCCTAATTCAGTGGATCTTCCCT

GGCCACCGTTTTGTATTGAGCTGCAATGCTTCCTTGACTGTTCTCCATGCCAGATTCTTATC

AATGATCTTTCACCTAAGAAACAGCAAAGATTCTGGCAAGCACACGATCTAGAGATACATCT

TATTGCGATTTTTCACAAAAATCAAAAGAAGAAAGAAGGCTTAGCTGGTGTTTAATTATTGT

TATTTTTTTCAATAGGGAAATCTGTACACAATGATTTATCTCCAGTGATTTGCCATTGATCA

ATTTTTTTCTCATTTCATTTTCTATTTTTTGTTTTTTGTTTTTCTTTATTTTTTATTTTTT

TCTCCTTTTTCTTTTTTTAAATTTTCTGTTTATCACAAATGATCATGTAATTATATGTTAAT

ACTATGTAACCCCAGTGTTTTCAACTGTTTGTGATTCAATGTTACCCAGTTTTCTTTTCTTA

ATTTTAAATAAATTTGAAAAATTATCTTAGAGTGTTTTGAGCCTGTGTTGGTACATTTAGTT

CTAGTTCATTGTGGTAAATCCACTTCAGTTTCTAAGTTTCCACCCTTTAGTAAAGACATATT
```

-continued

```
TCTAAATTTGGTTTATATCCTCAGTTACAAAAGATTCTAACTGCTAGTTTTGTGACAGCAAT

CACACATACCATCAAGGGATGGGCAGGCAGTTTTGGAATGTGCTGATGCTAGCATTTTTAT

AAGCCTATGGCTTTTATAGTCTAAATTGTTCTTATTTCTATTAATGCTTCAATTTTTGACAA

ACACACAACCATAGAAACAAATAATAAATTTGTTTTTTGGGAATTATCCAGGATTCTTGGTT

AAGTGGGGAATTTAGGCTTTGACAGCATAAAGGATCACGGATAAGTATTTTTCACGGTGGCT

CTAATTATAATGCTGAGCATGTGGCAGGCACAGAAATATTTACTCATTGACTGAATATAGCA

CATCGTAATGTTGATTTTTTTCCAACATAATTTTAGAGCTAGGCATATTGTATTCTATTACA

CTAGACTATATATCATTCTTAAATAGAACCAGCCTTGCTAGATAACACATGTTGGAGGAGAG

GCCCTTCTTCTTAGCCCTCAGTGTTTCCATCTATGGGGAAGAAGTTCCACCATACTAACATT

ACTATCGTCTCTCCACCTGCTCACTCACTTCTCCCCAAGGGAGGGGTGTTCGATATGGTTTC

TGAGCTTGGAAAGAAAACTCAGGCATGTGTAACATGGTTCCTTCAGTCCCATGACCCACTGT

CCACAAATGGGCTGCTCACAGAGTGCATGCCTTCACCCTTGTTCCTGGCCATGCAGGAAATT

GTATGAAACAGTCCTAGCTGAAGCCTGAGATTTTCCTGCATTGCCTAGTCCTGGTGGGTATC

TGTCTACTCCTGGAGTTTGGATTGGAAAGTCCACATGCCTGAAGGTATAAACCTATTCTACA

AAGGGGTGTTTTCTAGAATGAAGGTAATATTTTTATCTTACATTTGCAGAAAGAGACAGAAC

AATGTTATAGGTGAGTGCATGGACAATGACCTCAAACAGCTAAGATTCAAACCCCTGCGTTG

AATGATTGAATTGAAATGATTCAATGAGCTAATGTACATAAAGCATCCAGAATGTTGCCTGG

CACAAGGGACTGTATTGTCTGCTAGACCATTTATTCAAAGTGGGAGGATGATGTTCTAAAAG

CCAATGATAAAGCTCATGGCAATGCAGGGTATATCTGATGGCATGGAATGCTTTAGGATGGC

CAAGATTGCCCATCAAATGCCAAGTCACCGAAGGGTTCTGGGAAATAAGAAATCATTAGAAA

AAGATTTCTGCCTTCTAGAAGTACACAGTCTAATGGTGAGATAGGCAGGTTATTAATGGCTC

TCCTACTAGGAGCCTGACATCATGGTGAGCATCGAGAAAGGAATAACCTAAGCTGAAGACAC

GCCTTTTCAGGAGGCCAAGTTCCACGTTCTGTGCATGCTTTTGGCGAAAGTCAGGTAAAGCC

TCCAGAAATGCATGGTCTATTCTCTCGGACCATATGGCTGTGGGCAAACTCTGGCTTCTTGG

AGCCTCCATTAGCCACCTAGGGAAAGGTAATTGGCTTTATGTTTGGCTCCATCACTGCTGGC

GACAAGCTCCACTGCATTCTCAAGCAGTAGATGAAATACAACTGTGCTCCTGAATGCAGCAA

AGGAAAGAGAACCCAACTGGACCAGTGTGAAATTGGGACCTTTGGAGGCAAGAATGCACATA

TTTATAAATGAATAAACATAATTTTTCTCTCTTCTTCCCATTGGCAGCATATCTGAAGGCCC

TGACTCAACAGTAGTGGGTCTTAATGCTTGTGCTTGTCCACCCTTCTCGGCAGTGATTGATT

TCATTGTTGGCTTGTTTTCATGACTTGAATGTGCGATCTTCAGAGGGCCTAATTCCTTGCAA

GTTCCATTTGAGGGTGGAAGAGCTAGAACAAGCTATAACCAGTAGACAACTCCGTGACTCAG

GAGCTTAAGCATGTGACTAATTAGTAAGAAAAAATGTGGTGAAGATTTGTAGTTAATAAGAA

GGAAAGAAGAATCACTGGGGCTAGAATTATGCAAGCTTTTGTTTCCTTTTGGGACTATATCA

GAACTATGAGAGAAGAAAGGCTACCTTTTACCTTTGAGGAATTTTCAAAGCCTTTTTTTTTT

TTTTTGGTTGGTTTGTGACTGACAAAGGGCACAATTTCAACACCTCAGAAAAATGCCTCATC

ATTTCCTCTTGTGAAATCTGGGTGCTTCTGAATGAATCCATGTTAGGAATGTGTACTTCCAT

CCATTAAAGTCAATGTCCAGTCTCATTTTGGGCCAGAGGCTGTTACTAAGTTGTAGTACTGG

TGAGAAAAGGACAGAGCATTTACCTTCCCTGGGTATCCTGTGACCTACATGTGTCCTTGCAA

GGCAGGGAAATGTTACTAATTAAGAGCATAGCCTTTCGTCAGATGGGTTCAGATCCTAACAC

ATCCTCTTTCTGGTTACAGGACAGTCCTCTCTGAGCCTCAGTTTTCTCATCTCTAAGATGAG

GCTAATTATACCTACTTCCCAGGGGGGTACTAAGGATAAAGTAACAACACAAGAAAATTTTT
```

-continued

```
TATCCTTGATTTTCTTAGCTGGAAAATTAGGCTAGAAAGACCTCCATCCTTGGGGTATTTAA

AATAAAAGGACAAACATATGATGAGTCTAAGTGATCAATACATTGTGGCTTTTGTACTTACT

ATTCTGAAACATGGGTGTGGCCTAGATACTTTCCAAAATTCTGCCCTCTCCACCTAGCAAAA

TGACAACCAGACTTACAGATATGCCAACAAGCTAGTGTTTAATAATGGTGTTTGATGATAAA

TGGCATTTCTTTTCGACATTTGTCTCTTTTTAAAACTTGGTGCTCTTAAATGCATCATTGGA

TAAGTGATGACTGTTCCCATTCGCAAGAAGAGACCTGGAATCTAAGCATGAAGGACCTGTCC

TGATGTTGAGAAGTGTGGATCACATTTATTTGTAAACTTAGCTTCTTGCTCGTCTCATGGTT

GCTTTTTTTCTTTTTCCTTTTTCTTTTTTTTTTTTTTTTTTTTTTTTTTTGAGAGG

GAGTCTCACTCTGTCACCCAGGCTGGAGTGCAGTGGTGTGATCCCGGCTCACTGCAACCTCC

ACCTCCCGGTTTCAAGCAATTCTCCTGCTTCAGCCTCCCCAGAAGCTGGGATTACAGGCACG

TGCCAAGGATTTAATGGCAAGATGCCATTATAGACAAGAACAGGATTCAGACACTTTCGTGT

TATGTGTTCTTGTCCAAATACTGTGTCACTCTGCACTGGCATCCCAATCCCACCAACACCTT

TAGCAGGAACTTCCTGTTTCAATAACATTTCTCAATACTCTACCTGATTGCTTAGAATCCAT

GAGACAGCCATATTCTCCATGTCTAGGTCCCTATCTTATTTTGTTGAGATGGTGTTAAGAC

TTTATTTGTGAGGCTTCTGGGGAAGAGGAGTAAGGTATTGATCCCACTGACTGGATAATTTG

GGTCTCAAAATGGATAATAAATAAGCATTACATATTTTGACCACTTCCTTGGAGGAGAACTT

CTTGGAATGTGCACCATGTCCGCTGCACTTTTTTGCACAGATATCTAAGTTGGAGAAACAT

ACTACTAGATAAATCAATTTGTTCTCTTAGTACTCATGATATGGTTCCTGGGAACTTCTGAT

TCACCAAATTAATCTTGGCCAGGTACATACCTGGCAGGAATCCAAAAATTCCCCAAGTCTCC

TTGAAGTTCAGGATCATCATTCTTAATAAATACACCGAGGGAAAAACCATGGAGAGTTTGTC

CCAGATGCTGTGAATCTGGCCCGGGGTACATGAAGAAGTCCTTAATTGCAGTCATTTACATG

GTAGATTCTCTATAATCATTTAATTTGCTATAGGTCTATGATTTTTAGTCCTTCTTCTCTAA

ATGATTGAACATGTATAATTCCCATTTCAATCATATTACCTGGATGAACAAAAGTAACGCTA

GACTCATTCATGCATTCTGGTTGCCAAGGAAAAGGAAAAAAAAACAAAACAATCAACAGGAT

GTTTAAACTGTCTTAGGGCAACTTCAGGCCATAGTCACTGGTGTTCTTGCAGACTATGAGAT

ATTTTACATTCTGATAAGGGATAAAAATTCGTGCCTCACATGGCTCCCATCACACTAAGATC

TTGCAACAATAACACTACTGATTCAGACATTAATCTTAAGTATCCAGGGAGCCCTAAAACAT

TGTATCCCACTAGCAAGGACCATGGTAATTGCCACGTAAATCCCCTCCATTATGTGGCCCTT

ATTATGACCAGCCAGCCAAGGCTTGCCTTTAAATCATACCAATTGAACCGAGCCTTGTAGAA

ACACTATCACCTACGCATACCTCTGCTTCTTTTCATTAACCTGCTATCCTCTTTACAAATGG

GATTCTTCACCCACTCCCTTCTTCTAGATTAGCAATGCCCTGTTAAGTAAACGAACACGAAA

TTCAAAGGGAAACAGGAGCAATCATCATTACCAGCTGCCGTGTTAAGCATTGCGAAAACGCT

CACGATTCACAGAAAAATCCATGCTGTTCTTTGAAGGCATTCAAGCCTTAATAGCTAGCTGG

ATGAATGTTTAACTTCTAGGCCAGGCACTACTCTGTCCCAACAATAAGCCCTGTACATTGGG

AAAGGTGCCGAGACATGAACTTTGGTCTTCTCTGCAATCCATCTGGAGCATTCACTGACAAC

ATCGACTTTGAAGTTGCACTGACCTGGCCAGCCCTGCCACTTACCAGGTTGGGCTCTGTATG

GCTAAGCGTTTTCTCCTAAAATCCCTTGAAAACTGTGAGAAGACCATAAGAAGATCATATCT

TTAATTCTATTTCACAAGTCACACAATATTCCAATCAAATACAGATGGTTGAGAAAAGTCAT

CCATCTTCCCTCCCCACCCTCCCACAGCCCCTCAACCACTGCCCTGAAACTTATATGCTGTT

ATCCGCAGCTCCATCTGGAGCATCACAGCTACTGTCAACCCTGACGCTCTTTCTGAAAAAAC
```

-continued
```
ACCGGATGGACATCAGAACTATTTCTTTAAGGATGTTACTGAGCCACACAGGAAAACTTGCC

TTATGATTTTGAATGCACGGATCTGATTTGACTAAACATGATAACTAGAGAATCACCCAATC

TACTCCCATTTTCAACTCTAAATCATCAGAGTGTCTCAAATCCAAAGCACACACAGACCAGC

CTGGCCAACACGGTGAAACTCCACCCCTACTAAAAGTATAAAAATTATCCAGGTGTGGTGGC

GGGCGCCTGTAATCCAAGCTACTTGGGAGTCTGGAGGCAGGAGAATCCCTTGAACCTGGGAG

ATGGAGGTTGCAGTGAGCAGAGATCACACCACCGCACTCTAGCCTGGGCCACAAATCAACAA

CAACAACAACAACAAAAAACAAAGCGCACACAGAGACTGAGGTCCTCTTTGGCATTGAGAAG

ATGGCTATGCAAGTCCCAACTAGCAAGTGCAAACTTCCCAGCTTCACTTCTGCCAGTGTCCC

TTCACCCCTTCTCAACCCCACTGGGAGGCAGGAGGGTGCTTGACAATAACAGCCTTGGCATC

ACTCTGCCAGGGTGTAATAGGAACTGTTACAATTCTGAGATTCTGTGTAAGCACTGGCCTTT

CTGCCTAGAATGCCTTCTCCTCTCTTTTTAACTGCATGCTCCTATTTATCTTTCAAAGCCC

GGAAAAAATAACACTGCACACGGGAAATGCTCCCTTCCTACTGCAGTCATTTAGATGACTCT

ATGCCATTCCATTCATTTCTCTTTCCTACCACAGAAGTGCTTTGAGATTTTGGAGTCAGACT

GCTTGAACTTGAATCCTGGCCCTCTCATCAGAGACTTGACTTATTTTAGGCAAGTTATATAA

CCAATTTTACCTCAGTTCCTTACCCATAAAATGGGTCTAATGAGAGTACCTACCACACAGAA

TTTTGATGAAAACTGAATGAGATGAAGGCCTTTAAGGCAGTGGTCCCCAACCCTGGGGACAC

AGACAGGTACCATTTTGTGGCCTGTTAGGAACTGGGCCACACAGCAGGAGGTGAGCAGTGGG

TGAGTGAGATCAGCGTTATTTACAGCTGCTCCCCATTGCTCACCTTACTGCCTGAGCTCCAC

CTCCTGTCAGATCAGCAGTGGCATTAAATTCTCATAGCAGCACAAACCCTGTCATGAACTGC

ACATGCGAGGGATCTAGGTTGTGCGCTCCTTATGAGAATCTAATGCCTAATGACCTGTCACC

GTCTCCCATCACCCCTAGATGGGAGTGTCTAGTTGCAGGAAACAAGCTCAGGGCTTCCACTG

ATTCTACATTATGGTGAGTTGTATAATTATTTCATTATATAATACAATGTAATAATAATAGA

AACACAGTGCACAACAAATGTAATGTGCTTGAATCATCCCCAAACCATCCCAGTCCACGGTC

TTCCACATTTTGTCTTTTCACAAAATTGTCTTCCACAAAACTGGTCCCTGGTGCCAAAAAGG

CTTGGGACCACTGCTTTAAAGCCTTTGCATAGTGCTTAGAATTGAGGGGGAAAAAAAAACA

AAAACAATGTAGCTAGTTGCTACAATCACTATATTGGTGAGTTTCAAAAGGAAAAGAATTCT

GTCCCATTTATGCTTGAGCCTTGAGTTGCTAACCAAGCCTGACACAAAATTACTGTTGAAGG

GATGTGTGAGTCCTAATTGAAATGAGGCCTCTTAAGGGAATTGTGGACCAAACCCCAAGCAG

GCAGAAAGCCGTATCTTAATTATTGCAAGTATTTCAGGCAAGGTGTGGATGGCCATTTGAAT

TCAAGCAGACTAGGACCTGGGATGAGAAAGAAGGTGTGTACGTGACTTGATCTTTGAACTTT

AGCTCACCATCTGGAAGAAGGCTGAGTATTCTCTGCACTCACATAGTAGCTAATGCCTACTC

CCCAGCCACCCACAATTCTTTCTGTAGGAAGGCTCGCTAGAATACTTTGTGATATTGGATAT

TAGTTCCATATTCTACTGTGTATCTTAGTTCAACCAAATTGTAATCATCTGATATTTATTTC

TTTTAATATAAATATAAGTATATTAAGTCTTGGCATGCTTGCTCAGTCTCTCTCTCTCTCCC

ATTCCTCCCCGCTCCCCTCTCTCTTTCCCAACAGGCTTGGAAAGCAGGCATCACCATGCCTA

TTTAACAGTTGGGGTCCCTTGGCCACCAGGTGCTGGAGTAGGAATCTGAGCCCGGACATGCC

TGATCTGTAAATTTTGTGTTTTCCCCACTGTGCTGGGCAGATACACAGCTATCAGCGCCAAAT

TCATAGAAGGGGCGCCCCCTGTGGTCAATTGAGGGATTTGTGTTTGAGGTAGATCTCAAGAA

GGAATGGGTGGGGAACTTAGCCTAGGACAGAGCAGAAAGGAGCCCTCACTCCCAAGCACCA

ACGGCCTCAGTCCTTCCTGCTGACTCCAGCCTCTAGCTCTCACCCAGACTATCTGCATCCTT

CTCTCCACCACGCTCCTTTGGAACCTGCGTAAAACACAGATTAAAGGAATTCCGCCTTACTT
```

```
CCCTTTCCGCATTATGACCAAATGGTTTTACACTATCATTGAACAGTTTAGTACAAAACATG

CCACCTTTTAATCTATTCATTCATTTAACAAATACTTTGGAGTGTTTACCATGTGCCAAGTG

CTGTTCTAATAGACATAAGCTGTGAGGTTATGCTTATCTGATTCTCACAGCAACAGCTTTCG

AGATATGAATTGGTATACTCATTTGACAGATGAGGAAATTGAATTCATGTAGTGAGAAGGAA

GAGCTGCAATTCAGGGTTACTGGTTTCTCCTGCACTAAGCACTGAGCCACACTAGAAGAGAA

GGCATGAGGAAGACAAAAGTGAGGCTGTGGCTTGCCTTTTCACTTCTTGTGTCCTGTTTAAG

AAATATCTGCTATCCCAAGGTAAGATACTATACTTTTTTTAACATGTTATTTTGTTTTACCT

TTCACATTTGGTGTATACTACATTTGTAATTAATTTGTCCATATTATATGACATATAGCCAA

GATTTATTTTTTACCATACAGATACTCAATATTGCCATTTACGTAGAACATCGTTCTCTTCC

TACTCAATTGCCTTGGCACCTTTGTAATAAATCAGATGATCGTGTATGTGTAGTTCAGTTTC

TGGACTCTGTCTTCTGTTTCTTTAGTCTATTTGCCTATTCTTGTACCAATATGCACTGTGTT

AATAATCGTAGCTTGTAGTAGGTCTCGAAATCTGACAGTGTAATTCTTTTAGTTTCTTTCT

TCTGCAAATTTTCTTTAGCTGTTTTACGTCCTTTGCATTTGTATATAAACTTCAGAATCAGC

TTGTCTATTCCAAAAACAACAACAACAAATGAAAGTTTCAGAAACTTTAACTGAAATTGTAT

TGAATCTGTAGACAATTTTGGAGTAAATTGCATCTTAGCAATGTAGAGTCTTTCGAACCATA

ACCATGGTAAGTCTCTCCATTTGCTTAAATCTTCTTTAATTTATTTCAACAATGGCTTCCAA

TTTCCAGCGGGAGCTCTTGGAAACTACAATTTACATGAACTTCTAATTTGATATTTTCGGT

GTCATTATAAACATTGTTGTTTTAAAAGTTGTCTTCAATTTTTTGTTGTCAGGCACAGAAAT

ACAATTATTGATAACATTTATATATAAACTGTATCCAGTGATCTTGCTAGATTCACTGATGA

GTCTGATGTTGTAGATTCTTTGGGATTTTCTCCGTACATAATCATATCCTTTCTGAATAAGA

TAGTTTTACTTCTTCATTTTTAATATCTATGCCTTTTATTTATTTTTCTTTTGAACTTTTTG

CTGACTTCATTATTCACTCTCATGTTTTTCTCTTTCATTAGACTATGACTCCTCGATGGTAG

CAATTTGTAGTAATCAAATTTTTGTATTTTATTTTAGCATCTGGCATCTTTCTTGACATATG

TAGCAGTTGCTTTTTGACAGCTTGCTTCTTCAGTGAATGAATAAATTAATAAAGAGAAATGT

GATGTTCAGTGATCCATTTTGCAGGTAAGAAAACTGAGGCAGACAGAGGATGTTAGCAAGCA

AGAGGCCTTGGCCTACAATTTAGATCACTGGACTCTTACTCCAGATGCAATCTGCAGAACCC

ACATACTTTTAATTAGTCCCTTTGTCTATGTTCTGCCACTGTCACTTCTAAGGAAGGTGTGT

CATCCCAAATGGGGTAGTATCTTATTGGTAGACCTAAATCTGCTGTGTTCGCCATCTCACCT

ACATGAGTATCTATGTGTAGCATTCTGCATATTCATCTTTTCCACCTTCTGGAGGTTTTGTC

TTTTTATAGGCAGCATGTGAATAACAATGGGGCCAAACTGGGGACCAGAAGGGGCCATTTTC

TAGTTCTGAACATAGATAAGCATCACTAACTTTTCCCTCCTGGCAGTAATGGCCTCAAAAGT

TCCAACTTAGGAGAAAAAGGCAAAACCGTCTGCCAAAGTGTGTGAAAAGTTAGAGCAAACCT

TGGTTTTACCAAGAACCTGTGTCCCTCTTATGGAAATTCACACTTTCACACTTTTAGACAAA

TATTAAATGTGTGACATTCTATTACGTACAGTGCCTGGCACATCTAGACACGCAGCACACTT

TAGCCCCCTTCTTTCTTCTTCTAACTCCAAGTTCTAAACTAGAAAAAGCCCCACTTGAGTCT

GAGATTTGCTTTTTGAACTAGTTTATTTCAGATTGTAATCATGCTATCTAGGGTTGTGACAG

TGTTTGCTATTTCTAGGGCACTTTGACCTGATTCTTTTTGCACAGGAAACTTGTTCTACCCT

TTTGCCCACTTCACTGAAGTGAGGACTGAGACAGAGAAGGATTAAGTCACTTTTTATTTAAC

AAATATTTGTTCCACATTCCTCAGCATTTATTAAATACTGGTGCATAATGATGGAATAAATT

TTATACCGTAAGGATAAACCAGTATTCTGGACTAAGCCAACGTGGGAGACCCTAGGAGGCCT
```

-continued

```
GTTTGAGAAAGTGACATTTAAATTGAGACTTGGCGGTGGCTGTGGCTACATATCTAGTAAGT

GGCTGGGTTGGGATTTGAACTCATGCCTGCTTAGCTCTAAAGATGATGCTTTTGGCTTTGTA

CTCTGCTCTCTCTCTAGACAAACTCTGGTCCAAAATCGTTAAAGCTAACATTTATCCCTGCC

CAACTGGAATTGTCATGTTATGACAAATGGCTCTGTGGTCTCAGATGCCCAGCAGACCCATT

AGTGGAATTCTATGTGCTACAGACCTGGGCAAAATGCCAGAGCCTTATACACCCATCACATT

TCGTCTGGCAAAGGTCTTCAACAAAGAGAAGTAATTACAGCAATGAAAAGCAACAGGTCCAG

CAACACCATAAGAACAAAATAATTAATTTCCCTAAAATAGAAGAAACCATTTATAGAGTAAG

AGCCGATACAATCAATAATTGGAAGAAATAGAAGAGGCTTTAGTATTCTAGCCTTCTTTATT

TGTAGATGTAAATGTCGAGCCTCAGAGAAGTTATATATCTAATTAGTGTCACTCAGGTAGAT

AACAACAGAATTAGGATTAGAACTTAATTCTTATGACTCCCAGAGCAGGGAAAAGACAGGAT

GAAGTCCCAAAACATTGCGTGTGAACTCACATCTGACTCTGAATTGAGAGTCTGCTATTTAC

TCCCTATGTGACCAGAATCCTTCAGAGCCCATGAGATTCCCTGTCATAGAGTAGATTTTGAT

CCACACTAGGCATTTTTACCTCTTGCTCTTTGAGTTGGTGCCCCATGTTTACTCAGAAATAT

TCCAAAGGTGTTACATCTATTGGTTTTACATGTTGAGCACAGATCATTATAAGACAAATTGA

AATGAAAACATCAACAAGTCTCATTCATTGTCTAACTTACGCTGAGCAATATTTAATAACTA

GAATATCAAGAGAGTCCAAAGTGTTTGCCCATCCCCTCAAGACCAATGTAATGGAATTTTAC

TCTTATCACCTGCTCAGGGTAGTGGCAATTCAGGATACAGAGGACAGAAATAAAGAATCATG

ACACACAATCCACAGAATTCACAGATGCCAAACATCTACCCTTCTCTGTCACCACACATTGG

ACTCACATGGTGGAAATAGGCAACACAAGCAGAGAGGTGGCTTAACCTTTCATAATTTTTCA

ACGACCTATGGGAAGAGAGTTTTCTTGGTTCAAATCCCAGCTTAGCCACACAGAGTGTGGTA

ATATTGGGCAAGTCAACCAAGCTCTCTGTGCTTCAGTTTCCTCATTATTAAAATGGGGGAAA

TAATAGTGCCTGCATCAGAGGGTTGTTGTGAGAACTAAACGAAATAATTTATCTGAGCTTTA

GAACCCACACCATATTAGTTAAAAATTCATGCATTTTCTTTTATTATATTTCTCTACCTTAG

ACTGCAAACTCTAAGAGGAAAGGCCGGACTGTTATATTCATAAAGCATTACAGGAACAGTAA

TTAGAACTAGGAGCTTTTCAATGGCCTGCCTGAAATCTGAAAAATAGGTATATTATTTGAAA

TTTTGAAAAAATCAAATAATTAAAAATTAATAGATGTTAATAAAATATCTGTAATATGTAAT

ATCAAGGTCAACTCAACTCTTAATTGTTTATATAAAATATAGTGAAGTTTAAATTGCAAAAT

CTTACAGAAAATGTGCTATTAAAACTCAAAAGTATAATTCTTTCTAATATGTATATATATGT

ATATAGTTTTATTTTAAGTTCAGGGGCACATGTGCAAGTTTGTTACCTAGGGAAACTCACGT

CACAGGACTTTGTTATACAGATACTTTCATCACCCAGGTATTAAGCCTAGTGCTCATTAGTT

ATTTTTCCTGATCCTCTCCCTCCTCCCAACCTCCACCCTCAGGTAGGCCTCAGTATCTCTTG

TTCCCCTCTATGTGTTCATGAGTTCTTATCATTTAGCTCCCACTTACAAGTGAGAACATGTG

GCATTTGGTTTTCTGTTCCTGCCTTAGTTTGCTAAGGAAAGCACTGTGGCAATTTCTCAAAG

GACTAAAAACGGAATTACCATTCAACCCAGCAATCCCATTACTAGTTACGTACTCAAATATT

TTTAAGGCAAAACAAAGCTGCAACCAGAACACCTGGACTCCCTGAAACCCCTTCCACTGATG

TTGTTGTTGTTGTTTCTTTTTCCCCAGCTTCTCAGGCCAAAATACTGGATCATCTTGGGCAC

TGTTCTCTCCTGCCCACCCTTTCCCATATGCAGAGTGTTGTCACTTCTCTCTGCTTCCACTG

CTAACTCCCTGGTCCAAGCCGCTGCACCACTTTTCGTGATTATTGCCACAGTCTCCTCACTG

GTTCCCTGCCCCCACTCTTGCTCTGAACTATCCAGTTAAAACCTGAATTAGATCATCTCATC

CTCATCTCAGAGCTTTCTCGTGGCTCCTCTGCCCTCTCAGGAAAAAATCTAAATTCTAGATG

ACCTAAAAATCCCTTGTCTCTTACTGTTTATCTGACCTCATTTACTACCACCTTTTTCTTTG
```

-continued

```
ATCATTCTGTTCCAGCCACACTGGCCTCCTTACCACTCCTCAAATATGCCAAGCACAGCCCC

CACCCCCCAGGGCTTTGAACTGGCTGATCCCCCTTCCTGGAATGCCTTACCCCAAATATCAA

CTTAGCCAACTCCCTCCTCTCCTCCAAGTGTCTGTTTAAACATGGCTTCAGTAGGAGCTGTC

TTAACATCCTATTAATATTGTAATTCCTCTCATGACACTTTACACCCCCTTCCCTGATATGC

TTTCCATATACCATGCAATATCTGCTGAGATAATATATAATTCACTTATTTTCTTTATTGTC

ATTTCAAAGAGGGCGGTGTGTTCTGTGTTTTATTTAGTGCCAAAATACTTGCTGATGAAGAG

AGTTCCTGCCACATAGTAGGTGCTCAATATGTGCTTGTTGAATAAATGTGTCAATGTTTGAT

GTACAGACCTTTTATTATGTTTGATTTGCTGCCAGTGCTGCCTCCAAACACAGGAGTGCTTC

ATGAGATGTTCACAAAAGCTCTTAAAATATTCCACAAAAATCTTAAAATATTTCATGAGTTT

TCTTTCCTGTATTTTTATAGCAGCATCTGGAATTTAGCCTGCATAGGACCCTCTGTAAGCTG

ACCCTGTTTATCTATTCAGCTTTACTTCTCCCCTCTCTCCACTTTGTATTTTATTCTCTACT

ACTTCCAACTGATTGTAATTTGACCAGACTCCAGACTATCTTATGCCTCTTTGCTTTTGTTT

ACCTGTTACTTCTCTCTGGAATTCCCTGCCCCTTCTTAATTTTTCTGGCCAATTCTCACTCT

CTAGGACTCAGAGGTTTCTCCTCAGGAGACTTCCATGAGTCTCATGTTGAGTTAGGTGACCC

CAATCCTCTGTTCTTCATAGTCATTCGCGCATTTATCTAGCTCAGCATTTGCCATACTACAT

TGAAATTATTTCCTTATGTGCCCATCACTCCCCGTAGATTGCAAACTCCTAGAGAAGGGCTC

AACAGTGAGTGCTGAGGCTGCACAGAGGAGGAAGGCAGCACAATGATGGAAGGCTTCCTAAA

GAGGTATGTTCCAAGAGCCCCCACTTCCTTTCATGGGAGACTCATGCTGTTACACCTAGACT

ATCTAGGGATACATCTAATGTAGTCGTGGAAAGAACAGAGGACTTGAGTACTAGACTGACGT

GATTTTGAATCCTGGCTCCCTATTGACCAGATGTGTGTCTTGAACAAGTCCCTGAGCCTCAG

TGTCTTCATCTGCACAGTGAGGATAATGATACCACACTGCATATATGAGGTATCCGGCACAT

GTAAATGTCCACTACATGCTGATTTCTTCACCCGCTACTCACCCCTGGGAAAGAAGTAGACT

CACCTACTCTTGGTACCCATTCATTCCCCCTCAGTTGGAAGCATGAGGTGTGCAGCTGCCTG

ACCTGGGGAAGGGCTGCAAGCAGTAGGTGTTGTCAGATGTGGTGGAGCTTGTTGACTTCCT

CCCAGGGGCCCAGCTAACAACCTGCCTCTGTTCCTTGATAGTCAAGTTCAACTTTCACTTCT

TAGCACCACAGGAAGTTGACTGAACATTAACTGAAGTCTCTCTCAAACAGGAGACATCTTTG

CCAGGTCCCTGTACTTCCTAGCCTCATTCCTGCTCTCCCTAGTGAGCAGGCTGCCCTCCCTT

CTCGCCCCAGCACCACTGATAGGCAAGGGTACTCAGAACTACTACCTTGTGGGCCATGTCAT

GTGCCAGGAGCTGCACCCAGGACTTTAATACAGTAGTTGGCTCCCACTGAATGTTCATTGTT

ACCCCAGGATAAAAAGGGGACACTGTGATCATTTTCTATTTTGCTGTGATCAGGCTTGGTGA

GCTAAAGTCACCTACCTTCCCAGTCTCTACTAATAGAAGTCATGGATCAGTCCTATTGGTTC

TTCTGTTACAAGGATTCAGAATTCATAATCATGGAGCTGCATTTACAGGCAGAAGTTTCTTT

CATAGTTTTCTAAGTGTTCCTTTTAGCAACAATGGAGAAAATCAAAGAGGGCAAAGGTGAGG

GGAGAAAATAACATTTCCCTTTCTGTCCTTTGCTCTTGTAGTCTTTTGCTTTAGTTTCTTTA

CTATGACTGTGAGGGTGAAACTAGTGATCAGAGTGGTCCAGAATGGGTTTGATGAATCTGAT

TCTGGTGACACAAGATGAATTGGGTATATGTTTCCCTAAAGATAGAGAGACAATATAACATA

GTCTTTACATTAATAGACTCTGGAGCCAATTTTTTTAGGTTCACTCTCTTTCCTTTCATGTG

TGTTGATTTTCAACAAACATCTTGCACTCGAATTCCATCTCACTGTTTTATTTTCAAAAAAT

TTAATTTGAGAAAGTTAGCTGTATTAATTTTTTCTTTTTCTAAAATTCTTTTACTAATTGCA

ATTATTTCCATTGATGCTATTCCATTGAAACCATTTTAACATGGACTCAATAACTTCATTGT
```

-continued

```
ATGTTAATGTTTAATTTTCATTTCTTTACCTTCTTGGTTTTCTAGCTGTGTTTAATGTGGTT
GACCACTCATTCTTTGAAGCTCTATTCCTCTGGCTACTACAGTATGACACATTTTGTCTCCT
TCTTCAGTCTCTGTCTTCTCCACAGTCTTCTCTTCCTTTTATATACCTTTAAATATTAATGT
TTCCCAGAGATATTTTCTTAACTCACTTCTCTACTGATTCTAGGTACTTTTCTTGATCCAAC
TCTTCTGATTTTACCCATCTCGATGATTCTATAATTTGTATTTTCTGTTTTGATCTCTTTTC
AGTCTTCCAGACCTAAATATCCAAATGCCTGATGGATAGTGCTTTCTTTTTTACTACCAAGC
CCTCAAAGGCACTATGTTCAAAAGGAATTTGTCATCAGTCTCACGGCACATAAGCTTCCTCT
TGTGTTCAATCTGGAGACTTGAGAGTCTTCCTGTTCCCTTCTTCTCCTTATTTTCTCCATAA
TCAATCACAAAGTCATGTGGATTTTGCTCCTAAATATGTTAACTTCTTTCCTCTCTCACTTT
ATATCCCTTACATCTAGGTATTTCAGACCCTCAGTCTCTCTCACATAGACTTTGGCAATAAC
CTTCTAATATCAGTCAACCTGACCAATAGGCCACCAGTGCTTCATGTAGAATCTGGACAATG
TAGAGCACTGAGAATGCTCACACTGGTCATATATGTATGAGTTGGTATGACATCTAGGGAAG
TTGAAGACTTACATAGCCTTTGGCCCAGCAATATACACCATAATACATTAGAGAAACTCTAG
CATGTGTACACAGTGATATACACACAAGAATGTTCACAATGCCATTATTTTAATAGCAAAAT
TGTGGAAACAACACAAATGTTTATCAATAACAGAATGGATAAGTGAGCCATGGCATAGTCAT
ACAATGAAAAATAATATAATAGTCAAAATGAATGATCTGAAGAGATATCATTATTGGCAATC
TTATAAAAGACTGAGTTAAAAATGCAATTTGTGAAAATTTTTAATTATTTGATATTATTTAA
TGCAAAGTTTTAGAACATGCAAACAACTGTATATATTATTTATGTATATATGCAAATTCAGC
AATAGCATTTAATCATGCCTGGGAATGATAAGTATCAAAGTCAGAAAGTGGTTACCCTTGGG
AAGAGAGGTATGTATCAGCGGTGGGGCACATAGGATGTTGCAGCCATATCTGTAATGTTTCT
TTGCTTTAAAAAATTTGAATCAAGCTTGGCAAAGTGTGACATTTGATTAAGCAGGATAGTGA
GTGCATATCTGTTACTTATATTGTTCTTTATAATTTTCTCTATGCTAAAGCATTTTGTAATT
TAAAAAACCTGACAGTGTTACTCCCATGCTTAAAATATGCCAGTGGTCAAACCAAATCCAGC
AGCACATCAAAAAGCTTATCCACCATGATCAAGTGGGCTTCATCCCTGGGATGCAAGGCTGG
TTCAATATAAGCAAATCAATAAATGTAATCCAGCATATAAACAGAACCAAAGACAAAAACCA
CATGATTATCTCAATAGATGCAGAAAAGGCCTTTGACAAAATTCAACAACTCTTCATGCCAA
AAACTCTCAATAAATTAAGTATTGATGGGACGTATCTCAAAATAATAAGAGTTATCTATGAA
AAACCCACAGCCAATATCATACTGAATGGGCAAAAACTGGAAGCATTCCCTTTGAAAACTGG
CACAAGACAGGGATGCCCTCTCTCACCACTCCTATTCAACATGGTGTTGGAAGTTCTGGCCA
GGGCAATTAGGCAGGAGAAGGAAATAAAGGGTATTCAATTAGGAAAAGAGGAAATCAAATTG
TCCCTGTTTGCAGATGACATGTATATCTAGAAAACCCCATTGTCTCAGCCCAAAATCTCCTT
AAGCTGATAAGCAACTTCAGCAAAGTCTCAGGATATAAAAATCAATGTACAAAAATCAGAAG
CATTCTTATACACCAACAACAGACAAACAGAGAGCCAAATCATGAGTGAACTCCCATTCACA
ATTGCTTCAAAGAGAATAAAATACCTAGGAATCCAACTTACAAGGGACATGAAGGAACTCTT
CAAGGAGAACTACAAACCACTGCTCAATGAAATAAAAGAGGATACAAACAAATGGAAGAACA
TTCCATGCTCATGGGTAGGAAGAATCAATATCGTGAAAATGGCCATACTGCCCAAGGTAATT
TATAGATTCAATGCCATCCCCATCAAGCTACCAATGACTTTCTTCACAGAATTGGAAAAAAC
TGCTTTAAAGTTCATATGGCACCAAAAAAGAGCCCGCATCACCAAGTCAATCCTAAGCCAAA
AGAACAAAGCTGGAGGCATCACACTACCTGACTTCAAACTATACTACAAGGCTACAGTAACC
CAAACAGCATGGTACTGGTACCAAAACAGAGATATAGATCAATGGAACAGAACAGAGCCCTC
AGAAATAACGCCACATATCTACAACTCTCTGATCTTTGACAAACCTGAGAAAAACAAGCAAT
```

-continued

```
GGGGAAAGGATTCCCTATTTAATAAATGGTGCTGGGAAAACTGGCTAGCCATATGGAGAAAG

CTGAAACTGGATCCCTTCCTTACACCTTATACAAAAATTAATTCAAGATGGATTAAAGACTT

AAATGTTAGACCTAAAACCATAAAAACCCTAGAAGAAAACCTAGGCATTACCATTCAGGACA

TAGGCATGGGCAAGGACTTCATGTCTAAAACACCAAAAGCAATGGCAACAAAAGACAAAATT

GACAAAGGGGATCTAATTAAACTGAAGAGCTTCTGCACAGCAAAAGAAACTACCATCAGAGT

GAACAGGCAACCTACAAAATGGGAGAAAATTTTCACAACCTACTCATCTGACAAAGGGCTAA

TATCCAGAATCTACAATGAACTCAAACAAATTTACAAGAAAAAAACAAACAACCCCATCAAA

AAGTGGGCAAAGGACATGAACAGACACTTCTCAAAAGAAGACATTTATGCAGCCAAAAAACA

CATGAAAAAATGCTCATCATCACTGGCCATCAGAGAAATGCAAATCAAAACCACAATGAGAT

ACCATCTCACACCAGTTAGAATGGCAATCATTAAAAAGTCAGGAAACAACAGGTGCTCGAGA

GGATGTGGAGAAATAGGAACACTTTTACACTGTTAGTGGGACTGTAAACTAGTTCAACCATT

GTGGAAGTCAGTGTGGCGATTCCTCAGGGATCTAGAACTAGAAATACCATTTGACCCAGCCA

TCCCATTACTGGGTATATACCCAAAGGACTATAAATCATGCTGCTATAAAGACACATGCATA

CGTATGTTTATTGTGGCACTATTCACAATAGCAAAGACTTGGAACCAAGCCAAATGTCCAAC

AATGATAGACTGGATTAAGAGAATGTGGCACATATACACCATGGAATACTATGCAGCCATAA

AAAATGATGAGTTCATGTCCTTTGTAGGGACATGGATGAAATTGGAAATCATCATTCTCAGT

AAACTATCGCAAGGACAAAAACCAAACACCGCATGTTCTCACTCATAGGTGGGAACTGAACA

ATGAAAACACATGGACACAGGAAGGGGAACATCACACTCTGGGGACTGTTGTGGGGTGGGGG

GAGGGGGGAGGGATAGCATTAGGAGATATACCTAATGCTAAATGATGAGTTAATGGGTGCAG

CACACCAGCATGGCACACGTATACATATGTAACTAACCTGCACATTGTGCACATGTACCCTA

AAACTTAAAGTATAATAATAATTAAAAAAACCAATAGTTTATGAAACCCCCCCAAAAAAAA

TATATGCCAGTGGCCTCCAGTTGCCCACCAGGTAGCATCCACATTCTTTAATGGAAAGCCCT

TCCTTGCTTCGAACTTGCCAACTGGGATTGGACATTTGTAGTTGCATTTCTAAGAACTGTTC

CCTTTTGTCAATGGAGCCTGATTTCCACTTGGATATCTGGGTGATTTAGGGAAACTGACCTC

AAAACCCAATTCTACATTTCGACCATGTGACCTTGGCTTAATCAATTCACGCATCTTTTTCC

CTCACCTCAGGGGATGATCATATGAACTAAGCCAGTTGCAATAGAGTAAACCTCATGTTCCT

AATGAGAAATCCAGAACAAAATGCTTTATTTTTCTTCAATTTTTTATTAGGTCATCTCCTGA

ATCAATTAAAAAAAAAACCAACAGTGACAACAAAACTAAAAAATATGAAGAAGCTGAAACAT

GAAAGCTCTGCCAACTGCAATATGTAGCTGCTAAGGTTGCTGTATTTATTGGAATCAAGCAA

GTGTTCCAGTAAAGAGCACAGAAGATGTGTCTGGGAGCCTTTATGTGTAGGTCTGCAAGTGG

TGGATATCACTACTACTCACACGCCATTGGCTAGAACTGAGTTGCATGGATACACCTAATTG

TAAAAGAGGCTGGGAAATAGAGACTATTGTGCCCAGAAAGAAGAGAAAATTCATTTATGGAA

GAGGTAGCTAGTCTCTCACAGCCATGAAAAGAGAAGTGTTTAGCTAATTGAAGTGAATAGCA

GCCATCTTGGGTCCCTAAGGCAAGTTAGACTAATATTGAAGTGGAAACCATGAGGAAAGCAG

TGATACTGAAAGTAACCGCATCTTTGAGAACATGCATTCATTTCCTACAACATGAATTTATT

GAGGACCTACCTTAATACAGGCAGCGTGCTAGACACCAAGAGAACTGATGTCCTCTTCCTTC

CTGCCTGCCTGGAGCCTGTATTCTGGAGGGGACAGAGCTAGCAGATCAGACCTAACTGGAAA

TCTGCTGTGCCAGTATATATTTCAGTGATGTGAGCCAATATATCCCCTTGATTGCTCAAAGT

AGTTTGGTCGATATATTTTGTTGCTTTAAATTGAACACATTCTTATGTACAGCCTCTGTCTC

CTCATCTCCAACCAAGCAAAATAGCTTGTTCTCTTTATGCAGGGACACATGACATTTCCCAC
```

-continued

```
GTGGCTTTGTGCATATCTCCACCTCAATTTAAAATGCCTTCCAATCCCTGCTCAAAGTCAAA

CAGCTTAATAATGGTAGACATAGAATTTGACTTATTCTAATAATAGGTCTTTTAAACAATGC

CTTCTTCTCTTCATTCTTTCCTTCTTAGAGTGGGTATTCTTTCTGGTGCATCATGTAAAGGA

AGGTAACTACATGCATGTAATGATGAGAATATTTATATGTATTTATGATTATCACAAAAAAA

CAAAGATTCTACCATTCAAGAGGAACATTTATTTTATTTTTTATTTGAGAAAAGTATAATT

TTATTTATTTATTTATTTGTGCAAATTTATGGGGTACTTGAGAAAATGTGTTACATGTATAT

AATGTGTAGTGATCCAATCAGGATACTAAGGGTGTCCATCACCTGAGTGTATTACATTTTTG

TTAAGTATAATCATCCTACTCCAGGAGAACATTTTAAAAACTGTTCTGTAGAGATACTACTC

AAATTAAGTTCTCAGTCCTGAAACATCAGATCAGCTAGGAATCTGACAAAAATGCAAGTTCT

CAGATGACAGATGAGACCACTTCAATCAGAATTTCTGGAGTGGAGCCCACACATTTGTATTT

TTGCAACCTTTCCAATGATACTTATGTACATGCTCAAGCTTGAAAACCACTTTCCTAGGACA

TTAGTTCCTCGACAAGATTTGTGAGTAACCTTGTTTCATGAAAAAGTGTTTAGGAGATACTG

ATTCAATAAAAACTAATCAGGCTTTTATTGTTTGCAGGGCTTTCAAAACTTGCAATAGGCCA

CTGTGCATTGTTAATTTCTAAGAGGAAGATGCTTATGTCCTCAATGAATATCTTCCCACCAT

GAAGTACTCTTCTTCCCCCACTTTTTAAAACAATTACTAACACCTGGCAGAAGTAGGCAGAC

AGCTTACAGCTTAGAAAAAGTTGGCCTAAGATAATGGCTAATTTTCATACATTATTTATTTG

TCATCATGCTTATCTTTCTCTCTAAATTGTATATTTCATCTCTGTGATCACAGATTGAGC

CTCATATTTCATATCTGCCCCTGGCCTAATGGTTGTTTACAGAATGAGCTCAATGAATATTG

TTAAGTGAGTAGGATTTAATTTATTTGATAAATAGATAACCTTAAGTTTTAAACGGTGGATT

TCACATGAGGACATTTACTTACTATTGTTGAGCTGTAATTAATTTTTAATACTGTTTAGGTA

CTCATAATAAAGAACAGGATATTTGGAGAAGGAAGACAGTATCATTCCTGGTTCTTAGTCTT

ACCAGCTTATTGATCATGAGTATATAACCTCTCTGTGGCTCAGTGCCTTTCTCTGTAAAATG

GGAACACAGTGATGTTCACCTCACAGGATTGATTTGTAAAAGGGCTGGATAAGGTTATGAGA

ATGTTTTGCAAAGTGATATCGAAAGATTAATTGCAAACTTCATTTGAATCTTAAATTGTTTG

AGATAGGTCATGCTATGAATCAACTATGAAGTGCAGATATTGTCAAGATTCAATATTTCTTT

CCCAAGAGCTGAGAGGAGGGCTGCTTGTTTGTTTGTTTCTTTCTTTTTAGAAACATGCCAG

GACAGGCTCATTTTCGGGTTTTCCTCTCACTTGCTCATCTTACTTTTTCTTTAGTTTCTCTA

TTCATTAGGATACAGTACTGTAAAGCTTTATGGCATTTTTATTTTGTGGGAGATGAATCTGA

ATAAAGAATTACAGTTAAATCATTGCTAAGTTTGATGAATGAGCACCAAAGAACTCTTCAAG

ATGTCATTTTTAAAGTTTTGTAAATGATTGGCTTTCAGTGGTTTCCTCTAAGGAATTTTAAT

TTTGAATAATGCATAGAAAAATGTGCGCACACACAAATCATTCAGTATCCACCTCGAAGGGA

AATCAAAGTGCCTGTGAAGTGAAACTTTACCTTTCTATATCACCAGCTTCCTGTTAGAGCAG

ACTTTTTCTTTGCTCAAAGTCTAAGCATTGAAGAACTTCTTTTTAGTAGGTAGATTTTTGTG

TTTTTTTGTTTGTTTTTGAGACGGAGTCTCACTCTGTCGCCCAGGCTGTGGTGCAGTGGCAC

GATCTCGGCCCACTGCAAGCTCTGCCTCCCGGGTTCACACCATTCTCCTGCCTCAGCCTCCC

AAGTAGCTGGGACTACAGGTGCCAGCCACCACGCCTGGCTAATTTTTTGCATTTTTTAGTA

GAGATGGGGTTTCATCGTGTTAGCCAGGATGGTCTTGATCTCCTGACCTCATGATCCACCCG

CCTTGGCCTGCCAGAGTGCTGGAATTACAGGCGTGATTTAGTAGGTAGTTTTGAGTAGGGAG

TATACATTTAAAATGCTGAAACTCAGTTAAGGAATAATCTAATACTGTATTCAACTGAAACT

CAGTTGAGAAATTTCTTTCCAATAATAAAGGAAAATCAACTGCAGTAATGAGGGAGATGATT

TTGCTGCTAATTACAACAAATATTTACTACAGACCTGTTATGCACCAGGAACTGTGCTAAAT
```

```
GTTTTATACATATAACTTTATCTTGTGCTCCAACAACTTATTACATAGAAATTGCTATTATT

CCCATTTTCTAGATTAATAAATTGGTTTAGAGGGGTCGTATAGGTGAAACAACTCACTCAAT

ATCACAAGCTGTTATGTGGTGAAGTTTGCATGATCAGTACAGGGTTCTGGTCATCCCACTCA

TTGAGTGGTGCTAGTCAAGATCTGGAAGCTCTTCTGGTCTTAGTTTCTCTAGCCGTGAAGTG

ACAATGATTAGGTCTAATCATAGAACATGAGAGTACATGTGAAAAAATGCCTTTTTAAAGAG

TATGAAAAACTTGAGTTGTAAAATTTTCTTGTGGATAATTTATTATTGCTTTTCTTTTTTAG

ATAACACTAACAAAGTTGACCTTAGAATTGGAGTGCCTGGGTTAGAACCCTGCTGGTACCAC

CTGCTTACTGGCATGCTTCTGATGTGAGTTCAGGAGAAGACACTGGCAAGGACAGCAAAGAA

CAGGAGAACACTCTAGCTTCCCTGATAGCATTCAAGGTGCTGTCCAAAGCTGACTGTGATGG

CACCCTCCAGACAGACAGCGATGCCACATGTTCAAGATGGCAGAATCACTATCAGCTTCAAT

TCCTGAATGACTGCAGAGCAAAATTTCTTACCTGCAACATACACTCTATTTTCAGCCTCCCT

GGACTGTTACATAATGATACATAAAAATATTTCTTGTGTTGAGGCATCCCAAATTTGATTTA

TTTGTCATCACAGTCTATCCTATGAATATATTTCTGATCCAAATAATGCTAGATTCATGAGA

GTTTATAGTCCAGAGATTTTTTTTTTTTTGAGACAGAATCTGTCTCCCAGGCTGGGGTG

CAGTGGCATAATCTTAGCTCACTGCAACCTCTGCCTCCCGGGCTCAAGTGATCCTCCCTCCT

TAGCCTCCATGAGTAGCTGGGACCACAGGTGTGCACCACCACACCCCGCTAATTATTTTGTA

TTTTTTGCAGAGGGGGGTTTCACCACATTGCCCAAGCTGGTCTCAAACTCCTAGACTTAAGG

GATCTGCCTGCCTTGGCCTCCCAAAATGCTGAAATTACACTTGTTAGCCATAGTAATAGTTC

CTAGCCATAGTCCGGAGATATTTTAAAAACTTTAGTGTGAGTTATTTCTCTTTGCTATAATT

CTCTCATGCATTTTGAAAACCTTTTCTGCCATACAGTGGTTTTTGGGAAGTCCTTTTGGACA

GACATATCACAGGATGGAGAAACTAAAAAGAGAGAATGCATTAAAGAAAAAATAGTACTTCG

TATTTCAGAAATTACAAAAGGGTGTCATGCCCCACAGCATGGTGGGCAGTCATTTGTAACCC

ACAGAACATTGAGTTTCTAAAATTTGAGTGTTTTTAACTTACGAAGGCCAACTTTACTGATG

AAGTGATTACCCCAAATATGTGAAATCCATATTTCAAGTACAATAGTAGGAAATTGGAAATG

GGGCTCTTGAGTTTCTGCTTTCAAGTGACCCTCAGAAATTCCTCCATTCACTGCAGAGGTTC

TGTTTCTCCTTGCTTTGTTCTGACTTTACGGCAGAACTAAGCTAATGAGTTAGTTACTATGG

GTTATCACTTGGATTTGAAGAACCATCATTTCTAGGCATTGCTGCTCAGAGTGGGGTCTGCC

CTCAGGGGAAGCTGTCTAACCAGAGCCTAACCCACTAGGGTTTTATCAGAACCTAACTGACC

TGAGGAAAAGAAATACTCAACTCCAGCAAGCTCCAGCCTTCCAAATGGAGGAGGAGAAAACC

CAACTCCAGCCCACTTCAGCTATCTTGTCCCACATAAAGGGGAAGTGGAAGAAACCTGAGAA

GCAGGCATGAAGTTCACATGTATTCCACACCATTTCATATTCCATCGCATTCCATTCTACAC

AATTCCACATCTCCCCGGCCACATCAGCCTGAGAGTAATAAACAGACCTTGCCATCGTATCC

CCTTTTGGAGACACAAGCCAGGAAGGAAGCTCTTCAGTGCAGCTGTGAATAGAGAAATGCTG

GCTGAGGTTTTGGAGACACTGGGTGATCATTCCCAGTGAAATTTTTAGATCCCTGGGGACAT

GAGCTGCTTTGTCTTTTCCAAGGTCAGGATAAACAGAATAACTTCAGGCTTCTCTACCCAGA

AAGAACATGTGGCATAAATATCAACTGCAGAATAAATATGATTAATCTGGTACATGGACGAA

GATGTTTTCTAGGAGATGCTTATCCTGGGATGAGAGCTTTCATAAGCATTGATATTTACATG

ACTCTTACCGTGTGTCAGGAACTGTTCTAATTGTTTTACCTATGTCAATTCATTTGATAGTC

ACAACCACTGAAAGGAGTAAGTACTCTTATTACTTCCATTTTACAGATAGGGAAACTGAGGT

ATAGAGAAGTCAAGTGACTTGCCCGAGGTTATTAAACTACTTAATGTCAACACCAGGATTTG
```

-continued

```
AACCCAGATCATTTGTTTCTGAAGTACATGCTCACAATCACTGCATTACTGATACACTGTTT

TGTCTTTGCATACTTAAGTGGTCATAACTTAGTCTGAAACACTTTGTGAGAGCAGGAAGCAA

ACTGTCCCCTTATTAGGTGGACCAGTATAGTGATAATACAAAAGTGTATTGCATTTGAATTA

CTTGCTAATATCTTCTAATTGAGGCAATTTTGAACAGGAATATACATATCTAGCCTCTATTT

TTCTAGCTAGAAGTTCTGAAATCCCTGGGCTTAATATTGTATGGCAACAATTGGCTGGAGTT

GAGTTGCTGCCACTCTCTTTTAACTGAGCCATGCTCTCTCTAGTTTGCTACAGGCCCCACCA

CTCCCTATTGCCTCTCCAATACCAGGTCATTTGGCATCTTACTCAGCTCATTTCATGCACAT

GTGTTCCACAATTGGTAACATAACCCTAAAAGTATTTGAGTTTGTGGCTTCTGCTCTTGTGA

CAGAAGACTTTTCTCGAATTCCAAGGTCAACATATACCATATTGACTCTGGGCCACATTTTT

TAATGTGCTCAAGCTCAGTTTTTCTCCTTAAAAAATGAGGGGTTAAAAATAACACTTCGTAG

TTGCCTCATCTGTGGATTGGAAGAATGAATGCCTGTCATTTCTAGAGTTGTAGTAAGGGCCA

GTTGGGGCAGTGCCTGTGAATATACGCAATGGGCCATCAAGCAATCTCAGGGCTTCAGGCAA

TGCTGGGGTTTATAAAGCACTTTATGTTTTAAGTTCACTTTTATTTCTAAAGTCTCATTGAC

TGCTCTGAAAATCTCTCAAGTAAAGTGGGCACTAAAGGCTTTATACTCTCTCCAATTATACC

TTCCATTGTATAGATTTGGAAGCTGGGGTCCAAATGTGTTAAATGACTTGCCTAACATGGTC

CATTACTGTAAGTACAGAAACGGAATGAGACCCCAAATCTGCTTCATGGAGGGACACTCTTC

TAAGATACTGTGATGCTTCTTCCCAAGTAATTCCGTCTTCAGACTTCAAGGTCTCAATTCGA

ATGACAATTCAATATAGGACTTTCATAATCTTAAAAGCAACCTGACAGTCATTACAGTGGGC

TGTGAGAAATACTAACGCAGAGCCACATACTCTGGGCTTCATGCTAGGTTTTGCCACTCACT

ATCTTTGCTGAAAAAGTTTTGGAAGCCCTCCTAAGCAGGTGCCAGACCCTTTTTTGGCCAGA

GGACAGGATCTTACGCTGTTGCCCAGGCTGGAGTGCAATAGTGTCATCATGGCTCACTGTAG

CCTGGAACTGCTGGGCTCAAGGGATCCTCCCAGCTCAGCCTCCCAAGTAGCTAGGAGTAAAG

GTACATGCCATCATGCCTAGCTTTTTTTTTTTTAATTTTTGGAGAGATAAGTTCCCATCAT

GTTGCCCAGGCTGGTCTCTAACTCTTGGACTCAAGTGGTCCTCCCACATCAGCCTCTCAAAG

TGCTGAGATTGCAGGTGTTAGCCACTGCACTTGGCCTGGCCCCAGTATTCTTTGGGATCTGG

AGTTTGCTGTTGAATGAGAAGGCAAGATGAAATTCCATGTAGTCAGACTCCTACGCTGCTGT

TCTAAGCAGGGTTGGGCCTGATTAGTAGGTTATAGATGATGTTTTTCTGTGGTGCTATCTGG

ACCTAGTGCTCTTTGGCATCTGGGAAGGTATGGCCTTTAAAAAGCAAACTGCCATGAGAACT

GCTCTACCCCAAATTTTGGTTCACAGCCTTCATTTGATTATGTATTGGGGCAAAAATAGTTT

AGCCATGTGAACCTGTTTGTAAACTGGTGAGTTTCTATTGCTATTTCATAGCTAAAGTTTTG

AGGTAAATGCTATTGGATCTTTGTGTCTGTGTGTATACATATTTAGATTTTTTTTTTT

TTTTTTTTGGTTCTTTGAAACATTGCTGATTCTTTTGTTTTGTTTTCAGAGTCTGGAGA

ACACTTTTTCTTTTGAGCTGTTTACAACCTTTAGCAATTGAGTAGAGTGTACTCTTGTCAAT

AGAATTTGAAGCACATTTCTCTCTCTGCCTGATTTCTGTAGAATTTGTAAACTATTTGTGAA

TATTCTTAATTTATGGCAATATGGTTGCTTACATAAGTTCAATAATAATCTGTTTTCTTTTA

CAATGAGACACAGTTGGAGGAACTGGTTATTTTCCCAGGGCTTTGACTGAAATGGCCTTGTG

AATGGTTCCAGGAAAGCCAATTTTGGAGACCCTATGTGGATGATGATGCTTGCTGTACTTTC

TGTGGGTAATCGGGCCAAGTATATGGGACTGAAGCTAATTTTGCAGGGCAACATAGAGAGAC

TTGAGTTCCAGGGGGAAAGTTTTAGGATGGAGAGAAGCCCTCACTGGACTGTGATGTGGGGT

GAGAAAATGGAGGTCCAGAGAGAAAAGTGACTCACCCAAGCTGAAAACAGTTGCAGGAAGAA

AAGCCAGGACAGAACTGGGCTGTTAGAAACCTTGGTAGTGCACTTTTGATTTCACTCTTAAA
```

-continued

```
ATGCTCAAATGTCTTTTTCTGACAACATGTAGGGAGACCTGAGGTTGGACCTAAAGACACCA

TATATTGGATTCAGTGCTTCACACAAGTTAATCTAAATTATGAAGGAGTACACTAAAGATGA

GGAACTGAGTCACCGCAATGCCAAATGTAACACGCTGTGGGTCAAAATTTGGATGGTTGCGT

TGGAAATTATTCTGAAGCCACAGACAGGGCTAAAAGGAGTCTAGAATGTCCTACTAGCTGTT

GGAACCTGCTGGAGTTCTAAAGGCATGCGATGTCCTGAATGTGCTTGACCAATGGACACAGC

AGGTATTTGAAGAGTTTTGATGCTTCCTTTCTGTTTTCAGTGCTATTTTTTTGCTTTATTTC

TTTTAAAAAACTTTCCCCACAGAGGCTATTTATTACACAGCAGCAGCCAGCATGCACCAAGC

AGAACTGCTTTTCATAATAAACCTATTTATCTTCTGGCATGTCAGAAATTTCTCAAATTGAT

ACTTATAATAAATATGATTAATAACACATTGTATTTCAGTTGTTGCCGTAAAATAATTGGGA

ATAAATATCGTATTGTGATGTTGACAGTGTCAGGTTGGTTGGTGCCAAACAGCGGGAGCAGC

CAACTGTATTTCATTAACAGCCACATTGCTACAATGCTATTAAGTTTTTCATAATCTCTTCT

GCTCAAGGTTGATCATTCATTCTGTTAGACAAATTCTTGCAACAATCACACTGGAAGTAAAT

CTGCCAGCGACAATCTCAGCAAGATGGGTTCTCAC-5'

<128128655>

>CCAT1_JAX_2 Transcript sequence; Genomic location:
chr8:128128655-128232653 strand:-
<128232653>
                                              (SEQ ID NO: 2)
3'-

AAGGATTTAATGGCAAGATGCCATTATAGACAAGAACAGGATTCAGACACTTTCGTGTTATG

TGTTCTTGTCCAAATACTGTGTCACTCTGCACTGGCATCCCAATCCCACCAACACCTTTAGC

AGGAACTTCCTGTTTCAATAACATTTCTCAATACTCTACCTGATTGCTTAGAATCCATGAGA

CAGCCATATTCTCCATGTCTAGGTCCCTATCTTATTTTTGTTGAGATGGTGTTAAGACTTTA

TTTGTGAGGCTTCTGGGGAAGAGGAGTAAGGTATTGATCCCACTGACTGGATAATTTGGGTC

TCAAAATGGATAATAAATAAGCATTACATATTTTGACCACTTCCTTGGAGGAGAACTTCTTG

GAATGTGCACCATGTCCGCTGCACTTTTTTTGCACAGATATCTAAGTTGGAGAAACATACTA

CTAGATAAATCAATTTGTTCTCTTAGTACTCATGATATGGTTCCTGGGAACTTCTGATTCAC

CAAATTAATCTTGGCCAGGTACATACCTGGCAGGAATCCAAAAATTCCCCAAGTCTCCTTGA

AGTTCAGGATCATCATTCTTAATAAATACACCGAGGGAAAAACCATGGAGAGTTTGTCCCAG

ATGCTGTGAATCTGGCCCGGGGTACATGAAGAAGTCCTTAATTGCAGTCATTTACATGGTAG

ATTCTCTATAATCATTTAATTTGCTATAGGTCTATGATTTTTAGTCCTTCTTCTCTAAATGA

TTGAACATGTATAATTCCCATTTCAATCATATTACCTGGATGAACAAAAGTAACGCTAGACT

CATTCATGCATTCTGGTTGCCAAGGAAAAGGAAAAAAAAACAAAACAATCAACAGGATGTTT

AAACTGTCTTAGGGCAACTTCAGGCCATAGTCACTGGTGTTCTTGCAGACTATGAGATATTT

TACATTCTGATAAGGGATAAAAATTCGTGCCTCACATGGCTCCCATCACACTAAGATCTTGC

AACAATAACACTACTGATTCAGACATTAATCTTAAGTATCCAGGGAGCCCTAAAACATTGTA

TCCCACTAGCAAGGACCATGGTAATTGCCACGTAAATCCCCTCCATTATGTGGCCCTTATTA

TGACCAGCCAGCCAAGGCTTGCCTTTAAATCATACCAATTGAACCGAGCCTTGTAGAAACAC

TATCACCTACGCATACCTCTGCTTCTTTTCATTAACCTGCTATCCTCTTTACAAATGGGATT

CTTCACCCACTCCCTTCTTCTAGATTAGCAATGCCCTGTTAAGTAAACGAACACGAAATTCA

AAGGGAAACAGGAGCAATCATCATTACCAGCTGCCGTGTTAAGCATTGCGAAAACGCTCACG

ATTCACAGAAAAATCCATGCTGTTCTTTGAAGGCATTCAAGCCTTAATAGCTAGCTGGATGA
```

-continued

```
ATGTTTAACTTCTAGGCCAGGCACTACTCTGTCCCAACAATAAGCCCTGTACATTGGGAAAG
GTGCCGAGACATGAACTTTGGTCTTCTCTGCAATCCATCTGGAGCATTCACTGACAACATCG
ACTTTGAAGTTGCACTGACCTGGCCAGCCCTGCCACTTACCAGGTTGGGCTCTGTATGGCTA
AGCGTTTTCTCCTAAAATCCCTTGAAAACTGTGAGAAGACCATAAGAAGATCATATCTTTAA
TTCTATTTCACAAGTCACACAATATTCCAATCAAATACAGATGGTTGAGAAAGTCATCCAT
CTTCCCTCCCCACCCTCCCACAGCCCCTCAACCACTGCCCTGAAACTTATATGCTGTTATCC
GCAGCTCCATCTGGAGCATCACAGCTACTGTCAACCCTGACGCTCTTTCTGAAAAAACACCG
GATGGACATCAGAACTATTTCTTTAAGGATGTTACTGAGCCACACAGGAAAACTTGCCTTAT
GATTTTGAATGCACGGATCTGATTTGACTAAACATGATAACTAGAGAATCACCCAATCTACT
CCCATTTTCAACTCTAAATCATCAGAGTGTCTCAAATCCAAAGCACACACAGACCAGCCTGG
CCAACACGGTGAAACTCCACCCCTACTAAAAGTATAAAAATTATCCAGGTGTGGTGGCGGGC
GCCTGTAATCCAAGCTACTTGGGAGTCTGGAGGCAGGAGAATCCCTTGAACCTGGGAGATGG
AGGTTGCAGTGAGCAGAGATCACACCACCGCACTCTAGCCTGGGCCACAAATCAACAACAAC
AACAACAACAAAAAACAAAGCGCACACAGAGACTGAGGTCCTCTTTGGCATTGAGAAGATGG
CTATGCAAGTCCCAACTAGCAAGTGCAAACTTCCCAGCTTCACTTCTGCCAGTGTCCCTTCA
CCCCTTCTCAACCCCACTGGGAGGCAGGAGGGTGCTTGACAATAACAGCCTTGGCATCACTC
TGCCAGGGTGTAATAGGAACTGTTACAATTCTGAGATTCTGTGTAAGCACTGGCCTTTCTGC
CTAGAATGCCTTCTCCTCTCTTTTTTAACTGCATGCTCCTATTTATCTTTCAAAGCCCGGAA
AAAATAACACTGCACACGGGAAATGCTCCCTTCCTACTGCAGTCATTTAGATGACTCTATGC
CATTCCATTCATTTCTCTTTCCTACCACAGAAGTGCTTTGAGATTTTGGAGTCAGACTGCTT
GAACTTGAATCCTGGCCCTCTCATCAGAGACTTGACTTATTTTAGGCAAGTTATATAACCAA
TTTTACCTCAGTTCCTTACCCATAAAATGGGTCTAATGAGAGTACCTACCACACAGAATTTT
GATGAAAACTGAATGAGATGAAGGCCTTTAAGGCAGTGGTCCCCAACCCTGGGGACACAGAC
AGGTACCATTTTGTGGCCTGTTAGGAACTGGGCCACACAGCAGGAGGTGAGCAGTGGGTGAG
TGAGATCAGCGTTATTTACAGCTGCTCCCCATTGCTCACCTTACTGCCTGAGCTCCACCTCC
TGTCAGATCAGCAGTGGCATTAAATTCTCATAGCAGCACAAACCCTGTCATGAACTGCACAT
GCGAGGGATCTAGGTTGTGCGCTCCTTATGAGAATCTAATGCCTAATGACCTGTCACCGTCT
CCCATCACCCCTAGATGGGAGTGTCTAGTTGCAGGAAACAAGCTCAGGGCTTCCACTGATTC
TACATTATGGTGAGTTGTATAATTATTTCATTATATAATACAATGTAATAATAATAGAAACA
CAGTGCACAACAAATGTAATGTGCTTGAATCATCCCCAAACCATCCCAGTCCACGGTCTTCC
ACATTTTGTCTTTTCACAAAATTGTCTTCCACAAAACTGGTCCCTGGTGCCAAAAAGGCTTG
GGACCACTGCTTTAAAGCCTTTGCATAGTGCTTAGAATTGAGGGGGAAAAAAAAAACAAAAA
CAATGTAGCTAGTTGCTACAATCACTATATTGGTGAGTTTCAAAAGGAAAAGAATTCTGTCC
CATTTATGCTTGAGCCTTGAGTTGCTAACCAAGCCTGACACAAAATTACTGTTGAAGGGATG
TGTGAGTCCTAATTGAAATGAGGCCTCTTAAGGGAATTGTGGACCAAACCCCAAGCAGGCAG
AAAGCCGTATCTTAATTATTGCAAGTATTTCAGGCAAGGTGTGGATGGCCATTTGAATTCAA
GCAGACTAGGACCTGGGATGAGAAAGAAGGTGTGTACGTGACTTGATCTTTGAACTTTAGCT
CACCATCTGGAAGAAGGCTGAGTATTCTCTGCACTCACATAGTAGCTAATGCCTACTCCCCA
GCCACCCACAATTCTTTCTGTAGGAAGGCTCGCTAGAATACTTTGTGATATTGGATATTAGT
TCCATATTCTACTGTGTATCTTAGTTCAACCAAATTGTAATCATCTGATATTTATTTCTTTT
AATATAAATATAAGTATATTAAGTCTTGGCATGCTTGCTCAGTCTCTCTCTCTCTCCCATTC
```

-continued

CTCCCCGCTCCCCTCTCTCTTTCCCAACAGGCTTGGAAAGCAGGCATCACCATGCCTATTTA

ACAGTTGGGGTCCCTTGGCCACCAGGTGCTGGAGTAGGAATCTGAGCCCGGACATGCCTGAT

CTGTAAATTTTGTGTTTTCCCCACTGTGCTGGGCAGATCACAGCTATCAGCGCCAAATTCAT

AGAAGGGGCGCCCCCTGTGGTCAATTGAGGGATTTGTGTTTGAGGTAGATCTCAAGAAGGAA

TGGGTGGGGAACTTAGCCTAGGACAGAGCAGAAAGGAGCCCTCACTCCCCAAGCACCAACGG

CCTCAGTCCTTCCTGCTGACTCCAGCCTCTAGCTCTCACCCAGACTATCTGCATCCTTCTCT

CCACCACGCTCCTTTGGAACCTGCGTAAAACACAGATTAAAGGAATTCCGCCTTACTTCCCT

TTCCGCATTATGACCAAATGGTTTTACACTATCATTGAACAGTTTAGTACAAAACATGCCAC

CTTTTAATCTATTCATTCATTTAACAAATACTTTGGAGTGTTTACCATGTGCCAAGTGCTGT

TCTAATAGACATAAGCTGTGAGGTTATGCTTATCTGATTCTCACAGCAACAGCTTTCGAGAT

ATGAATTGGTATACTCATTTGACAGATGAGGAAATTGAATTCATGTAGTGAGAAGGAAGAGC

TGCAATTCAGGGTTACTGGTTTCTCCTGCACTAAGCACTGAGCCACACTAGAAGAGAAGGCA

TGAGGAAGACAAAAGTGAGGCTGTGGCTTGCCTTTTCACTTCTTGTGTCCTGTTTAAGAAAT

ATCTGCTATCCCAAGGTAAGATACTATACTTTTTTTAACATGTTATTTTGTTTTACCTTTCA

CATTTGGTGTATACTACATTTGTAATTAATTTGTCCATATTATATGACATATAGCCAAGATT

TATTTTTTACCATACAGATACTCAATATTGCCATTTACGTAGAACATCGTTCTCTTCCTACT

CAATTGCCTTGGCACCTTTGTAATAAATCAGATGATCGTGTATGTGTAGTTCAGTTTCTGGA

CTCTGTCTTCTGTTTCTTTAGTCTATTTGCCTATTCTTGTACCAATATGCACTGTGTTAATA

ATCGTAGCTTTGTAGTAGGTCTCGAAATCTGACAGTGTAATTCTTTTAGTTTCTTTCTTCTG

CAAATTTTCTTTAGCTGTTTTACGTCCTTTGCATTTGTATATAAACTTCAGAATCAGCTTGT

CTATTCCAAAAACAACAACAAATGAAAGTTTCAGAAACTTTAACTGAAATTGTATTGAA

TCTGTAGACAATTTTGGAGTAAATTGCATCTTAGCAATGTAGAGTCTTTCGAACCATAACCA

TGGTAAGTCTCTCCATTTGCTTAAATCTTCTTTAATTTATTTCAACAATGGCTTCCAATTTC

CAGCGGGAGCTCTTGGAAACTACAATTTACATGAACTTCTAATTTGATATTTTTCGGTGTCA

TTATAAACATTGTTGTTTTAAAAGTTGTCTTCAATTTTTTGTTGTCAGGCACAGAAATACAA

TTATTGATAACATTTATATATAAACTGTATCCAGTGATCTTGCTAGATTCACTGATGAGTCT

GATGTTGTAGATTCTTTGGGATTTTCTCCGTACATAATCATATCCTTTCTGAATAAGATAGT

TTTACTTCTTCATTTTTAATATCTATGCCTTTTATTTATTTTTCTTTTGAACTTTTTGCTGA

CTTCATTATTCACTCTCATGTTTTTCTCTTTCATTAGACTATGACTCCTCGATGGTAGCAAT

TTGTAGTAATCAAATTTTTGTATTTTATTTTAGCATCTGGCATCTTTCTTGACATATGTAGC

AGTTGCTTTTTGACAGCTTGCTTCTTCAGTGAATGAATAAATTAATAAAGAGAAATGTGATG

TTCAGTGATCCATTTTGCAGGTAAGAAAACTGAGGCAGACAGAGGATGTTAGCAAGCAAGAG

GCCTTGGCCTACAATTTAGATCACTGGACTCTTACTCCAGATGCAATCTGCAGAACCCACAT

ACTTTTAATTAGTCCCTTTGTCTATGTTCTGCCACTGTCACTTCTAAGGAAGGTGTGTCATC

CCAAATGGGTAGTATCTTATTGGTAGACCTAAATCTGCTGTGTTCGCCATCTCACCTACAT

GAGTATCTATGTGTAGCATTCTGCATATTCATCTTTTCCACCTTCTGGAGGTTTTGTCTTTT

TATAGGCAGCATGTGAATAACAATGGGGCCAAACTGGGGACCAGAAGGGGCCATTTTCTAGT

TCTGAACATAGATAAGCATCACTAACTTTTCCCTCCTGGCAGTAATGGCCTCAAAAGTTCCA

ACTTAGGAGAAAAAGGCAAAACCGTCTGCCAAAGTGTGTGAAAAGTTAGAGCAAACCTTGGT

TTTACCAAGAACCTGTGTCCCTCTTATGGAAATTCACACTTTCACACTTTTAGACAAATATT

```
AAATGTGTGACATTCTATTACGTACAGTGCCTGGCACATCTAGACACGCAGCACACTTTAGC

CCCCTTCTTTCTTCTTCTAACTCCAAGTTCTAAACTAGAAAAAGCCCCACTTGAGTCTGAGA

TTTGCTTTTTGAACTAGTTTATTTCAGATTGTAATCATGCTATCTAGGGTTGTGACAGTGTT

TGCTATTTCTAGGGCACTTTGACCTGATTCTTTTTGCACAGGAAACTTGTTCTACCCTTTTG

CCCACTTCACTGAAGTGAGGACTGAGACAGAGAAGGATTAAGTCACTTTTTATTTAACAAAT

ATTTGTTCCACATTCCTCAGCATTTATTAAATACTGGTGCATAATGATGGAATAAATTTTAT

ACCGTAAGGATAAACCAGTATTCTGGACTAAGCCAACGTGGGAGACCCTAGGAGGCCTGTTT

GAGAAAGTGACATTTAAATTGAGACTTGGCGGTGGCTGTGGCTACATATCTAGTAAGTGGCT

GGGTTGGGATTTGAACTCATGCCTGCTTAGCTCTAAAGATGATGCTTTTGGCTTTGTACTCT

GCTCTCTCTCTAGACAAACTCTGGTCCAAAATCGTTAAAGCTAACATTTATCCCTGCCCAAC

TGGAATTGTCATGTTATGACAAATGGCTCTGTGGTCTCAGATGCCCAGCAGACCCATTAGTG

GAATTCTATGTGCTACAGACCTGGGCAAAATGCCAGAGCCTTATACACCCATCACATTTCGT

CTGGCAAAGGTCTTCAACAAAGAGAAGTAATTACAGCAATGAAAAGCAACAGGTCCAGCAAC

ACCATAAGAACAAAATAATTAATTTCCCTAAAATAGAAGAAACCATTTATAGAGTAAGAGCC

GATACAATCAATAATTGGAAGAAATAGAAGAGGCTTTAGTATTCTAGCCTTCTTTATTTGTA

GATGTAAATGTCGAGCCTCAGAGAAGTTATATATCTAATTAGTGTCACTCAGGTAGATAACA

ACAGAATTAGGATTAGAACTTAATTCTTATGACTCCCAGAGCAGGGAAAAGACAGGATGAAG

TCCCAAAACATTGCGTGTGAACTCACATCTGACTCTGAATTGAGAGTCTGCTATTTACTCCC

TATGTGACCAGAATCCTTCAGAGCCCATGAGATTCCCTGTCATAGAGTAGATTTTGATCCAC

ACTAGGCATTTTTACCTCTTGCTCTTTGAGTTGGTGCCCCATGTTTACTCAGAAATATTCCA

AAGGTGTTACATCTATTGGTTTTACATGTTGAGCACAGATCATTATAAGACAAATTGAAATG

AAAACATCAACAAGTCTCATTCATTGTCTAACTTACGCTGAGCAATATTTAATAACTAGAAT

ATCAAGAGAGTCCAAAGTGTTTGCCCATCCCCTCAAGACCAATGTAATGGAATTTTACTCTT

ATCACCTGCTCAGGGTAGTGGCAATTCAGGATACAGAGGACAGAAATAAAGAATCATGACAC

ACAATCCACAGAATTCACAGATGCCAAACATCTACCCTTCTCTGTCACCACACATTGGACTC

ACATGGTGGAAATAGGCAACACAAGCAGAGAGGTGGCTTAACCTTTCATAATTTTTCAACGA

CCTATGGGAAGAGAGTTTTCTTGGTTCAAATCCCAGCTTAGCCACACAGAGTGTGGTAATAT

TGGGCAAGTCAACCAAGCTCTCTGTGCTTCAGTTTCCTCATTATTAAAATGGGGGAAATAAT

AGTGCCTGCATCAGAGGGTTGTTGTGAGAACTAAACGAAATAATTTATCTGAGCTTTAGAAC

CCACACCATATTAGTTAAAAATTCATGCATTTTCTTTTATTATATTTCTCTACCTTAGACTG

CAAACTCTAAGAGGAAAGGCCGGACTGTTATATTCATAAAGCATTACAGGAACAGTAATTAG

AACTAGGAGCTTTTCAATGGCCTGCCTGAAATCTGAAAAATAGGTATATTATTTGAAATTTT

GAAAAAATCAAATAATTAAAAATTAATAGATGTTAATAAAATATCTGTAATATGTAATATCA

AGGTCAACTCAACTCTTAATTGTTTATATAAAATATAGTGAAGTTTAAATTGCAAATCTTA

CAGAAAATGTGCTATTAAAACTCAAAAGTATAATTCTTTCTAATATGTATATATATGTATAT

AGTTTTATTTTAAGTTCAGGGGCACATGTGCAAGTTTGTTACCTAGGGAAACTCACGTCACA

GGACTTTGTTATACAGATACTTTCATCACCCAGGTATTAAGCCTAGTGCTCATTAGTTATTT

TTCCTGATCCTCTCCCTCCTCCCAACCTCCACCCTCAGGTAGGCCTCAGTATCTCTTGTTCC

CCTCTATGTGTTCATGAGTTCTTATCATTTAGCTCCCACTTACAAGTGAGAACATGTGGCAT

TTGGTTTTCTGTTCCTGCCTTAGTTTGCTAAGGAAAGCACTGTGGCAATTTCTCAAAGGACT

AAAAACGGAATTACCATTCAACCCAGCAATCCCATTACTAGTTACGTACTCAAATATTTTA
```

```
AGGCAAAACAAAGCTGCAACCAGAACACCTGGACTCCCTGAAACCCCTTCCACTGATGTTGT
TGTTGTTGTTTCTTTTTCCCCAGCTTCTCAGGCCAAAATACTGGATCATCTTGGGCACTGTT
CTCTCCTGCCCACCCTTTCCCATATGCAGAGTGTTGTCACTTCTCTCTGCTTCCACTGCTAA
CTCCCTGGTCCAAGCCGCTGCACCACTTTTCGTGATTATTGCCACAGTCTCCTCACTGGTTC
CCTGCCCCACTCTTGCTCTGAACTATCCAGTTAAAACCTGAATTAGATCATCTCATCCTCA
TCTCAGAGCTTTCTCGTGGCTCCTCTGCCCTCTCAGGAAAAAATCTAAATTCTAGATGACCT
AAAAATCCCTTGTCTCTTACTGTTTATCTGACCTCATTTACTACCACCTTTTTCTTTGATCA
TTCTGTTCCAGCCACACTGGCCTCCTTACCACTCCTCAAATATGCCAAGCACAGCCCCCACC
CCCCAGGGCTTTGAACTGGCTGATCCCCCTTCCTGGAATGCCTTACCCCAAATATCAACTTA
GCCAACTCCCTCCTCTCCTCCAAGTGTCTGTTTAAACATGGCTTCAGTAGGAGCTGTCTTAA
CATCCTATTAATATTGTAATTCCTCTCATGACACTTTACACCCCCTTCCCTGATATGCTTTC
CATATACCATGCAATATCTGCTGAGATAATATATAATTCACTTATTTTCTTTATTGTCATTT
CAAAGAGGGCGGTGTGTTCTGTGTTTTATTTAGTGCCAAAATACTTGCTGATGAAGAGAGTT
CCTGCCACATAGTAGGTGCTCAATATGTGCTTGTTGAATAAATGTGTCAATGTTTGATGTAC
AGACCTTTTATTATGTTTGATTTGCTGCCAGTGCTGCCTCCAAACACAGGAGTGCTTCATGA
GATGTTCACAAAAGCTCTTAAAATATTCCACAAAAATCTTAAAATATTTCATGAGTTTTCTT
TCCTGTATTTTTATAGCAGCATCTGGAATTTAGCCTGCATAGGACCCTCTGTAAGCTGACCC
TGTTTATCTATTCAGCTTTACTTCTCCCCTCTCTCCACTTTGTATTTTATTCTCTACTACTT
CCAACTGATTGTAATTTGACCAGACTCCAGACTATCTTATGCCTCTTTGCTTTTGTTTACCT
GTTACTTCTCTCTGGAATTCCCTGCCCCTTCTTAATTTTTCTGGCCAATTCTCACTCTCTAG
GACTCAGAGGTTTCTCCTCAGGAGACTTCCATGAGTCTCATGTTGAGTTAGGTGACCCCAAT
CCTCTGTTCTTCATAGTCATTCGCGCATTTATCTAGCTCAGCATTTGCCATACTACATTGAA
ATTATTTCCTTATGTGCCCATCACTCCCCGTAGATTGCAAACTCCTAGAGAAGGGCTCAACA
GTGAGTGCTGAGGCTGCACAGAGGAGGAAGGCAGCACAATGATGGAAGGCTTCCTAAAGAGG
TATGTTCCAAGAGCCCCCACTTCCTTTCATGGGAGACTCATGCTGTTACACCTAGACTATCT
AGGGATACATCTAATGTAGTCGTGGAAAGAACAGAGGACTTGAGTACTAGACTGACGTGATT
TTGAATCCTGGCTCCCTATTGACCAGATGTGTGTCTTGAACAAGTCCCTGAGCCTCAGTGTC
TTCATCTGCACAGTGAGGATAATGATACCACACTGCATATATGAGGTATCCGGCACATGTAA
ATGTCCACTACATGCTGATTTCTTCACCCGCTACTCACCCCTGGGAAAGAAGTAGACTCACC
TACTCTTGGTACCCATTCATTCCCCCTCAGTTGGAAGCATGAGGTGTGCAGCTGCCTGACCT
GGGGGAAGGGCTGCAAGCAGTAGGTGTTGTCAGATGTGGTGGAGCTTGTTGACTTCCTCCCA
GGGGCCCAGCTAACAACCTGCCTCTGTTCCTTGATAGTCAAGTTCAACTTTCACTTCTTAGC
ACCACAGGAAGTTGACTGAACATTAACTGAAGTCTCTCTCAAACAGGAGACATCTTTGCCAG
GTCCCTGTACTTCCTAGCCTCATTCCTGCTCTCCCTAGTGAGCAGGCTGCCCTCCCTTCTCG
CCCCAGCACCACTGATAGGCAAGGGTACTCAGAACTACTACCTTGTGGGCCATGTCATGTGC
CAGGAGCTGCACCCAGGACTTTAATACAGTAGTTGGCTCCCACTGAATGTTCATTGTTACCC
CAGGATAAAAAGGGGACACTGTGATCATTTTCTATTTTGCTGTGATCAGGCTTGGTGAGCTA
AAGTCACCTACCTTCCCAGTCTCTACTAATAGAAGTCATGGATCAGTCCTATTGGTTCTTCT
GTTACAAGGATTCAGAATTCATAATCATGGAGCTGCATTTACAGGCAGAAGTTTCTTTCATA
GTTTTCTAAGTGTTCCTTTTAGCAACAATGGAGAAAATCAAAGAGGGCAAAGGTGAGGGGAG
```

-continued

```
AAAATAACATTTCCCTTTCTGTCCTTTGCTCTTGTAGTCTTTTGCTTTAGTTTCTTTACTAT
GACTGTGAGGGTGAAACTAGTGATCAGAGTGGTCCAGAATGGGTTTGATGAATCTGATTCTG
GTGACACAAGATGAATTGGGTATATGTTTCCCTAAAGATAGAGAGACAATATAACATAGTCT
TTACATTAATAGACTCTGGAGCCAATTTTTTTAGGTTCACTCTCTTTCCTTTCATGTGTGTT
GATTTTCAACAAACATCTTGCACTCGAATTCCATCTCACTGTTTTATTTTCAAAAAATTTAA
TTTGAGAAAGTTAGCTGTATTAATTTTTTCTTTTTCTAAAATTCTTTTACTAATTGCAATTA
TTTCCATTGATGCTATTCCATTGAAACCATTTTAACATGGACTCAATAACTTCATTGTATGT
TAATGTTTAATTTTCATTTCTTTACCTTCTTGGTTTTCTAGCTGTGTTTAATGTGGTTGACC
ACTCATTCTTTGAAGCTCTATTCCTCTGGCTACTACAGTATGACACATTTTGTCTCCTTCTT
CAGTCTCTGTCTTCTCCACAGTCTTCTCTTCCTTTTATATACCTTTAAATATTAATGTTTCC
CAGAGATATTTTCTTAACTCACTTCTCTACTGATTCTAGGTACTTTTCTTGATCCAACTCTT
CTGATTTTACCCATCTCGATGATTCTATAATTTGTATTTTCTGTTTTGATCTCTTTTCAGTC
TTCCAGACCTAAATATCCAAATGCCTGATGGATAGTGCTTTCTTTTTTACTACCAAGCCCTC
AAAGGCACTATGTTCAAAAGGAATTTGTCATCAGTCTCACGGCACATAAGCTTCCTCTTGTG
TTCAATCTGGAGACTTGAGAGTCTTCCTGTTCCCTTCTTCTCCTTATTTTCTCCATAATCAA
TCACAAAGTCATGTGGATTTTGCTCCTAAATATGTTAACTTCTTTCCTCTCTCACTTTATAT
CCCTTACATCTAGGTATTTCAGACCCTCAGTCTCTCTCACATAGACTTTGGCAATAACCTTC
TAATATCAGTCAACCTGACCAATAGGCCACCAGTGCTTCATGTAGAATCTGGACAATGTAGA
GCACTGAGAATGCTCACACTGGTCATATATGTATGAGTTGGTATGACATCTAGGGAAGTTGA
AGACTTACATAGCCTTTGGCCCAGCAATATACACCATAATACATTAGAGAAACTCTAGCATG
TGTACACAGTGATATACACACAAGAATGTTCACAATGCCATTATTTTAATAGCAAAATTGTG
GAAACAACACAAATGTTTATCAATAACAGAATGGATAAGTGAGCCATGGCATAGTCATACAA
TGAAAAATAATATAATAGTCAAATGAATGATCTGAAGAGATATCATTATTGGCAATCTTAT
AAAAGACTGAGTTAAAAATGCAATTTGTGAAAATTTTTAATTATTTGATATTATTTAATGCA
AAGTTTTAGAACATGCAAACAACTGTATATATTATTTATGTATATATGCAAATTCAGCAATA
GCATTTAATCATGCCTGGGAATGATAAGTATCAAAGTCAGAAAGTGGTTACCCTTGGGAAGA
GAGGTATGTATCAGCGGTGGGGCACATAGGATGTTGCAGCCATATCTGTAATGTTTCTTTGC
TTTAAAAAATTTGAATCAAGCTTGGCAAAGTGTGACATTTGATTAAGCAGGATAGTGAGTGC
ATATCTGTTACTTATATTGTTCTTTATAATTTTCTCTATGCTAAAGCATTTTGTAATTTAAA
AAACCTGACAGTGTTACTCCCATGCTTAAAATATGCCAGTGGTCAAACCAAATCCAGCAGCA
CATCAAAAAGCTTATCCACCATGATCAAGTGGGCTTCATCCCTGGGATGCAAGGCTGGTTCA
ATATAAGCAAATCAATAAATGTAATCCAGCATATAAACAGAACCAAAGACAAAAACCACATG
ATTATCTCAATAGATGCAGAAAAGGCCTTTGACAAAATTCAACAACTCTTCATGCCAAAAAC
TCTCAATAAATTAAGTATTGATGGGACGTATCTCAAAATAATAAGAGTTATCTATGAAAAAC
CCACAGCCAATATCATACTGAATGGGCAAAAACTGGAAGCATTCCCTTTGAAAACTGGCACA
AGACAGGGATGCCCTCTCTCACCACTCCTATTCAACATGGTGTTGGAAGTTCTGGCCAGGGC
AATTAGGCAGGAGAAGGAAATAAAGGGTATTCAATTAGGAAAAGAGGAAATCAAATTGTCCC
TGTTTGCAGATGACATGTATATCTAGAAAACCCCATTGTCTCAGCCCAAAATCTCCTTAAGC
TGATAAGCAACTTCAGCAAAGTCTCAGGATATAAAAATCAATGTACAAAAATCAGAAGCATT
CTTATACACCAACAACAGACAAACAGAGAGCCAAATCATGAGTGAACTCCCATTCACAATTG
CTTCAAAGAGAATAAAATACCTAGGAATCCAACTTACAAGGGACATGAAGGAACTCTTCAAG
```

-continued

```
GAGAACTACAAACCACTGCTCAATGAAATAAAAGAGGATACAAACAAATGGAAGAACATTCC

ATGCTCATGGGTAGGAAGAATCAATATCGTGAAAATGGCCATACTGCCCAAGGTAATTTATA

GATTCAATGCCATCCCCATCAAGCTACCAATGACTTTCTTCACAGAATTGGAAAAAACTGCT

TTAAAGTTCATATGGCACCAAAAAAGAGCCCGCATCACCAAGTCAATCCTAAGCCAAAAGAA

CAAAGCTGGAGGCATCACACTACCTGACTTCAAACTATACTACAAGGCTACAGTAACCCAAA

CAGCATGGTACTGGTACCAAAACAGAGATATAGATCAATGGAACAGAACAGAGCCCTCAGAA

ATAACGCCACATATCTACAACTCTCTGATCTTTGACAAACCTGAGAAAAACAAGCAATGGGG

AAAGGATTCCCTATTTAATAAATGGTGCTGGGAAAACTGGCTAGCCATATGGAGAAAGCTGA

AACTGGATCCCTTCCTTACACCTTATACAAAAATTAATTCAAGATGGATTAAAGACTTAAAT

GTTAGACCTAAAACCATAAAAACCCTAGAAGAAAACCTAGGCATTACCATTCAGGACATAGG

CATGGGCAAGGACTTCATGTCTAAAACACCAAAAGCAATGGCAACAAAAGACAAAATTGACA

AAGGGGATCTAATTAAACTGAAGAGCTTCTGCACAGCAAAAGAAACTACCATCAGAGTGAAC

AGGCAACCTACAAAATGGGAGAAAATTTTCACAACCTACTCATCTGACAAAGGGCTAATATC

CAGAATCTACAATGAACTCAAACAAATTTACAAGAAAAAAACAAACAACCCCATCAAAAAGT

GGGCAAAGGACATGAACAGACACTTCTCAAAAGAAGACATTTATGCAGCCAAAAAACACATG

AAAAAATGCTCATCATCACTGGCCATCAGAGAAATGCAAATCAAAACCACAATGAGATACCA

TCTCACACCAGTTAGAATGGCAATCATTAAAAAGTCAGGAAACAACAGGTGCTCGAGAGGAT

GTGGAGAAATAGGAACACTTTTACACTGTTAGTGGGACTGTAAACTAGTTCAACCATTGTGG

AAGTCAGTGTGGCGATTCCTCAGGGATCTAGAACTAGAAATACCATTTGACCCAGCCATCCC

ATTACTGGGTATATACCCAAAGGACTATAAATCATGCTGCTATAAAGACACATGCATACGTA

TGTTTATTGTGGCACTATTCACAATAGCAAAGACTTGGAACCAAGCCAAATGTCCAACAATG

ATAGACTGGATTAAGAGAATGTGGCACATATACACCATGGAATACTATGCAGCCATAAAAAA

TGATGAGTTCATGTCCTTTGTAGGGACATGGATGAAATTGGAAATCATCATTCTCAGTAAAC

TATCGCAAGGACAAAAACCAAACACCGCATGTTCTCACTCATAGGTGGGAACTGAACAATGA

AAACACATGGACACAGGAAGGGGAACATCACACTCTGGGGACTGTTGTGGGGTGGGGGAGG

GGGGAGGGATAGCATTAGGAGATATACCTAATGCTAAATGATGAGTTAATGGGTGCAGCACA

CCAGCATGGCACACGTATACATATGTAACTAACCTGCACATTGTGCACATGTACCCTAAAAC

TTAAAGTATAATAATAATTAAAAAAACCAATAGTTTATGAAACCCCCCCCAAAAAAAATATA

TGCCAGTGGCCTCCAGTTGCCCACCAGGTAGCATCCACATTCTTTAATGGAAAGCCCTTCCT

TGCTTCGAACTTGCCAACTGGGATTGGACATTTGTAGTTGCATTTCTAAGAACTGTTCCCTT

TTGTCAATGGAGCCTGATTTCCACTTGGATATCTGGGTGATTTAGGGAAACTGACCTCAAAA

CCCAATTCTACATTTCGACCATGTGACCTTGGCTTAATCAATTCACGCATCTTTTTCCCTCA

CCTCAGGGGATGATCATATGAACTAAGCCAGTTGCAATAGAGTAAACCTCATGTTCCTAATG

AGAAATCCAGAACAAAATGCTTTATTTTTCTTCAATTTTTTATTAGGTCATCTCCTGAATCA

ATTAAAAAAAAAACCAACAGTGACAACAAAACTAAAAAATATGAAGAAGCTGAAACATGAAA

GCTCTGCCAACTGCAATATGTAGCTGCTAAGGTTGCTGTATTTATTGGAATCAAGCAAGTGT

TCCAGTAAAGAGCACAGAAGATGTGTCTGGGAGCCTTTATGTGTAGGTCTGCAAGTGGTGGA

TATCACTACTACTCACACGCCATTGGCTAGAACTGAGTTGCATGGATACACCTAATTGTAAA

AGAGGCTGGGAAATAGAGACTATTGTGCCCAGAAAGAAGAGAAAATTCATTTATGGAAGAGG

TAGCTAGTCTCTCACAGCCATGAAAAGAGAAGTGTTTAGCTAATTGAAGTGAATAGCAGCCA
```

-continued

```
TCTTGGGTCCCTAAGGCAAGTTAGACTAATATTGAAGTGGAAACCATGAGGAAAGCAGTGAT

ACTGAAAGTAACCGCATCTTTGAGAACATGCATTCATTTCCTACAACATGAATTTATTGAGG

ACCTACCTTAATACAGGCAGCGTGCTAGACACCAAGAGAACTGATGTCCTCTTCCTTCCTGC

CTGCCTGGAGCCTGTATTCTGGAGGGGACAGAGCTAGCAGATCAGACCTAACTGGAAATCTG

CTGTGCCAGTATATATTTCAGTGATGTGAGCCAATATATCCCCTTGATTGCTCAAAGTAGTT

TGGTCGATATATTTTGTTGCTTTAAATTGAACACATTCTTATGTACAGCCTCTGTCTCCTCA

TCTCCAACCAAGCAAAATAGCTTGTTCTCTTTATGCAGGGACACATGACATTTCCCACGTGG

CTTTGTGCATATCTCCACCTCAATTTAAAATGCCTTCCAATCCCTGCTCAAAGTCAAACAGC

TTAATAATGGTAGACATAGAATTTGACTTATTCTAATAATAGGTCTTTTAAACAATGCCTTC

TTCTCTTCATTCTTTCCTTCTTAGAGTGGGTATTCTTTCTGGTGCATCATGTAAAGGAAGGT

AACTACATGCATGTAATGATGAGAATATTTATATGTATTTATGATTATCACAAAAAAACAAA

GATTCTACCATTCAAGAGGAACATTTATTTTATTTTTTATTTGAGAAAAGTATAATTTTAT

TTATTTATTTATTTGTGCAAATTTATGGGGTACTTGAGAAAATGTGTTACATGTATATAATG

TGTAGTGATCCAATCAGGATACTAAGGGTGTCCATCACCTGAGTGTATTACATTTTTGTTAA

GTATAATCATCCTACTCCAGGAGAACATTTTAAAAACTGTTCTGTAGAGATACTACTCAAAT

TAAGTTCTCAGTCCTGAAACATCAGATCAGCTAGGAATCTGACAAAAATGCAAGTTCTCAGA

TGACAGATGAGACCACTTCAATCAGAATTTCTGGAGTGGAGCCCACACATTTGTATTTTTGC

AACCTTTCCAATGATACTTATGTACATGCTCAAGCTTGAAAACCACTTTCCTAGGACATTAG

TTCCTCGACAAGATTTGTGAGTAACCTTGTTTCATGAAAAAGTGTTTAGGAGATACTGATTC

AATAAAAACTAATCAGGCTTTTATTGTTTGCAGGGCTTTCAAAACTTGCAATAGGCCACTGT

GCATTGTTAATTTCTAAGAGGAAGATGCTTATGTCCTCAATGAATATCTTCCCACCATGAAG

TACTCTTCTTCCCCCACTTTTTAAAACAATTACTAACACCTGGCAGAAGTAGGCAGACAGCT

TACAGCTTAGAAAAAGTTGGCCTAAGATAATGGCTAATTTTCATACATTATTTATTTGTCAT

CATGCTTATCTTTCTCTCTAAATTGTATATTTCATCTCTGTGATCACAGATTGAGCCTCA

TATTTCATATCTGCCCCTGGCCTAATGGTTGTTTACAGAATGAGCTCAATGAATATTGTTAA

GTGAGTAGGATTTAATTTATTTGATAAATAGATAACCTTAAGTTTTAAACGGTGGATTTCAC

ATGAGGACATTTACTTACTATTGTTGAGCTGTAATTAATTTTTAATACTGTTTAGGTACTCA

TAATAAAGAACAGGATATTTGGAGAAGGAAGACAGTATCATTCCTGGTTCTTAGTCTTACCA

GCTTATTGATCATGAGTATATAACCTCTCTGTGGCTCAGTGCCTTTCTCTGTAAAATGGGAA

CACAGTGATGTTCACCTCACAGGATTGATTTGTAAAAGGGCTGGATAAGGTTATGAGAATGT

TTTGCAAAGTGATATCGAAAGATTAATTGCAAACTTCATTTGAATCTTAAATTGTTTGAGAT

AGGTCATGCTATGAATCAACTATGAAGTGCAGATATTGTCAAGATTCAATATTTCTTTCCCA

AGAGCTGAGAGGAGGGGCTGCTTGTTTGTTTGTTTCTTTCTTTTTAGAAACATGCCAGGACA

GGCTCATTTTCGGGTTTTCCTCTCACTTGCTCATCTTACTTTTTCTTTAGTTTCTCTATTCA

TTAGGATACAGTACTGTAAAGCTTTATGGCATTTTTATTTTGTGGGAGATGAATCTGAATAA

AGAATTACAGTTAAATCATTGCTAAGTTTGATGAATGAGCACCAAAGAACTCTTCAAGATGT

CATTTTTAAAGTTTTGTAAATGATTGGCTTTCAGTGGTTTCCTCTAAGGAATTTTAATTTTG

AATAATGCATAGAAAAATGTGCGCACACACAAATCATTCAGTATCCACCTCGAAGGGAAATC

AAAGTGCCTGTGAAGTGAAACTTTACCTTTCTATATCACCAGCTTCCTGTTAGAGCAGACTT

TTTCTTTGCTCAAAGTCTAAGCATTGAAGAACTTCTTTTTAGTAGGTAGATTTTTGTGTTTT

TTTGTTTGTTTTTGAGACGGAGTCTCACTCTGTCGCCCAGGCTGTGGTGCAGTGGCACGATC
```

```
TCGGCCCACTGCAAGCTCTGCCTCCCGGGTTCACACCATTCTCCTGCCTCAGCCTCCCAAGT

AGCTGGGACTACAGGTGCCAGCCACCACGCCTGGCTAATTTTTTGCATTTTTTAGTAGAGA

TGGGGTTTCATCGTGTTAGCCAGGATGGTCTTGATCTCCTGACCTCATGATCCACCCGCCTT

GGCCTGCCAGAGTGCTGGAATTACAGGCGTGATTTAGTAGGTAGTTTTGAGTAGGGAGTATA

CATTTAAAATGCTGAAACTCAGTTAAGGAATAATCTAATACTGTATTCAACTGAAACTCAGT

TGAGAAATTTCTTTCCAATAATAAAGGAAAATCAACTGCAGTAATGAGGGAGATGATTTTGC

TGCTAATTACAACAAATATTTACTACAGACCTGTTATGCACCAGGAACTGTGCTAAATGTTT

TATACATATAACTTTATCTTGTGCTCCAACAACTTATTACATAGAAATTGCTATTATTCCCA

TTTTCTAGATTAATAAATTGGTTTAGAGGGGTCGTATAGGTGAAACAACTCACTCAATATCA

CAAGCTGTTATGTGGTGAAGTTTGCATGATCAGTACAGGGTTCTGGTCATCCCACTCATTGA

GTGGTGCTAGTCAAGATCTGGAAGCTCTTCTGGTCTTAGTTTCTCTAGCCGTGAAGTGACAA

TGATTAGGTCTAATCATAGAACATGAGAGTACATGTGAAAAAATGCCTTTTTAAAGAGTATG

AAAAACTTGAGTTGTAAAATTTTCTTGTGGATAATTTATTATTGCTTTTCTTTTTTAGATAA

CACTAACAAAGTTGACCTTAGAATTGGAGTGCCTGGGTTAGAACCCTGCTGGTACCACCTGC

TTACTGGCATGCTTCTGATGTGAGTTCAGGAGAAGACACTGGCAAGGACAGCAAAGAACAGG

AGAACACTCTAGCTTCCCTGATAGCATTCAAGGTGCTGTCCAAAGCTGACTGTGATGGCACC

CTCCAGACAGACAGCGATGCCACATGTTCAAGATGGCAGAATCACTATCAGCTTCAATTCCT

GAATGACTGCAGAGCAAAATTTCTTACCTGCAACATACACTCTATTTTCAGCCTCCCTGGAC

TGTTACATAATGATACATAAAAATATTTCTTGTGTTGAGGCATCCCAAATTTGATTTATTTG

TCATCACAGTCTATCCTATGAATATATTTCTGATCCAAATAATGCTAGATTCATGAGAGTTT

ATAGTCCAGAGATTTTTTTTTTTTTGAGACAGAATCTGTCTCCCAGGCTGGGGTGCAGT

GGCATAATCTTAGCTCACTGCAACCTCTGCCTCCCGGGCTCAAGTGATCCTCCCTCCTTAGC

CTCCATGAGTAGCTGGGACCACAGGTGTGCACCACCACACCCCGCTAATTATTTTGTATTTT

TTGCAGAGGGGGTTTCACCACATTGCCCAAGCTGGTCTCAAACTCCTAGACTTAAGGGATC

TGCCTGCCTTGGCCTCCCAAAATGCTGAAATTACACTTGTTAGCCATAGTAATAGTTCCTAG

CCATAGTCCGGAGATATTTTAAAAACTTTAGTGTGAGTTATTTCTCTTTGCTATAATTCTCT

CATGCATTTTGAAAACCTTTTCTGCCATACAGTGGTTTTTGGGAAGTCCTTTTGGACAGACA

TATCACAGGATGGAGAAACTAAAAAGAGAGAATGCATTAAAGAAAAAATAGTACTTCGTATT

TCAGAAATTACAAAAGGGTGTCATGCCCCACAGCATGGTGGGCAGTCATTTGTAACCCACAG

AACATTGAGTTTCTAAAATTTGAGTGTTTTTAACTTACGAAGGCCAACTTTACTGATGAAGT

GATTACCCCAAATATGTGAAATCCATATTTCAAGTACAATAGTAGGAAATTGGAAATGGGGC

TCTTGAGTTTCTGCTTTCAAGTGACCCTCAGAAATTCCTCCATTCACTGCAGAGGTTCTGTT

TCTCCTTGCTTTGTTCTGACTTTACGGCAGAACTAAGCTAATGAGTTAGTTACTATGGGTTA

TCACTTGGATTTGAAGAACCATCATTTCTAGGCATTGCTGCTCAGAGTGGGGTCTGCCCTCA

GGGGAAGCTGTCTAACCAGAGCCTAACCCACTAGGGTTTTATCAGAACCTAACTGACCTGAG

GAAAAGAAATACTCAACTCCAGCAAGCTCCAGCCTTCCAAATGGAGGAGGAGAAAACCCAAC

TCCAGCCCACTTCAGCTATCTTGTCCCACATAAAGGGGAAGTGGAAGAAACCTGAGAAGCAG

GCATGAAGTTCACATGTATTCCACACCATTTCATATTCCATCGCATTCCATTCTACACAATT

CCACATCTCCCCGGCCACATCAGCCTGAGAGTAATAAACAGACCTTGCCATCGTATCCCCTT

TTGGAGACACAAGCCAGGAAGGAAGCTCTTCAGTGCAGCTGTGAATAGAGAAATGCTGGCTG
```

-continued

```
AGGTTTTGGAGACACTGGGTGATCATTCCCAGTGAAATTTTTAGATCCCTGGGGACATGAGC

TGCTTTGTCTTTTCCAAGGTCAGGATAAACAGAATAACTTCAGGCTTCTCTACCCAGAAAGA

ACATGTGGCATAAATATCAACTGCAGAATAAATATGATTAATCTGGTACATGGACGAAGATG

TTTTCTAGGAGATGCTTATCCTGGGATGAGAGCTTTCATAAGCATTGATATTTACATGACTC

TTACCGTGTGTCAGGAACTGTTCTAATTGTTTTACCTATGTCAATTCATTTGATAGTCACAA

CCACTGAAAGGAGTAAGTACTCTTATTACTTCCATTTTACAGATAGGGAAACTGAGGTATAG

AGAAGTCAAGTGACTTGCCCGAGGTTATTAAACTACTTAATGTCAACACCAGGATTTGAACC

CAGATCATTTGTTTCTGAAGTACATGCTCACAATCACTGCATTACTGATACACTGTTTTGTC

TTTGCATACTTAAGTGGTCATAACTTAGTCTGAAACACTTTGTGAGAGCAGGAAGCAAACTG

TCCCCTTATTAGGTGGACCAGTATAGTGATAATACAAAAGTGTATTGCATTTGAATTACTTG

CTAATATCTTCTAATTGAGGCAATTTTGAACAGGAATATACATATCTAGCCTCTATTTTTCT

AGCTAGAAGTTCTGAAATCCCTGGGCTTAATATTGTATGGCAACAATTGGCTGGAGTTGAGT

TGCTGCCACTCTCTTTTAACTGAGCCATGCTCTCTAGTTTGCTACAGGCCCCACCACTCC

CTATTGCCTCTCCAATACCAGGTCATTTGGCATCTTACTCAGCTCATTTCATGCACATGTGT

TCCACAATTGGTAACATAACCCTAAAAGTATTTGAGTTTGTGGCTTCTGCTCTTGTGACAGA

AGACTTTTCTCGAATTCCAAGGTCAACATATACCATATTGACTCTGGGCCACATTTTTTAAT

GTGCTCAAGCTCAGTTTTTCTCCTTAAAAAATGAGGGGTTAAAAATAACACTTCGTAGTTGC

CTCATCTGTGGATTGGAAGAATGAATGCCTGTCATTTCTAGAGTTGTAGTAAGGGCCAGTTG

GGGCAGTGCCTGTGAATATACGCAATGGGCCATCAAGCAATCTCAGGGCTTCAGGCAATGCT

GGGGTTTATAAAGCACTTTATGTTTTAAGTTCACTTTTATTTCTAAAGTCTCATTGACTGCT

CTGAAAATCTCTCAAGTAAAGTGGGCACTAAAGGCTTTATACTCTCTCCAATTATACCTTCC

ATTGTATAGATTTGGAAGCTGGGGTCCAAATGTGTTAAATGACTTGCCTAACATGGTCCATT

ACTGTAAGTACAGAAACGGAATGAGACCCCAAATCTGCTTCATGGAGGGACACTCTTCTAAG

ATACTGTGATGCTTCTTCCCAAGTAATTCCGTCTTCAGACTTCAAGGTCTCAATTCGAATGA

CAATTCAATATAGGACTTTCATAATCTTAAAAGCAACCTGACAGTCATTACAGTGGGCTGTG

AGAAATACTAACGCAGAGCCACATACTCTGGGCTTCATGCTAGGTTTTGCCACTCACTATCT

TTGCTGAAAAGTTTTGGAAGCCCTCCTAAGCAGGTGCCAGACCCTTTTTTGGCCAGAGGAC

AGGATCTTACGCTGTTGCCCAGGCTGGAGTGCAATAGTGTCATCATGGCTCACTGTAGCCTG

GAACTGCTGGGCTCAAGGGATCCTCCCAGCTCAGCCTCCCAAGTAGCTAGGAGTAAAGGTAC

ATGCCATCATGCCTAGCTTTTTTTTTTTTAATTTTTGGAGAGATAAGTTCCCATCATGTTG

CCCAGGCTGGTCTCTAACTCTTGGACTCAAGTGGTCCTCCCACATCAGCCTCTCAAAGTGCT

GAGATTGCAGGTGTTAGCCACTGCACTTGGCCTGGCCCCAGTATTCTTTGGGATCTGGAGTT

TGCTGTTGAATGAGAAGGCAAGATGAAATTCCATGTAGTCAGACTCCTACGCTGCTGTTCTA

AGCAGGGTTGGGCCTGATTAGTAGGTTATAGATGATGTTTTCTGTGGTGCTATCTGGACCT

AGTGCTCTTTGGCATCTGGGAAGGTATGGCCTTTAAAAAGCAAACTGCCATGAGAACTGCTC

TACCCCAAATTTTGGTTCACAGCCTTCATTTGATTATGTATTGGGCAAAAATAGTTTAGCC

ATGTGAACCTGTTTGTAAACTGGTGAGTTTCTATTGCTATTTCATAGCTAAAGTTTTGAGGT

AAATGCTATTGGATCTTTGTGTCTGTGTGTATACATATTTAGATTTTTTTTTTTTTTT

TTTTTGGTTCTTTGAAACATTGCTGATTCTTTTGTTTTGTTTTCAGAGTCTGGAGAACAC

TTTTTCTTTTGAGCTGTTTACAACCTTTAGCAATTGAGTAGAGTGTACTCTTGTCAATAGAA

TTTGAAGCACATTTCTCTCTCTGCCTGATTTCTGTAGAATTTGTAAACTATTTGTGAATATT
```

-continued

```
CTTAATTTATGGCAATATGGTTGCTTACATAAGTTCAATAATAATCTGTTTTCTTTTACAAT

GAGACACAGTTGGAGGAACTGGTTATTTTCCCAGGGCTTTGACTGAAATGGCCTTGTGAATG

GTTCCAGGAAAGCCAATTTTGGAGACCCTATGTGGATGATGATGCTTGCTGTACTTTCTGTG

GGTAATCGGGCCAAGTATATGGGACTGAAGCTAATTTTGCAGGGCAACATAGAGAGACTTGA

GTTCCAGGGGAAAGTTTTAGGATGGAGAGAAGCCCTCACTGGACTGTGATGTGGGTGAGA

AAATGGAGGTCCAGAGAGAAAAGTGACTCACCCAAGCTGAAAACAGTTGCAGGAAGAAAAGC

CAGGACAGAACTGGGCTGTTAGAAACCTTGGTAGTGCACTTTTGATTTCACTCTTAAAATGC

TCAAATGTCTTTTTCTGACAACATGTAGGGAGACCTGAGGTTGGACCTAAAGACACCATATA

TTGGATTCAGTGCTTCACACAAGTTAATCTAAATTATGAAGGAGTACACTAAAGATGAGGAA

CTGAGTCACCGCAATGCCAAATGTAACACGCTGTGGGTCAAAATTTGGATGGTTGCGTTGGA

AATTATTCTGAAGCCACAGACAGGGCTAAAAGGAGTCTAGAATGTCCTACTAGCTGTTGGAA

CCTGCTGGAGTTCTAAAGGCATGCGATGTCCTGAATGTGCTTGACCAATGGACACAGCAGGT

ATTTGAAGAGTTTTGATGCTTCCTTTCTGTTTTCAGTGCTATTTTTTGCTTTATTTCTTTT

AAAAAACTTTCCCCACAGAGGCTATTTATTACACAGCAGCAGCCAGCATGCACCAAGCAGAA

CTGCTTTTCATAATAAACCTATTTATCTTCTGGCATGTCAGAAATTTCTCAAATTGATACTT

ATAATAAATATGATTAATAACACATTGTATTTCAGTTGTTGCCGTAAAATAATTGGGAATAA

ATATCGTATTGTGATGTTGACAGTGTCAGGTTGGTTGGTGCCAAACAGCGGGAGCAGCCAAC

TGTATTTCATTAACAGCCACATTGCTACAATGCTATTAAGTTTTTCATAATCTCTTCTGCTC

AAGGTTGATCATTCATTCTGTTAGACAAATTCTTGCAACAATCACACTGGAAGTAAATCTGC

CAGCGACAATCTCAGCAAGATGGGTTCTCAC-5'

<128128655>

>CCAT1_JAX_3 Transcript sequence; Genomic location:
chr8:128152989-128231094 strand:-
<128231094>
                                              (SEQ ID NO: 3)
3'-

GTTGCACTGACCTGGCCAGCCCTGCCACTTACCAGGTTGGGGCTTTGACTGAAATGGCCTTG

TGAATGGTTCCAGGAAAGCCAATTTTGGAGACCCTATGTGGATGATGATGCTTGCTGTACTT

TCTGTGGGTAATCGGGCCAAGTATATGGGACTGAAGCTAATTTTGCAGGCAACATAGAGAGA

CTTGAGTTCCAGGGGAAAGTTTTAGGATGGAGAGAAGCCCTCACTGGACTGTGATGTGGGT

GAGAAAATGGAGGTCCAGAGAGAAAAGTGACTCACCCAAGCTGAAAACAGTTGCAGGAAGAA

AAGCCAGGACAGAACTGGGCTGTTAGAAACCTTGATGAAGGAGTACACTAAAGATGAGGAAC

TGAGTCACCGCAATGCCAAATGTAACACGCTGTGGGTCAAAATTTGGATGGTTGCGTTGGAA

ATTATICTGAAGCCACAGACAGGGCTAAAAG-5' <128152989>
```

>CCAT1_JAX_4 Transcript sequence; Genomic location:
chr8:128160497-128232653 strand:-
<128232653>
(SEQ ID NO: 4)
3'-

```
AAGGATTTAATGGCAAGATGCCATTATAGACAAGAACAGGATTCAGACACTTTCGTGTTATG

TGTTCTTGTCCAAATACTGTGTCACTCTGCACTGGCATCCCAATCCCACCAACACCTTTAGC

AGGAACTTCCTGTTTCAATAACATTTCTCAATACTCTACCTGATTGCTTAGAATCCATGAGA

CAGCCATATTCTCCATGTCTAGGTCCCTATCTTATTTTTGTTGAGATGGTGTTAAGACTTTA

TTTGTGAGGCTTCTGGGGAAGAGGAGTAAGGTATTGATCCCACTGACTGGATAATTTGGGTC
```

```
-continued
TCAAAATGGATAATAAATAAGCATTACATATTTTGACCACTTCCTTGGAGGAGAACTTCTTG

GAATGTGCACCATGTCCGCTGCACTTTTTTTGCACAGATATCTAAGTTGGAGAAACATACTA

CTAGATAAATCAATTTGTTCTCTTAGTACTCATGATATGGTTCCTGGGAACTTCTGATTCAC

CAAATTAATCTTGGCCAGGTACATACCTGGCAGGAATCCAAAAATTCCCCAAGTCTCCTTGA

AGTTCAGGATCATCATTCTTAATAAATACACCGAGGGAAAAACCATGGAGAGTTTGTCCCAG

ATGCTGTGAATCTGGCCCGGGGTACATGAAGAAGTCCTTAATTGCAGTCATTTACATGGTAG

ATTCTCTATAATCATTTAATTTGCTATAGGTCTATGATTTTTAGTCCTTCTTCTCTAAATGA

TTGAACATGTATAATTCCCATTTCAATCATATTACCTGGATGAACAAAAGTAACGCTAGACT

CATTCATGCATTCTGGTTGCCAAGGAAAAGGAAAAAAAACAAAACAATCAACAGGATGTTTA

AACTGTCTTAGGGCAACTTCAGGCCATAGTCACTGGTGTTCTTGCAGACTATGAGATATTTT

ACATTCTGATAAGGGATAAAAATTCGTGCCTCACATGGCTCCCATCACACTAAGATCTTGCA

ACAATAACACTACTGATTCAGACATTAATCTTAAGTATCCAGGGAGCCCTAAAACATTGTAT

CCCACTAGCAAGGACCATGGTAATTGCCACGTAAATCCCCTCCATTATGTGGCCCTTATTAT

GACCAGCCAGCCAAGGCTTGCCTTTAAATCATACCATTGAACCGAGCCTTGTAGAAACACTA

TCACCTACGCATACCTCTGCTTCTTTTCATTAACCTGCTATCCTCTTTACAAATGGGATTCT

TCACCCACTCCCTTCTTCTAGATTAGCAATGCCCTGTTAAGTAAACGAACACGAAATTCAAA

GGGAAACAGGAGCAATCATCATTACCAGCTGCCGTGTTAAGCATTGCGAAAACGCTCACGAT

TCACAGAAAAATCCATGCTGTTCTTTGAAGGCATTCAAGCCTTAATAGCTAGCTGGATGAAT

GTTTAACTTCTAGGCCAGGCACTACTCTGTCCCAACAATAAGCCCTGTACATTGGGAAAGGT

GCCGAGACATGAACTTTGGTCTTCTCTGCAATCCATCTGGAGCATTCACTGACAACATCGAC

TTTGAAGTTGCACTGACCTGGCCAGCCCTGCCACTTACCAGGTTGGGCTGTGGCTTGCCTTT

TCACTTCTTGTGTCCTGTTTAAGAAATATCTGCTATCCCAAGGTAAGATACTATACTTTTTT

TAACATGTTATTTTGTTTTACCTTTCACATTTGGTGTATACTACATTTGTAATTAATTTGTC

CATATTATATGACATATAGCCAAGATTTATTTTTTACCATACAGATACTCAATATTGCCATT

TACGTAGAACATCGTTCTCTTCCTACTCAATTGCCTTGGCACCTTTGTAATAAATCAGATGA

TCGTGTATGTGTAGTTCAGTTTCTGGACTCTGTCTTCTGTTTCTTTAGTCTATTTGCCTATT

CTTGTACCAATATGCACTGTGTTAATAATCGTAGCTTTGTAGTAGGTCTCGAAATCTGACAG

TGTAATTCTTTTAGTTTCTTTCTTCTGCAAATTTTCTTTAGCTGTTTTACGTCCTTTGCATT

TGTATATAAACTTCAGAATCAGCTTGTCTATTCCAAAAACAACAACAACAAATGAAAGTTTC

AGAAACTTTAACTGAAATTGTATTGAATCTGTAGACAATTTTGGAGTAAATTGCATCTTAGC

AATGTAGAGTCTTTCGAACCATAACCATGGTAAGTCTCTCCATTTGCTTAAATCTTCTTTAA

TTTATTTCAACAATGGCTTCCAATTTCCAGCGGGAGCTCTTGGAAACTACAATTTACATGAA

CTTCTAATTTGATATTTTTCGGTGTCATTATAAACATTGTTGTTTTAAAAGTTGTCTTCAAT

TTTTTGTTGTCAGGCACAGAAATACAATTATTGATAACATTTATATATAAACTGTATCCAGT

GATCTTGCTAGATTCACTGATGAGTCTGATGTTGTAGATTCTTTGGGATTTTCTCCGTACAT

AATCATATCCTTTCTGAATAAGATAGTTTTACTTCTTCATTTTTAATATCTATGCCTTTTAT

TTATTTTTCTTTTGAACTTTTTGCTGACTTCATTATTCACTCTCATGTTTTTCTCTTTCATT

AGACTATGACTCCTCGATGGTAGCAATTTGTAGTAATCAAATTTTTGTATTTTATTTTAGCA

TCTGGCATCTTTCTTGACATATGTAGCAGTTGCTTTTTGACAGCTTGCTTCTTCAGTGAATG

AATAAATTAATAAAGAGAAATGTGATGTTCAGTGATCCATTTTGCAGGTAAGAAAACTGAGG

CAGACAGAGGATGTTAGCAAGCAAGAGGCCTTGGCCTACAATTTAGATCACTGGACTCTTAC
```

```
TCCAGATGCAATCTGCAGAACCCACATACTTTTAATTAGTCCCTTTGTCTATGTTCTGCCAC

TGTCACTTCTAAGGAAGGTGTGTCATCCCAAATGGGGTAGTATCTTATTGGTAGACCTAAAT

CTGCTGTGTTCGCCATCTCACCTACATGAGTATCTATGTGTAGCATTCTGCATATTCATCTT

TTCCACCTTCTGGAGGTTTTGTCTTTTTATAGGCAGCATGTGAATAACAATGGGGCCAAACT

GGGGACCAGAAGGGGCCATTTTCTAGTTCTGAACATAGATAAGCATCACTAACTTTTCCCTC

CTGGCAGTAATGGCCTCAAAAGTTCCAACTTAGGAGAAAAAGGCAAAACCGTCTGCCAAAGT

GTGTGAAAAGTTAGAGCAAACCTTGGTTTTACCAAGAACCTGTGTCCCTCTTATGGAAATTC

ACACTTTCACACTTTTAGACAAATATTAAATGTGTGACATTCTATTACGTACAGTGCCTGGC

ACATCTAGACACGCAGCACACTTTAGCCCCCTTCTTTCTTCTTCTAACTCCAAGTTCTAAAC

TAGAAAAAGCCCCACTTGAGTCTGAGATTTGCTTTTTGAACTAGTTTATTTCAGATTGTAAT

CATGCTATCTAGGGTTGTGACAGTGTTTGCTATTTCTAGGGCACTTTGACCTGATTCTTTTT

GCACAGGAAACTTGTTCTACCCTTTTGCCCACTTCACTGAAGTGAGGACTGAGACAGAGAAG

GATTAAGTCACTTTTTATTTAACAAATATTTGTTCCACATTCCTCAGCATTTATTAAATACT

GGTGCATAATGATGGAATAAATTTTATACCGTAAGGATAAACCAGTATTCTGGACTAAGCCA

ACGTGGGAGACCCTAGGAGGCCTGTTTGAGAAAGTGACATTTAAATTGAGACTTGGCGGTGG

CTGTGGCTACATATCTAGTAAGTGGCTGGGTTGGGATTTGAACTCATGCCTGCTTAGCTCTA

AAGATGATGCTTTTGGCTTTGTACTCTGCTCTCTCTAGACAAACTCTGGTCCAAAATCGT

TAAAGCTAACATTTATCCCTGCCCAACTGGAATTGTCATGTTATGACAAATGGCTCTGTGGT

CTCAGATGCCCAGCAGACCCATTAGTGGAATTCTATGTGCTACAGACCTGGGCAAAATGCCA

GAGCCTTATACACCCATCACATTTCGTCTGGCAAAGGTCTTCAACAAAGAGAAGTAATTACA

GCAATGAAAAGCAACAGGTCCAGCAACACCATAAGAACAAAATAATTAATTTCCCTAAAATA

GAAGAAACCATTTATAGAGTAAGAGCCGATACAATCAATAATTGGAAGAAATAGAAGAGGCT

TTAGTATTCTAGCCTTCTTTATTTGTAGATGTAAATGTCGAGCCTCAGAGAAGTTATATATC

TAATTAGTGTCACTCAGGTAGATAACAACAGAATTAGGATTAGAACTTAATTCTTATGACTC

CCAGAGCAGGGAAAAGACAGGATGAAGTCCCAAAACATTGCGTGTGAACTCACATCTGACTC

TGAATTGAGAGTCTGCTATTTACTCCCTATGTGACCAGAATCCTTCAGAGCCCATGAGATTC

CCTGTCATAGAGTAGATTTTGATCCACACTAGGCATTTTTACCTCTTGCTCTTTGAGTTGGT

GCCCCATGTTTACTCAGAAATATTCCAAAGGTGTTACATCTATTGGTTTTACATGTTGAGCA

CAGATCATTATAAGACAAATTGAAATGAAAACATCAACAAGTCTCATTCATTGTCTAACTTA

CGCTGAGCAATATTTAATAACTAGAATATCAAGAGAGTCCAAAGTGTTTGCCCATCCCCTCA

AGACCAATGTAATGGAATTTTACTCTTATCACCTGCTCAGGGTAGTGGCAATTCAGGATACA

GAGGACAGAAATAAAGAATCATGACACACAATCCACAGAATTCACAGATGCCAAACATCTAC

CCTTCTCTGTCACCACACATTGGACTCACATGGTGGAAATAGGCAACACAAGCAGAGAGGTG

GCTTAACCTTTCATAATTTTTCAACGACCTATGGGAAGAGAGTTTTCTTGGTTCAAATCCCA

GCTTAGCCACACAGAGTGTGGTAATATTGGGCAAGTCAACCAAGCTCTCTGTGCTTCAGTTT

CCTCATTATTAAAATGGGGGAAATAATAGTGCCTGCATCAGAGGGTTGTTGTGAGAACTAAA

CGAAATAATTTATCTGAGCTTTAGAACCCACACCATATTAGTTAAAAATTCATGCATTTTCT

TTTATTATATTTCTCTACCTTAGACTGCAAACTCTAAGAGGAAAGGCCGGACTGTTATATTC

ATAAAGCATTACAGGAACAGTAATTAGAACTAGGAGCTTTTCAATGGCCTGCCTGAAATCTG

AAAAATAGGTATATTATTTGAAATTTTGAAAAAATCAAATAATTAAAAATTAATAGATGTTA
```

-continued

```
ATAAAATATCTGTAATATGTAATATCAAGGTCAACTCAACTCTTAATTGTTTATATAAAATA
TAGTGAAGTTTAAATTGCAAAATCTTACAGAAAATGTGCTATTAAAACTCAAAAGTATAATT
CTTTCTAATATGTATATATGTATATAGTTTTATTTTAAGTTCAGGGGCACATGTGCAAGT
TTGTTACCTAGGGAAACTCACGTCACAGGACTTTGTTATACAGATACTTTCATCACCCAGGT
ATTAAGCCTAGTGCTCATTAGTTATTTTTCCTGATCCTCTCCCTCCTCCCAACCTCCACCCT
CAGGTAGGCCTCAGTATCTCTTGTTCCCCTCTATGTGTTCATGAGTTCTTATCATTTAGCTC
CCACTTACAAGTGAGAACATGTGGCATTTGGTTTTCTGTTCCTGCCTTAGTTTGCTAAGGAA
AGCACTGTGGCAATTTCTCAAAGGACTAAAAACGGAATTACCATTCAACCCAGCAATCCCAT
TACTAGTTACGTACTCAAATATTTTTAAGGCAAAACAAAGCTGCAACCAGAACACCTGGACT
CCCTGAAACCCCTTCCACTGATGTTGTTGTTGTTGTTTCTTTTTCCCCAGCTTCTCAGGCCA
AAATACTGGATCATCTTGGGCACTGTTCTCTCCTGCCCACCCTTTCCCATATGCAGAGTGTT
GTCACTTCTCTCTGCTTCCACTGCTAACTCCCTGGTCCAAGCCGCTGCACCACTTTTCGTGA
TTATTGCCACAGTCTCCTCACTGGTTCCCTGCCCCCACTCTTGCTCTGAACTATCCAGTTAA
AACCTGAATTAGATCATCTCATCCTCATCTCAGAGCTTTCTCGTGGCTCCTCTGCCCTCTCA
GGAAAAAATCTAAATTCTAGATGACCTAAAAATCCCTTGTCTCTTACTGTTTATCTGACCTC
ATTTACTACCACCTTTTTCTTTGATCATTCTGTTCCAGCCACACTGGCCTCCTTACCACTCC
TCAAATATGCCAAGCACAGCCCCCACCCCCCAGGGCTTTGAACTGGCTGATCCCCCTTCCTG
GAATGCCTTACCCCAAATATCAACTTAGCCAACTCCCTCCTCTCCTCCAAGTGTCTGTTTAA
ACATGGCTTCAGTAGGAGCTGTCTTAACATCCTATTAATATTGTAATTCCTCTCATGACACT
TTACACCCCCTTCCCTGATATGCTTTCCATATACCATGCAATATCTGCTGAGATAATATATA
ATTCACTTATTTTCTTTATTGTCATTTCAAAGAGGGCGGTGTGTTCTGTGTTTTATTTAGTG
CCAAAATACTTGCTGATGAAGAGAGTTCCTGCCACATAGTAGGTGCTCAATATGTGCTTGTT
GAATAAATGTGTCAATGTTTGATGTACAGACCTTTTATTATGTTTGATTTGCTGCCAGTGCT
GCCTCCAAACACAGGAGTGCTTCATGAGATGTTCACAAAAGCTCTTAAAATATTCCACAAAA
ATCTTAAAATATTTCATGAGTTTTCTTTCCTGTATTTTTATAGCAGCATCTGGAATTTAGCC
TGCATAGGACCCTCTGTAAGCTGACCCTGTTTATCTATTCAGCTTTACTTCTCCCCTCTCTC
CACTTTGTATTTTATTCTCTACTACTTCCAACTGATTGTAATTTGACCAGACTCCAGACTAT
CTTATGCCTCTTTGCTTTTGTTTACCTGTTACTTCTCTCTGGAATTCCCTGCCCCTTCTTAA
TTTTTCTGGCCAATTCTCACTCTCTAGGACTCAGAGGTTTCTCCTCAGGAGACTTCCATGAG
TCTCATGTTGAGTTAGGTGACCCCAATCCTCTGTTCTTCATAGTCATTCGCGCATTTATCTA
GCTCAGCATTTGCCATACTACATTGAAATTATTTCCTTATGTGCCCATCACTCCCCGTAGAT
TGCAAACTCCTAGAGAAGGGCTCAACAGTGAGTGCTGAGGCTGCACAGAGGAGGAAGGCAGC
ACAATGATGGAAGGCTTCCTAAAGAGGCTGAAAAAGTTTTGGAAGCCCTCCTAAGCAGGTGC
CAGACCCTTTTTGGCCAGAGACAGGATCTTACGCTGTTGCCCAGGCTGGAGTGCAATAGTG
TCATCATGGCTCACTGTAGCCTGGAACTGCTGGGCTCAAGGGATCCTCCCAGCTCAGCCTCC
CAAGTAGCTAGGAGTAAAGGTACATGCCATCATGCCTAGCTTTTTTTTTTTTAATTTTTGG
AGAGATAAGTTCCCATCATGTTGCCCAGGCTGGTCTCTAACTCTTGGACTCAAGTGGTCCTC
CCACATCAGCCTCTCAAAGTGCTGAGATTGCAGGTGTTAGCCACTGCACTTGGCCTGGCCCC
AGTATTCTTTGGGATCTGGAGTTTGCTGTTGAATGAGAAGGCAAGATGAAATTCCATGTAGT
CAGACTCCTACGCTGCTGTTCTAAGCAGGGTTGGGCCTGATTAGTAGGTTATAGATGATGTT
TTTCTGTGGTGCTATCTGGACCTAGTGCTCTTTGGCATCTGGGAAGGTATGGCCTTTAAAAA
```

GCAAACTGCCATGAGAACTGCTCTACCCCAAATTTTGGTTCACAGCCTTCATTTGATTATGT

ATTGGGGCAAAAATAGTTTAGCCATGTGAACCTGTTTGTAAACTGGTGAGTTTCTATTGCTA

TTTCATAGCTAAAGTTTTGAGGTAAATGCTATTGGATCTTTGTGTCTGTGTGTGTATACATA

TTTAGA-5'

<128160497>

>CCAT1_JAX_5 Transcript sequence; Genomic location: chr8:128172634-128231094 strand:-
<128231094>

(SEQ ID NO: 5)

3'-

GTTGCACTGACCTGGCCAGCCCTGCCACTTACCAGGTTGGTGTATTCCACACCATTTCATAT

TCCATCGCATTCCATTCTACACAATTCCACATCTCCCCGGCCACATCAGCCTGAGAGTAATA

AACAACCTTGCCATCGTATCCCCTTTTGGAGACACAAGCCAGGAAGGAAGCTCTTCAGTGCA

GCTGTGAATAGAGAAATGCTGGCTGAGGTTTTGGAGACACTGGGTGATCATTCCCAGTGAAA

TTTTTAGATCCCTGGGGACATGAGCTGCTTTGTCTTTTCCAAGGTCAGGATAAACAGAATAA

CTTCAGGCTTCTCTACCCAGAAAGAACATGTGGCATAAATATCAACTGCAGAATAAATATGA

TTAATCTGGTACATGGACGAAGATGTTTTCTAGGAGATGCTTATCCTGGGATGAGAGCTTTC

ATAAGCATTGATATTTACATGACTCTTACCGTGTGTCAGGAACTGTTCTAATTGTTTTACCT

ATGTCAATTCATTTGATAGTCACAACCACTGAAAGGAGTAAGTACTCTTATTACTTCCATTT

TACAGATAGGGAAACTGAGGTATAGAGAAGTCAAGTGACTTGCCCGAGGTTATTAAACTACT

TAATGTCAACACCAGGATTTGAACCCAGATCATTTGTTTCTGAAGTACATGCTCACAATCAC

TGCATTACTGATACACTGTTTTGTCTTTGCATACTTAAGTGGTCATAACTTAGTCTGAAACA

CTTTGTGAGAGCAGGAAGCAAACTGTCCCCTTATTAGGTGGACCAGTATAGTGATAATACAA

AAGTGTATTGCATTTGAATTACTTGCTAATATCTTCTAATTGAGGCAATTTTGAACAGGAAT

ATACATATCTAGCCTCTATTTTTCTAGCTAGAAGTTCTGAAATCCCTGGGCTTAATATTGTA

TGGCAACAATTGGCTGGAGTTGAGTTGCTGCCACTCTCTTTTAACTGAGCCATGCTCTCTCT

AGTTTGCTACAGGCCCCACCACTCCCTATTGCCTCTCCAATACCAGGTCATTTGGCATCTTA

CTCAGCTCATTTCATGCACATGTGTTCCACAATTGGTAACATAACCCTAAAAGTATTTGAGT

TTGTGGCTTCTGCTCTTGTGACAGAAGACTTTTCTCGAATTCCAAGGTCAACATATACCATA

TTGACTCTGGGCCACATTTTTTAATGTGCTCAAGCTCAGTTTTTCTCCTTAAAAAATGAGGG

GTTAAAAATAACACTTCGTAGTTGCCTCATCTGTGGATTGGAAGAATGAATGCCTGTCATTT

CTAGAGTTGTAGTAAGGGCCAGTTGGGGCAGTGCCTGTGAATATACGCAATGGGCCATCAAG

CAATCTCAGGGCTTCAGGCAATGCTGGGGTTTATAAAGCACTTTATGTTTTAAGTTCACTTT

TATTTCTAAAGTCTCATTGACTGCTCTGAAAATCTCTCAAGTAAAGTGGGCACTAAAGGCTT

TATACTCTCTCCAATTATACCTTCCATTGTATAGATTTGGAAGCTGGGGTCCAAATGTGTTA

AATGACTTGCCTAACATGGTCCATTACTGTAAGTACAGAAACGGAATGAGACCCCAAATCTG

CTTCATGGAGGGACACTCTTCTAAGATACTGTGATGCTTCTTCCCAAGTAATTCCGTCTTCA

GACTTCAAGGTCTCAATTCGAATGACAATTCAATATAGGACTTTCATAATCTTAAAAGCAAC

CTGACAGTCATTACAGTGGGCTGTGAGAAATACTAACGCAGAGCCACATACTCTGGGCTTCA

TGCTAGGTTTTGCCACTCACTATCTT-5'

<128172634>

>CCAT1_JAX_6 Transcript sequence; Genomic location:
chr8:128197810-128240377 strand:-
<128240377>

(SEQ ID NO: 6)

3'-

GCATGTGGCAGGCACAGAAATATTTACTCATTGACTGAATATAGCACATCGTAATGTTGATT

TTTTTCCAACATAATTTTAGAGCTAGGCATATTGTATTCTATTACACTAGACTATATATCAT

TCTTAAATAGAACCAGCCTTGCTAGATAACACATGTTGGAGGAGAGGCCCTTCTTCTTAGCC

CTCAGTGTTTCCATCTATGGGAAGAAGTTCCACCATACTAACATTACTATCGTCTCTCCAC

CTGCTCACTCACTTCTCCCCAAGGGAGGGGTGTTCGATATGGTTTCTGAGCTTGGAAAGAAA

ACTCAGGCATGTGTAACATGGTTCCTTCAGTCCCATGACCCACTGTCCACAAATGGGCTGCT

CACAGAGTGCATGCCTTCACCCTTGTTCCTGGCCATGCAGGAAATTGTATGAAACAGTCCTA

GCTGAAGCCTGAGATTTTCCTGCATTGCCTAGTCCTGGTGGGTATCTGTCTACTCCTGGAGT

TTGGATTGGAAAGTCCACATGCCTGAAGGTATAAACCTATTCTACAAAGGGGTGTTTTCTAG

AATGAAGGTAATATTTTTATCTTACATTTGCAGAAAGAGACAGAACAATGTTATAGGTGAGT

GCATGGACAATGACCTCAAACAGCTAAGATTCAAACCCCTGCGTTGAATGATTGAATTGAAA

TGATTCAATGAGCTAATGTACATAAAGCATCCAGAATGTTGCCTGGCACAAGGACTGTATTG

TCTGCTAGACCATTTATTCAAAGTGGGAGGATGATGTTCTAAAAGCCAATGATAAAGCTCAT

GGCAATGCAGGGTATATCTGATGGCATGGAATGCTTTAGGATGGCCAAGATTGCCCATCAAA

TGCCAAGTCACCGAAGTTATTAATGGCTCTCCTACTAGGAGCCTGACATCATGGTGAGCATC

GAGAAAGGAATAACCTAAGCTGAAGACACGCCTTTTCAGGAGGCCAAGTTCCACGTTCTGTG

CATGCTTTTGGCGAAAGTCAGGCCAGGCACTACTCTGTCCCAACAATAAGCCCTGTACATTG

GGAAAGGTGCCGAGACATGAACTTTGGTCTTCTCTGCAATCCATCTGGAGCATTCACTGACA

ACATCGACTTGAAGTTGCACTGACCTGGCCAGCCCTGCCACTTACCAGGTTGGGCTGTGGCT

TGCCTTTTCACTTCTTGTGTCCTGTTTAAGAAATATCTGCTATCCCAAGATTGCAAACTCCT

AGAGAAGGGCTCAACAGTGAGTGCTGAGGCTGCACAGAGGAGGAAGGCAGCACAATGATGGA

AGGCTTCCTAAAGAGGTATGTTCCAAGAGCCCCCACTTCCTTTCATGGGAGACTCATGCTGT

TACACCTAGACTATCTAGGGATACATCTAATGTAGTCGTGGAAAGAACAGAGGACTTGAGTA

CTAGACTGACGTGATTTTGAATCCTGGCTCCCTATTGACCAGATGTGTGTCTTGAACAAGTC

CCTGAGCCTCAGTGTCTTCATCTGCACAGTGAGGATAATGATACCACACTGCATATATGAGG

TATCCGGCACATGTAAATGTCCACTACATGCTGATTTCTTCACCCGCTACTCACCCCTGGGA

AAGAAGTAGACTCACCTACTCTTGGTACCCATTCATTCCCCCTCAGTTGGAAGCATGAGGTG

TGCAGCTGCCTGACCTGGGGGAAGGGCTGCAAGCAGTAGGTGTTGTCAGATGTGGTGGAGCT

TGTTGACTTCCTCCCAGGGGCCCAGCTAACAACCTGCCTCTGTTCCTTGATAGTCAAGTTCA

ACTTTCACTTCTTAGCACCACAGGAAGTTGACTGAACATTAACTGAAGTCTCTCTCAAACAG

GAGACATCTTTGCCAGGTCCCTGTACTTCCTAGCCTCATTCCTGCTCTCCCTAGTGAGCAGG

CTGCCCTCCCTTCTCGCCCCAGCACCACTGATAGGCAAGGGTACTCAGAACTACTACCTTGT

GGGCCATGTCATGTGCCAGGAGCTGCACCCAGGACTTTAATACAGTAGTTGGCTCCCACTGA

ATGTTCATTGTTACCCCAGGATAAAAAGGGGACACTGTGATCATTTTCTATTTTGCTGTGAT

CAGGCTTGGTGAGCTAAAGTCACCTACCTTCCCAGTCTCTACTAATAGAAGTCATGGATCAG

TCCTATTGGTTCTTCTGTTACAAGGATTCAGAATTCATAATCATGGAGCTGCATTTACAGGC

AGAAGTTTCTTTCATAGTTTTCTAAGTGTTCCTTTTAGCAACAATGGAGAAAATCAAAGAGG

```
-continued
GCAAAGGTGAGGGGAGAAAATAACATTTCCCTTTCTGTCCTTTGCTCTTGTAGTCTTTTGCT

TTAGTTTCTTTACTATGACTGTGAGGGTGAAACTAGTGATCAGAGTGGTCCAGAATGGGTTT

GATGAATCTGATTCTGGTGACACAAGATGAATTGGGTATATGTTTCCCTAAAGATAGAGAGA

CAATATAACATAGTCTTTACATTAATAGACTCTGGAGCCAATTTTTTAGGTTCACTCTCTT

TCCTTTCATGTGTGTTGATTTTCAACAAACATCTTGCACTCGAATTCCATCTCACTGTTTTA

TTTTCAAAAAATTTAATTTGAGAAAGTTAGCTGTATTAATTTTTTCTTTTTCTAAAATTCTT

TTACTAATTGCAATTATTTCCATTGATGCTATTCCATTGAAACCATTTTAACATGGACTCAA

TAACTTCATTGTATGTTAATGTTTAATTTTCATTTCTTTACCTTCTTGGTTTTCTAGCTGTG

TTTAATGTGGTTGACCACTCATTCTTTGAAGCTCTATTCCTCTGGCTACTACAGTATGACAC

ATTTTGTCTCCTTCTTCAGTCTCTGTCTTCTCCACAGTCTTCTCTTCCTTTTATATACCTTT

AAATATTAATGTTTCCCAGAGATATTTTCTTAACTCACTTCTCTACTGATTCTAGGTACTTT

TCTTGATCCAACTCTTCTGATTTTACCCATCTCGATGATTCTATAATTTGTATTTTCTGTTT

TGATCTCTTTTCAGTCTTCCAGACCTAAATATCCAAATGCCTGATGGATAGTGCTTTCTTTT

TTACTACCAAGCCCTCAAAGGCACTATGTTCAAAAGGAATTTGTCATCAGTCTCACGGCACA

TAAGCTTCCTCTTGTGTTCAATCTGGAGACTTGAGAGTCTTCCTGTTCCCTTCTTCTCCTTA

TTTTCTCCATAATCAATCACAAAGTCATGTGGATTTTGCTCCTAAATATGTTAACTTCTTTC

CTCTCTCACTTTATATCCCTTACATCTAGGTATTTCAGACCCTCAGTCTCTCTCACATAGAC

TTTGGCAATAACCTTCTAATATCAGTCAACCTGACCAATAGGCCACCAGTGCTTCATGTAGA

ATCTGGACAATGTAGAGCACTGAGAATGCTCACACTGGTCATATATGTATGAGTTGGTATGA

CATCTAGGGAAGTTGAAGACTTACATAGCCTTTGGCCCAGCAATATACACCATAATACATTA

GAGAAACTCTAGCATGTGTACACAGTGATATACACACAAGAATGTTCACAATGCCATTATTT

TAATAGCAAAATTGTGGAAACAACACAAATGTTTATCAATAACAGAATGGATAAGTGAGCCA

TGGCATAGTCATACAATGAAAATAATATAATAGTCAAATGAATGATCTGAAGAGATATCA

TTATTGGCAATCTTATAAAAGACTGAGTTAAAAATGCAATTTGTGAAAATTTTTAATTATTT

GATATTATTTAATGCAAAGTTTTAGAACATGCAAACAACTGTATATATTATTTATGTATATA

TGCAAATTCAGCAATAGCATTTAATCATGCCTGGGAATGATAAGTATCAAAGTCAGAAAGTG

GTTACCCTTGGGAAGAGAGGTATGTATCAGCGGTGGGGCACATAGGATGTTGCAGCCATATC

TGTAATGTTTCTTTGCTTTAAAAAATTTGAATCAAGCTTGGCAAAGTGTGACATTTGATTAA

GCAGGATAGTGAGTGCATATCTGTTACTTATATTGTTCTTTATAATTTTCTCTATGCTAAAG

CATTTTGTAATTTAAAAAACCTGACAGTGTTACTCCCATGCTTAAAATATGCCAGTGGTCAA

ACCAAATCCAGCAGCACATCAAAAAGCTTATCCACCATGATCAAGTGGGCTTCATCCCTGGG

ATGCAAGGCTGGTTCAATATAAGCAAATCAATAAATGTAATCCAGCATATAAACAGAACCAA

AGACAAAAACCACATGATTATCTCAATAGATGCAGAAAAGGCCTTTGACAAAATTCAACAAC

TCTTCATGCCAAAAACTCTCAATAAATTAAGTATTGATGGGACGTATCTCAAAATAATAAGA

GTTATCTATGAAAAACCCACAGCCAATATCATACTGAATGGGCAAAAACTGGAAGCATTCCC

TTTGAAAACTGGCACAAGACAGGGATGCCCTCTCTCACCACTCCTATTCAACATGGTGTTGG

AAGTTCTGGCCAGGGCAATTAGGCAGGAGAAGGAAATAAAGGGTATTCAATTAGGAAAAGAG

GAAATCAAATTGTCCCTGTTTGCAGATGACATGTATATCTAGAAAACCCCATTGTCTCAGCC

CAAAATCTCCTTAAGCTGATAAGCAACTTCAGCAAAGTCTCAGGATATAAAAATCAATGTAC

AAAAATCAGAAGCATTCTTATACACCAACAACAGACAAACAGAGAGCCAAATCATGAGTGAA

CTCCCATTCACAATTGCTTCAAAGAGAATAAAATACCTAGGAATCCAACTTACAAGGGACAT
```

-continued

```
GAAGGAACTCTTCAAGGAGAACTACAAACCACTGCTCAATGAAATAAAAGAGGATACAAACA

AATGGAAGAACATTCCATGCTCATGGGTAGGAAGAATCAATATCGTGAAAATGGCCATACTG

CCCAAGGTAATTTATAGATTCAATGCCATCCCCATCAAGCTACCAATGACTTTCTTCACAGA

ATTGGAAAAAACTGCTTTAAAGTTCATATGGCACCAAAAAAGAGCCCGCATCACCAAGTCAA

TCCTAAGCCAAAAGAACAAAGCTGGAGGCATCACACTACCTGACTTCAAACTATACTACAAG

GCTACAGTAACCCAAACAGCATGGTACTGGTACCAAAACAGAGATATAGATCAATGGAACAG

AACAGAGCCCTCAGAAATAACGCCACATATCTACAACTCTCTGATCTTTGACAAACCTGAGA

AAAACAAGCAATGGGGAAAGGATTCCCTATTTAATAAATGGTGCTGGGAAAACTGGCTAGCC

ATATGGAGAAAGCTGAAACTGGATCCCTTCCTTACACCTTATACAAAAATTAATTCAAGATG

GATTAAAGACTTAAATGTTAGACCTAAAACCATAAAAACCCTAGAAGAAAACCTAGGCATTA

CCATTCAGGACATAGGCATGGGCAAGGACTTCATGTCTAAAACACCAAAAGCAATGGCAACA

AAAGACAAAATTGACAAGGGGATCTAATTAAACTGAAGAGCTTCTGCACAGCAAAAGAAAC

TACCATCAGAGTGAACAGGCAACCTACAAAATGGGAGAAAATTTTCACAACCTACTCATCTG

ACAAAGGGCTAATATCCAGAATCTACAATGAACTCAAACAAATTTACAAGAAAAAAACAAAC

AACCCCATCAAAAAGTGGGCAAAGGACATGAACAGACACTTCTCAAAAGAAGACATTTATGC

AGCCAAAAAACACATGAAAAAATGCTCATCATCACTGGCCATCAGAGAAATGCAAATCAAAA

CCACAATGAGATACCATCTCACACCAGTTAGAATGGCAATCATTAAAAAGTCAGGAAACAAC

AGGTGCTCGAGAGGATGTGGAGAAATAGGAACACTTTTACACTGTTAGTGGGACTGTAAACT

AGTTCAACCATTGTGGAAGTCAGTGTGGCGATTCCTCAGGGATCTAGAACTAGAAATACCAT

TTGACCCAGCCATCCCATTACTGGGTATATACCCAAAGGACTATAAATCATGCTGCTATAAA

GACACATGCATACGTATGTTTATTGTGGCACTATTCACAATAGCAAAGACTTGGAACCAAGC

CAAATGTCCAACAATGATAGACTGGATTAAGAGAATGTGGCACATATACACCATGGAATACT

ATGCAGCCATAAAAAATGATGAGTTCATGTCCTTTGTAGGGACATGGATGAAATTGGAAATC

ATCATTCTCAGTAAACTATCGCAAGGACAAAAACCAAACACCGCATGTTCTCACTCATAGGT

GGGAACTGAACAATGAAAACACATGGACACAGGAAGGGGAACATCACACTCTGGGGACTGTT

GTGGGGTGGGGGGAGGGGGAGGGATAGCATTAGGAGATATACCTAATGCTAAATGATGAGT

TAATGGGTGCAGCACACCAGCATGGCACACGTATACATATGTAACTAACCTGCACATTGTGC

ACATGTACCCTAAAACTTAAAGTATAATAATAATTAAAAAAACCAATAGTTTATGAAACCCC

CCCCAAAAAAAATATATGCCAGTGGCCTCCAGTTGCCCACCAGGTAGCATCCACATTCTTTA

ATGGAAAGCCCTTCCTTGCTTCGAACTTGCCAACTGGGATTGGACATTTGTAGTTGCATTTC

TAAGAACTGTTCCCTTTTGTCAATGGAGCCTGATTTCCACTTGGATATCTGGGTGATTTAGG

GAAACTGACCTCAAAACCCAATTCTACATTTCGACCATGTGACCTTGGCTTAATCAATTCAC

GCATCTTTTTCCCTCACCTCAGGGGATGATCATATGAACTAAGCCAGTTGCAATAGAGTAAA

CCTCATGTTCCTAATGAGAAATCCAGAACAAAATGCTTTATTTTTCTTCAATTTTTTATTAG

GTCATCTCCTGAATCAATTAAAAAAAAAACCAACAGTGACAACAAAACTAAAAAATATGAAG

AAGCTGAAACATGAAAGCTCTGCCAACTGCAATATGTAGCTGCTAAGGTTGCTGTATTTATT

GGAATCAAGCAAGTGTTCCAGTAAAGAGCACAGAAGATGTGTCTGGGAGCCTTTATGTGTAG

GTCTGCAAGTGGTGGATATCACTACTACTCACACGCCATTGGCTAGAACTGAGTTGCATGGA

TACACCTAATTGTAAAAGAGGCTGGGAATAGAGACTATTGTGCCCAGAAAGAAGAGAAAAT

TCATTTATGGAAGAGGTAGCTAGTCTCTCACAGCCATGAAAAGAGAAGTGTTTAGCTAATTG
```

-continued

```
AAGTGAATAGCAGCCATCTTGGGTCCCTAAGGCAAGTTAGACTAATATTGAAGTGGAAACCA
TGAGGAAAGCAGTGATACTGAAAGTAACCGCATCTTTGAGAACATGCATTCATTTCCTACAA
CATGAATTTATTGAGGACCTACCTTAATACAGGCAGCGTGCTAGACACCAAGAGAACTGATG
TCCTCTTCCTTCCTGCCTGCCTGGAGCCTGTATTCTGGAGGGGACAGAGCTAGCAGATCAGA
CCTAACTGGAAATCTGCTGTGCCAGTATATATTTCAGTGATGTGAGCCAATATATCCCCTTG
ATTGCTCAAAGTAGTTTGGTCGATATATTTTGTTGCTTTAAATTGAACACATTCTTATGTAC
AGCCTCTGTCTCCTCATCTCCAACCAAGCAAAATAGCTTGTTCTCTTTATGCAGGGACACAT
GACATTTCCCACGTGGCTTTGTGCATATCTCCACCTCAATTTAAAATGCCTTCCAATCCCTG
CTCAAAGTCAAACAGCTTAATAATGGTAGACATAGAATTTGACTTATTCTAATAATAGGTCT
TTTAAACAATGCCTTCTTCTCTTCATTCTTTCCTTCTTAGAGTGGGTATTCTTTCTGGTGCA
TCATGTAAAGGAAGGTAACTACATGCATGTAATGATGAGAATATTTATATGTATTTATGATT
ATCACAAAAAAACAAAGATTCTACCATTCAAGAGGAACATTTATTTTATTTTTTATTTGAG
AAAAGTATAATTTTATTTATTTATTTATTTGTGCAAATTTATGGGGTACTTGAGAAAATGTG
TTACATGTATATAATGTGTAGTGATCCAATCAGGATACTAAGGGTGTCCATCACCTGAGTGT
ATTACATTTTTGTTAAGTATAATCATCCTACTCCAGGAGAACATTTTAAAAACTGTTCTGTA
GAGATACTACTCAAATTAAGTTCTCAGTCCTGAAACATCAGATCAGCTAGGAATCTGACAAA
AATGCAAGTTCTCAGATGACAGATGAGACCACTTCAATCAGAATTTCTGGAGTGGAGCCCAC
ACATTTGTATTTTTGCAACCTTTCCAATGATACTTATGTACATGCTCAAGCTTGAAAACCAC
TTTCCTAGGACATTAGTTCCTCGACAAGATTTGTGAGTAACCTTGTTTCATGAAAAAGTGTT
TAGGAGATACTGATTCAATAAAAACTAATCAGGCTTTTATTGTTTGCAGGGCTTTCAAAACT
TGCAATAGGCCACTGTGCATTGTTAATTTCTAAGAGGAAGATGCTTATGTCCTCAATGAATA
TCTTCCCACCATGAAGTACTCTTCTTCCCCCACTTTTTAAAACAATTACTAACACCTGGCAG
AAGTAGGCAGACAGCTTACAGCTTAGAAAAAGTTGGCCTAAGATAATGGCTAATTTTCATAC
ATTATTTATTTGTCATCATGCTTATCTTTCTCTCTAAATTGTATATTTCATCTCTGTGAT
CACAGATTGAGCCTCATATTTCATATCTGCCCCTGGCCTAATGGTTGTTTACAGAATGAGCT
CAATGAATATTGTTAAGTGAGTAGGATTTAATTTATTTGATAAATAGATAACCTTAAGTTTT
AAACGGTGGATTTCACATGAGGACATTTACTTACTATTGTTGAGCTGTAATTAATTTTTAAT
ACTGTTTAGGTACTCATAATAAAGAACAGGATATTTGGAGAAGGAAGACAGTATCATTCCTG
GTTCTTAGTCTTACCAGCTTATTGATCATGAGTATATAACCTCTCTGTGGCTCAGTGCCTTT
CTCTGTAAAATGGGAACACAGTGATGTTCACCTCACAGGATTGATTTGTAAAAGGGCTGGAT
AAGGTTATGAGAATGTTTTGCAAAGTGATATCGAAAGATTAATTGCAAACTTCATTTGAATC
TTAAATTGTTTGAGATAGGTCATGCTATGAATCAACTATGAAGTGCAGATATTGTCAAGATT
CAATATTCTTTCCCAAGAGCTGAGAGGAGGGGCTGCTTGTTTGTTTGTTTCTTTCTTTTTA
GAAACATGCCAGGACAGGCTCATTTTCGGGTTTTCCTCTCACTTGCTCATCTTACTTTTTCT
TTAGTTTCTCTATTCATTAGGATACAGTACTGTAAAGCTTTATGGCATTTTTATTTTGTGGG
AGATGAATCTGAATAAAGAATTACAGTTAAATCATTGCTAAGTTTGATGAATGAGCACCAAA
GAACTCTTCAAGATGTCATTTTTAAAGTTTTGTAAATGATTGGCTTTCAGTGGTTTCCTCTA
AGGAATTTTAATTTTGAATAATGCATAGAAAAATGTGCGCACACACAAATCATTCAGTATCC
ACCTCGAAGGGAAATCAAAGTGCCTGTGAAGTGAAACTTTACCTTTCTATATCACCAGCTTC
CTGTTAGAGCAGACTTTTTCTTTGCTCAAAGTCTAAGCATTGAAGAACTTCTTTTTAGTAGG
TAGATTTTTGTGTTTTTTTGTTTGTTTTTGAGACGGAGTCTCACTCTGTCGCCCAGGCTGTG
```

-continued

```
GTGCAGTGGCACGATCTCGGCCCACTGCAAGCTCTGCCTCCCGGGTTCACACCATTCTCCTG

CCTCAGCCTCCCAAGTAGCTGGGACTACAGGTGCCAGCCACCACGCCTGGCTAATTTTTTG

CATTTTTTAGTAGAGATGGGGTTTCATCGTGTTAGCCAGGATGGTCTTGATCTCCTGACCTC

ATGATCCACCCGCCTTGGCCTGCCAGAGTGCTGGAATTACAGGCGTGATTTAGTAGGTAGTT

TTGAGTAGGGAGTATACATTTAAAATGCTGAAACTCAGTTAAGGAATAATCTAATACTGTAT

TCAACTGAAACTCAGTTGAGAAATTTCTTTCCAATAATAAAGGAAAATCAACTGCAGTAATG

AGGGAGATGATTTTGCTGCTAATTACAACAAATATTTACTACAGACCTGTTATGCACCAGGA

ACTGTGCTAAATGTTTTATACATATAACTTTATCTTGTGCTCCAACAACTTATTACATAGAA

ATTGCTATTATTCCCATTTTCTAGATTAATAAATTGGTTTAGAGGGGTCGTATAGGTGAAAC

AACTCACTCAATATCACAAGCTGTTATGTGGTGAAGTTTGCATGATCAGTACAGGGTTCTGG

TCATCCCACTCATTGAGTGGTGCTAGTCAAGATCTGGAAGCTCTTCTGGTCTTAGTTTCTCT

AGCCGTGAAGTGACAATGATTAGGTCTAATCATAGAACATGAGAGTACATGTGAAAAAATGC

CTTTTTAAAGAGTATGAAAAACTTGAGTTGTAAAATTTTCTTGTGGATAATTTATTATTGCT

TTTCTTTTTTAGATAACACTAACAAAGTTGACCTTAGAATTGGAGTGCCTGGGTTAGAACCC

TGCTGGTACCACCTGCTTACTGCATGCTTCTGATGTGAGTTCAGGAGAAGACACTGGCAAGG

ACAGCAAAGAACAGGAGAACACTCTAGCTTCCCTGATAGCATTCAAGGTGCTGTCCAAACTG

ACTGTGATGGCACCCTCCAGACAGACAGCGATGCCACATGTTCAAGATGGCAGAATCACTAT

CAGCTTCAATTCCTGAATGACTGCAGAGCAAAATTTCTTACCTGCAACATACACTCTATTTT

CAGCCTCCCTGGACTGTTACATAATGATACATAAAAATATTTCTTGTGTTGAGGCATCCCAA

ATTTGATTTATTTGTCA-5'

<128197810>

>CCAT1_JAX_7 Transcript sequence; Genomic location:
chr8:128186443-128240377 strand:-
<128240377>
                                            (SEQ ID NO: 7)
3'-

GTAATGTTGATTTTTTTCCAACATAATTTTAGAGCTAGGCATATTGTATTCTATTACACTAG

ACTATATATCATTCTTAAATAGAACCAGCCTTGCTAGATAACACATGTTGGAGGAGAGGCCC

TTCTTCTTAGCCCTCAGTGTTTCCATCTATGGGGAAGAAGTTCCACCATACTAACATTACTA

TCGTCTCTCCACCTGCTCACTCACTTCTCCCCAAGGGAGGGGTGTTCGATATGGTTTCTGAG

CTTGGAAAGAAAACTCAGGCATGTGTAACATGGTTCCTTCAGTCCCATGACCCACTGTCCAC

AAATGGGCTGCTCACAGAGTGCATGCCTTCACCCTTGTTCCTGGCCATGCAGGAAATTGTAT

GAAACAGTCCTAGCTGAAGCCTGAGATTTTCCTGCATTGCCAGTCCTGGTGGGTATCTGTC

TACTCCTGGAGTTTGGATTGGAAAGTCCACATGCCTGAAGGTATAAACCTATTCTACAAAGG

GGTGTTTTCTAGAATGAAGGTAATATTTTTATCTTACATTTGCAGAAAGAGACAGAACAATG

TTATAGGACTGTATTGTCTGCTAGACCATTTATTCAAAGTGGGAGGATGATGTTCTAAAAGC

CAATGATAAAGCTCATGGCAATGCAGGGTATATCTGATGGCATGAATGCTTTAGGATGGCC

AAGATTGCCCATCAAATGCCAAGTCACCGAAGTTATTAATGGCTCTCCTACTAGGAGCCTGA

CATCATGGTGAGCATCGAGAAAGGAATAACCTAAGCTGAAGACACGCCTTTTCAGGAGGCCA

AGTTCCACGTTCTGTGCATGCTTTTGGCGAAAGTCAGGCCAGGCACTACTCTGTCCCAACAA

TAAGCCCTGTACATTGGGAAAGGTGCCGAGACATGAACTTTGGTCTTCTCTGCAATCCATCT

GGAGCATTCACTGACAACATCGACTTGAAGTTGCACTGACCTGGCCAGCCCTGCCACTTACC
```

-continued
AGGTTGGGCTCTTGAGTTTCTGCTTTCAAGTGACCCTCAGAAATTCCTCCATTCACTGCAGA

GGTTCTGTTTCTCCTTGCTTTGTTCTGACTTTACGGCAGAACTAAGCTAATGAGTTAGTTAC

TATGGGTTATCACTTGGATTTGAAGAACCATCATTTCTAGGCATTGCTGC-5'

<128186443>

>CCAT1_JAX_8 Transcript sequence; Genomic location:
chr8:128218833-128240377 strand = -
<128240377>
(SEQ ID NO: 8)
3'-

GCATGTGGCAGGCACAGAAATATTTACTCATTGACTGAATATAGCACATCGTAATGTTGATT

TTTTTCCAACATAATTTTAGAGCTAGGCATATTGTATTCTATTACACTAGACTATATATCAT

TCTTAAATAGAACCAGCCTTGCTAGATAACACATGTTGGAGGAGAGGCCCTTCTTCTTAGCC

CTCAGTGTTTCCATCTATGGGAAGAAGTTCCACCATACTAACATTACTATCGTCTCTCCAC

CTGCTCACTCACTTCTCCCCAAGGGAGGGGTGTTCGATATGGTTTCTGAGCTTGGAAAGAAA

ACTCAGGCATGTGTAACATGGTTCCTTCAGTCCCATGACCCACTGTCCACAAATGGGCTGCT

CACAGAGTGCATGCCTTCACCCTTGTTCCTGGCCATGCAGGAAATTGTATGAAACAGTCCTA

GCTGAAGCCTGAGATTTTCCTGCATTGCCTAGTCCTGGTGGGTATCTGTCTACTCCTGGAGT

TTGGATTGGAAAGTCCACATGCCTGAAGGTATAAACCTATTCTACAAAGGGGTGTTTTCTAG

AATGAAGGTAATATTTTTATCTTACATTTGCAGAAAGAGACAGAACAATGTTATAGGTTCTG

GGAAATAAGAAATCATTAGAAAAAGATTTCTGCCTTCTAGAAGTACACAGTCTAATGGTGAG

ATAGGCAGTTATTAATGGCTCTCCTACTAGGAGCCTGACATCATGGTGAGCATCGAGAAAGG

AATAACCTAAGCTGAAGACACGCCTTTTCAGGAGGCCAAGTTCCACGTTCTGTGCATGCTTT

TGGCGAAAGTCAGGCCAGGCACTACTCTGTCCCAACAATAAGCCCTGTACATTGGGAAAGGT

GCCGAGACATGAACTTTGGTCTTCTCTGCAATCCATCTGGAGCATTCACTGACAACATCGAC

TTGAAGTTGCACTGACCTGGCCAGCCCTGCCACTTACCAGGTTGGCTCTGTATGGCTAAGCG

TTTTCTCCTAAAATCCCTTGAAAACTGTGAGAAGACCATAAGAAGATCATATCTTTAATTCT

ATTTCACAAGTCACACAATATTCCAATCAAATACAGATGGTTGAGAAAAGTCATCCATCTTC

CCTCCCCACCCTCCCACAGCCCCTCAACCACTGCCCTGAAACTTATATGCTGTTATCCGCAG

CTCCATCTGGAGCATCACAGCTACTGTCAACCCTGACGCTCTTTCTGAAAAAACACCGGATG

GACATCAGAACTATTTCTTTAAGGATGTTACTGAGCCACACAGGAAAACTTGCCTTATGATT

TTGAATGCACGGATCTGATTTGACTAAACATGATAACTAGAGAATCACCCAATCTACTCCCA

TTTTCAACTCTAAATCATCAGAGTGTCTCAAATCCAAAGCACACACAGACCAGCCTGGCCAA

CACGGTGAAACTCCACCCCTACTAAAAGTATAAAAATTATCCAGGTGTGGTGGCGGGCGCCT

GTAATCCAAGCTACTTGGGAGTCTGGAGGCAGGAGAATCCCTTGAACCTGGGAGATGGAGGT

TGCAGTGAGCAGAGATCACACCACCGCACTCTAGCCTGGGCCACAAATCAACAACAACAACA

ACAACAAAAAACAAAGCGCACACAGAGACTGAGGTCCTCTTTGGCATTGAGAAGATGGCTAT

GCAAGTCCCAACTAGCAAGTGCAAACTTCCCAGCTTCACTTCTGCCAGTGTCCCTTCACCCC

TTCTCAACCCCACTGGGAGGCAGGAGGGTGCTTGACAATAACAGCCTTGGCATCACTCTGCC

AGGGTGTAATAGGAACTGTTACAATTCTGAGATTCTGTGTAAGCACTGGCCTTTCTGCCTAG

AATGCCTTCTCCTCTCTTTTTAACTGCATGCTCCTATTTATCTTTCAAAGCCCGGAAAAAA

TAACACTGCACACGGGAAATGCTCCCTTCCTACTGCAGTCATTTAGATGACTCTATGCCATT

CCATTCATTTCTCTTTCCTACCACAGAAGTGCTTTGAGATTTTGGAGTCAGACTGCTTGAAC

TTGAATCCTGGCCCTCTCATCAGAGACTTGACTTATTTTAGGCAAGTTATATAACCAATTTT

-continued

```
ACCTCAGTTCCTTACCCATAAAATGGGTCTAATGAGAGTACCTACCACACAGAATTTTGATG

AAAACTGAATGAGATGAAGGCCTTTAAGGCAGTGGTCCCCAACCCTGGGGACACAGACAGGT

ACCATTTTGTGGCCTGTTAGGAACTGGGCCACACAGCAGGAGGTGAGCAGTGGGTGAGTGAG

ATCAGCGTTATTTACAGCTGCTCCCCATTGCTCACCTTACTGCCTGAGCTCCACCTCCTGTC

AGATCAGCAGTGGCATTAAATTCTCATAGCAGCACAAACCCTGTCATGAACTGCACATGCGA

GGGATCTAGGTTGTGCGCTCCTTATGAGAATCTAATGCCTAATGACCTGTCACCGTCTCCCA

TCACCCCTAGATGGGAGTGTCTAGTTGCAGGAAACAAGCTCAGGGCTTCCACTGATTCTACA

TTATGGTGAGTTGTATAATTATTTCATTATATAATACAATGTAATAATAATAGAAACACAGT

GCACAACAAATGTAATGTGCTTGAATCATCCCCAAACCATCCCAGTCCACGGTCTTCCACAT

TTTGTCTTTTCACAAAATTGTCTTCCACAAAACTGGTCCCTGGTGCCAAAAAGGCTTGGGAC

CACTGCTTTAAAGCCTTTGCATAGTGCTTAGAATTGAGGGGAAAAAAAAACAAAAACAAT

GTAGCTAGTTGCTACAATCACTATATTGGTGAGTTTCAAAAGGAAAAGAATTCTGTCCCATT

TATGCTTGAGCCTTGAGTTGCTAACCAAGCCTGACACAAAATTACTGTTGAAGGGATGTGTG

AGTCCTAATTGAAATGAGGCCTCTTAAGGGAATTGTGGACCAAACCCCAAGCAGGCAGAAAG

CCGTATCTTAATTATTGCAAGTATTTCAGGCAAGGTGTGGATGGCCATTTGAATTCAAGCAG

ACTAGGACCTGGGATGAGAAAGAAGGTGTGTACGTGACTTGATCTTTGAACTTTAGCTCACC

ATCTGGAAGAAGGCTGAGTATTCTCTGCACTCACATAGTAGCTAATGCCTACTCCCAGCCA

CCCACAATTCTTTCTGTAGGAAGGCTCGCTAGAATACTTTGTGATATTGGATATTAGTTCCA

TATTCTACTGTGTATCTTAGTTCAACCAAATTGTAATCATCTGATATTTATTTCTTTTAATA

TAAATATAAGTATATTAAGTCTTGGCATGCTTGCTCAGTCTCTCTCTCTCTCCCATTCCTCC

CCGCTCCCCTCTCTCTTTCCCAACAGGCTTGGAAAGCAGGCATCACCATGCCTATTTAACAG

TTGGGGTCCCTTGGCCACCAGGTGCTGGAGTAGGAATCTGAGCCCGGACATGCCTGATCTGT

AAATTTTGTGTTTTCCCCACTGTGCTGGGCAGATCACAGCTATCAGCGCCAAATTCATAGAA

GGGGCGCCCCCTGTGGTCAATTGAGGGATTTGTGTTTGAGGTAGATCTCAAGAAGGAATGGG

TGGGGAACTTAGCCTAGGACAGAGCAGAAAGGAGCCCTCACTCCCCAAGCACCAACGGCCTC

AGTCCTTCCTGCTGACTCCAGCCTCTAGCTCTCACCCAGACTATCTGCATCCTTCTCTCCAC

CACGCTCCTTTGGAACCTGCGTAAAACACAGATTAAAGGAATTCCGCCTTACTTCCCTTTCC

GCATTATGACCAAATGGTTTTACACTATCATTGAACAGTTTAGTACAAAACATGCCACCTTT

TAATCTATTCATTCATTTAACAAATACTTTGGAGTGTTTACCATGTGCCAAGTGCTGTTCTA

ATAGACATAAGCTGTGAGGTTATGCTTATCTGATTCTCACAGCAACAGCTTTCGAGATATGA

ATTGGTATACTCATTTGACAGATGAGGAAATTGAATTCATGTAGTGAAAGGAAGAGCTGCAA

TTCAGGGTTACTGGTTTCTCCTGCACTAAGCACTGAGCCACACTAGAAGAGAAGGCATGAGG

AAGACAAAAGT-5'

<128218833>
```

For each of SEQ ID NOs: 1-8, the cDNA sequence "-" strand having the same sequence (except that the U's in RNA are replaced with T's in cDNA) as the respective CCAT1 ncRNA transcript isoform is shown, from 3' end to 5' end. In addition, the first and the last nucleotides of each cDNA "-" strand, as they are mapped to the corresponding nucleotides on the genomic sequence, are also shown (e.g., in SEQ ID NO:1, the first cDNA nucleotide C at the 5' end corresponds to nucleotide 128128655 on Chromosome 8 of the human genome, and the last cDNA nucleotide T at the 5' end corresponds to nucleotide 128241571 on Chromosome 8 of the human genome).

Furthermore, the following table lists additional information for the 8 transcripts, CCAT1_JAX_1 to CCAT1_JAX_8 (SEQ ID NOs: 1-8, respectively), including the start and end nucleotide positions for each exon of each CCAT1 transcript as represented by the nucleotide positions on human chromosome 8, the length of each exon, and the corresponding genomic sequence spans.

| Name | Feature | Start | End | Genomic span | Transcript length |
|---|---|---|---|---|---|
| CCAT1_JAX_1 | Transcript | 128128655 | 128241571 | 112917 | 29299 |
| CCAT1_JAX_1 | Exon1 | 128128655 | 128129210 | 556 | 556 |
| CCAT1_JAX_1 | Exon2 | 128152988 | 128153109 | 122 | 122 |
| CCAT1_JAX_1 | Exon3 | 128153590 | 128153816 | 227 | 227 |
| CCAT1_JAX_1 | Exon4 | 128155104 | 128155178 | 75 | 75 |
| CCAT1_JAX_1 | Exon5 | 128156007 | 128156437 | 431 | 431 |
| CCAT1_JAX_1 | Exon6 | 128160496 | 128161163 | 668 | 668 |
| CCAT1_JAX_1 | Exon7 | 128161860 | 128161917 | 58 | 58 |
| CCAT1_JAX_1 | Exon8 | 128172633 | 128174329 | 1697 | 1697 |
| CCAT1_JAX_1 | Exon9 | 128176683 | 128176771 | 89 | 89 |
| CCAT1_JAX_1 | Exon10 | 128181151 | 128181362 | 212 | 212 |
| CCAT1_JAX_1 | Exon11 | 128186434 | 128186609 | 176 | 176 |
| CCAT1_JAX_1 | Exon12 | 128197071 | 128198015 | 945 | 945 |
| CCAT1_JAX_1 | Exon13 | 128200029 | 128200129 | 101 | 101 |
| CCAT1_JAX_1 | Exon14 | 128200289 | 128215467 | 15179 | 15179 |
| CCAT1_JAX_1 | Exon15 | 128218832 | 128218920 | 89 | 89 |
| CCAT1_JAX_1 | Exon16 | 128218922 | 128221962 | 3041 | 3041 |
| CCAT1_JAX_1 | Exon17 | 128231054 | 128231498 | 445 | 445 |
| CCAT1_JAX_1 | Exon18 | 128231499 | 128231806 | 308 | 308 |
| CCAT1_JAX_1 | Exon19 | 128231808 | 128232653 | 846 | 846 |
| CCAT1_JAX_1 | Exon20 | 128234035 | 128235911 | 1877 | 1877 |
| CCAT1_JAX_1 | Exon21 | 128236644 | 128236720 | 77 | 77 |
| CCAT1_JAX_1 | Exon22 | 128236779 | 128236929 | 151 | 151 |
| CCAT1_JAX_1 | Exon23 | 128239643 | 128241571 | 1929 | 1929 |
| CCAT1_JAX_2 | Transcript | 128128655 | 128232653 | 103999 | 25265 |
| CCAT1_JAX_2 | Exon1 | 128128655 | 128129210 | 556 | 556 |
| CCAT1_JAX_2 | Exon2 | 128152988 | 128153109 | 122 | 122 |
| CCAT1_JAX_2 | Exon3 | 128153590 | 128153816 | 227 | 227 |
| CCAT1_JAX_2 | Exon4 | 128155104 | 128155178 | 75 | 75 |
| CCAT1_JAX_2 | Exon5 | 128156007 | 128156437 | 431 | 431 |
| CCAT1_JAX_2 | Exon6 | 128160496 | 128161163 | 668 | 668 |
| CCAT1_JAX_2 | Exon7 | 128161860 | 128161917 | 58 | 58 |
| CCAT1_JAX_2 | Exon8 | 128172633 | 128174329 | 1697 | 1697 |
| CCAT1_JAX_2 | Exon9 | 128176683 | 128176771 | 89 | 89 |
| CCAT1_JAX_2 | Exon10 | 128181151 | 128181362 | 212 | 212 |
| CCAT1_JAX_2 | Exon11 | 128186434 | 128186609 | 176 | 176 |
| CCAT1_JAX_2 | Exon12 | 128197071 | 128198015 | 945 | 945 |
| CCAT1_JAX_2 | Exon13 | 128200029 | 128200129 | 101 | 101 |
| CCAT1_JAX_2 | Exon14 | 128200289 | 128215467 | 15179 | 15179 |
| CCAT1_JAX_2 | Exon15 | 128218832 | 128218920 | 89 | 89 |
| CCAT1_JAX_2 | Exon16 | 128218922 | 128221962 | 3041 | 3041 |
| CCAT1_JAX_2 | Exon17 | 128231054 | 128231498 | 445 | 445 |
| CCAT1_JAX_2 | Exon18 | 128231499 | 128231806 | 308 | 308 |
| CCAT1_JAX_2 | Exon19 | 128231808 | 128232653 | 846 | 846 |
| CCAT1_JAX_3 | Transcript | 128152989 | 128231094 | 78106 | 465 |
| CCAT1_JAX_3 | Exon1 | 128152989 | 128153109 | 121 | 121 |
| CCAT1_JAX_3 | Exon2 | 128153719 | 128153816 | 98 | 98 |
| CCAT1_JAX_3 | Exon3 | 128155105 | 128155178 | 74 | 74 |
| CCAT1_JAX_3 | Exon4 | 128156008 | 128156139 | 132 | 132 |
| CCAT1_JAX_3 | Exon5 | 128231055 | 128231094 | 40 | 40 |
| CCAT1_JAX_4 | Transcript | 128160497 | 128232653 | 72157 | 8066 |
| CCAT1_JAX_4 | Exon1 | 128160497 | 128161163 | 667 | 667 |
| CCAT1_JAX_4 | Exon2 | 128161861 | 128161917 | 57 | 57 |
| CCAT1_JAX_4 | Exon3 | 128209720 | 128215465 | 5746 | 5746 |
| CCAT1_JAX_4 | Exon4 | 128231055 | 128231498 | 444 | 444 |
| CCAT1_JAX_4 | Exon5 | 128231500 | 128231806 | 307 | 307 |
| CCAT1_JAX_4 | Exon6 | 128231809 | 128232653 | 845 | 845 |
| CCAT1_JAX_5 | Transcript | 128172634 | 128231094 | 58461 | 1824 |
| CCAT1_JAX_5 | Exon1 | 128172634 | 128174329 | 1696 | 1696 |
| CCAT1_JAX_5 | Exon2 | 128176684 | 128176771 | 88 | 88 |
| CCAT1_JAX_5 | Exon3 | 128231055 | 128231094 | 40 | 40 |
| CCAT1_JAX_6 | Transcript | 128197810 | 128240377 | 42568 | 11053 |
| CCAT1_JAX_6 | Exon1 | 128197810 | 128198015 | 206 | 206 |
| CCAT1_JAX_6 | Exon2 | 128200030 | 128200129 | 100 | 100 |
| CCAT1_JAX_6 | Exon3 | 128200290 | 128209809 | 9520 | 9520 |
| CCAT1_JAX_6 | Exon4 | 128215408 | 128215465 | 58 | 58 |
| CCAT1_JAX_6 | Exon5 | 128231055 | 128231098 | 44 | 44 |
| CCAT1_JAX_6 | Exon6 | 128231100 | 128231211 | 112 | 112 |
| CCAT1_JAX_6 | Exon7 | 128235783 | 128235911 | 129 | 129 |
| CCAT1_JAX_6 | Exon8 | 128236780 | 128236929 | 150 | 150 |
| CCAT1_JAX_6 | Exon9 | 128239644 | 128240377 | 734 | 734 |
| CCAT1_JAX_7 | Transcript | 128186443 | 128240377 | 53935 | 1216 |
| CCAT1_JAX_7 | Exon1 | 128186443 | 128186609 | 167 | 167 |
| CCAT1_JAX_7 | Exon2 | 128231055 | 128231098 | 44 | 44 |
| CCAT1_JAX_7 | Exon3 | 128231100 | 128231212 | 113 | 113 |
| CCAT1_JAX_7 | Exon4 | 128235784 | 128235911 | 128 | 128 |
| CCAT1_JAX_7 | Exon5 | 128236780 | 128236929 | 150 | 150 |
| CCAT1_JAX_7 | Exon6 | 128239764 | 128240377 | 614 | 614 |

-continued

| Name | Feature | Start | End | Genomic span | Transcript length |
|---|---|---|---|---|---|
| CCAT1_JAX_8 | Transcript | 128218833 | 128240377 | 21545 | 4103 |
| CCAT1_JAX_8 | Exon1 | 128218833 | 128218920 | 88 | 88 |
| CCAT1_JAX_8 | Exon2 | 128218923 | 128221962 | 3040 | 3040 |
| CCAT1_JAX_8 | Exon3 | 128231055 | 128231098 | 44 | 44 |
| CCAT1_JAX_8 | Exon4 | 128231100 | 128231211 | 112 | 112 |
| CCAT1_JAX_8 | Exon5 | 128235783 | 128235911 | 129 | 129 |
| CCAT1_JAX_8 | Exon6 | 128236645 | 128236720 | 76 | 76 |
| CCAT1_JAX_8 | Exon7 | 128239764 | 128240377 | 614 | 614 |

These CCAT1 transcripts are different from the CCAT1 transcript described below in NCBI Reference Sequence: XR_133500.3:

```
                                                         (SEQ ID NO: 9)
   1 TCATCATTAC CAGCTGCCGT GTTAAGCATT GCGAAAACGC TCACGATTCA CAGAAAAATC

61 CATGCTGTTC TTTGAAGGCA TTCAAGCCTT AATAGCTAGC TGGATGAATG TTTAACTTCT

121 AGGCCAGGCA CTACTCTGTC CCAACAATAA GCCCTGTACA TTGGGAAAGG TGCCGAGACA

181 TGAACTTTGG TCTTCTCTGC AATCCATCTG GAGCATTCAC TGACAACATC GACTTTGAAG

241 TTGCACTGAC CTGGCCAGCC CTGCCACTTA CCAGGTTGGC TCTGTATGGC TAAGCGTTTT

301 CTCCTAAAAT CCCTTGAAAA CTGTGAGAAG ACCATAAGAA GATCATATCT TTAATTCTAT

361 TTCACAAGTC ACACAATATT CCAATCAAAT ACAGATGGTT GAGAAAGTC ATCCATCTTC

421 CCTCCCCACC CTCCCACAGC CCCTCAACCA CTGCCCTGAA ACTTATATGC TGTTATCCGC

481 AGCTCCATCT GGAGCATCAC AGCTACTGTC AACCCTGACG CTCTTTCTGA AAAACACCG

541 GATGGACATC AGAACTATTT CTTTAAGGAT GTTACTGAGC CACACAGGAA AACTTGCCTT

601 ATGATTTTGA ATGCACGGAT CTGATTTGAC TAAACATGAT AACTAGAGGA TCACCCAATC

661 TACTCCCATT TTCAACTCTA AATCATCAGA GTGTCTCAAA TCCAAAGCAC ACACAGACCA

721 GCCTGGCCAA CGCGGTGAAA CTCCACCCCT ACTAAAAGTA TAAAAATTAT CCAGGTGTGG

781 TGGCGGGCGC CTGTAATCCA AGCTACTTGG GAGTCTGAGG CAGGAGAATC CCTTGAACCT

841 GGGAGATGGA GGTTGCAGTG AGCAGAGATC ACACCACCGC ACTCTAGCCT GGGCCACAAA

901 TCAACAACAA CAACAACAAC AAAAAACAAA GCGCACACAG AGACTGAGGT CCTCTTTGGC

961 ATTGAGAAGA TGGCTATGCA AGTCCCAACT AGCAAGTGCA AACTTCCCAG CTTCACTTCT

1021 GCCAGTGTCC CTTCACCCCT TCTCAACCCC ACTGGGAGGC AGGAGGGTGC TTGACAATAA

1081 CAGCCTTGGC ATCACTCTGC CAGGGTGTAA TAGGAACTGT ACAATTCTG AGATTCTGTG

1141 TAAGCACTGG CCTTTCTGCC TAGAATGCCT TCTCCTCTCT TTTTTAACTG CATGCTCCTA

1201 TTTATCTTTC AAAGCCCGGA AAAATAACA CTGCACACGG GAAATGCTCC CTTCCTACTG

1261 CAGTCATTTA GATGACTCTA TGCCATTCCA TTCATTTCTC TTTCCTACCA CAGAAGTGCT

1321 TTGAGATTTT GGAGTCAGAC TGCTTGAACT TGAATCCTGG CCCTCTCATC AGAGACTTGA

1381 CTTATTTTAG GCAAGTTATA TAACCAATTT TACCTCAGTT CCTTACCCAT AAAATGGGTC

1441 TAATGAGAGT ACCTACCACA CAGAATTTTG ATGAAAACTG AATGAGATGA AGGCCTTTAA

1501 GGCAGTGGTC CCCAACCCTG GGGACACAGA CAGGTACCAT TTTGTGGCCT GTTAGGAACT

1561 GGGCCACACA GCAGGAGGTG AGCAGTGGGT GAGTGAGATC AGCGTTATTT ACAGCTGCTC

1621 CCCATTGCTC ACCTTACTGC CTGAGCTCCA CCTCCTGTCA GATCAGCAGT GGCATTAAAT

1681 TCTCATAGCA GCACAAACCC TGTCATGAAC TGCACATGCG AGGGATCTAG GTTGTGCGCT

1741 CCTTATGAGA ATCTAATGCC TAATGACCTG TCACCGTCTC CCATCACCCC TAGATGGGAG
```

```
-continued
1801  TGTCTAGTTG CAGGAAACAA GCTCAGGGCT TCCACTGATT CTACATTATG GTGAGTTGTA

1861  TAATTATTTC ATTATATAAT ACAATGTAAT AATAATAGAA ACACAGTGCA CAACAAATGT

1921  AATGTGCTTG AATCATCCCC AAACCATCCC AGTCCACGGT CTTCCACATT TTGTCTTTTC

1981  ACAAAATTGT CTTCCACAAA ACTGGTCCCT GGTGCCAAAA AGGCTTGGGA CCACTGCTTT

2041  AAAGCCTTTG CATAGTGCTT AGAATTGAGG GGGAAAAAAA AAACAAAAAC AATGTAGCTA

2101  GTTGCTACAA TCACTATATT GGTGAGTTTC AAAAGGAAAA GAATTCTGTC CCATTTATGC

2161  TTGAGCCTTG AGTTGCTAAC CAAGCCTGAC ACAAAATTAC TGTTGAAGGG ATGTGTGAGT

2221  CCTAATTGAA ATGAGGCCTC TTAAGGGAAT TGTGGACCAA ACCCCAAGCA GGCAGAAAGC

2281  CGTATCTTAA TTATTGCAAG TATTTCAGGC AAGGTGTGGA TGGCCATTTG AATTCAAGCA

2341  GACTAGGACC TGGGATGAGA AGAAGGTGT GTACGTGACT TGATCTTTGA ACTTTAGCTC

2401  ACCATCTGGA AGAAGGCTGA GTATTCTCTG CACTCACATA GTAGCTAATG CCTACTCCCC

2461  AGCCACCCAC AATTCTTTCT GTAGGAAGGC TCGCTAGAAT ACTTTGTGAT ATTGGATATT

2521  AGTTCCATAT TCTACTGTGT ATCTTAGTTC AACCAAATTG TAATCATCTG ATATTTATTT

2581  CTTTTAATAT AAATATAAGT ATATTAAGTC TT
```

Thus in one aspect, the invention provides cDNA sequences of the CCAT1 ncRNA transcripts, wherein the cDNA sequences are represented by a sequence selected from the group consisting of SEQ ID NOs: 1-8.

In a related aspect, the invention provides an antagonist sequence of a CCAT1 ncRNA, wherein the antagonist sequence antagonizes a function of the CCAT1 ncRNA.

In certain embodiments, the antagonizing sequence does not antagonize a function of the CCAT1 ncRNA corresponding to SEQ ID NO: 9.

In certain embodiments, the antagonist sequence is an antisense sequence to any one of the "-" strand cDNA sequences shown in SEQ ID NOs: 1-8.

In certain embodiments, the antisense sequence hybridizes to any one of the "-" strand cDNA sequences shown in SEQ ID NOs: 1-8 (but not SEQ ID NO: 9), under physiological conditions (e.g., in the nucleus of a cell), or under a high stringency hybridization condition, such as one described in *Molecular Cloning: A Laboratory Manual* by Sambrook and Russell, Third Edition, 2001, published by Cold Spring Harbor Laboratory Press (incorporated herein by reference). One such high stringency hybridization condition may include 6× sodium chloride/sodium citrate (SSC) at approximately 45° C., followed by one or more washes in 0.2×SSC and 0.1% SDS at 50° C., at 55° C., or at about 60° C., or about 65° C. or more.

In certain embodiments, the antisense sequence is at least about 40%, 50%, 60%, 70%, 80%, 85%, 90%, 95%, 97%, 99% or more identical to any one of the "-" strand cDNA sequences shown in SEQ ID NOs: 1-8, at least in a region to which the antisense sequence hybridizes with the cDNA sequence. In certain embodiments, the antisense sequence is no more than about 50%, 40%, 30%, 20% identical to SEQ ID NO: 9.

In certain embodiments, the antisense sequence is about 10, 12, 14, 16, 20, 22, 24, 26, 28, 30 or more nucleotides in length.

In certain embodiments, the antagonist sequence is an siRNA or miRNA sequence that targets the destruction of any one or more of the CCAT1 ncRNA isoforms represented by the "-" strand cDNA sequences shown in SEQ ID NOs: 1-8 (but not SEQ ID NO: 9).

In certain embodiments, the antagonist sequence is a vector that encodes the siRNA/miRNA, or a dsRNA substrate for RNase III (such as Dicer) that can be processed to the siRNA or miRNA.

In certain embodiments, the siRNA or miRNA comprises a guide sequence of about 20-25 nucleotides that targets the destruction of the CCAT1 ncRNA isoforms.

In a related aspect, the invention provides a method of diagnosing cancer or precancerous lesions, comprising measuring the level of expression of any one of SEQ ID NOs: 1-8 or a fragment thereof in a biological sample, wherein expression of any one of SEQ ID NOs: 1-8 or a fragment thereof in the biological sample is indicative of cancer or a precancerous lesion. In certain embodiments, the fragment is not a fragment of SEQ ID NO: 9.

In certain embodiments, the method further comprises comparing the expression level measured in the biological sample with a standard, wherein a higher level of expression of any one of SEQ ID NOs: 1-8 or a fragment thereof in the biological sample is indicative of cancer or a precancerous lesion. In certain embodiments, the fragment is not a fragment of SEQ ID NO: 9.

In certain embodiments, the method comprising: (a) isolating nucleic acids from a biological sample obtained from a subject; (b) hybridizing a probe capable of recognizing to any one of SEQ ID NOs: 1-8 with the nucleic acids, under conditions allowing the formation of hybridization complexes; and (c) comparing hybridization complex formation with a standard; wherein a higher level of hybridization complexes in the biological sample is indicative of cancer or a precancerous lesion. In certain embodiments, the probe does not hybridize to SEQ ID NO:9.

In certain embodiments, the method comprising: (a) isolating nucleic acids from a biological sample obtained from a subject; (b) amplifying any one of SEQ ID NOs: 1-8 or any fragment thereof in the isolated nucleic acids; (c) visualizing the amplified CCAT1 product; and (d) comparing the amount of the CCAT1 amplification product with a standard; wherein the presence of a higher level of a CCAT-1 amplification product is indicative of cancer or a precancerous lesion. In certain embodiments, the fragment is not a fragment of SEQ ID NO: 9.

In certain embodiments, the amplification is performed by PCR (such as real-time quantitative PCR) using a probe specific for one or more of SEQ ID NOs: 1-8.

In certain embodiments, the standard is determined by measuring the level of expression of CCAT-1 in a subject not afflicted with cancer. In a related embodiment, the standard is determined by measuring the level of expression of CCAT-1 in a non-cancerous tissue of the same subject.

In certain embodiments, the cancer is selected from the group consisting of: colon cancer (e.g., adenocarcinoma of the colon), rectal cancer, cervical cancer, lung cancer, gastric carcinoma, liver cancer and, metastases thereof.

In certain embodiments, the precancerous lesion is an adenomatous polyp.

In certain embodiments, the biological sample is selected from the group consisting of tissue, blood, saliva, urine, stool, and bone marrow samples.

A related aspect of the invention provides an oligonucleotide comprising at least 8 contiguous nucleotides of any one of SEQ ID NOs: 1-8 or a complement thereof, useful as a probe or a primer. In certain embodiments, the oligonucleotide does not hybridize to SEQ ID NO: 9.

A related aspect of the invention provides a method for detecting the expression of CCAT-1 in a biological sample, the method comprising: (a) isolating nucleic acids from the biological sample; (b) hybridizing the CCAT1 oligonucleotide probe of the invention to the nucleic acids under conditions allowing the formation of hybridization complexes; and (c) comparing hybridization complex formation with a standard, wherein a higher level of hybridization complexes in the biological sample indicates expression of CCAT-1 in the sample.

Another related aspect of the invention provides a vector comprising a cDNA or a fragment thereof, wherein the cDNA is selected from the group consisting of SEQ ID NOs: 1-8. In certain embodiments, the cDNA fragment does not hybridize to SEQ ID NO: 9.

Another related aspect of the invention provides a host cell comprising the subject vector.

Another related aspect of the invention provides a method of imaging cancer or precancerous lesions, comprising: (a) administering to a subject a CCAT1 probe of the invention; wherein the probe is conjugated to an indicator molecule; and (b) detecting the indicator molecule (e.g., a radioisotope, a fluorescent dye, a visible dye or a nano-particle) conjugated to the probe by an imaging device.

A further related aspect of the invention provides a method to antagonize the function of a CCAT1 ncRNA transcript represented by any one or more of SEQ ID NOs: 1-8, comprising contacting the CCAT1 ncRNA with a subject antagonist sequence of CCAT1 (e.g., antisense, miRNA or siRNA).

In certain embodiments, the method is carried out in vitro, and the CCAT1 ncRNA transcript is present in cells from a tissue culture sample.

In certain embodiments, the method is carried out in vivo, comprising administering to a subject in need thereof the subject antagonist sequence of CCAT1 (e.g., antisense, miRNA or siRNA).

Yet another related aspect of the invention provides a pharmaceutical composition comprising a subject antagonist sequence of CCAT1 (e.g., antisense, miRNA or siRNA), and a pharmaceutically acceptable excipient and/or carrier.

It should be understood that any embodiments described in the application, including embodiments only described under one aspect of the invention, can be combined with other embodiments of other aspects of the invention.

A person of ordinary skill in the art will appreciate that techniques not specifically taught herein may be found in standard molecular biology reference books, such as *Molecular Cloning: A Laboratory Manual* by Sambrook and Russell, Third Edition, 2001, published by Cold Spring Harbor Laboratory Press; *Oligonucleotide Synthesis* (M. J. Gait, ed., 1984); *Nucleic Acid Hybridization* (B. D. Hames and S. J. Higgins. eds., 1984); PCR Technology—principles and applications for DNA amplification, 1989, (ed. H. A. Erlich) Stockton Press, New York; *PCR Protocols: A Guide to Methods and Applications,* 1990, (ed. M. A. Innis et al.) Academic Press, San Diego; and PCR Strategies, 1995, (ed. M. A. Innis et al.) Academic Press, San Diego; all of which are incorporated herein by reference.

EXAMPLES

The invention generally described above will be more readily understood through reference to the following illustrative examples that are for illustration only, and are not intended to be limiting in any respect.

Example 1 General RICh-PET Methodology

Using RNA-DNA ligation followed by paired-end-tag sequencing (RICH-PET), Applicants have developed an exemplary method described below to study ncRNA (non-coding RNA) and chromatin interactions in an unbiased and genome-wide manner.

A principal concept behind the method is based on the realization that most of the ncRNA regulatory functions, particularly those adopted by long ncRNAs (lncRNAs), likely have direct or indirect contacts in specific chromatin loci through any combinations of RNA-protein, RNA-DNA, and/or RNA-RNA interactions. Therefore, a comprehensive collection of ncRNA contact addresses of chromatin locations in the entire genome would provide a large structural framework and the detail contents of genomic elements in order to understand the global impact as well as specific functions mediated by individual and/or collective ncRNAs.

Through crosslinking, RNA-chromatin interactions can be captured. After fragmentation of chromatin fibers by sonication, ncRNA and DNA fragments tethered together via protein bindings in each chromatin complex are then subjective for RNA-DNA ligation using the subject RNA and DNA linkers, in order to establish an artificial connectivity relationship of the RNA molecules and the DNA fragments for high throughput analysis with specificity.

The RNA linker of the invention may comprise a random oligonucleotide sequence, e.g., random hexonucleotides, for annealing to the 3'-end of any tethered RNA molecules, and as the primer for reverse transcription to convert the RNA templates into first-strand cDNA molecules. Meanwhile, the DNA linker of the invention is ligated to the blunt-ended chromatin DNA fragments. The RNA linker and the DNA linker each has a sticky end complementary to each other but not to itself. Hence, once the linkers are attached accordingly to their intended targets, the RNA and DNA fragments can be covalently connected through ligation. The hybrid ligation products are then subjective for paired end tag (PET) library construction and subsequent high throughput sequencing analysis. A schematic drawing for this method is depicted in FIG. 1A.

Figure 1B:
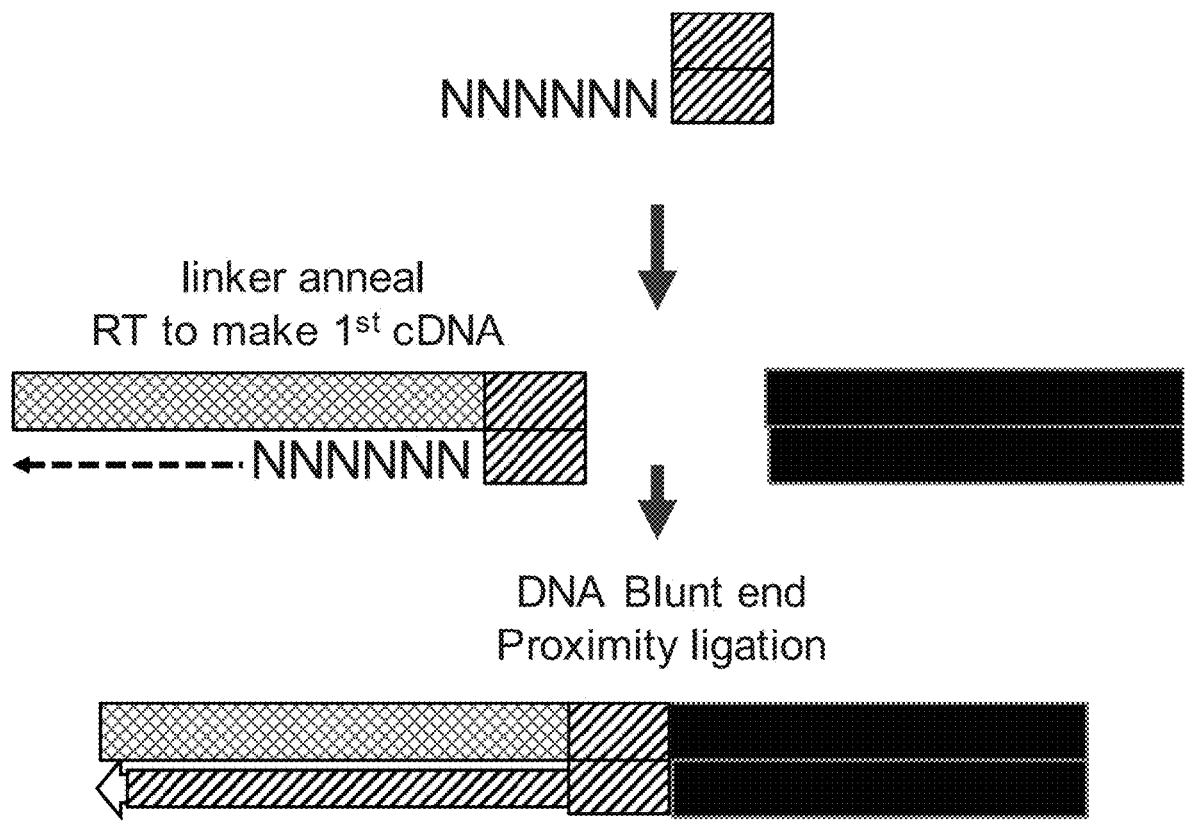
FIG. 1B shows a schematic flow of a typical setting of the RICh-PET method using the modified RNA linker.

Alternatively, a modified RNA linker may be used to carry out the RNA-DNA ligation step. A schematic drawing for this method is depicted in FIG. 1B.

Figure 1C:
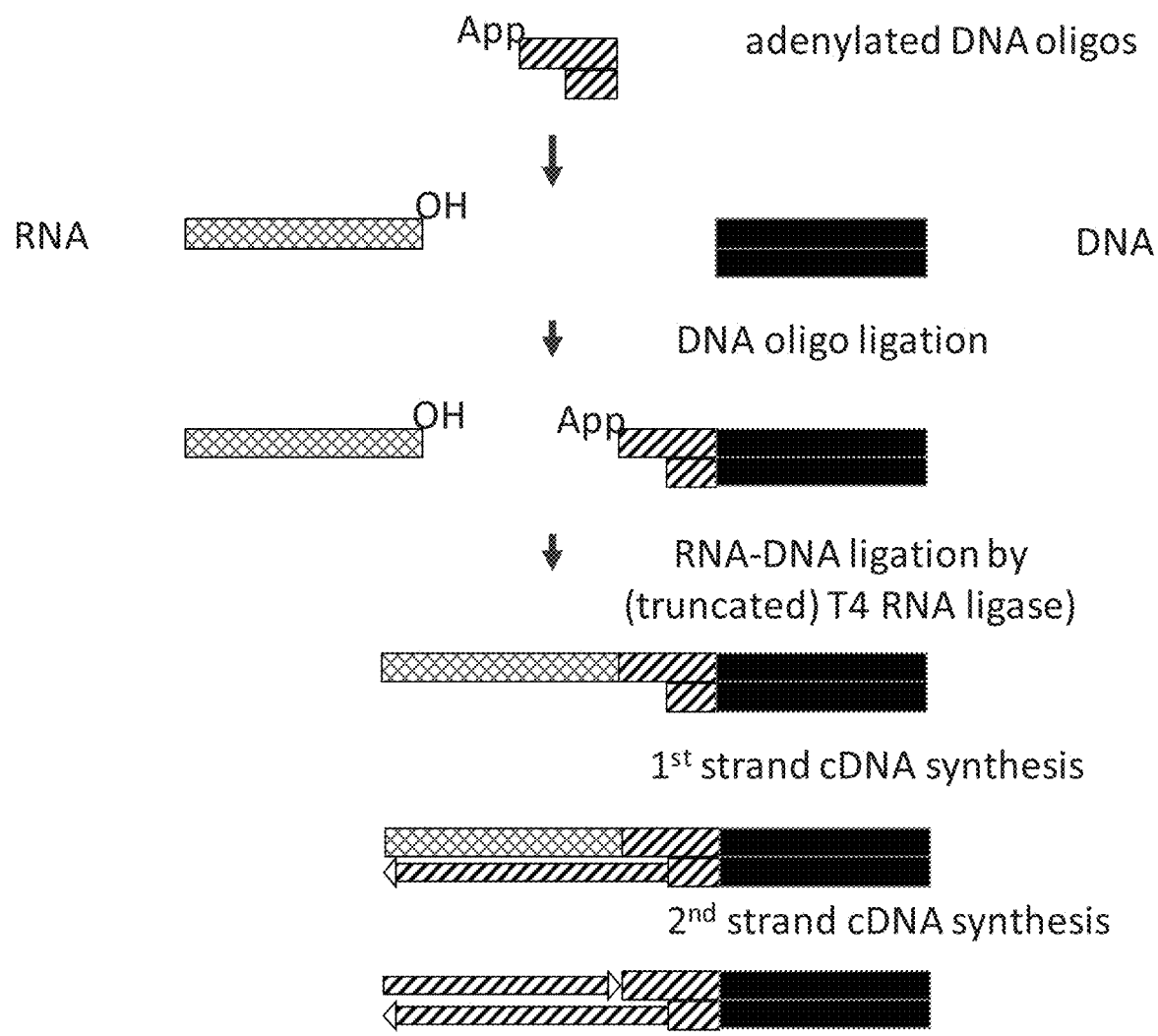
FIG. 1C shows a schematic flow of a typical setting of the RICh-PET method using the direct RNA linker. "App" stands for the 5' adenylation at the 5'-end of the first polynucleotide.

Additionally, a direct RNA linker may be used to carry out the RNA-DNA ligation step by taking advantage of certain enzymes (such as the truncated RNL2) that can directly link RNA 3'-end to 5' adenylated ssDNA or 5' adenylated overhang, a schematic drawing for the latter method is depicted in FIG. 1C.

To further distinguish the tag sequences from their original nature as RNA or DNA, specific nucleotide bar codes may be incorporated into RNA and/or DNA linker sequence designs, which then allow accurate calling of the paired RNA-tag and DNA-tag in a RICh-PET library dataset. The processed RNA-tag and DNA-tag sequences are then mapped to reference genome (e.g., a reference human genome for human originated sequences) to identify ncRNAs and their chromatin target loci (data not shown).

Certain experimental details are provided below for illustration purpose.

I. Cell Culture and Crosslinking

HeLa S3 cells were grown in Ham's F-12 Nutrient Mix (Life Technologies, cat. 11765-054) supplemented with 5% Fetal Bovine Serum (FBS) (Life Technologies, cat. 10082147). For each batch of crosslinked cells, EGS (spacer Arm: 16.1 A; Thermo Scientific, cat. 21565) and formaldehyde (spacer Arm: 2.0 A; Merck—Calbiochem, cat. 344198-250ML) were used to treat the cells for dual-crosslinking of protein-DNA, protein-RNA and protein-protein, which could provide better connectivity than using only formaldehyde.

Around $1 \times 10^8$ cells in 245 mm square plate (Corning, cat. 431110) were crosslinked with 45 ml of 1.5 mM EGS in pre-warmed DPBS (Life Technologies, cat. 14190250), first shaking at 75 rpm for 40 min, then adding 1% formaldehyde (Merck—Calbiochem, cat. 344198-250ML), and keeping for 20 min, followed by quenching with 0.125 M glycine (Promega, cat. H5071) for 10 min, then washing with ice-cold DPBS twice. Then 3 to 5 ml of ice-cold DPBS containing proteinase inhibitor (Roche, cat. 11873580001) and RNase inhibitor (such as the SUPERase• In™ RNase Inhibitor, Life Technologies, cat. AM2696) were added, and then cells were scraping and transferred to 15 ml-Falcon tube (Life Technologies, cat. AM1250). This process was repeated as necessary to ensure that all cells were collected. Cells were spun down at 2000 rpm for 5 min at 4° C., then the cell pellet were stored at −80° C. until use.

II. Cell Lysis and Chromatin Biotinylation

Cell lysis was performed as described previously (Goh et al., *J. Vis. Exp.*, (62), e3770, doi:10.3791/3770, 2012; Fullwood et al., *Nature*, 462:58-64, 2009, both incorporate herein by reference). Briefly, the nuclei pellet was washed twice with an ice-cold wash buffer (50 mM Tris-HCl pH=8.0, 150 mM Nacl, 1 mM EDTA, 1% TritonX-100, 0.1% SDS), and suspended in 1 mL of the same buffer. Chromatin was sheared to fragments with average size of about 500 bp by, for example, sonication. SDS was then added to the final concentration of about 0.5% to the shearing chromatin, and the mixture was then incubated at 37° C. for 15 min, before mixing with EZlink Iodoacetyl-PEG2-Biotin (IPB) (Thermo Scientific, cat. 21334) and rotating at room temperature for 60 min as described previously (Kalhor et al., *Nat. Biotechnol.*, 30:90-98, 2012, incorporate herein by reference). The streptavidin beads-bound chromatin was then subjected to RICh-PET library construction.

III. RICh-PET Library Construction

The DNA fragments present in streptavidin beads-bound chromatin were end-repaired using T4 polymerase (Promega, R0191), followed by first-strand cDNA synthesis using Superscript III First Strand Synthesis System (Life Technologies, cat. 18080051).

Briefly, 1 μg of biotinylated RNA linker a (tube 1) and RNA linker b (tube 2) containing a flanking MmeI site (IDT), were added to two tubes containing annealing mixture (5 μl 10 mM dNTPs, 40 μl DEPC-treated water), respectively, and incubated at 65° C. for 5 min, then placed on ice for at least about 1 min, then mixed with cDNA synthesis mixture (10 μl 10×RT (reverse transcription) buffer, 20 μl 25 mM MgCl$_2$, 10 μl 0.1 M DTT, 5 μl RNaseOUT, 5 μl SuperScript III RT) for incubation for 10 min at 25° C., followed by 30 min at 50° C.

Overnight ligation was performed using 1 μg of DNA linker A (tube 1) and DNA linker B (tube 2), respectively, in ligation mixture (140 μl 5×T4 DNA ligase buffer with PEG, 3.5 μl RNase inhibitor, 546.5 μl nuclease free water) using 5 μl of T4 DNA ligase at 16° C. The linker-added DNA fragments were then phosphorylated with 14 μl of T4 polynucleotide kinase (NEB) in PNK master mix buffers (70 μl 10×T4 DNA ligase buffer, 3.5 μl RNase inhibitor, 612.5 μl Nuclease free water), followed by the two tubes proximity ligation with 34 μl of T4 DNA ligase in reaction buffer (1000 μl 10×T4 DNA ligase buffer, 50 μl RNase, 8916 μl Nuclease free water) overnight at 16° C.

Chromatin DNA fragments with linkers were subjected to second-strand cDNA synthesis with Superscript Double-stranded cDNA Synthesis Kit (Life Technologies, cat. 1197-020). Specifically, chromatin fragments were mixed with second-strand cDNA mixture (111 μl DEPC-treated water, 30 μl 5× Second-strand reaction buffer, 3 μl 10 mM dNTP mix, 1 μl *E. coli* DNA ligase, 4 μl *E. coli* DNA Polymerase I, 1 μl *E. coli* RNase H), and were incubated at 16° C. for 2 hours. Following the reaction, 2 μL of T4 DNA polymerase was added for continued incubation at 16° C. for 5 min.

The crosslinks in DNA/RNA/protein complexes were then reversed by incubation at 65° C. overnight with 0.3% SDS (Ambion) and proteinase K (Ambion). The cDNA-DNA fragments were purified by phenol/chloroform isopropanol precipitation. The purified cDNA-DNA was then digested by 1 μl of MmeI (NEB) in suitable buffer (5 μl 10× NEBuffer 4, 5 μl Half linker non-Biotinylated to quench excess MmeI, 5 μl 10×SAM) for at least 2 hrs at 37° C. to release the cDNA tag-RNA linker-DNA linker-DNA tag structure (paired end tag, PET).

The biotinylated PETs were then immobilized on streptavidin-conjugated magnetic Dynabeads (Life Technologies, cat. 11206D-10ML) in 50 μl of 2×B&W buffer (10 mM Tris-HCl pH7.5, 1 mM EDTA, 1 M NaCl), rocked at room temperature for 45 min. The ends of each PET structure were then ligated to an adaptor by 1 μl of T4 DNA ligase (Thermo Scientific, cat. EL0013) in Adaptor ligation buffer (4 μl Adaptor A, 4 μl Adaptor B, 5 μl μ10× T4 DNA ligase buffer, 36 μl Nuclease free water) at 16° C. overnight with mixing. The beads were then washed three times with 1× B&W buffer (5 mM Tris-HCl pH7.5, 0.5 mM EDTA, 1 M NaCl).

Nick translation was performed with 4 μl of *E. coli* DNA polymerase I in a reaction mixture (38.5 μl Nuclease free water, 10× NEBuffer 2, 2.5 μl 10 mM dNTPs), which was incubated at room temperature for 2 hours with rotation on an Intelli-Mixer (F8, 30 rpm, U=50, u=60; ELMI Ltd., Riga, Latvia). This was followed by 16 rounds of PCR to amplify the PETs. RICh-PET libraries were sequenced on an Illumina HiSeq2000 (2×36 bp reads).

All steps were performed in buffer with protease inhibitor and RNase-inhibitors to prevent or minimize protein and RNA degradation.

The various polynucleotides or primers used herein are listed below:

| Polynucleotides | Name | Sequences |
|---|---|---|
| DNA linker A2 | Rb-top-6 | 5'-Phos-GTTGGACTTGTAC GATAGCTCTC-3' |
| | Rb-bot-6 | 5'-OH-GCTA/iBIOdT/CGT ACAAGTCCAACNNNNNV-3' |
| DNA linker B2 | DB-top-6 | 5'-OH-GCGATATCACTGTTC CAAC-3' |
| | DB-bot-6 | 5'-OH-GTTGGAACAGTGATA TCGCGAGA-3' |
| Linker without biotin for sequencing access MmeI | top | 5'-GGCCGCGATATCGGATCC AAC-3' |
| | bottom | 5'-GTTGGATCCGATATCG C-3' |
| Adaptor A | top | 5'-CCATCTCATCCCTGCGTG TCCCATCTGTTCCCTCCCTGT CTCAGNN-3' |
| | bottom | 5'-CTGAGACAGGGAGGGAAC AGATGGGACACGCAGGGATGA GATGG-3' |
| Adaptor B | top | 5'-CTGAGACACGCAACAGGG GATAGGCAAGGCACACAGGGG ATAGG-3' |
| | bottom | 5'-CCTATCCCCTGTGTGCCT TGCCTATCCCCTGTTGCGTGT CTCAGNN-3' |
| PCR primer 1 | | 5'-AATGATACGGCGACCACC GAGATCTACACCCTATCCCCT GTGTGCCTTG-3' |
| PCR primer 2 | | 5'-CAAGCAGAAGACGGCATA CGAGATCGGTCCATCTCATCC CTGCGTGTC-3' |
| Sequencing primer 1 | | 5'-GTGCCTTGCCTATCCCCT GTTGCGTGTCTCAG-3' |
| Sequencing primer 2 | | 5'-TGCGTGTCCCATCTGTTC CCTCCCTGTCTCAG-3' |

Example 2 RICh-PET Library Statistics

Three RICh-PET library datasets were generated using technical and biological replicates from HeLa S3 cells.

HeLa S3 RICh-PET data mapping results

| Libraries | Replicates | Reads | Unique PET | Cluster (≥PET2) |
|---|---|---|---|---|
| CHH2430 | 1 (Tec) | 52,254,130 | 2,367,898 | 5,371 |
| JCHH2430 | 2 (Tec) | 211,837,204 | 2,920,369 | 9,089 |
| JCHH2431 | 3 (Bio) | 83,143,999 | 2,049,942 | 3,128 |

Figure 2A:
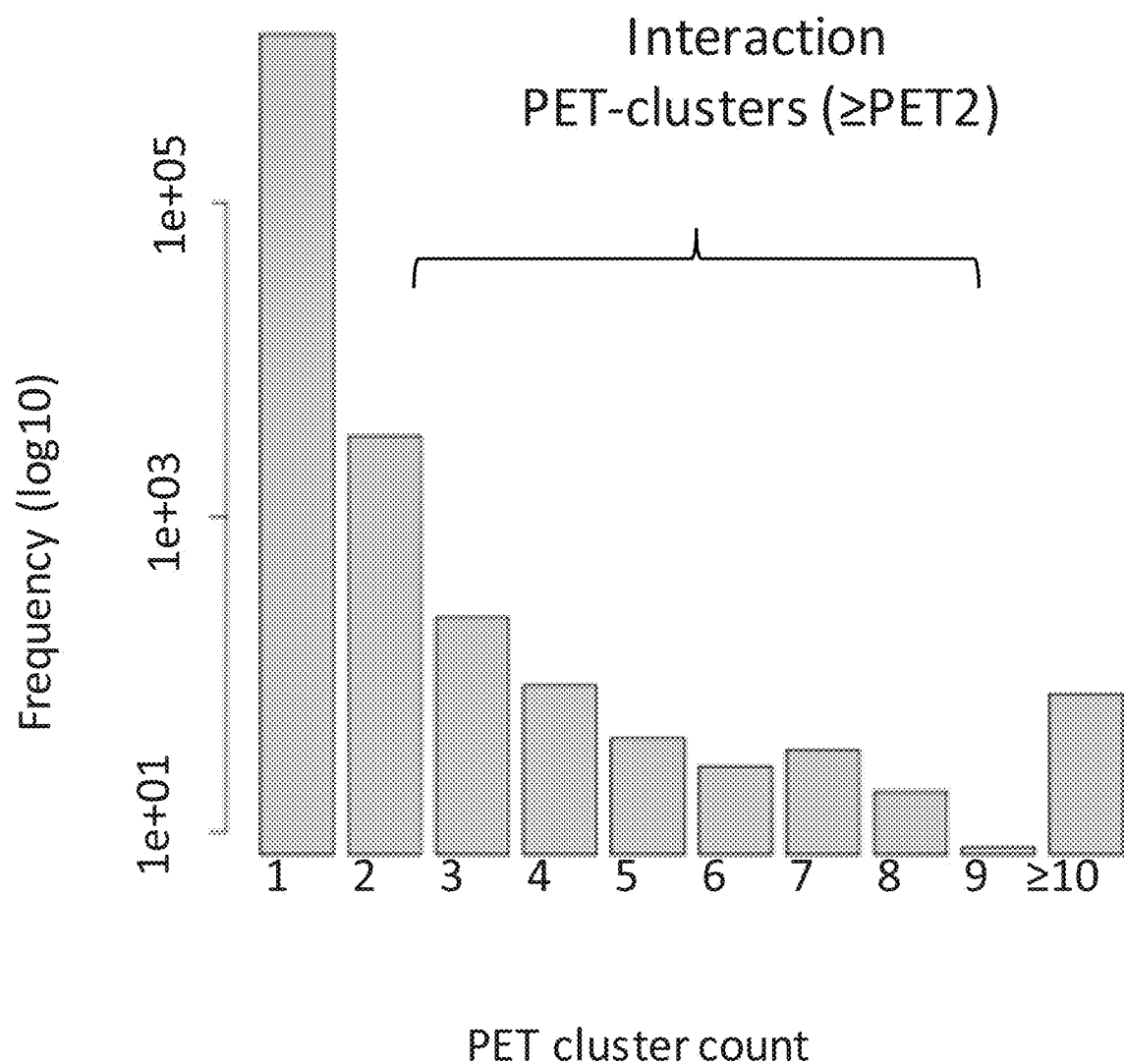
FIGS. 2A-2C present statistics of selected RICh-PET libraries, and sequencing and mapping data.

RICh-PET data is classified either as singleton PET (i.e., no overlap on both RNA-tag and DNA-tag with other PET sequences) or as PET cluster (i.e., both of the paired RNA-tag and DNA-tag sequences overlap with other PETs) with 2 and more PET sequences. The PET clusters are considered to be more reliable, or as high confidence data reflecting recurrent detection of more reliable events of ncRNA-chromatin interactions, whereas the singleton PETs may represent weak linking signals, but are indistinguishable from random background noises. Using the clustering criterion, approximately 700 putative RNA loci that are connected to about 5000 chromatin loci were identified (FIG. 2A).

Figure 2B:
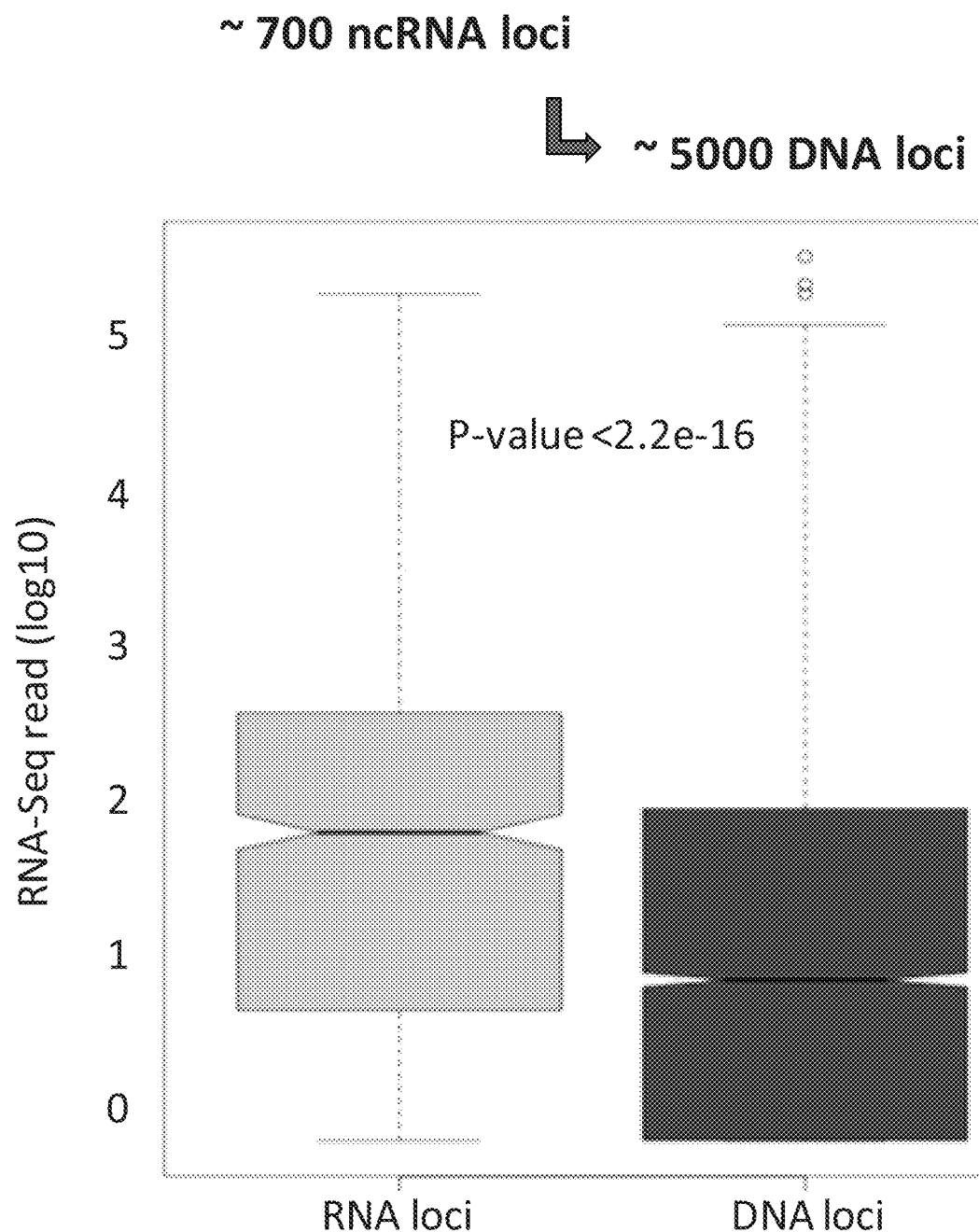

As a quick verification, RNA-seq signals for these RNA and DNA loci were checked, and it was found that the RNA loci indeed had significantly higher RNA counts than the DNA loci, suggesting that the RICh-PET data are as expected (FIG. 2B).

Figure 2C:
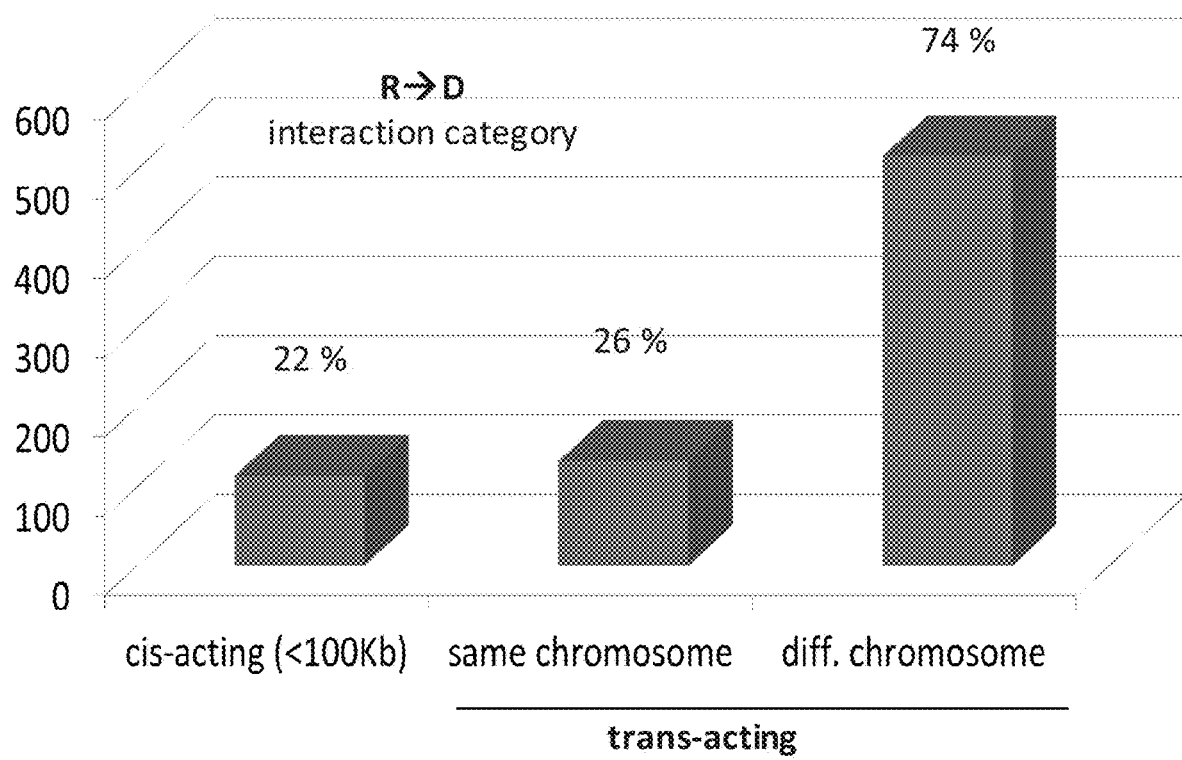

About one fifth (about 22%) of the obtained RNA-DNA connectivity data can be considered as cis-acting in nature (i.e., <100 kb from the RNA to DNA mapping sites), while the majority of the RNA-DNA connectivity data is trans-acting (FIG. 2C).

One concern was that the chromatin RNA-DNA ligation approach may capture mostly the nascent mRNA when transcription is still in process. Surprisingly, the data shows that most nascent mRNA transcripts appear to have their 3'-ends hidden within the center of the RNA polymerase complex, such that the method of the invention, which is partly based on using the supposedly free 3'-ends of ncRNA molecules, largely avoids the interference from nascent mRNA.

Specifically, mapping paired RICh-PET data reveals the distance between the paired RNA and DNA tags, thus suggesting possible mode of interacting action, cis or trans. The mapping results showed that only a small set of the data was cis-acting, and the majority was trans-acting and inter-chromosomal, indicating that the likelihood of capturing nascent transcripts in the RICh-PET protocol is low.

Further annotation analysis of the RNA tag clusters (see below) showed that only 3% of the RNA tags mapped to mRNA exons, while the vast majority mapped to ncRNAs.

Another concern was the abundance of rRNAs in cells, which is a general issue for RNA related analysis because in some cells, rRNA could be as high as 80% of total RNAs. One strategy to deal with rRNAs includes the avoidance approach, such as the polyA+ selection approach for mRNA and subtractive depletion of rRNA, used prior to the start of specific analysis. We assessed the abundance level of rRNA sequences in one of the RICh-PET libraries, and found that rRNA sequences constitute about 26% of the total RNA tags. In contrast, almost none (0.23%) of the DNA tags correspond to rRNA sequences. Thus a digital depletion approach may be used to remove all rRNA sequences before any further analysis to reduce data noise due to rRNA.

| RICh-PET | Total | Non-rRNA | rRNA |
|---|---|---|---|
| RNA Tag | 2308959 | 1699014 (73.58%) | 609945 (26.42%) |
| DNA Tag | 2308959 | 2303550 (99.77%) | 5409 (0.23%) |

Example 3 Reproducibility and Sensitivity of the RICh-PET Method

Figure 3:
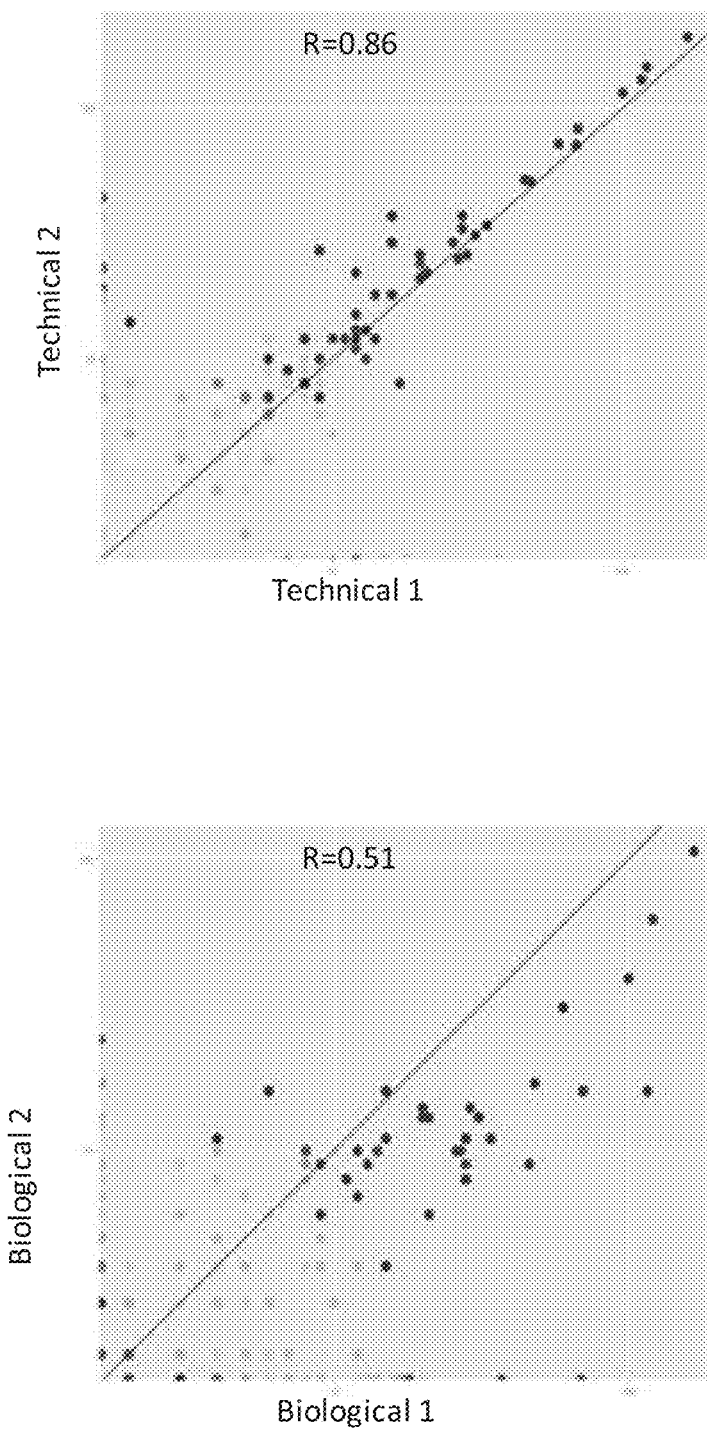
FIG. 3 demonstrates reproducibility and sensitivity of the subject method. The figure shows representative scatter plots showing the comparison of RNA interacting sites identified in technical and biological replicates. Known lncRNAs MALAT1 (PET count 174) and NEAT1 (PET 18) were repeatedly detected in RICh-PET data (not shown). RNAPII ChIA-PET data also shows that these two lncRNAs are also connected spatially within the same RNAPII transcriptional complex possibly for co-regulation. In addition, RNA-Seq and RNA-PET data were used to assess the expression level of ncRNA genes in HeLa S3 (data not shown). Both data showed that MALAT1 was highly expressed, NEAT1 was expressed at middle level, and HOTAIR was expressed at very low level. RICh-PET mapping at the HOTAIR locus shows poor RICh-PET data in this region (data not shown).

To assess the reproducibility of the RICh-PET data, two technical replicates (same cell preparations split into two aliquots for parallel library construction and sequencing analysis) and two biological replicates (different cell preparations collected at different times for use in library construction using nearly identical procedures with slight modifications) were performed. The resulting replicate results showed genuine reproducibility (FIG. 3). For example, the two well studied lncRNAs NEAT1 and MALAT1, known to be involved in cancers, were reproducibly detected in all three libraries (data not shown).

It is noteworthy that the two lncRNA genes were found to be spatially organized in an extensive chromatin interaction loop structure mediated by RNA polymerase II (RNAPII or RNA Pol2), indicating that their expressions are most likely co-regulated under a common transcription complex of machinery.

In RICh-PET data obtained herein, both MALAT1 and NEAT1 were highly expressed in HeLa S3 cells, and were abundantly detected in all three RICh-PET datasets. Specifically, NEAT1 was expressed relatively less compared to MALAT1 in the cells, thus the RICH-PET data counts to NEAT1 was less than that to MALAT1 (data not shown). As a control, HOTAIR is another known lncRNA expressed in low level in HeLa S3 cells, and it was not detected in the obtained RICh-PET data (data not shown).

Thus it appeared that the detection of ncRNA in RICh-PET data was well correlated with ncRNA expression levels.

Example 4 Validation of the RICh-PET Data

Figure 4A:
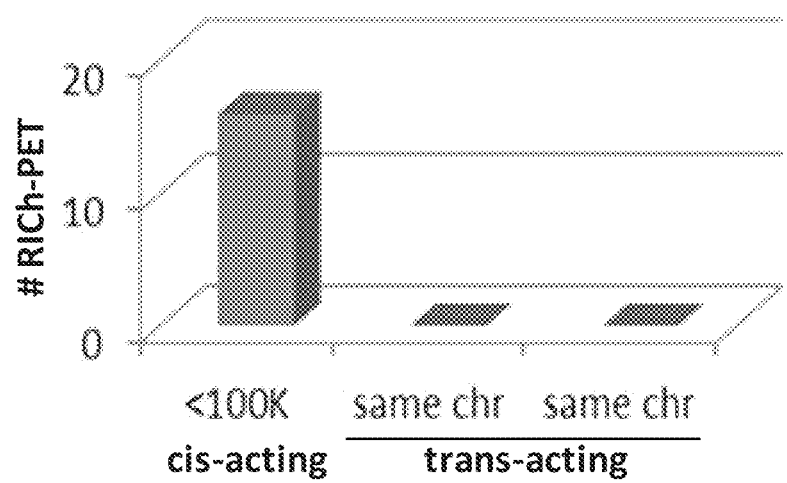
FIGS. 4A-4B show data for validation of NEAT1 and MALAT1 RICh-PET data.
Figure 4A:
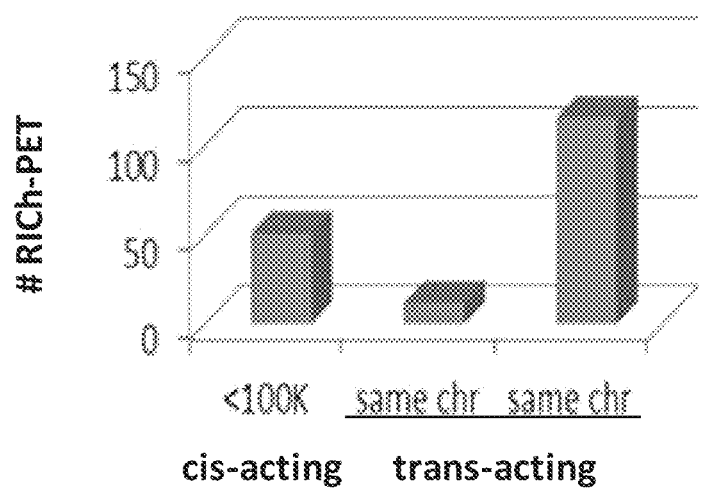

Based on the obtained RICh-PET mapping data, it is intriguing that even though these two ncRNAs are co-transcribed in the same transcription factory, their interaction properties are very different. Specifically, NEAT1 RNA is restrictively in cis, binding only to where it was transcribed; whereas MALAT1 is mostly out going in trans, interacting with many loci in the genome (FIG. 4A).

Figure 4B:
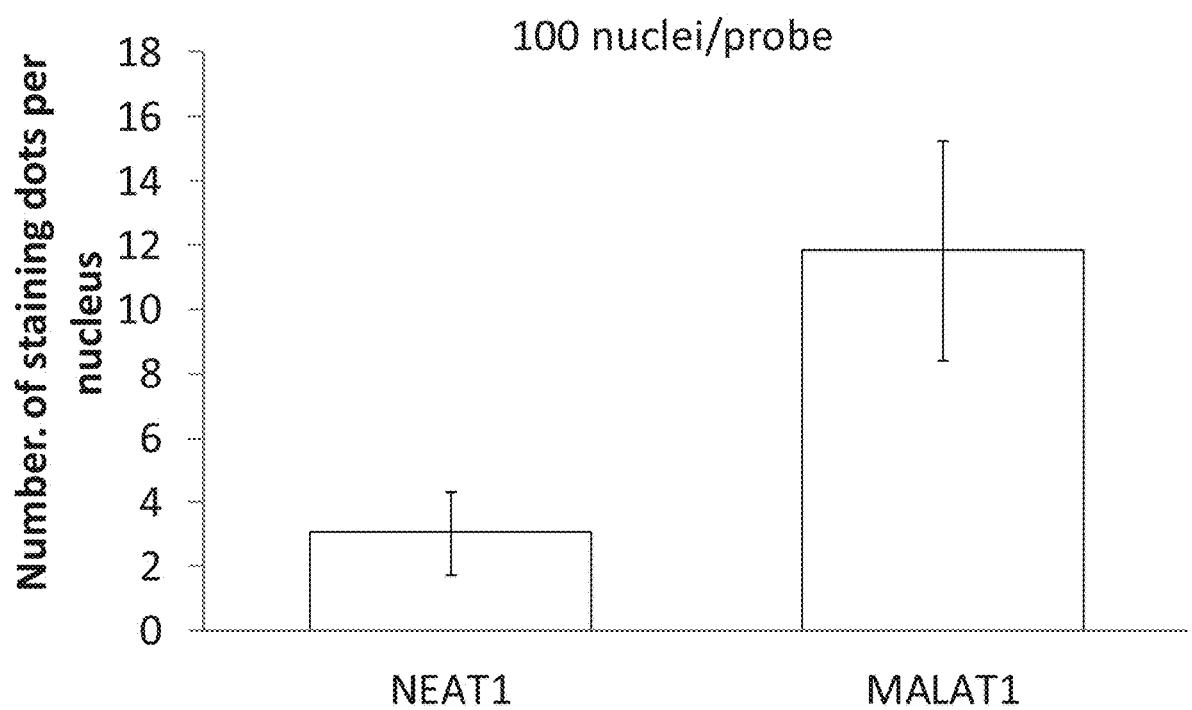

To validate this observation, RNA-FISH experiments were conducted using NEAT1 and MALAT1 RNAs as fluorescent probes to examine HeLa nuclei (FIG. 4B). As expected, the NEAT1 probe yielded only 1 or 2 spots per nucleus, whereas the MALAT1 probe spotted all over the nuclear space, consistent to what were observed in the RICh-PET data. Similar RNA-FISH result for NEAT1 and MALAT1 in A549 cells was also obtained. This validation suggests that RICh-PET data is qualitative and accurate in detecting and distinguishing authentic cis and trans interactions.

Example 5 Characterization of the RICh-PET Data

Figure 5A:
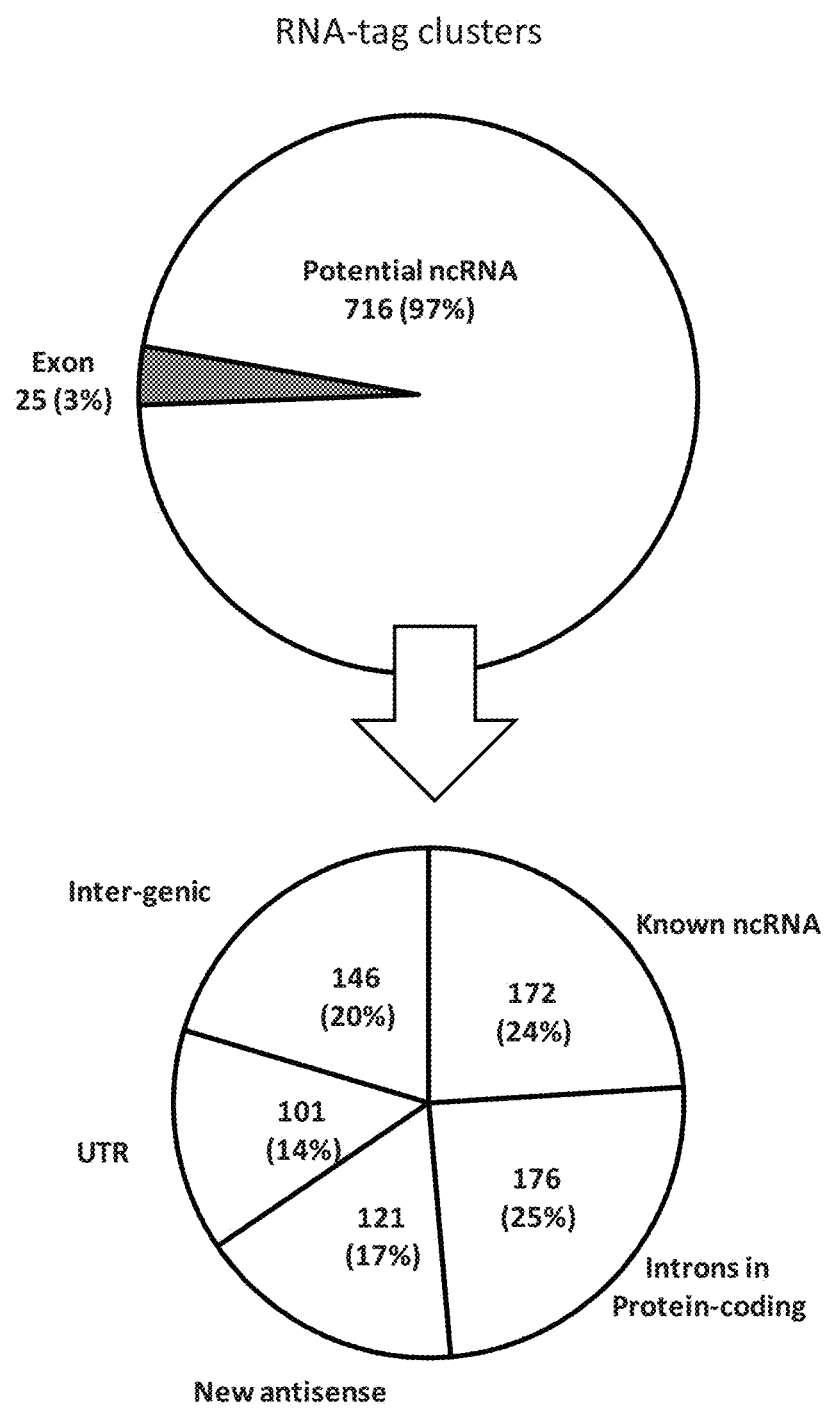
FIGS. 5A-5B characterize the RICh-PET data.

The RNA and DNA tag clusters were characterized based on Genecode V14 annotation of the human genome. Only 3% of the RNA tag clusters overlapped with protein-coding exons, and the vast majority of the RNA tag clusters were mapped to non-coding regions, many of which are previously known ncRNAs (172, 24%). The rest are potentially novel ncRNAs located in protein-coding intron regions, antisense, and inter-genetic regions (FIG. 5A).

Figure 5B:
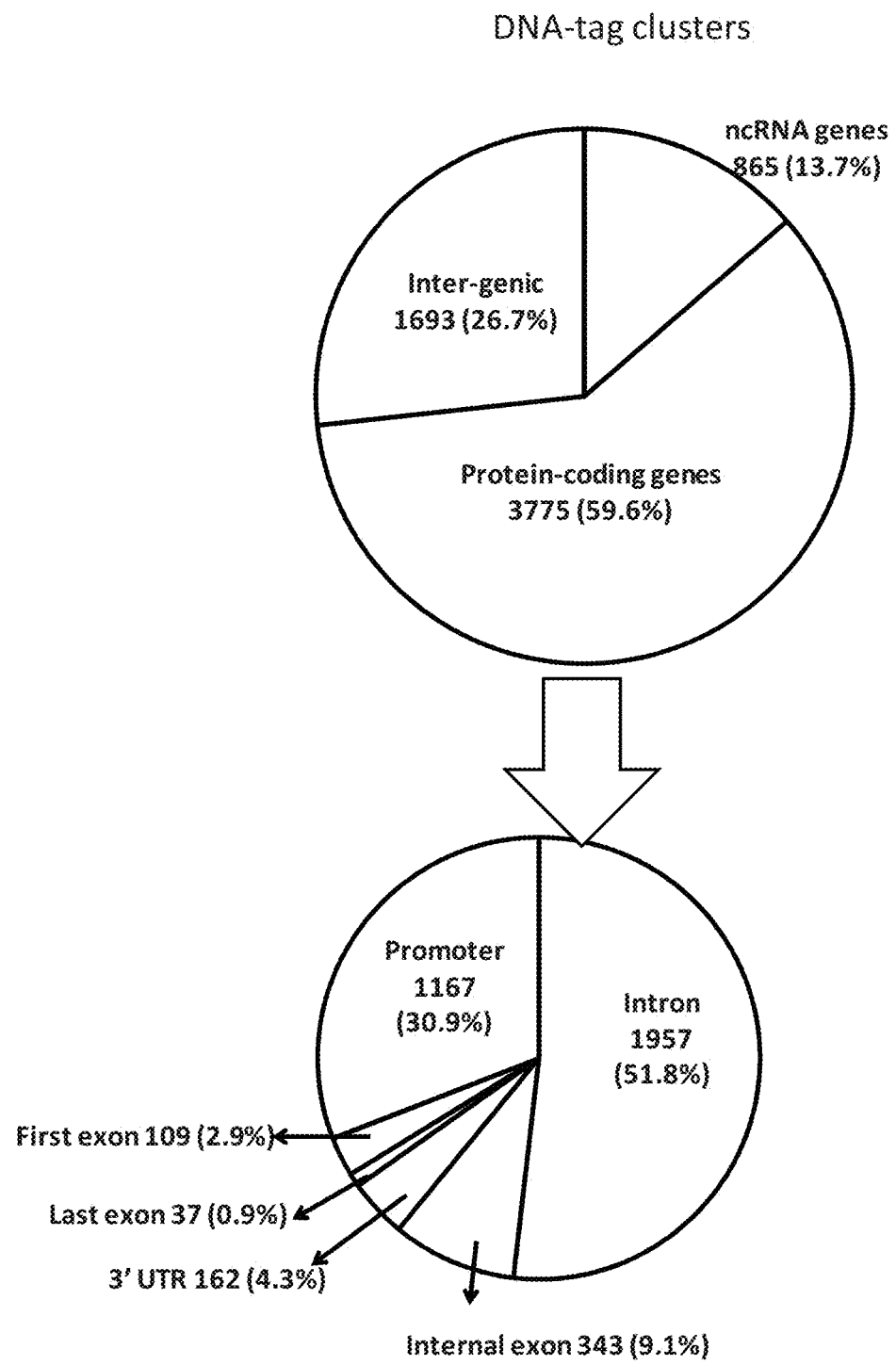

All putative ncRNAs identified in the RICh-PET data have RNA-Seq data support, indicating that they are actively transcribed in HeLa cells. In contrary, the DNA tag clusters of the RICh-PET data mapped mostly to protein-coding genes, and a significant portion to gene promoters (FIG. 5B).

A set of chromatin activity marks around the RNA and DNA tag clusters were subjected to further analysis. It is interesting to note that the center of RNA tag clusters are off the peaks of transcription activity defined by the signals of RNA Pol2 and DHS for open chromatin state, and such "off-center" property is strand specific (data not shown). This strand-specific "off-center" property is consistent with the RICh-PET methodology, as it is designed to capture the 3'-end of RNAs. Therefore, the RNA tag clusters are expected to be downstream of transcription start sites. In contrast, the chromatin activity signals are symmetrically peaked around the center of DNA tag clusters (data not shown), reflecting the random shearing of chromatin fibers by sonication.

Figure 6A:
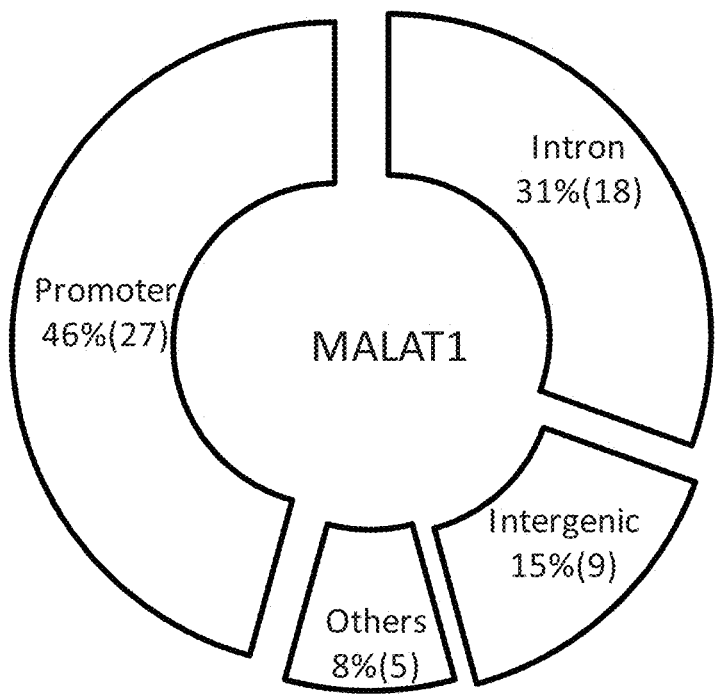
FIGS. 6A-6B show multi-targets and multi-functions by MALAT1 interactions.
Figure 6B:
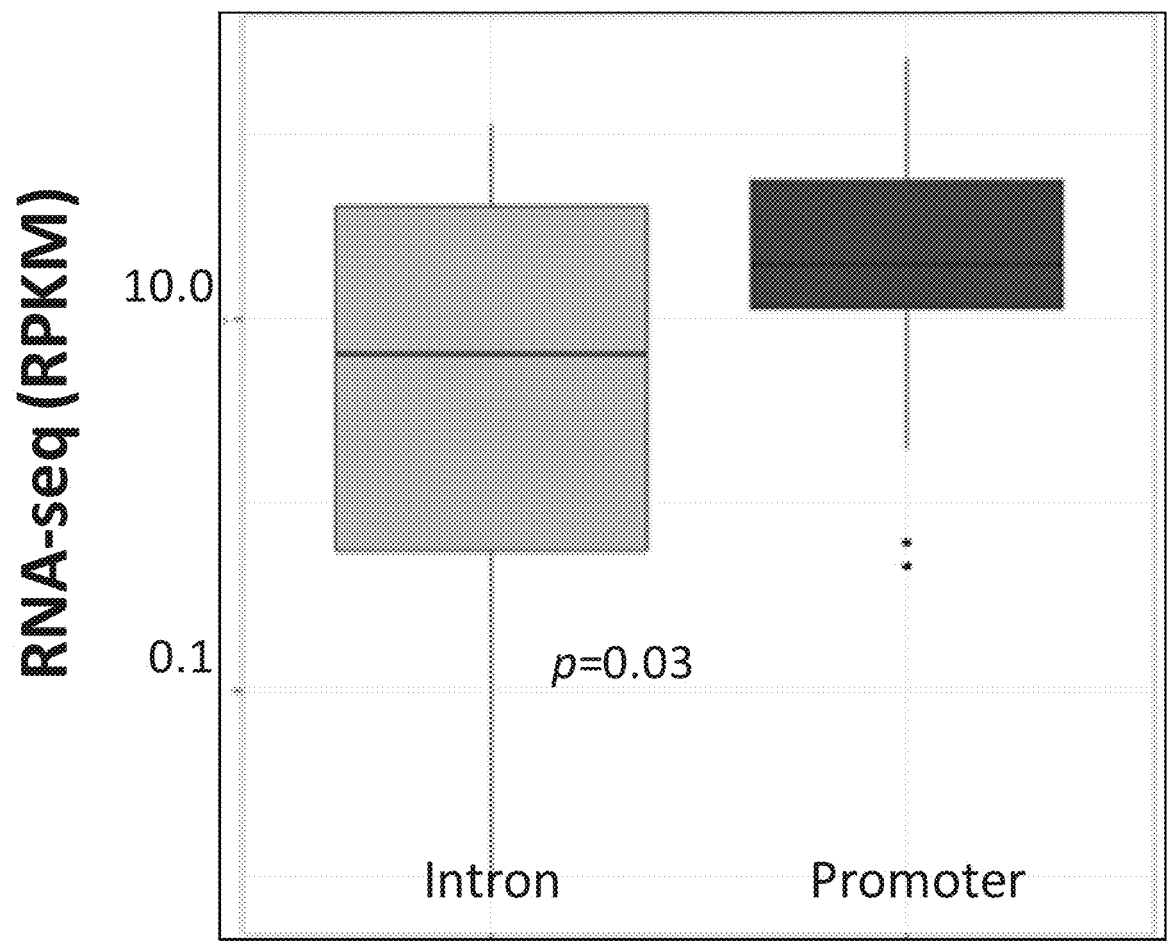
Figure 7:
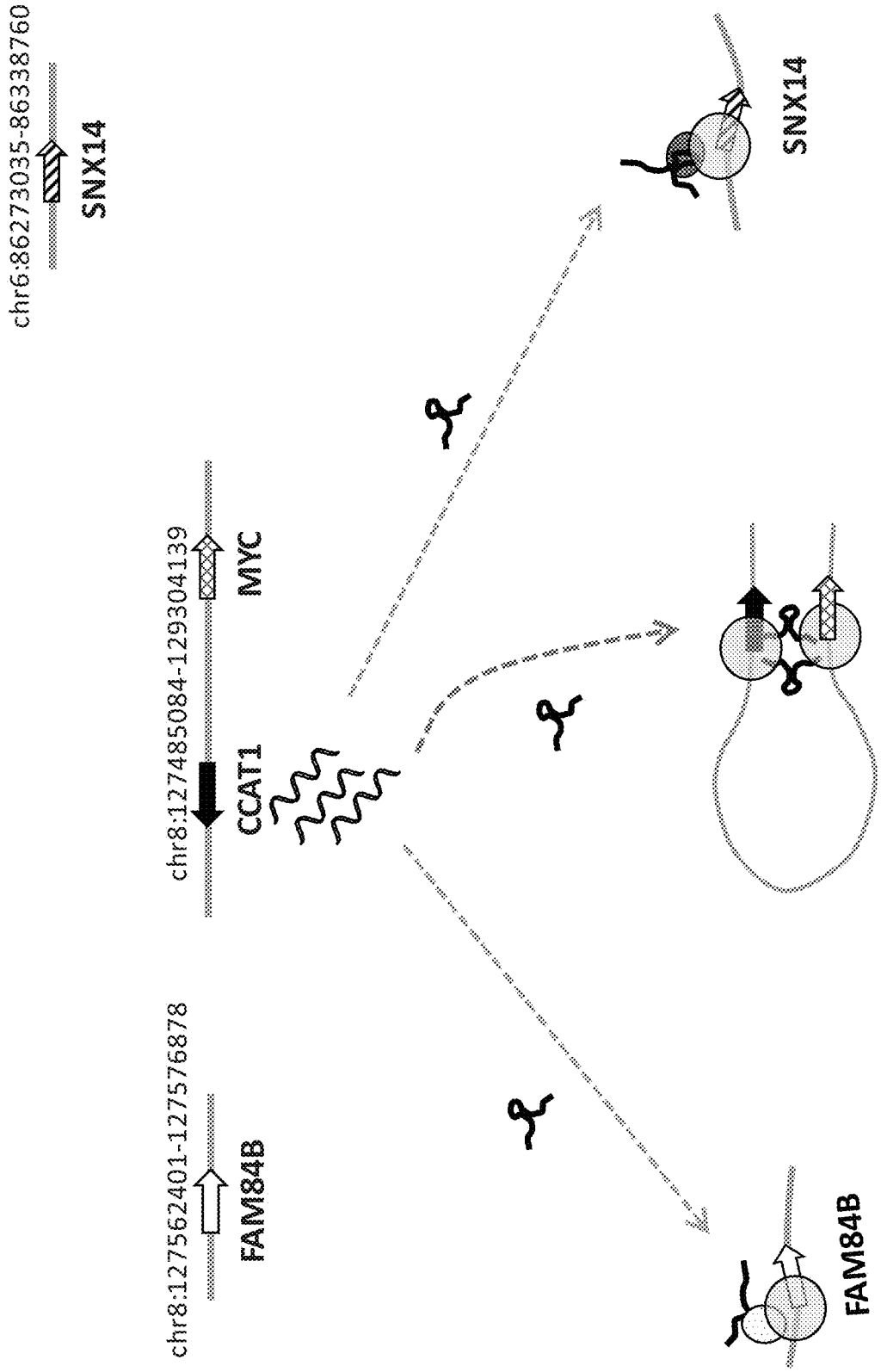
FIG. 7 shows a schematic drawing of CCAT1 and its lncRNA transcript acting as transcription activator or co-activator for several target genes.
Figure 8A:
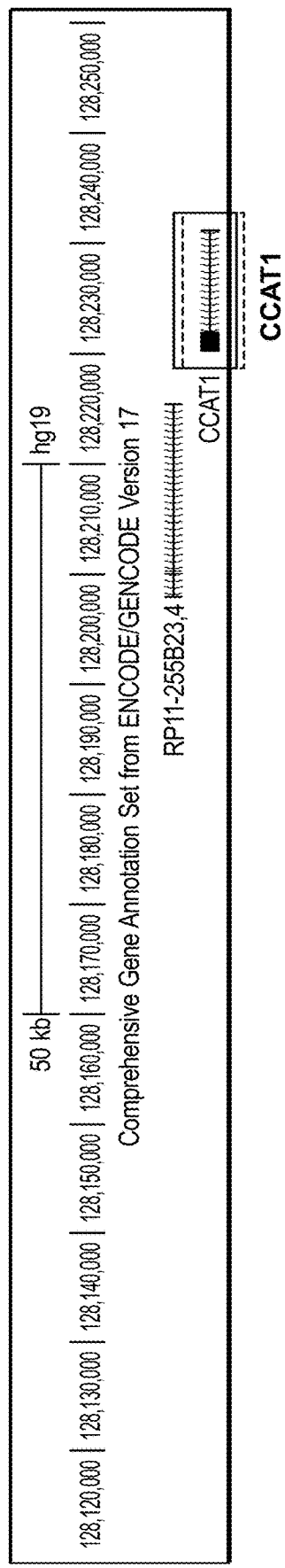
FIG. 8A shows the location on the human chromosome 8 of the CCAT1 genomic and cDNA sequences corresponding to SEQ ID NO: 9.
Figure 8B:
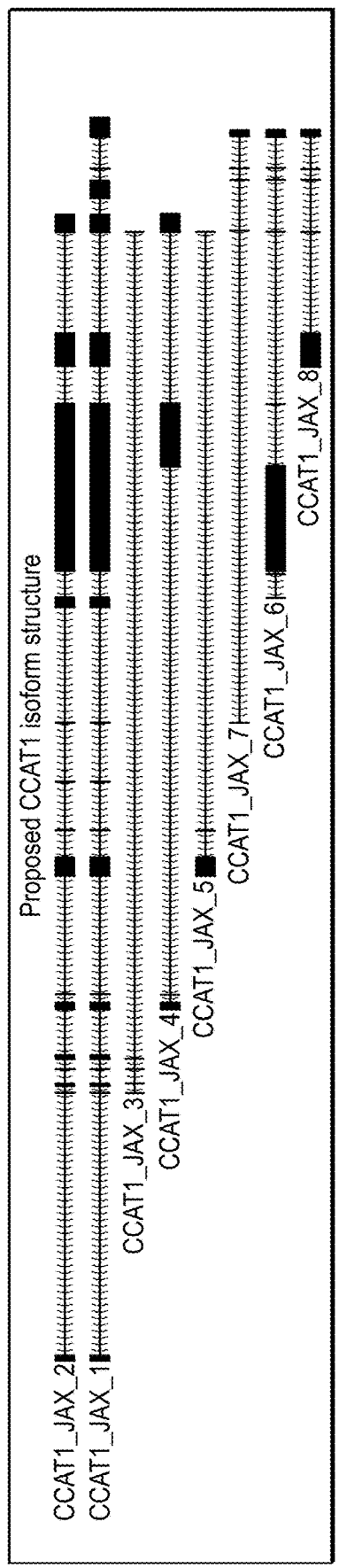
FIG. 8B shows the location on the human chromosome 8 of the eight additional CCAT1 genomic and cDNA sequences corresponding to SEQ ID NOs: 1-8 (CCAT1_JAX_1 to _8, respectively). Filled boxes represent exon sequences, while lines linking the exon sequences represent intron sequences.

Example 6 MALAT1 Interacts with Many Genomic Features and May Function for Both Gene Activation and Gene Repression Using all RICh-PET data connected to MALAT1 (including singleton PETs), Applicants generated the chromosome-wide and genome-wide MALAT1-interaction profile, showing that MALAT1 has a potential to interact with a large territory in the genome (data not shown). Of more than 50 high-confidence interactions (PET cluster with tag counts≥2) sites, about half are located in promoters and a quarter in intron regions of known genes (FIG. 6A). RNA-Seq and RNA Pol2 ChIP-seq data from the same cells showed that genes with MALAT1 presence in their promoters have significantly higher transcriptional activities than those with MALAT1 interacting at their intron regions (FIG. 6B; data not shown). It had been reported that MALAT1 was involved in modulating splicing functions through interacting with a number of splicing factors including SRSF2 (Tripathi et al., 2011).

Applicants also found that MALAT1 RNA may be directly involved in modulating the expression of SRSF2 by interacting with its promoter (data not shown). These observations suggest that MALAT1 may have multiple functional roles in regulating gene activation and repression.

Example 7 XIST's Function Beyond X-Chromosome

The most well characterized lncRNA is XIST, which is transcribed from one copy of the X chromosome and binds (cis-acting) to the same site in the other copy of the X chromosome, and further extends to coat the entire chromosome for inactivation (not shown). The RICh-PET mapping data indeed showed that the DNA tags paired with the RNA tags of XIST were highly enriched in the X chromosome, while the background noise was scattered throughout the genome, indicating that XIST is specifically bound to the X chromosome as expected.

Interestingly, it also appeared that there was some level of XIST-binding enrichment in one non-X chromosome, and somehow depleted to another non-X chromosome. More data and further analysis are being obtained to further validate this observation.

Example 8 Complex Interaction Networks by ncRNAs

The RICh-PET data presented here provided a first glimpse into the complex systems of ncRNA interaction networks. In addition to the classic view that one ncRNA may have multiple targets in the genome (MALAT1), it had been found that many putative ncRNA loci have "in-and-out" RICh-PET data, in that a locus was found to be interacted by an ncRNA and from where an interactive ncRNA was also detected to interact with another locus.

In many sense, this ncRNA interaction network is similar to transcription factor (TF) binding networks, in which many TFs bind to each other's genes for transcriptional modulation. More data will help to further illustrate how ncRNAs function, and how the ncRNA interaction networks impact the genome system.

Example 9 lncRNA Encoded by CCAT1 is a Transcription Co-Activator

The RICh-PET method was used to identify global ncRNA—genomic DNA interaction. Among the identified interactions, one ncRNA—the Colon Cancer Associated Transcript 1—was of particular interest.

Colon Cancer Associated Transcript 1 (CCAT1) is a 2628 nucleotide-long, non-coding RNA recently discovered using Representational Difference Analysis (RDA), cDNA cloning, and rapid amplification of cDNA ends (RACE) (Nissan et al., "Colon cancer associated transcript-1: A novel RNA expressed in malignant and pre-malignant human tissues," *Int. J. Cancer*, 13:1598-1606, 2012). It is recently found to be over-expressed in colon cancer (CC), but not in normal tissues, thereby making it a potential disease-specific biomarker (Nissan et al., *Int. J. Cancer*, 130(7):1598-606, 2012; Alaiyan et al., *BMC Cancer*, 13:196, 2013).

Careful analysis based on the RICh-PET data revealed a new complex model of isoform transcripts in this locus (data not shown). In addition, CCAT1 is highly transcribed in the cervical cancer cell line HeLa cells.

RICh-PET data also revealed that the CCAT1 lncRNA transcripts targets many other loci in the genome (data not shown), including all the human chromosomes except for chromosomes 15, 16, 20, X and Y.

Among the CCAT1 chromatin targets having at least 2 CCAT1 tags, many show the strongest lncRNA-genomic DNA association in enhancers or promoters (data not shown). For example, for the 122 CCAT1 genomic target loci associated with at least 3 CCAT1 RNA tags, 88 target loci are in the enhancer region, including 6 of the enhancer loci with RNAPII interaction. Another 34 genomic target loci of CCAT1 are in promoters.

These CCAT1 target genes have an average expression level several folds higher than randomly selected collections of control genes, suggesting that CCAT1 lncRNA promotes target gene expression.

One of these CCAT1 target genes is c-myc, an oncogene overexpressed in a wide variety of human cancers, including about 80% of breast cancers, 70% of colon cancers, 90% of gynecological cancers, 50% of hepatocellular carcinomas, and a variety of hematological tumors (such as Burkitt's lymphoma) possessing abnormal myc expression. Additional data suggests that the CCAT1 lncRNA functions by binding to the CCAT1 locus itself as well as the myc locus, thus bringing the CCAT1 and myc loci to close physical proximity, and allowing the enhancers in the CCAT1 locus to stimulate myc transcription. In addition, the CCAT1 transcribed lncRNA may bind to protein factors and serve as transcription co-activators, thus directly enhancing transcription of myc, as well as other CCAT1 target genes such as FAM84B and SNX14.

Example 10 Additional Applications in Human B-Lymphoblastoid Cells GM12878 and *Drosophila* S2 Cells Using substantially the same RICh-PET methods described above, Applicants obtained additional data from the human B-lymphoblastoid cells GM12878 and the *Drosophila* S2 cells to further support the general applicability of the RICh-PET methods.

Specifically, the human GM12878 cells were used for RICh-PET analysis because the ncRNA gene XIST is highly expressed in this cell line, while the previous HeLa cells used for RICh-PET analysis have low level of XIST expression, and HCT116 is derived from a male, thus having no XIST expression. Hence, GM12878 is a much better cell type for RICh-PET analysis when using XIST as a model to evaluate the performance of RICh-PET analysis to detect ncRNA interaction with chromatin.

Figure 9A:
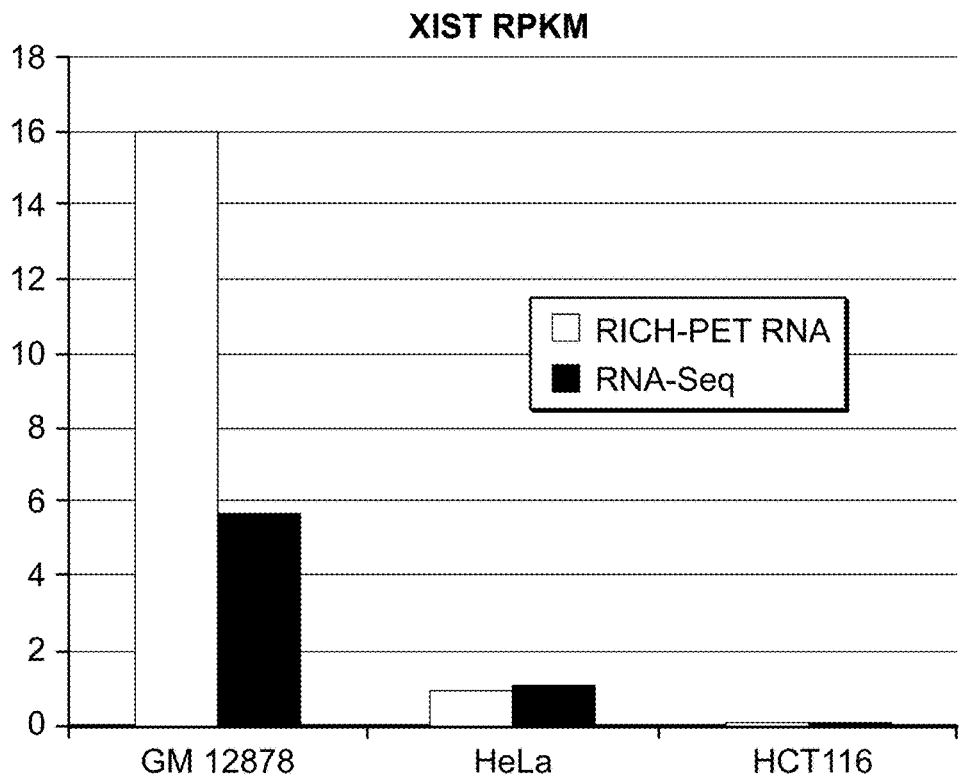
FIG. 9A shows the counts of XIST (which specifically targets the X chromosome in female cells) measured by RNA-Seq data, in reads per kb per million reads (RPKM).
Figure 9B:
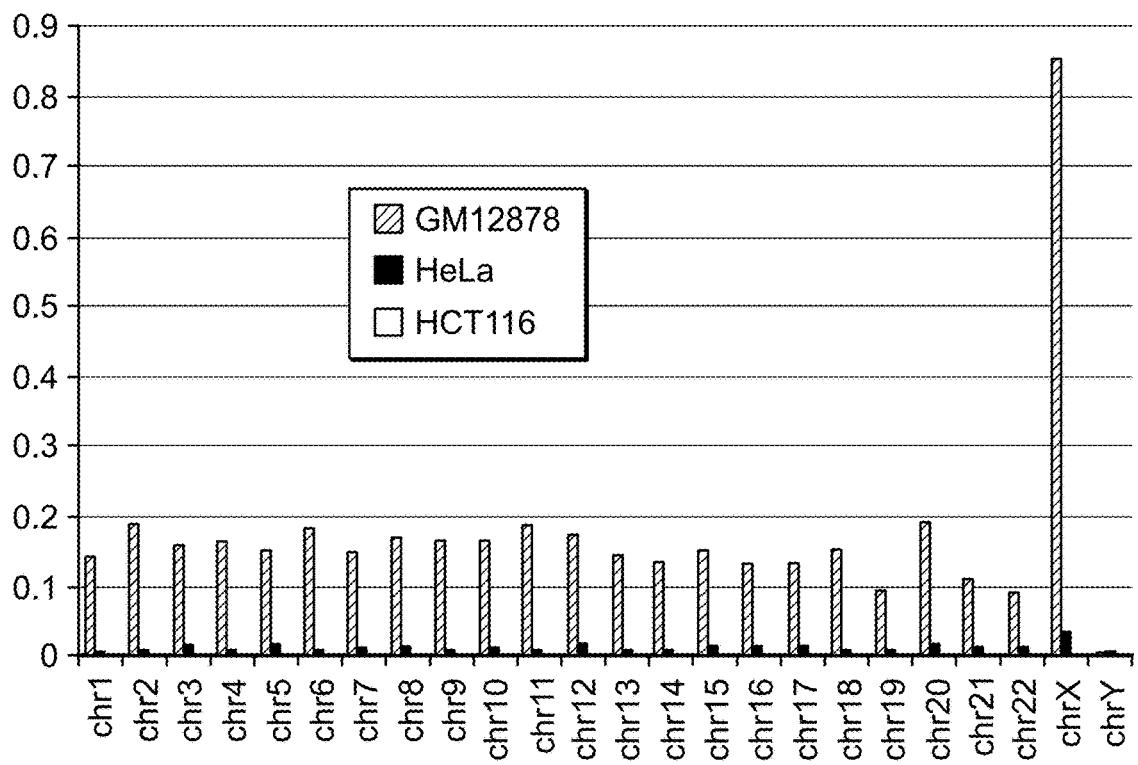
FIG. 9B shows the proportion of each chromosome covered by XIST binding.

As previously described, XIST specifically or preferentially binds to the X-chromosome. See FIG. 9A, which shows the counts of XIST measured by RNA-Seq data, in reads per kb per million reads (RPKM); and FIG. 9B, which shows the proportion of each chromosome covered by XIST binding. In GM12878 cells, most of the chromosomes were only covered by XIST in 10-20% of the total chromosome space, whereas the X-chromosome was covered by nearly 90% by XIST. This coverage represents almost 6-fold (5.9-fold) specificity of the XIST to its targeting chromosome over the other non-specific chromosomes. In contrast, in HeLa cells, the coverage represented about 3.4-fold specificity of the XIST to its targeting chromosome over the other non-specific chromosomes, and in HCT116 cells, there was no observed X-chromosome enrichment, as expected.

Similarly, in *Drosophila* S2 cells, the ncRNA gene rox2—an equivalent to XIST of human—showed similar enrichment of rox2 binding to X-chromosome: 5-fold over the other chromosomes (data not shown). Specifically, rox2 binding data in whole *Drosophila* genome was obtained. More than 80% of the rox2-linked DNA-tags bind to the X-chromosome, representing a 5-fold enrichment to the X-chromosome. There was a reasonably strong correlation value (0.6) observed between rox2 mapping on X-chromosome by CHART-seq, and by the RICh-PET method, demonstrating the suitability of the RICh-PET method.

The majority of the RNA-tags of the RICh-PET data mapped to non-coding regions, while only about 26% are in coding regions, indicating the method has enrichment for ncRNA (data not shown). Comparison of the RNA-tags of RICh-PET data with the RNA-seq data from *Drosophila* S2 cells showed significant enrichment for know ncRNAs (data not shown).

In summary, data presented in the examples above demonstrates that the method of the invention (e.g., RICh-PET method) works as designed. The vast majority of the RNA tags in the RICh-PET data were mapped to non-coding regions, and some of them mapped to known lncRNAs such as MALAT1 and NEAT1. This is a strong indication that this method performed as expected. More importantly, through the RNA-DNA connectivity mapping data, Applicants are able to identify potential ncRNA-chromatin interaction loci genome-wide. Several lines of preliminary validations done so far have suggested that RICh-PET identified ncRNA interactions are bonafide.

We claim:

1. A paired-end tag (PET) polynucleotide comprising a central region comprising a double-stranded region of a modified RNA linker, the modified linker comprising:
   (i) a first polynucleotide; and,
   (ii) a second polynucleotide,
wherein the first and the second polynucleotides form a double-stranded region flanked by a genomic DNA ligation compatible end, and a 3-overhang at the 3-end of the first polynucleotide, wherein the 3-overhang comprises a random-sequence primer, and optionally wherein the random-sequence primer comprises 4, 5, 6, 7, 8, or more nucleotides, wherein the central region is flanked by:
   (a) at a site proximal to the random-sequence primer, a sequence tag of a non-coding RNA (ncRNA); and
   (b) at a site proximal to the genomic DNA ligation compatible end, a sequence tag of a genomic DNA.

2. The PET polynucleotide of claim 1, wherein the sequence tag of the ncRNA has a free end resulting from digestion by a first restriction enzyme recognizing a first recognition site in the double-stranded region, or, wherein the sequence tag of the ncRNA uniquely identifies a genomic region from which the ncRNA is transcribed, or, wherein the sequence tag of the ncRNA is about 8-30 base pairs in length, or, wherein the sequence tag of the genomic DNA has a free end resulting from digestion by a second restriction enzyme recognizing a second recognition site in the double-stranded region, or, wherein the sequence tag of the genomic DNA uniquely identifies a genomic region at which the genomic DNA is located, or, wherein the sequence tag of the genomic DNA is about 8-30 base pairs in length.

3. A library of the PET polynucleotide of claim 1, comprising two or more PET polynucleotides, each comprising the same central region, and different RNA sequence tag of the ncRNA, different DNA sequence tag of the genomic DNA, or both.

4. A vector or recombinant vector comprising the PET polynucleotide of claim 1.

5. A kit comprising a direct RNA linker comprising:
   (a) a first polynucleotide; and,
   (b) a second polynucleotide,
wherein the first and the second polynucleotides form a double-stranded region flanked by a genomic DNA ligation compatible end, and a 5'-overhang at the 5'-end of the first polynucleotide, and optionally wherein the 5'-overhang is 5' adenylated.

6. A paired-end tag (PET) polynucleotide comprising a central region comprising the double-stranded region of the direct RNA linker of claim 5 flanked by:
   (a) a sequence tag of an ncRNA a site proximal to the 5' end of the first polynucleotide, wherein the site is 5' adenylated or suitable to be 5' adenylated; and
   (b) a sequence tag of a genomic DNA at a site proximal to the ligation compatible end.

7. A library of the PET polynucleotide of claim 6, comprising two or more PET polynucleotides, each comprising the same central region, and different RNA sequence tag of the ncRNA, different DNA sequence tag of the genomic DNA, or both.

8. A vector or recombinant vector comprising the PET polynucleotide of claim 6.

* * * * *